United States Patent
He et al.

(10) Patent No.: US 11,053,260 B2
(45) Date of Patent: Jul. 6, 2021

(54) TRI-CYCLE COMPOUND AND APPLICATIONS THEREOF

(71) Applicant: FUJIAN COSUNTER PHARMACEUTICAL CO., LTD., Fujian (CN)

(72) Inventors: Haiying He, Shanghai (CN); Jing Wang, Shanghai (CN); Zhigan Jiang, Shanghai (CN); Yaxun Yang, Shanghai (CN); Peng Shao, Shanghai (CN); Chen Zhang, Shanghai (CN); Jian Li, Shanghai (CN); Shuhui Chen, Shanghai (CN)

(73) Assignee: FUJIAN COSUNTER PHARMACEUTICAL CO., LTD., Ningde (CN)

( * ) Notice: Subject to any disclaimer, the term of this patent is extended or adjusted under 35 U.S.C. 154(b) by 3 days.

(21) Appl. No.: 16/488,244

(22) PCT Filed: Feb. 9, 2018

(86) PCT No.: PCT/CN2018/075995
§ 371 (c)(1),
(2) Date: Aug. 23, 2019

(87) PCT Pub. No.: WO2018/153285
PCT Pub. Date: Aug. 30, 2018

(65) Prior Publication Data
US 2020/0247819 A1    Aug. 6, 2020

(30) Foreign Application Priority Data

| Feb. 23, 2017 | (CN) | 201710100309.1 |
| Aug. 1, 2017 | (CN) | 201710648155.X |
| Jan. 4, 2018 | (CN) | 201810008592.X |

(51) Int. Cl.
C07D 513/04 (2006.01)
A61P 31/12 (2006.01)
C07D 519/00 (2006.01)

(52) U.S. Cl.
CPC ............ C07D 513/04 (2013.01); A61P 31/12 (2018.01); C07D 519/00 (2013.01)

(58) Field of Classification Search
CPC .................................................. C07D 513/04
USPC ................................................... 514/210.18
See application file for complete search history.

(56) References Cited

U.S. PATENT DOCUMENTS

2018/0319819 A1    11/2018 Yogo et al.

FOREIGN PATENT DOCUMENTS

| CA | 2691056 A1 | 12/2008 |
| CA | 2922302 A1 | 10/2014 |
| CN | 102060786 A | 5/2011 |
| CN | 105102451 A | 11/2015 |
| CN | 106255684 A | 12/2016 |
| CN | 106413402 A | 2/2017 |
| CN | 106459032 A | 2/2017 |
| JP | 2016-515598 A | 5/2016 |
| JP | 2016-537368 A | 12/2016 |
| WO | 2008154817 A1 | 12/2008 |
| WO | 2014161888 A1 | 10/2014 |
| WO | 2015138895 A1 | 9/2015 |
| WO | 2015173164 A1 | 11/2015 |
| WO | 2017048954 A1 | 3/2017 |
| WO | 2017069279 A1 | 4/2017 |
| WO | 2018053157 A1 | 3/2018 |

OTHER PUBLICATIONS

Office Action issued in the counterpart Israeli application No. 268827 dated Dec. 12, 2019.
Extended European Search Report issued in the counterpart European application No. 18757445.4 dated Jan. 21, 2020.
Notification of Reasons for Refusal issued in the counterpart Japanese application No. 2019-557752 dated Jan. 21, 2020.
Office Action issued in the counterpart Canadian application No. 3,054,324 dated Nov. 26, 2019.
Office Action issued in the counterpart Korean application No. 10-2019-7027723 dated Nov. 25, 2019.
Third Office Action issued in the counterpart Chinese application No. 201880001646.8 dated Oct. 30, 2019.
International Search Report and Written Opinion of PCT/CN2018/075995 dated May 9, 2018.
First Office Action and Search Report issued in counterpart Chinese patent application No. 201880001646.8 dated May 15, 2019.
Second Office Action issued in counterpart Chinese patent application No. 201880001646.8 dated Aug. 7, 2019.
The Second Office Action issued in the counterpart Canadian application No. 3,054,324 dated Mar. 4, 2020.
The First Office Action issued in the counterpart Malaysian application No. PI2019004841 dated May 27, 2020.
The Written Opinion issued in the counterpart Singaporean application No. 11201907725S dated Jun. 11, 2020.
The Second Office Action issued in the counterpart Japanese application No. 2019-557752 dated Jun. 16, 2020.

(Continued)

*Primary Examiner* — Kahsay Habte

(57) ABSTRACT

Disclosed in the present invention are a compound represented by formula (I), a tautomer thereof or a pharmaceutically acceptable salt, and applications thereof in the preparation of drugs for treating HBV-related diseases.

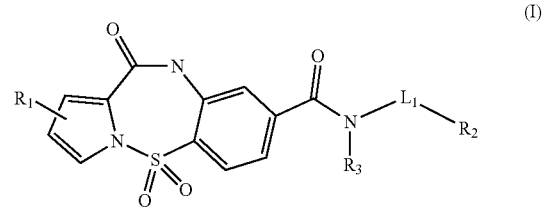

(I)

18 Claims, 1 Drawing Sheet
Specification includes a Sequence Listing.

(56) References Cited

OTHER PUBLICATIONS

The First Office Action issued in the counterpart Mexican application No. MX/a/2019/010042 dated Aug. 13, 2020.
The First Office Action issued in the counterpart Australian application No. 2018223435 dated Aug. 13, 2020.
The First Office Action issued in the counterpart Eurasian application No. 201991910 dated Sep. 15, 2020.
Mar. 15, 2021 Indian Office Action issued in Indian Patent Application No. 201947036066.

TRI-CYCLE COMPOUND AND APPLICATIONS THEREOF

CROSS REFERENCE TO RELATED APPLICATIONS

The present application claims priorities of the Chinese Patent Application No. CN201810008592.X filed on Jan. 4, 2018, the Chinese Patent Application No. CN201710648155.X filed on Aug. 1, 2017 and the Chinese Patent Application No. CN201710100309.1 filed on Feb. 23, 2017, the contents of which are incorporated herein by reference in their entireties.

REFERENCE TO SEQUENCE LISTING

The Sequence Listing is submitted concurrently with the specification as an ASCII formatted text file via EFS-Web, with a file name of "BSHING-19054-USPT_SEQ.TXT", a creation date of Apr. 8, 2021, and a size of 1,108 bytes. The Sequence Listing filed via EFS-Web is part of the specification and is incorporated in its entirety by reference herein.

FIELD OF THE INVENTION

The invention relates to a compound represented by formula (I), a tautomer thereof or a pharmaceutically acceptable salt thereof, and a use thereof in manufacturing a medicament for treating diseases associated with HBV.

BACKGROUND OF THE INVENTION

Hepatitis B is an inflammatory response caused by hepatitis B virus invasion, which can lead to a series of disorders such as liver pain, hepatosplenomegaly, liver fibrosis, severe cirrhosis and even liver cancer. According to statistics, there are about 350-400 million carriers of hepatitis B virus in the world, and one third of them are in China. In China, the number of deaths caused by hepatitis B reaches up to 500,000 per year.

At this stage, there is no efficacious drug to cure hepatitis B in the world. The first-line drugs for hepatitis B treatment in China are mainly nucleosides drugs, interferon and traditional Chinese medicine, which are accompanied with problems such as high cost and easy recurrence. Therefore, the development of a new type of anti-hepatitis B drug is imperative.

WO2008154817A1 discloses the structure of GLS4 as follows:

GLS4

Content of the Invention

The invention provides a compound of formula (I), an isomer thereof or a pharmaceutically acceptable salt thereof, (I)

$L_1$ is a single bond or —$C_{1-6}$ alkyl-;

$R_1$ is H, Cl, F, Br I or $C_{1-3}$ alkyl which is optionally substituted by 1, 2 or 3 R;

$R_2$ is selected from the group consisting of $C_{1-3}$ heteroalkyl, 4-8 membered heterocycloalkyl, 5-10 membered heteroaryl, 4-8 membered partially unsaturated heterocycloalkyl, phenyl, $C_{1-3}$ alkyl, $C_{3-8}$ cycloalkyl, 4-8 membered heterocycloalkyl-O— and 5-10 membered heteroaryl-O—, each of which is optionally substituted by 1, 2 or 3 R;

$R_3$ is H or $C_{1-3}$ alkyl;

each of R is independently H, Cl, F, Br, I, $NH_2$, OH or CN, or selected from the group consisting of $C_{1-6}$ alkyl, $C_{1-6}$ heteroalkyl, phenyl, phenyl-O—C(=O)— and 5-6 membered heteroaryl, each of which is optionally substituted by 1, 2 or 3 R';

each of R' is independently selected from the group consisting of Cl, F, Br, I, $NH_2$, $CH_3$, CN and $N(CH_3)_2$;

each of the "hetero" in the $C_{1-3}$ heteroalkyl, 4-8 membered heterocycloalkyl, 5-10 membered heteroaryl, $C_{1-6}$ heteroalkyl, 5-6 membered heteroaryl and 4-8 membered partially unsaturated heterocycloalkyl is independently selected from the group consisting of —S—, —O—, —NH—, N, —C(=O)—, —O—C(=O)—, —S(=O)$_2$—, —S(=O)—, —NH—C(=O)— and —NH—C(=O)—O—;

in any of the above cases, the number of the heteroatom or the heteroatomic group is independently 1, 2, 3 or 4.

In some embodiments of the invention, R is H, Cl, F, Br, I, $NH_2$, OH or CN, or selected from the group consisting of $C_{1-3}$ alkyl, $C_{1-6}$ alkyl-O—C(=O)—, $C_{1-6}$ alkyl-C(=O)—, $C_{1-3}$ alkyl-S(=O)$_2$—, $C_{1-3}$ alkyl-S(=O)—, $C_{1-3}$ alkylamino, phenyl, phenyl-O—C(=O)— and pyridyl, each of which is optionally substituted by 1, 2 or 3 R', and other variables are as defined in the invention.

In some embodiments of the invention, R is H, Cl, F, Br, I, $NH_2$, OH or CN, or selected from the group consisting of $CH_3$, -continued

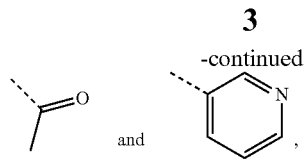

each of which is optionally substituted by 1, 2 or 3 R, and other variables are as defined in the invention.

In some embodiments of the invention, R is selected from the group consisting of H, Cl, F, Br, I, $NH_2$, OH, $CH_3$, CN,

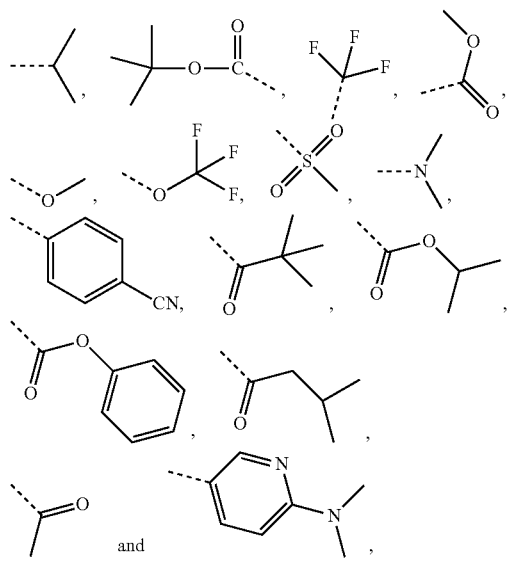

and other variables are as defined in the invention.

In some embodiments of the invention, $R_1$ is selected from the group consisting of H, Cl, F, Br, I, Me, Et,

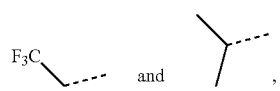

and other variables are as defined in the invention.

In some embodiments of the invention, $R_2$ is selected from the group consisting of $C_{1-3}$ alkoxy, tetrahydrofuranyl, thiazolyl, 3-azabicyclo[3.1.0]hexyl, pyridyl, benzimidazolyl, thienyl, pyrazolyl, benzothiazolyl, imidazo[1,2-a]pyridyl, methyl, $C_{1-3}$ alkylthio, $C_{1-3}$ alkyl-S(=O)$_2$—, cyclopentyl, phenyl, azetidinyl, piperidinyl, pyrrolidinyl, oxazolyl, 2-oxo-pyrrolidinyl, 2(1H)-oxo-pyridinyl, cyclohexyl, cyclopropyl, 1,1-dioxo-isothiazolidinyl, pyrimidinyl, 1,3,4-thiadiazolyl, 2-oxo-oxazolidinyl, tetrahydropyranyl, cyclopentyl-O—, pyridyl-O—, oxepanyl, 1,4-dioxanyl, 1,4-dioxepanyl, morpholinyl and 2,3-dihydrobenzo[b][1,4]dioxinyl, each of which is optionally substituted by 1, 2 or 3 R, and other variables are as defined in the invention.

In some embodiments of the invention, $R_2$ is selected from the group consisting of $CH_3$,

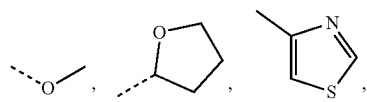

-continued

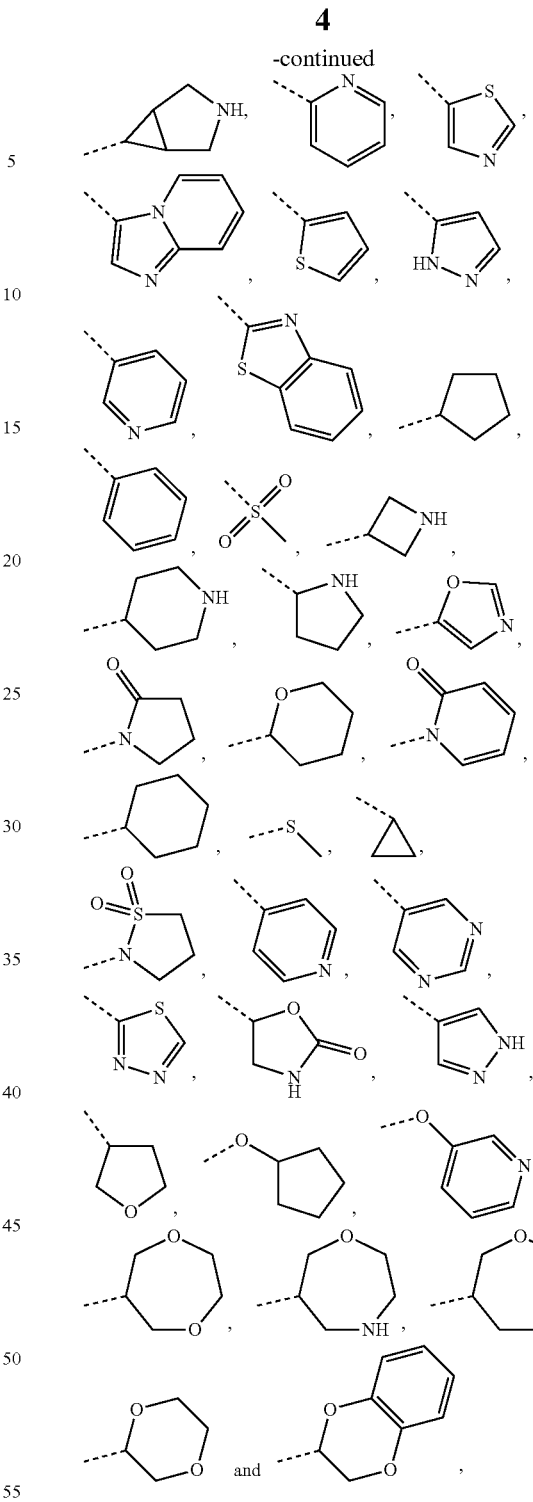

each of which is optionally substituted by 1, 2 or 3 R, and other variables are as defined in the invention.

In some embodiments of the invention, $R_2$ is selected from the group consisting of

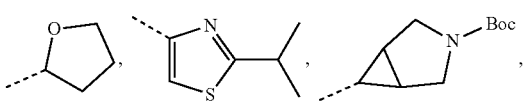

-continued
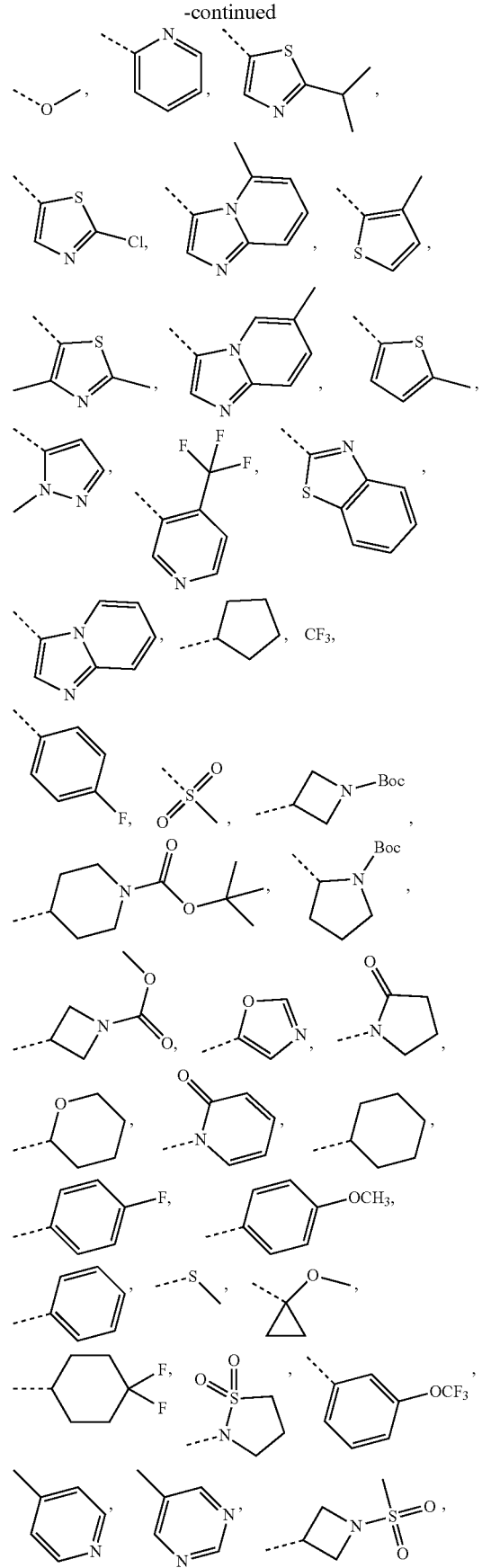
-continued
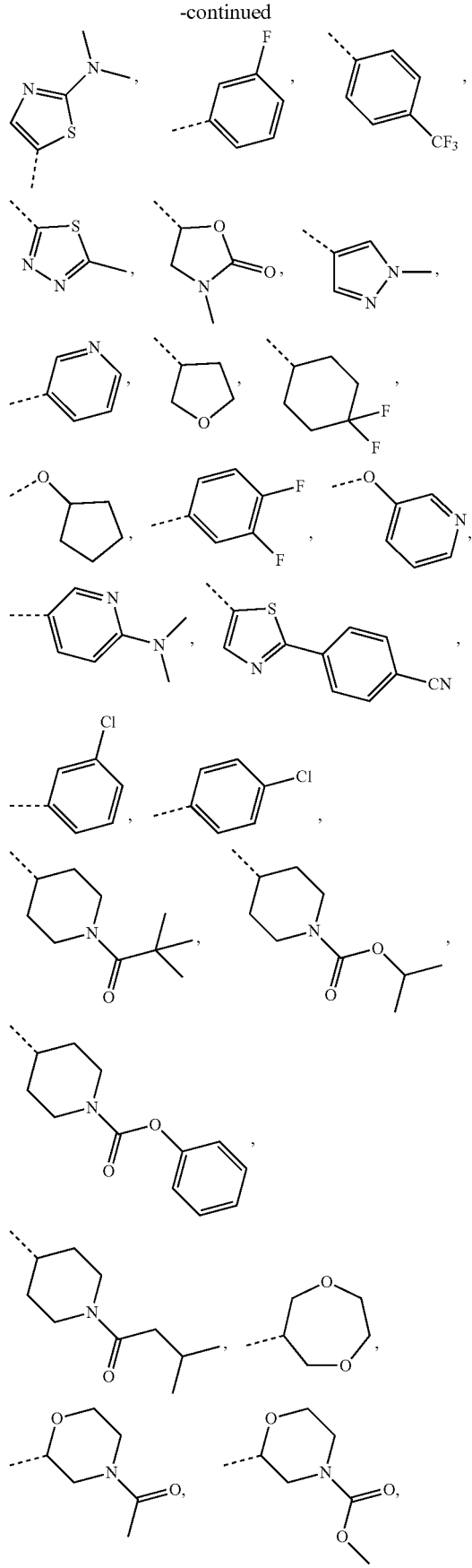

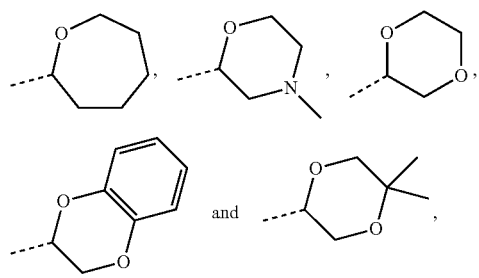

and other variables are as defined in the invention.

In some embodiments of the invention, $L_1$ is a single bond, $CH_2$,

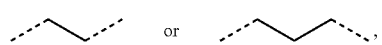

and other variables are as defined in the invention.

In some embodiments of the invention, $R_3$ is H, $CH_3$ or $-CH_2CH_3$, and other variables are as defined in the invention.

In some embodiments of the invention, the moiety

is selected from the group consisting of

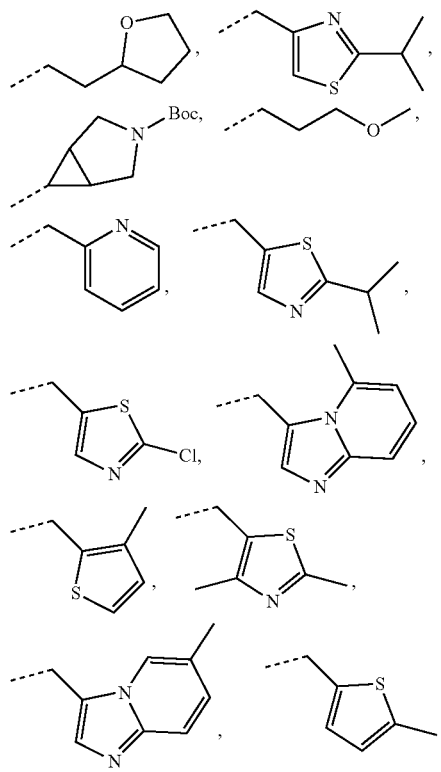

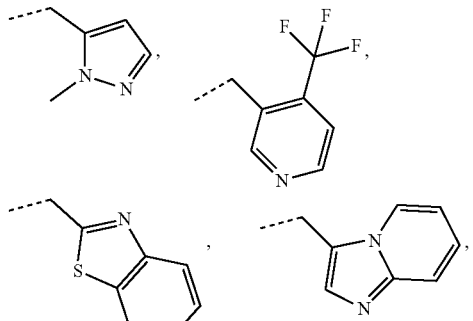

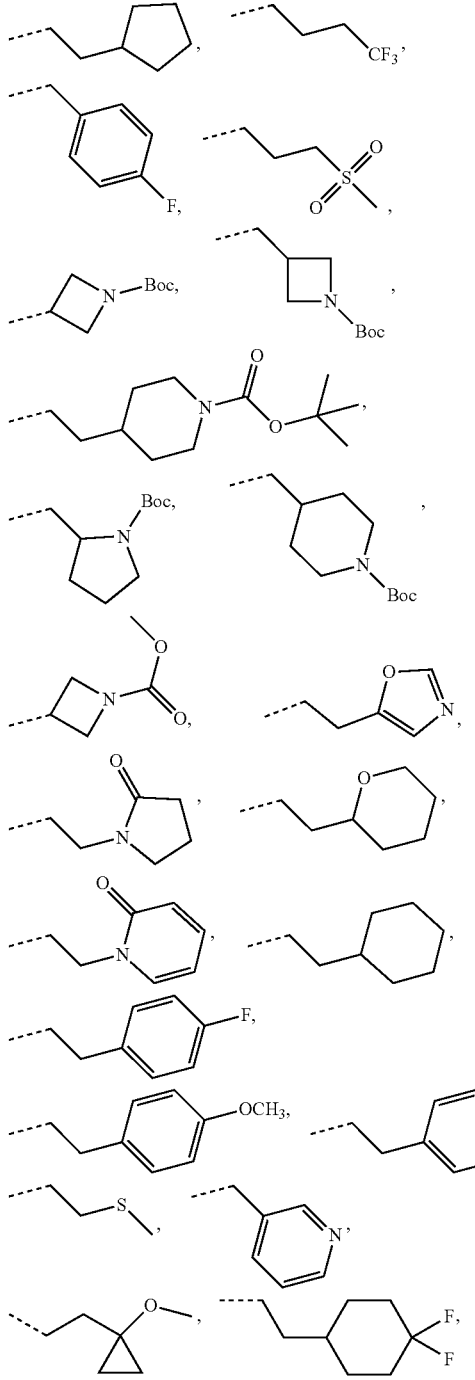

-continued
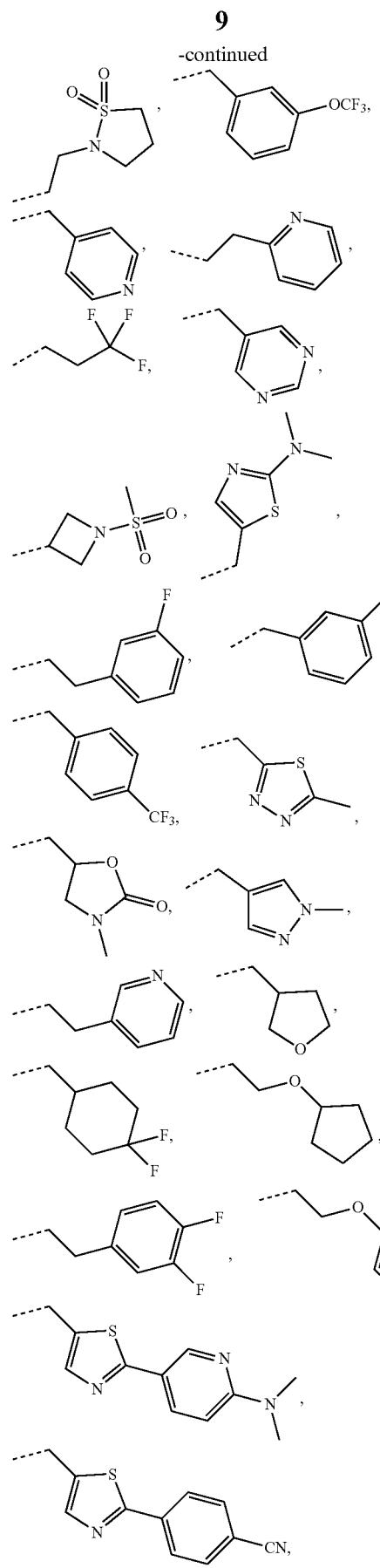
-continued
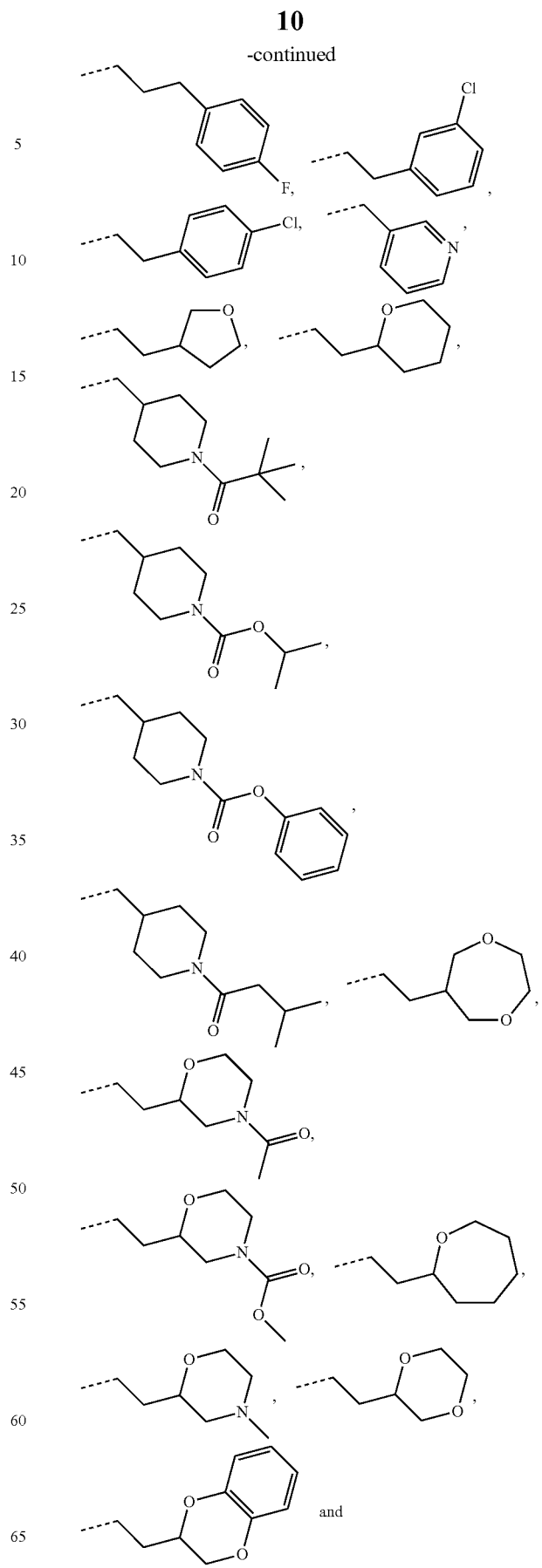
and

-continued

[Structure showing a dioxane-containing fragment]

and other variables are as defined in the invention.

Other embodiments of the invention can be obtained by the arbitrary combination of the above variables.

In some embodiments of the invention, the compound, the isomer thereof or the pharmaceutically acceptable salt thereof is selected from the group consisting of:

(I-1)

(I-2)

(I-3)

(I-4)

(I-5)

(I-6)

wherein, m is 1, 2 or 3;

n is 1 or 2;

r is 0 or 1;

$T_1$ is N or CH;

R, $L_1$, $R_1$ and $R_3$ are as defined in the invention.

In some embodiments of the invention, the compound, the isomer thereof or the pharmaceutically acceptable salt thereof is selected from the group consisting of:

(I-7)

(I-8)

(I-9)

(I-10)

and

-continued (I-11)

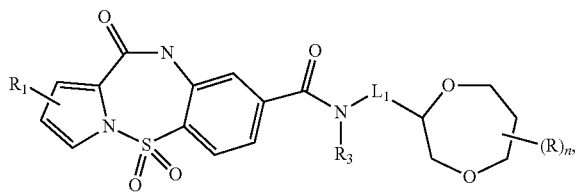

wherein,

R, L₁, R₁, R₃ and n are as defined in the invention.

The invention provides a compound of formula (I), an isomer thereof or a pharmaceutically acceptable salt thereof, (I)

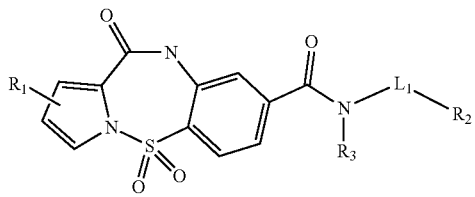

$L_1$ is a single bond or —$C_{1-6}$ alkyl-;

$R_1$ is H, Cl, F, Br, I, or $C_{1-3}$ alkyl which is optionally substituted by 1, 2 or 3 R;

$R_2$ is selected from the group consisting of $C_{1-3}$ heteroalkyl, 4-8 membered heterocycloalkyl, 5-10 membered heteroaryl, 4-8 membered partially unsaturated heterocycloalkyl, phenyl, $C_{1-3}$ alkyl, $C_{3-8}$ cycloalkyl, 4-8 membered heterocycloalkyl-O— and 5-10 membered heteroaryl-O—, each of which is optionally substituted by 1, 2 or 3 R;

$R_3$ is H or $C_{1-3}$ alkyl;

R is H, Cl, F, Br, I, $NH_2$, OH or CN, or selected from the group consisting of $C_{1-6}$ alkyl, $C_{1-6}$ heteroalkyl, phenyl, phenyl-O—C(=O)— and 5-6 membered heteroaryl, each of which is optionally substituted by 1, 2 or 3 R';

R' is selected from the group consisting of Cl, F, Br, I, $NH_2$, $CH_3$, CN and $N(CH_3)_2$;

each of the "hetero" in the $C_{1-3}$ heteroalkyl, 4-8 membered heterocycloalkyl, 5-10 membered heteroaryl, $C_{1-6}$ heteroalkyl, 5-6 membered heteroaryl and 4-8 membered partially unsaturated heterocycloalkyl is independently selected from the group consisting of —S—, —O—, —NH—, N, —C(=O)—, —O—C(=O)—, —S(=O)₂—, —S(=O)—, —NH—C(=O)— and —NH—C(=O)—O—;

in any of the above cases, the number of the heteroatom or the heteroatomic group is independently 1, 2, 3 or 4.

In some embodiments of the invention, R is H, Cl, F, Br, I, $NH_2$, OH or CN, or selected from the group consisting of $C_{1-3}$ alkyl, $C_{1-6}$ alkyl-O—C(=O)—, $C_{1-6}$ alkyl-C(=O)—, $C_{1-3}$ alkyl-S(=O)₂—, $C_{1-3}$ alkyl-S(=O)—, $C_{1-3}$ alkylamino, phenyl, phenyl-O—C(=O)— and pyridyl, each of which is optionally substituted by 1, 2 or 3 R'.

In some embodiments of the invention, R is H, Cl, F, Br, I, $NH_2$, OH or CN, or selected from the group consisting of $CH_3$,

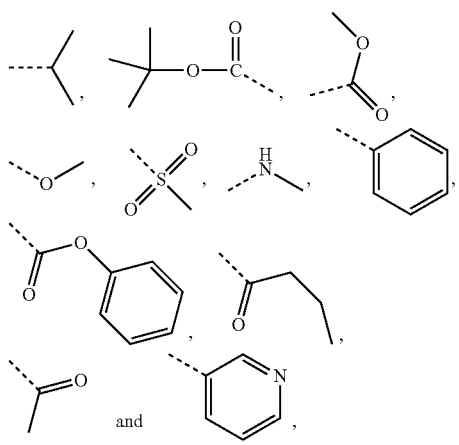

each of which is optionally substituted by 1, 2 or 3 R'.

In some embodiments of the invention, R is selected from the group consisting of H, Cl, F, Br, I, $NH_2$, OH, $CH_3$, CN,

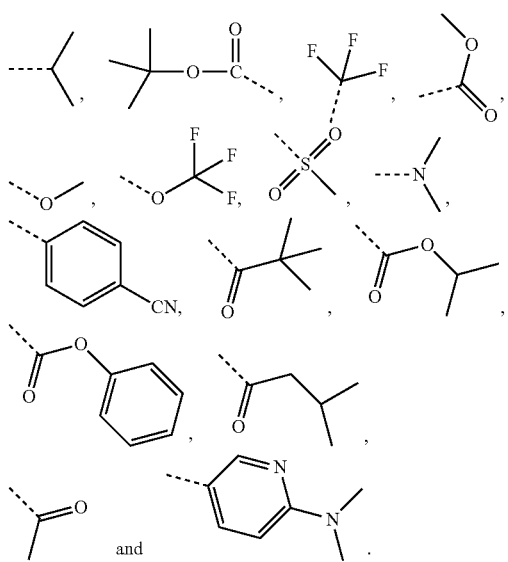

In some embodiments of the invention, $R_1$ is selected from the group consisting of H, Cl, F, Br, I, Me, Et and

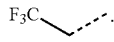

In some embodiments of the invention, $R_2$ is selected from the group consisting of $C_{1-3}$ alkoxy, tetrahydrofuranyl, thiazolyl, 3-azabicyclo[3.1.0]hexyl, pyridyl, benzimidazolyl, thienyl, pyrazolyl, benzothiazolyl, imidazo[1,2-a]pyridyl, methyl, $C_{1-3}$ alkylthio, $C_{1-3}$ alkyl-S(=O)₂—, cyclopentyl, phenyl, azetidinyl, piperidinyl, pyrrolidinyl, oxazolyl, 2-oxo-pyrrolidinyl, 2(1H)-oxo-pyridinyl, cyclohexyl, cyclopropyl, 1,1-dioxo-isothiazolidinyl, pyrimidinyl, 1,3,4-thiadiazolyl, 2-oxo-oxazolidinyl, tetrahydropyranyl, cyclopentyl-O—, pyridyl-O—, oxepanyl, 1,4-dioxanyl, 1,4-dioxepanyl and morpholinyl, each of which is optionally substituted by 1, 2 or 3 R.

In some embodiments of the invention, $R_2$ is selected from the group consisting of

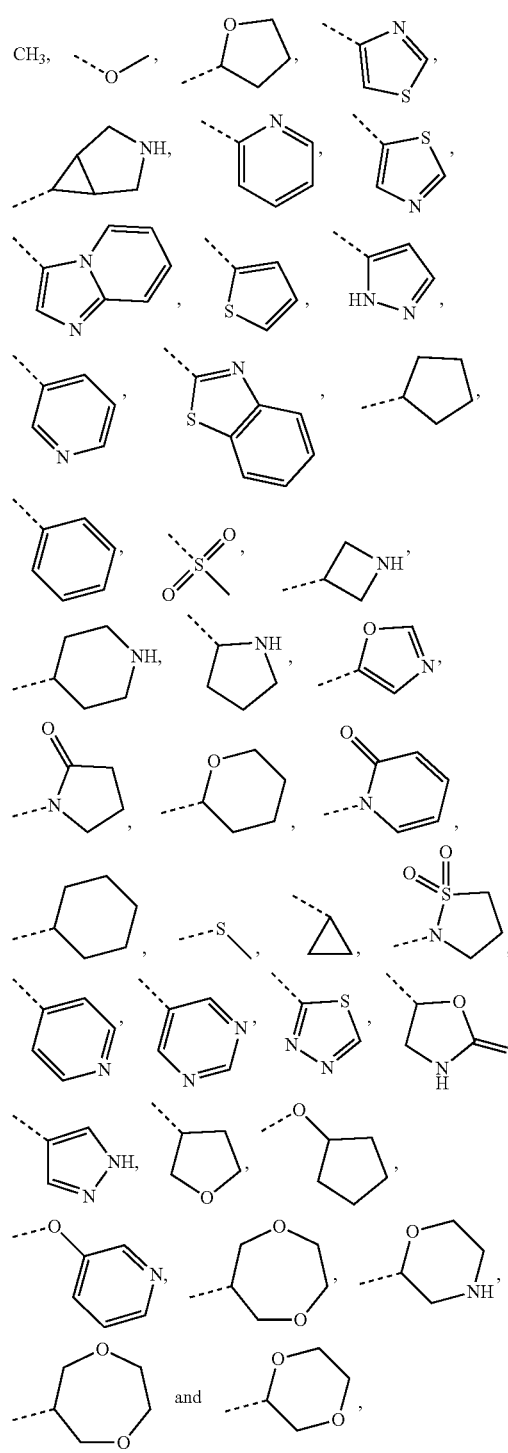
each of which is optionally substituted by 1, 2 or 3 R.
In some embodiments of the invention, the $R_2$ is selected from the group consisting of
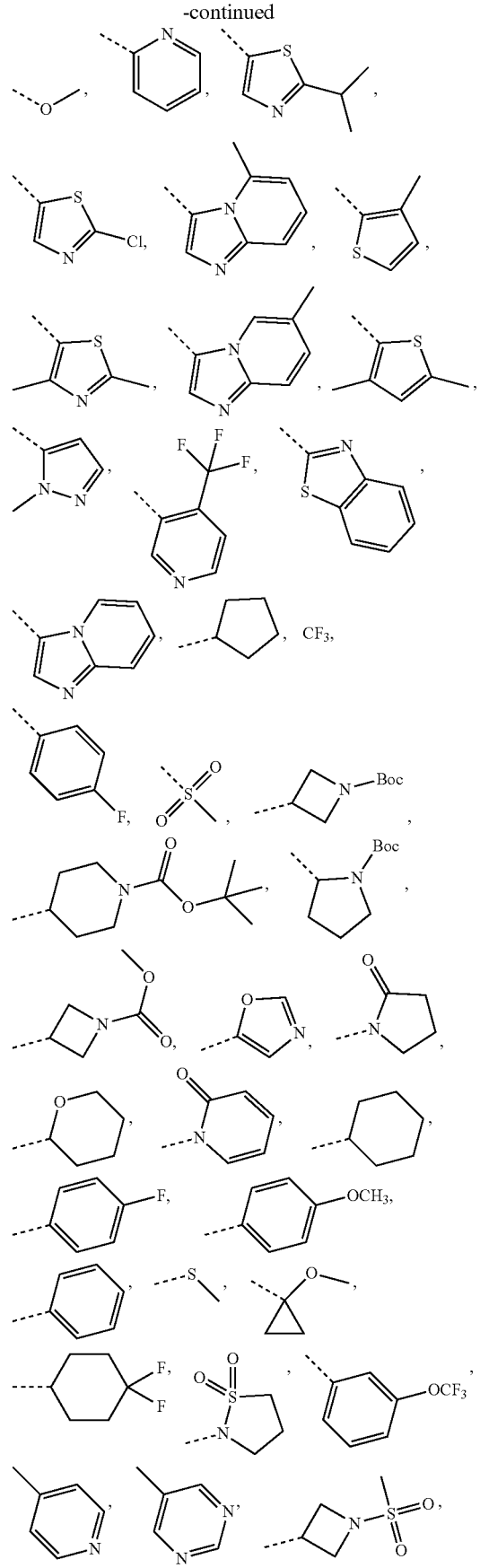

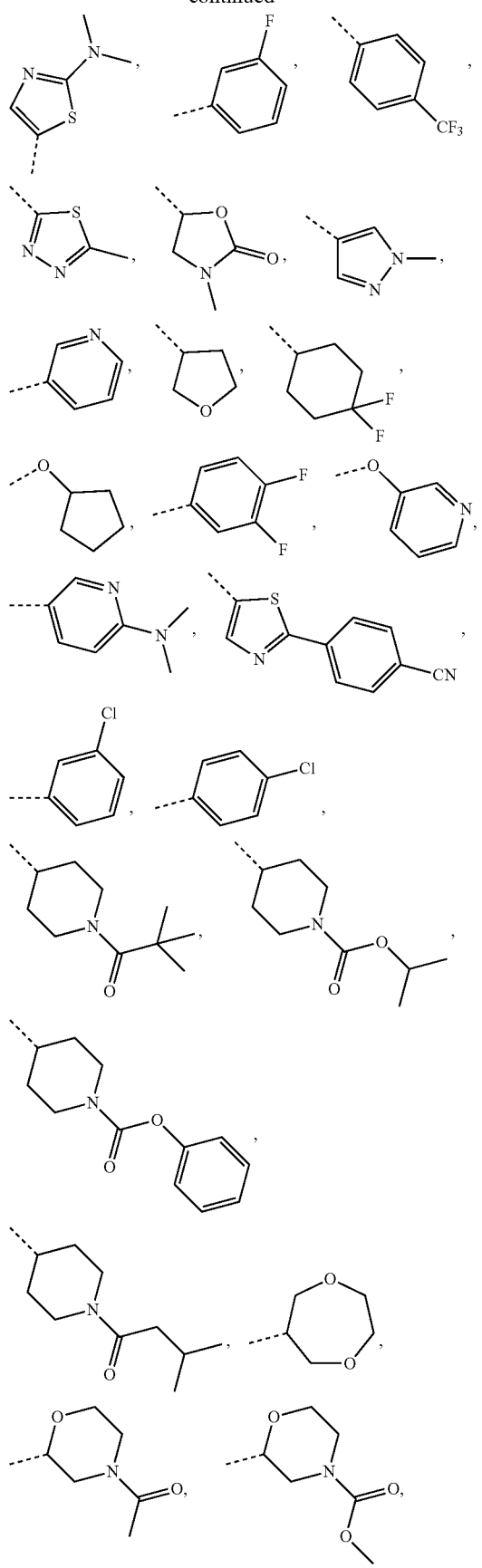
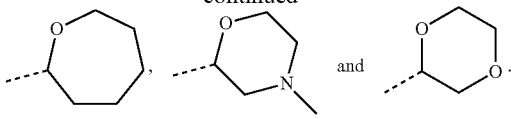
In some embodiments of the invention, $L_1$ is a single bond, $CH_2$,
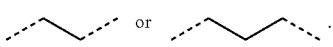
In some embodiments of the invention, $R_3$ is H, $CH_3$ or $-CH_2CH_3$.
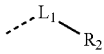
In some embodiments of the invention, the moiety is selected from the group consisting of
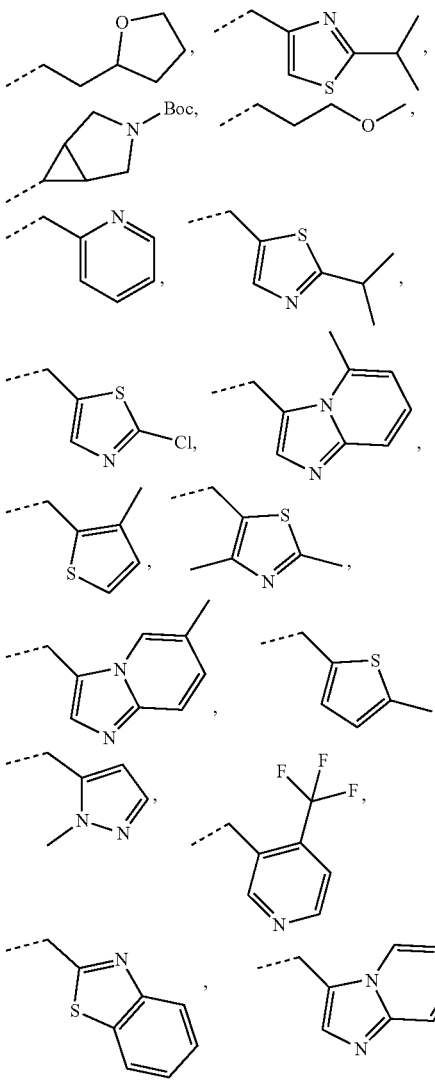

-continued
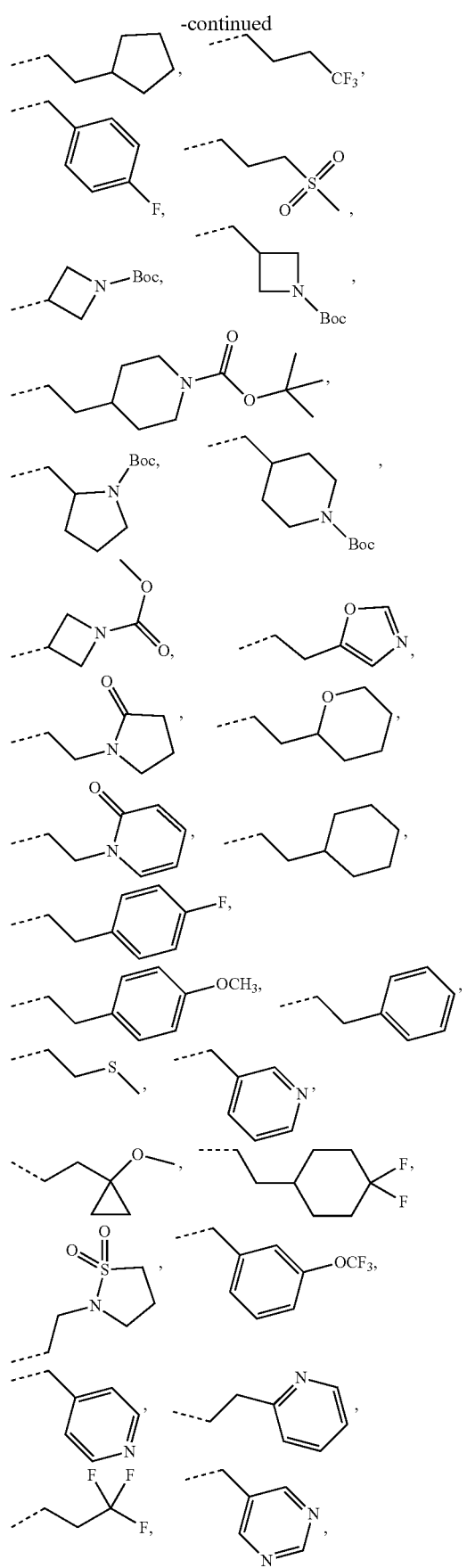
-continued
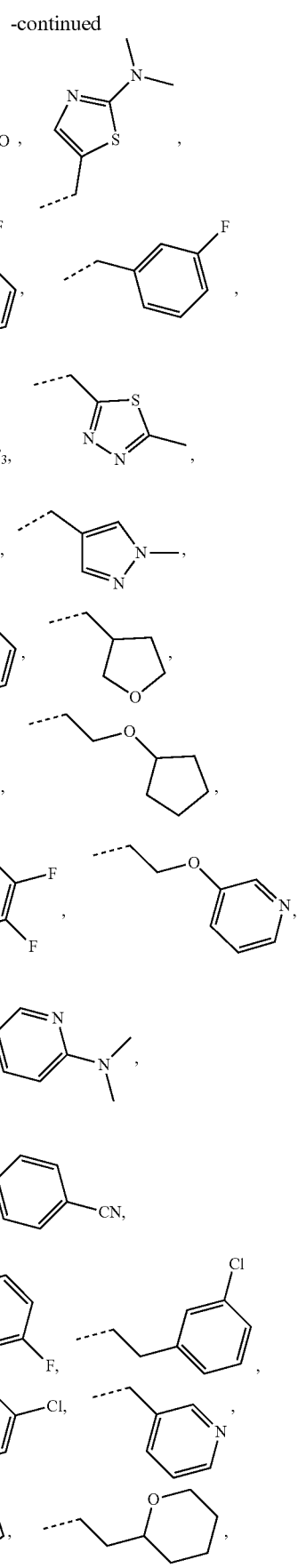

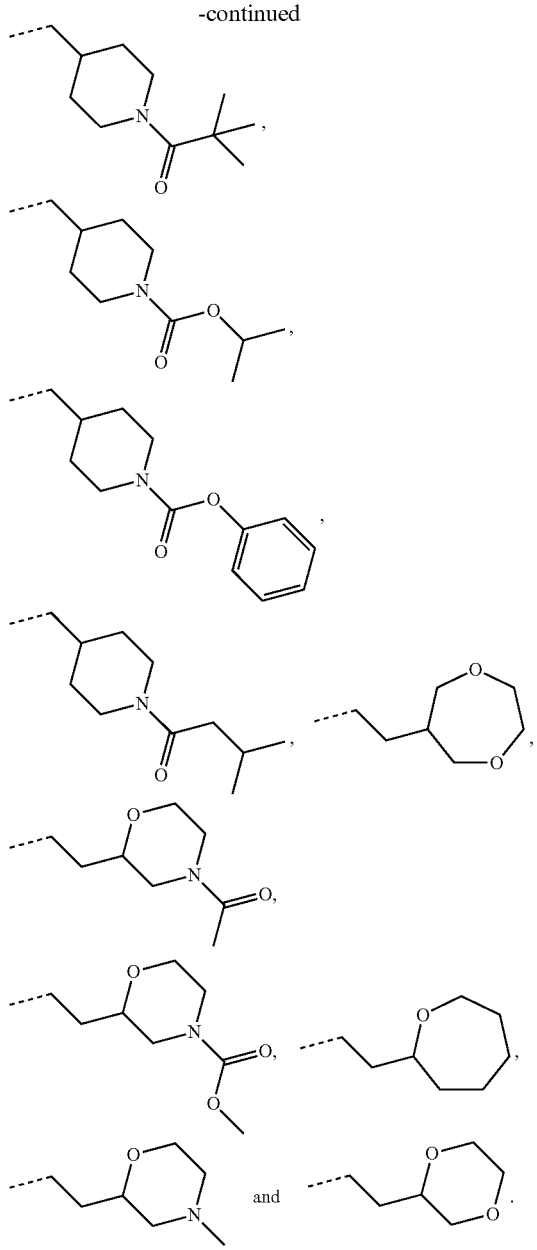

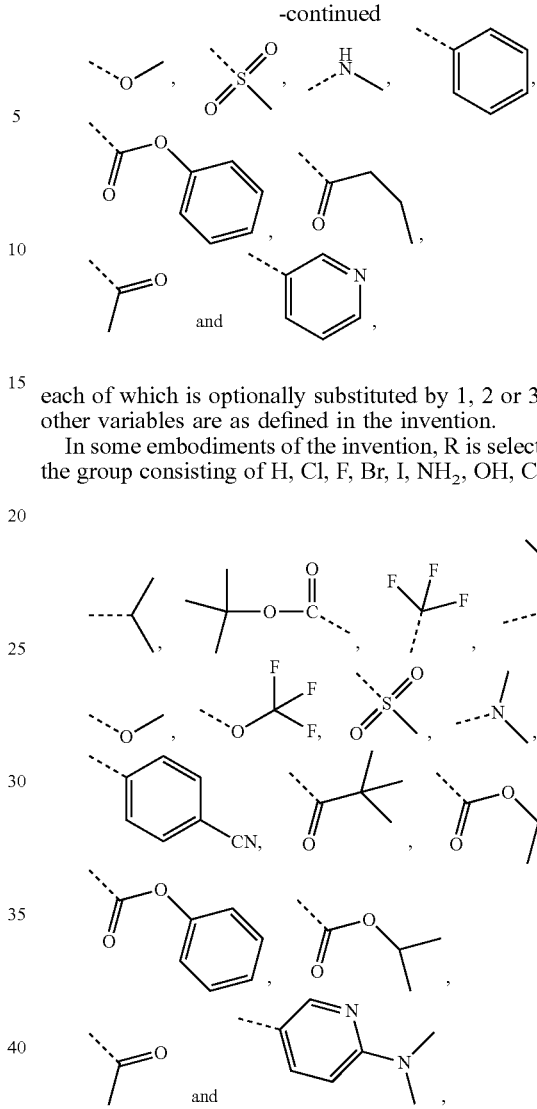

each of which is optionally substituted by 1, 2 or 3 R', and other variables are as defined in the invention.

In some embodiments of the invention, R is selected from the group consisting of H, Cl, F, Br, I, $NH_2$, OH, $CH_3$, CN,

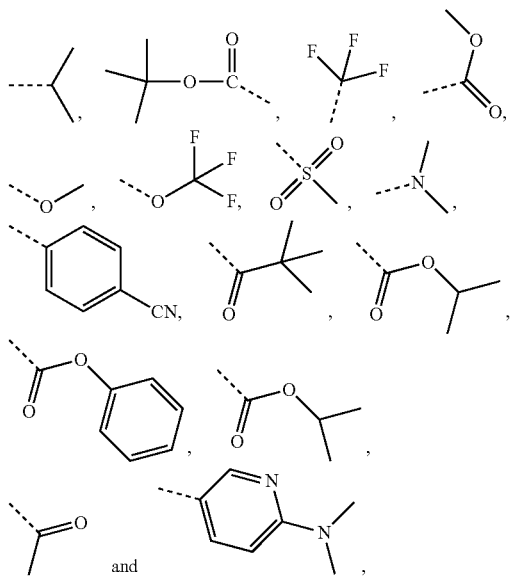

and other variables are as defined in the invention.

In some embodiments of the invention, $R_1$ is selected from the group consisting of H, Cl, F, Br, I, Me, Et and $F_3C$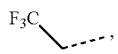, and other variables are as defined in the invention.

In some embodiments of the invention, $R_2$ is selected from the group consisting of $C_{1-3}$ alkoxy, tetrahydrofuranyl, thiazolyl, 3-azabicyclo[3.1.0]hexyl, pyridyl, benzimidazolyl, thienyl, pyrazolyl, benzothiazolyl, imidazo[1,2-a]pyridyl, methyl, $C_{1-3}$ alkylthio, $C_{1-3}$ alkyl-S(=O)$_2$—, cyclopentyl, phenyl, azetidinyl, piperidinyl, pyrrolidinyl, oxazolyl, 2-oxo-pyrrolidinyl, 2(1H)-oxo-pyridinyl, cyclohexyl, cyclopropyl, 1,1-dioxo-isothiazolidinyl, pyrimidinyl, 1,3,4-thiadiazolyl, 2-oxo-oxazolidinyl, tetrahydropyranyl, cyclopentyl-O—, pyridyl-O—, oxepanyl, 1,4-dioxanyl, 1,4-dioxepanyl and morpholinyl, each of which is optionally substituted by 1, 2 or 3 R, and other variables are as defined in the invention.

In some embodiments of the invention, $R_2$ is selected from the group consisting of In some embodiments of the invention, R is H, Cl, F, Br, I, $NH_2$, OH or CN, or selected from the group consisting of $C_{1-3}$ alkyl, $C_{1-6}$ alkyl-O—C(=O)—, $C_{1-6}$ alkyl-C(=O)—, $C_{1-3}$ alkyl-S(=O)$_2$—, $C_{1-3}$ alkyl-S(=O)—, $C_{1-3}$ alkylamino, phenyl, phenyl-O—C(=O)— and pyridyl, each of which is optionally substituted by 1, 2 or 3 R', and other variables are as defined in the invention.

In some embodiments of the invention, R is H, Cl, F, Br, I, $NH_2$, OH or CN, or selected from the group consisting of $CH_3$,

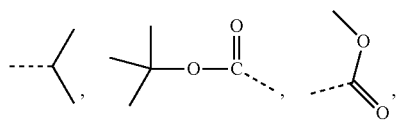

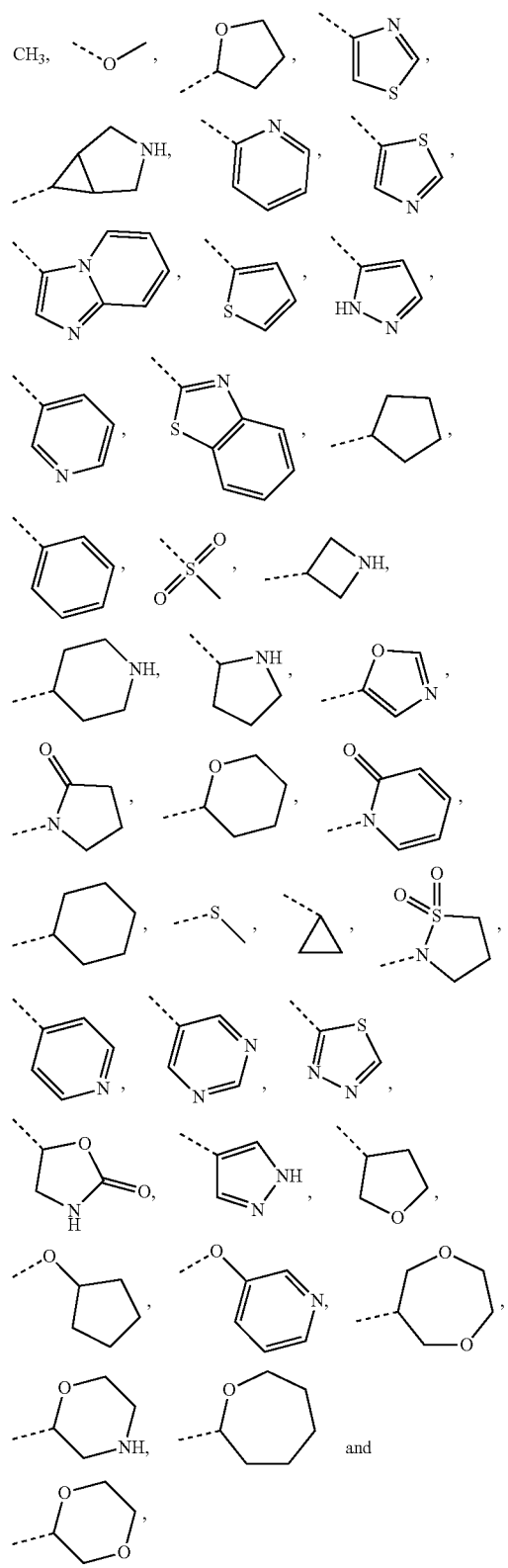
each of which is optionally substituted by 1, 2 or 3 R, and other variables are as defined in the invention.
In some embodiments of the invention, $R_2$ is selected from
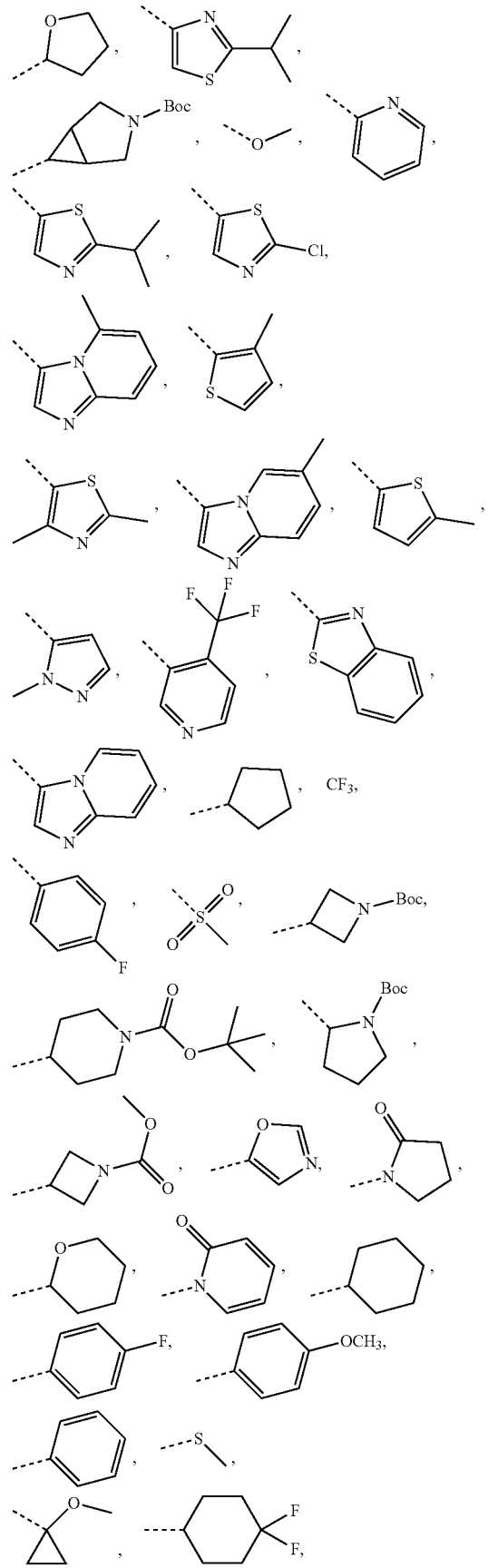

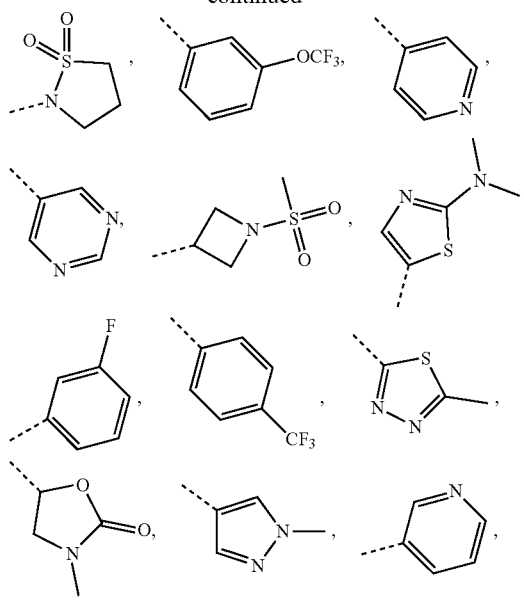
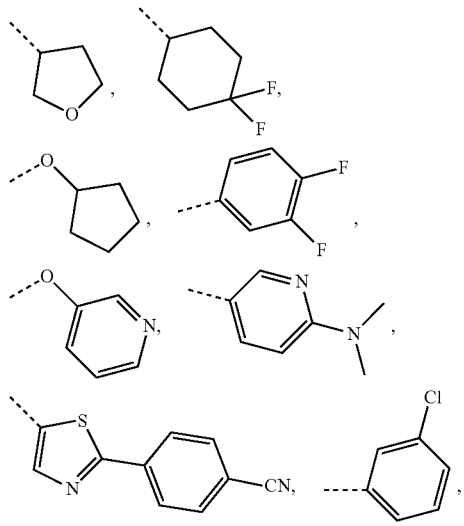
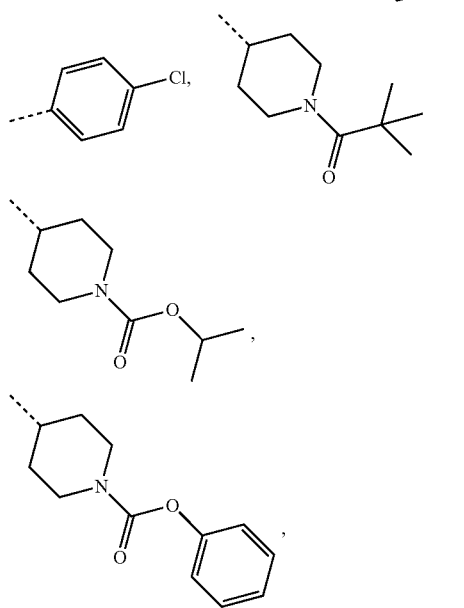
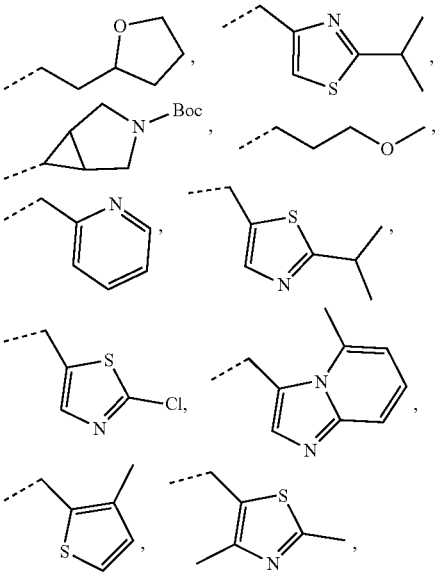

and other variables are as defined in the invention.

In some embodiments of the invention, $L_1$ is or a single bond, $CH_2$,

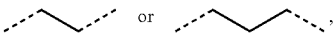

and other variables are as defined in the invention.

In some embodiments of the invention, $R_3$ is H, $CH_3$ or $-CH_2CH_3$, and other variables are as defined in the invention.

In some embodiments of the invention, the moiety

is selected from the group consisting of

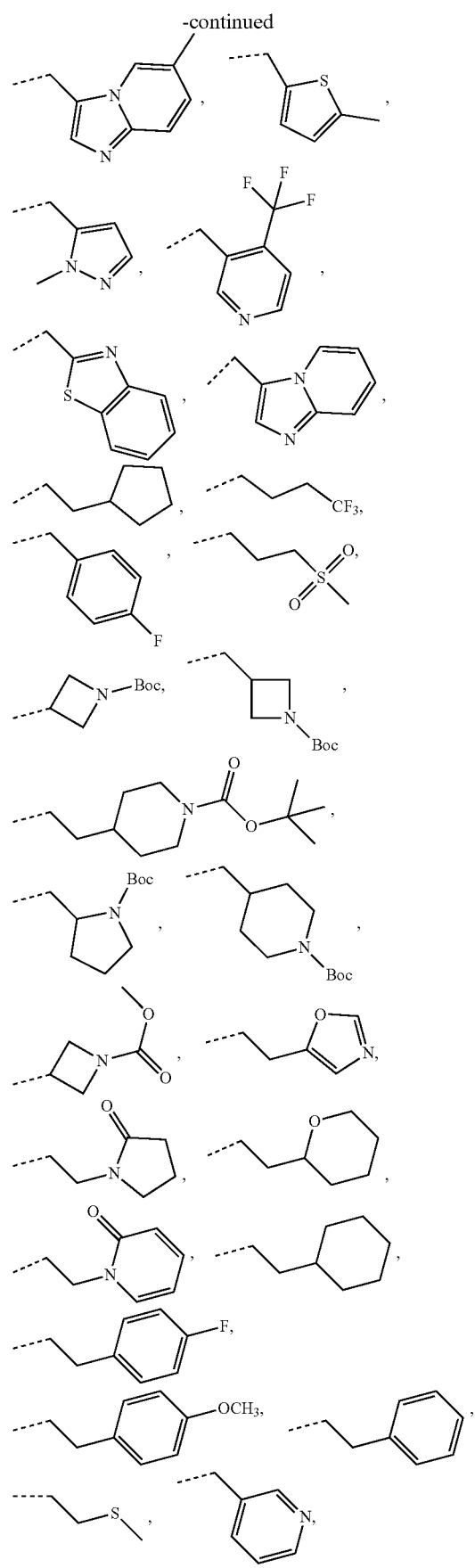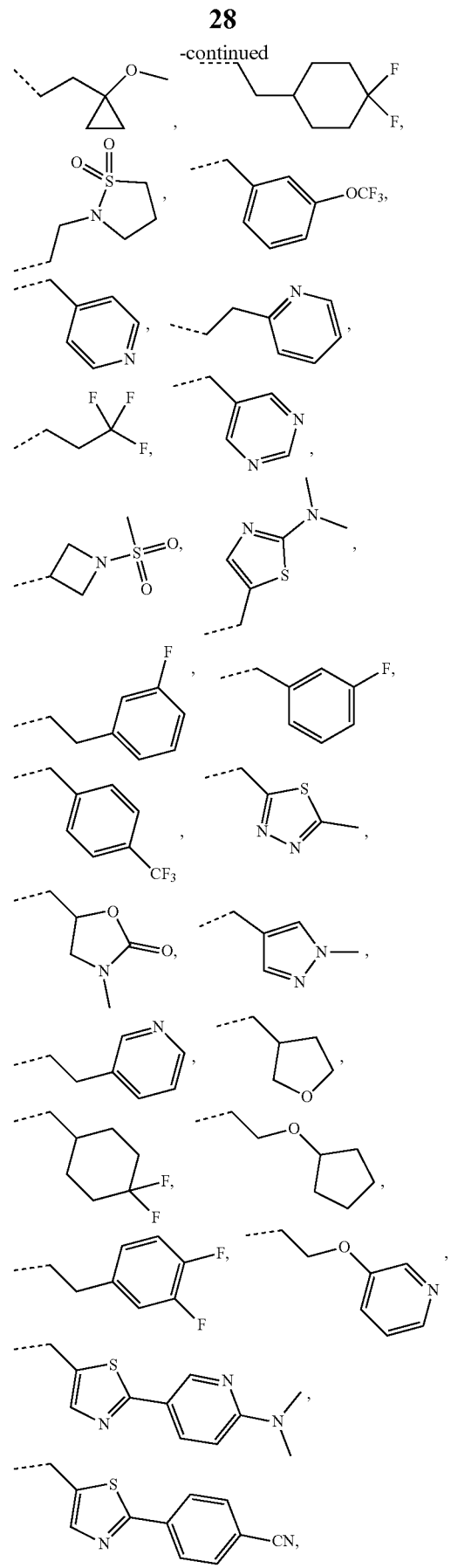

-continued

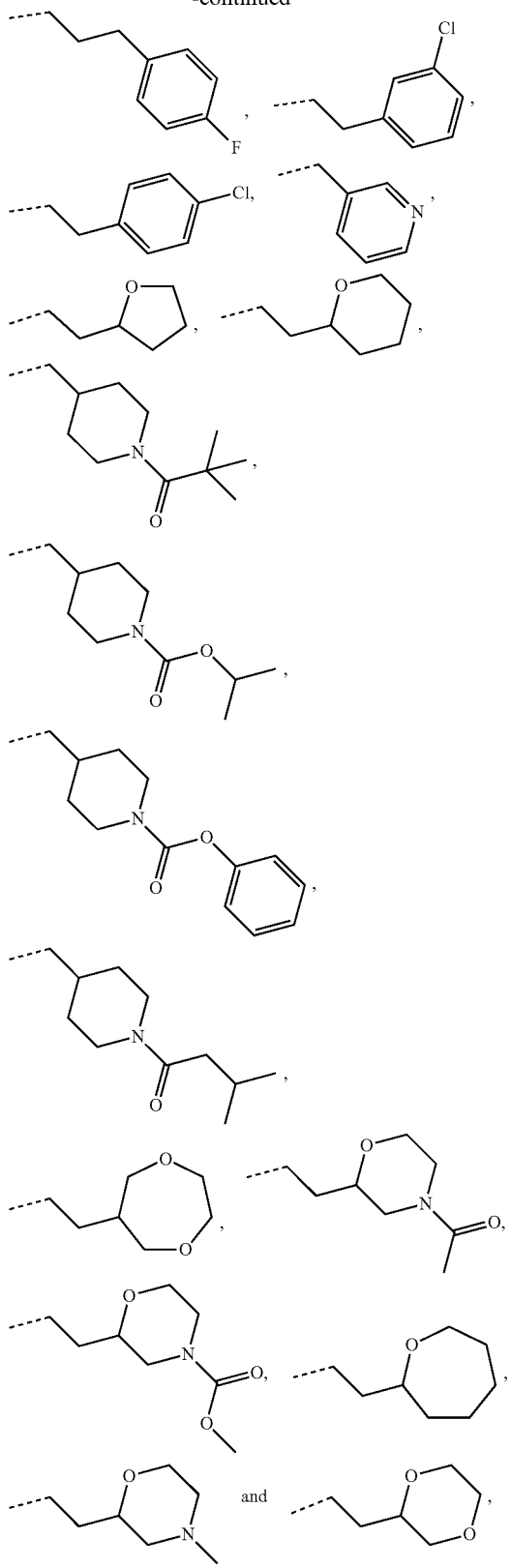

and other variables are as defined in the invention.

Other embodiments can be obtained by the arbitrary combination of the variables of the invention.

In some embodiments of the invention, the above compound, the isomer thereof or the pharmaceutically acceptable salt thereof is selected from the group consisting of:

(I-1)
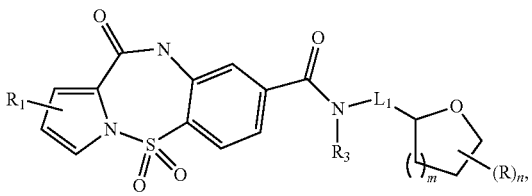

(I-2)
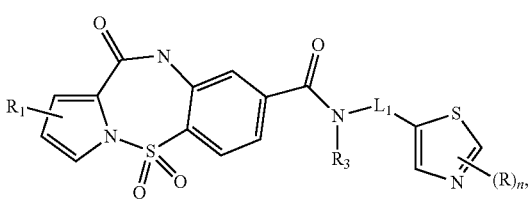

(I-3)
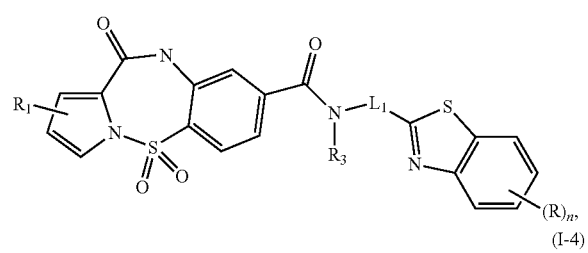

(I-4)
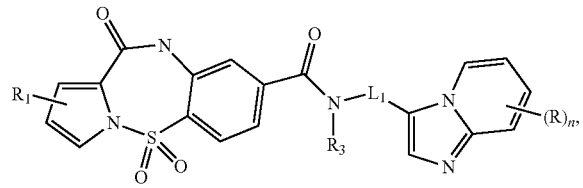

(I-5)
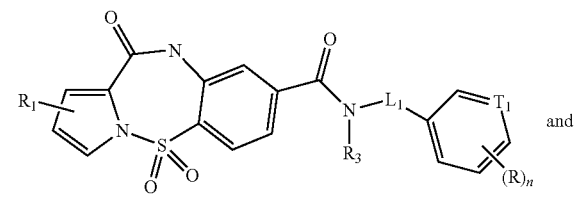

(I-6)
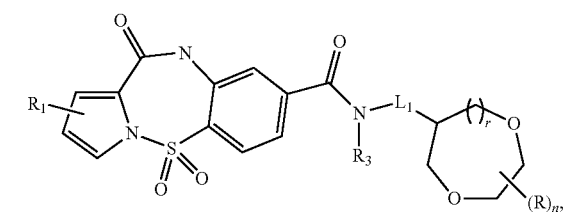

wherein,
m is 1, 2 or 3;
n is 1 or 2;
r is 0 or 1;
$T_1$ is N or CH;
R, $L_1$, $R_1$ and $R_3$ are as defined in the invention.

The invention provides a compound of formula (I), an isomer thereof or a pharmaceutically acceptable salt thereof,

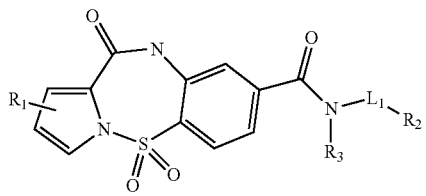

(I)

$L_1$ is a single bond or —$C_{1-6}$ alkyl-;

$R_1$ is H, Cl, F, Br or $C_{1-3}$ alkyl which is optionally substituted by 1, 2 or 3 R;

$R_2$ is selected from the group consisting of $C_{1-3}$ heteroalkyl, 4-8 membered heterocycloalkyl and 5-10 membered heteroaryl, each of which is optionally substituted by 1, 2 or 3 R;

$R_3$ is H or $C_{1-3}$ alkyl;

R is H, Cl, F, Br, $NH_2$ or OH, or selected from the group consisting of $C_{1-3}$ alkyl and $C_{1-6}$ alkyl-O—C(=O)—, each of which is optionally substituted by 1, 2 or 3 R';

R' is selected from the group consisting of Cl, F, Br and $NH_2$;

each of the "hetero" in the 4-8 membered heterocycloalkyl and the 5-10 membered heteroaryl is independently selected from the group consisting of —S—, —O—, —NH— and N;

in any of the above cases, the number of the heteroatom or the heteroatomic group is independently 1, 2 or 3.

In some embodiments of the invention, R is H, Cl, F, Br, $NH_2$ or OH, or selected from the group consisting of $CH_3$,

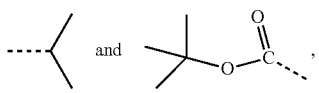

each of which is optionally substituted by 1, 2 or 3 R'.

In some embodiments of the invention, R is selected from the group consisting of H, Cl, F, Br, $NH_2$, OH, $CH_3$, CN,

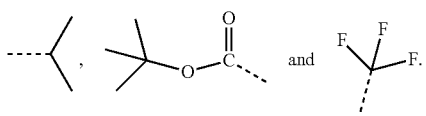

In some embodiments of the invention, $R_1$ is selected from the group consisting of H, Cl, F, Br, Me and Et.

In some embodiments of the invention, $R_2$ is selected from the group consisting of $C_{1-3}$ alkoxy, tetrahydrofuranyl, thiazolyl, 3-azabicyclo[3.1.0]hexyl, pyridyl, benzimidazolyl, thienyl, pyrazolyl, benzothiazolyl and imidazo[1,2-a]pyridyl, each of which is optionally substituted by 1, 2 or 3 R.

In some embodiments of the invention, $R_2$ is selected from the group consisting of

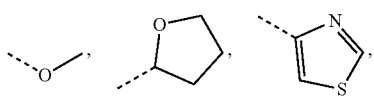

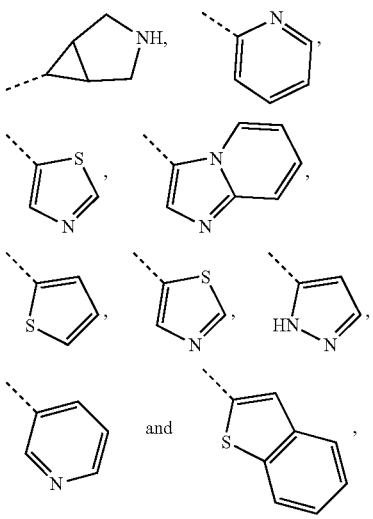

each of which is optionally substituted by 1, 2 or 3 R.

In some embodiments of the invention, $R_2$ is selected from the group consisting of

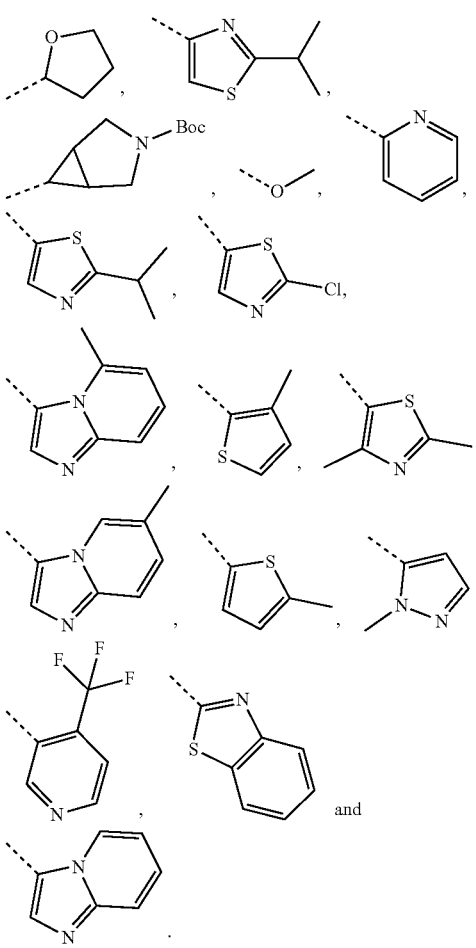

In some embodiments of the invention, $L_1$ is a single bond, $CH_2$,

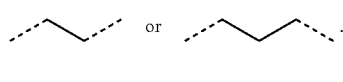

In some embodiments of the invention, $R_3$ is H, $CH_3$ or —$CH_2CH_3$.

In some embodiments of the invention, the moiety

is selected from the group consisting of

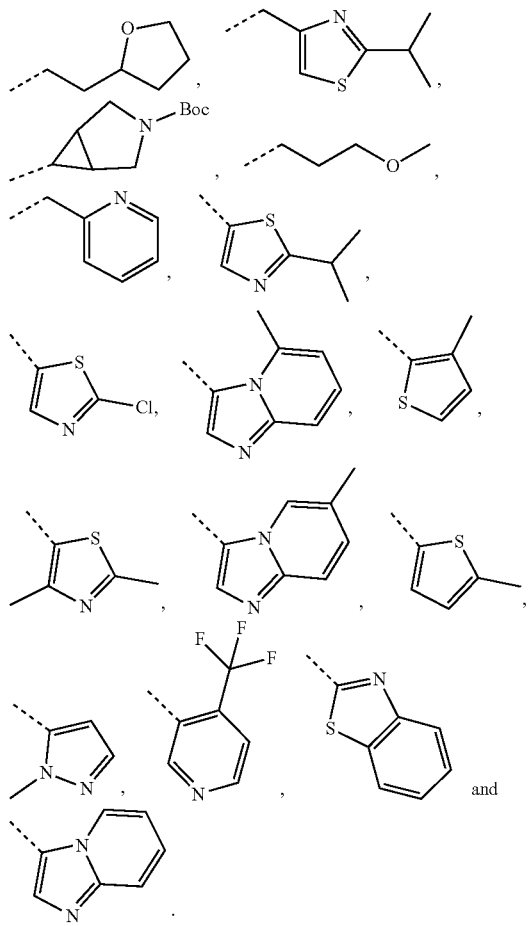

In some embodiments of the invention, R is H, Cl, F, Br, $NH_2$ or OH, or selected from the group consisting of $CH_3$,

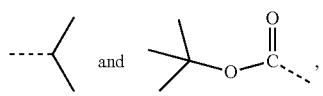

each of which is optionally substituted by 1, 2 or 3 R', and other variables are as defined in the invention.

In some embodiments of the invention, R is selected from the group consisting of H, Cl, F, Br, $NH_2$, OH, $CH_3$,

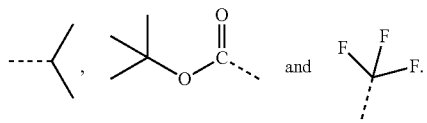

and other variables are as defined in the invention.

In some embodiments of the invention, $R_1$ is selected from the group consisting of H, Cl, F, Br, Me and Et, and other variables are as defined in the invention.

In some embodiments of the invention, $R_2$ is selected from the group consisting of $C_{1-3}$ alkoxy, tetrahydrofuranyl, thiazolyl, 3-azabicyclo[3.1.0]hexyl, pyridyl, benzimidazolyl, thienyl, pyrazolyl, benzothiazolyl and imidazo[1,2-a]pyridyl, each of which is optionally substituted by 1, 2 or 3 R, and other variables are as defined in the invention.

In some embodiments of the invention, $R_2$ is selected from the group consisting of

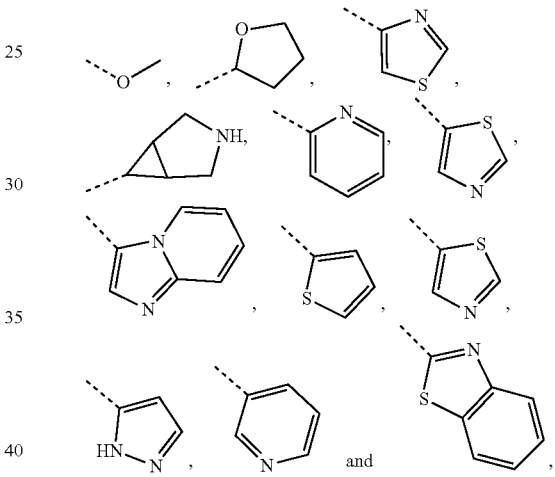

each of which is optionally substituted by 1, 2 or 3 R, and other variables are as defined in the invention.

In some embodiments of the invention, $R_2$ is selected from the group consisting of

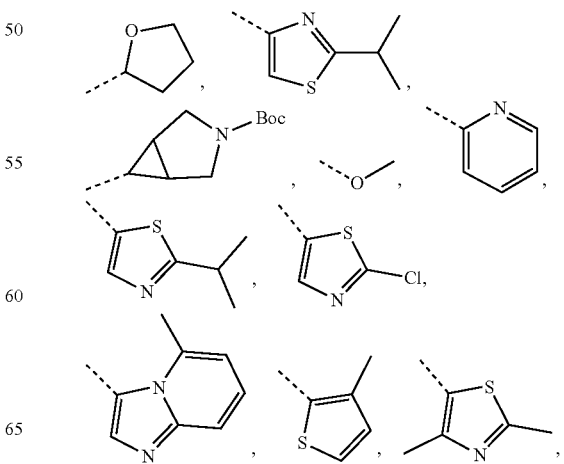

-continued

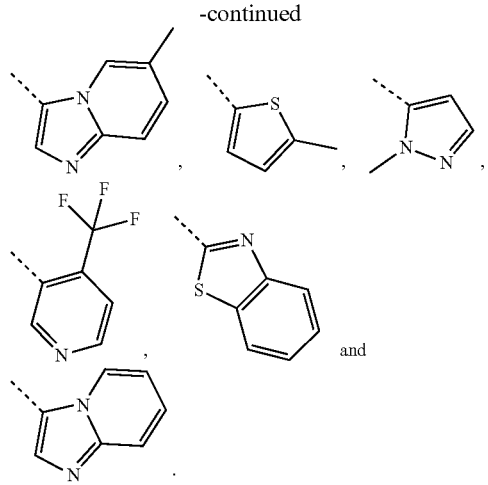

and other variables are as defined in the invention.

In some embodiments of the invention, $L_1$ is a single bond, $CH_2$,

[diagram]  or  [diagram], and other variables are as defined in the invention.

In some embodiments of the invention, $R_3$ is H, $CH_3$ or —$CH_2CH_3$, and other variables are as defined in the invention.

In some embodiments of the invention, the moiety

[diagram of $L_1$—$R_2$]

is selected from the group consisting of

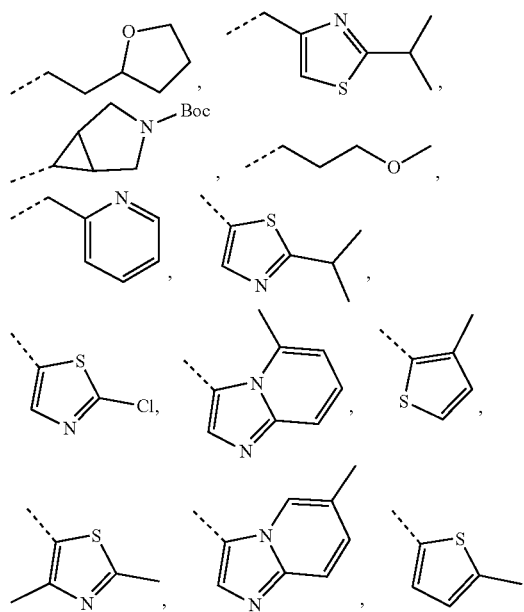

-continued

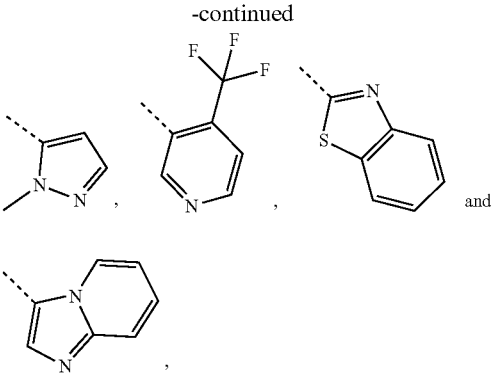

and other variables are as defined in the invention.

In some embodiments of the invention, the compound, the isomer thereof or the pharmaceutically acceptable salt thereof is selected from the group consisting of:

(I-1)

[structure with $R_1$, $L_1$, $R_3$, $(R)_n$, $m$]

(I-2)

[structure with $R_1$, $L_1$, $R_3$, $(R)_n$]

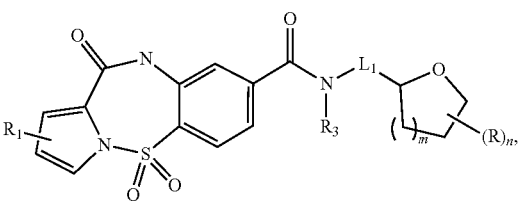

(I-3)

and

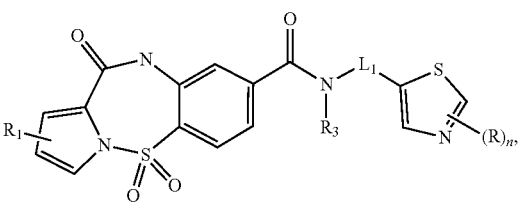

(I-4)

wherein, R, $L_1$, $R_1$ and $R_3$ are as defined in the invention; n is 1 or 2.

The invention also provides a compound, an isomer thereof or a pharmaceutically acceptable salt thereof which is selected from the group consisting of

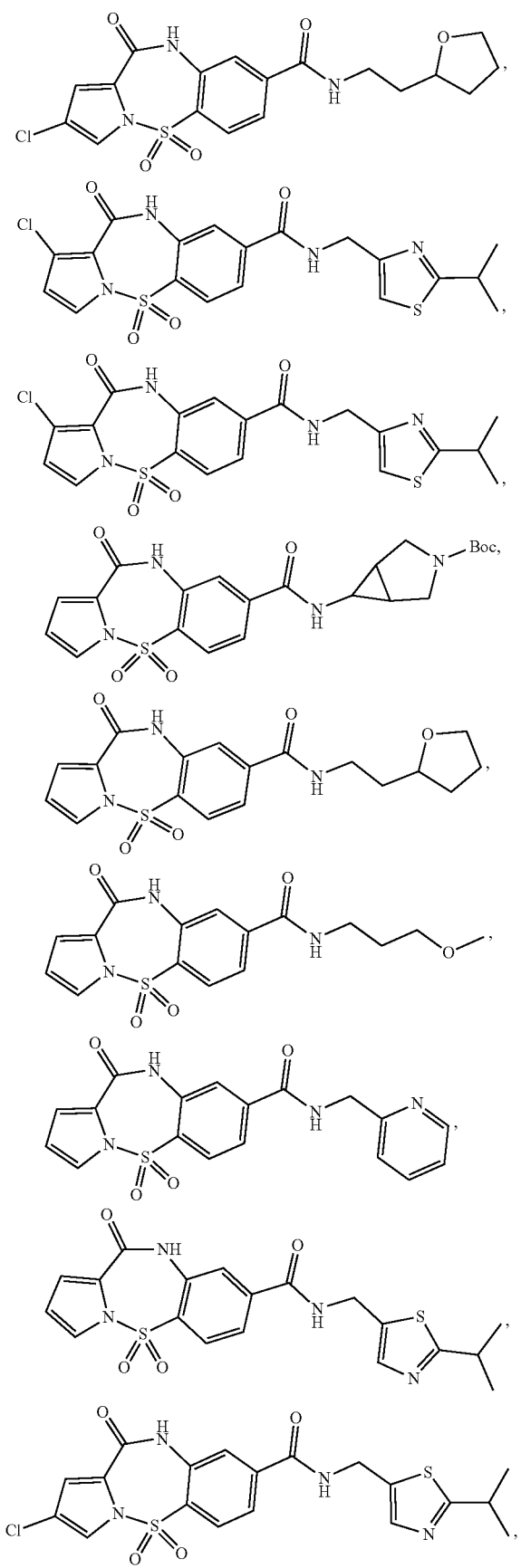
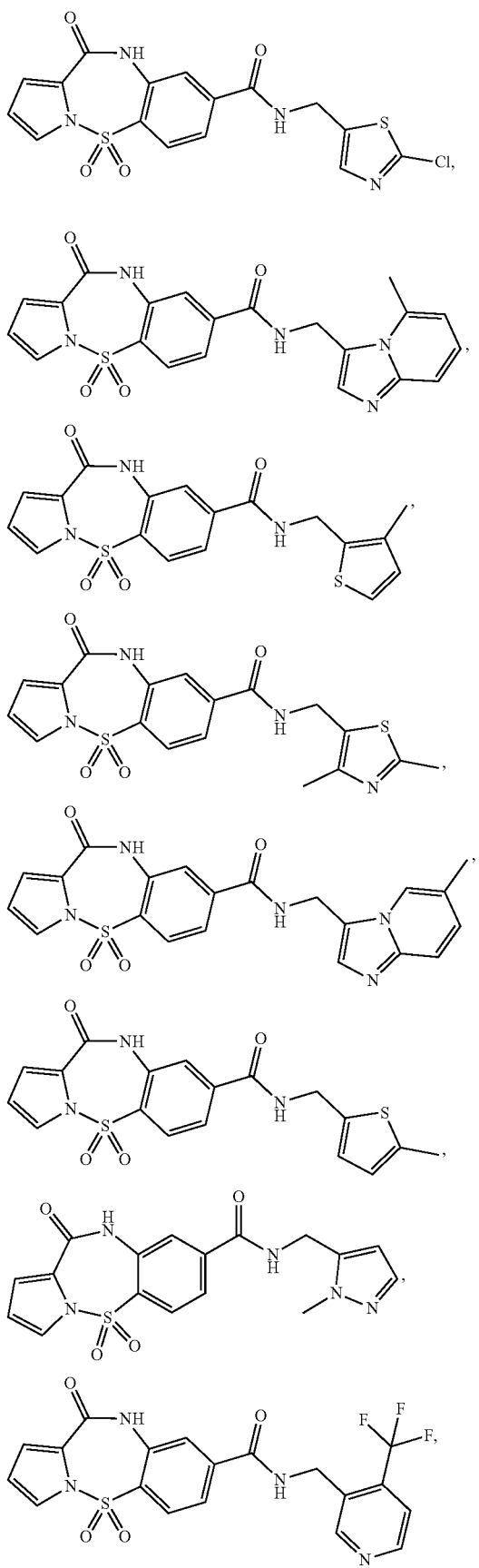

39
-continued
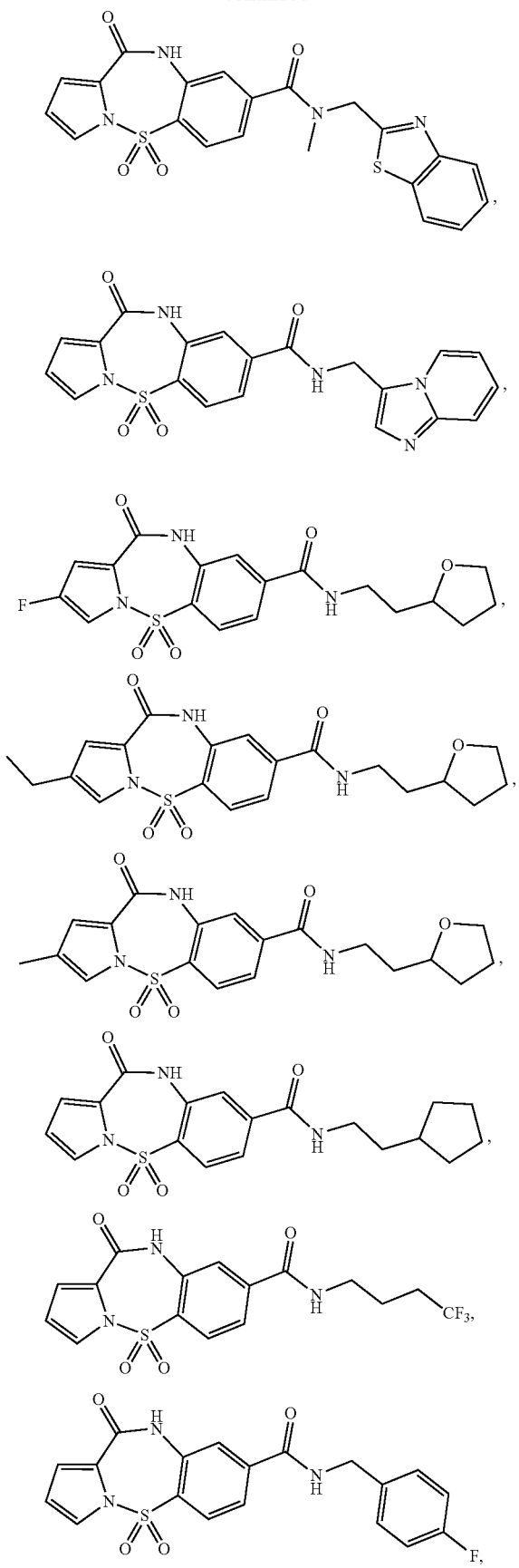
40
-continued
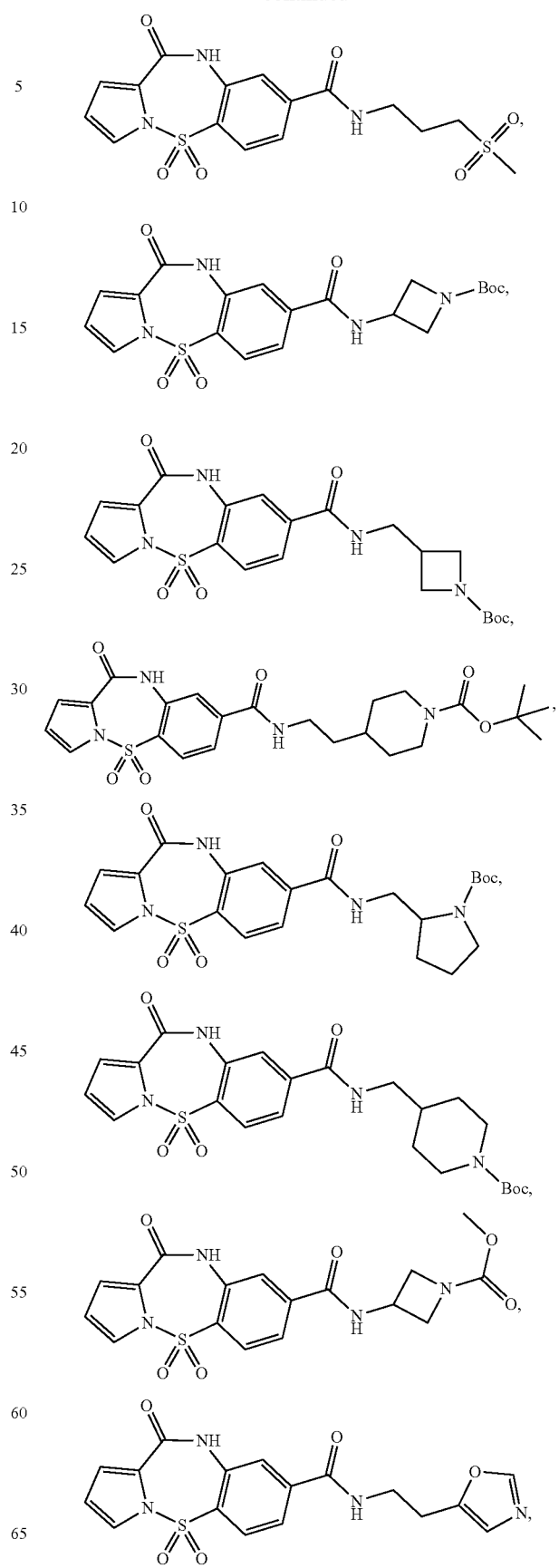

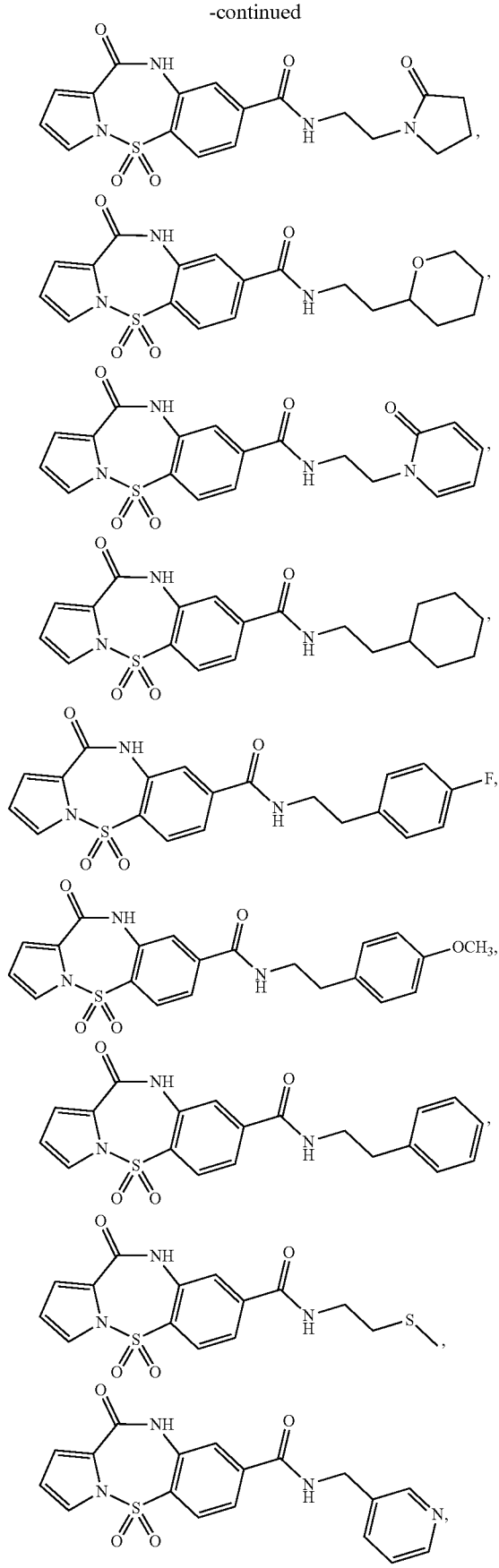
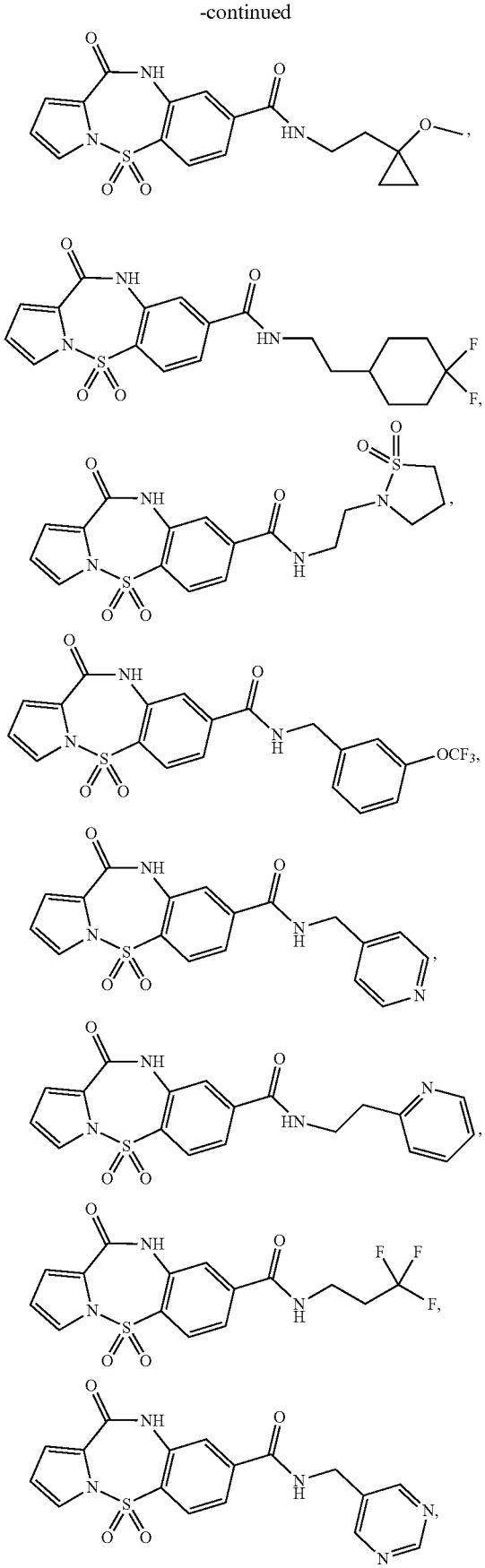

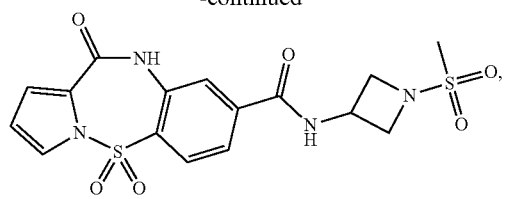
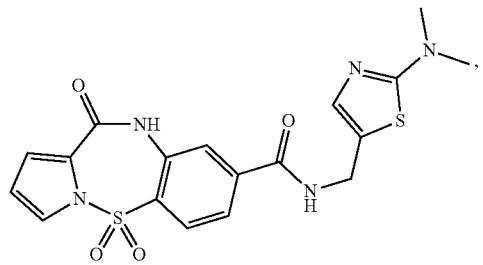
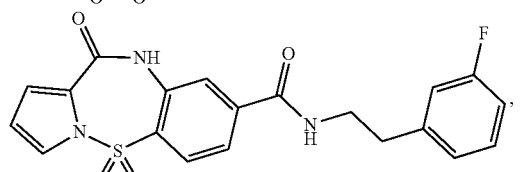
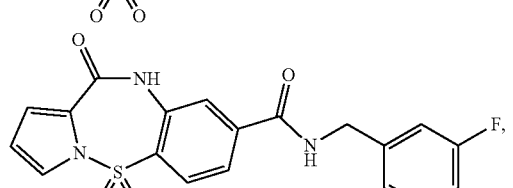
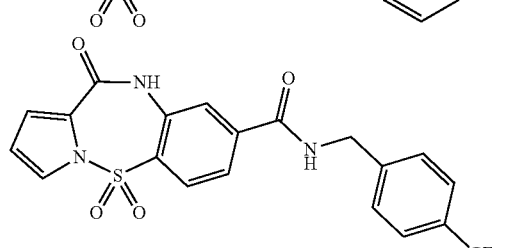
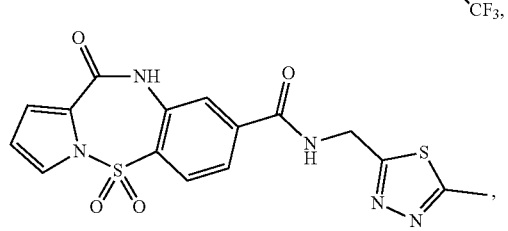
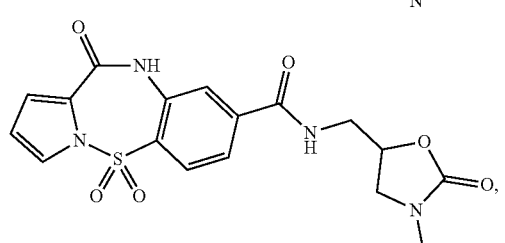
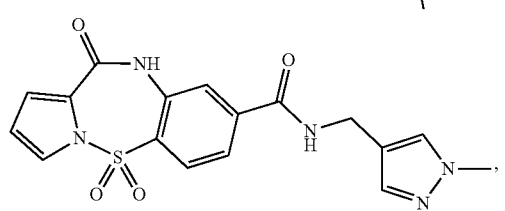
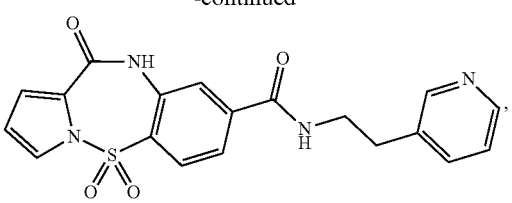
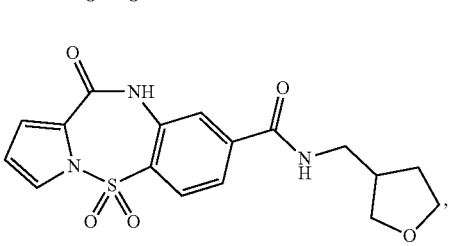
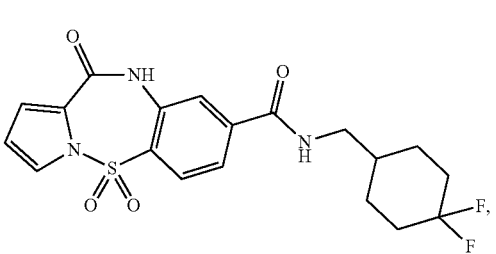
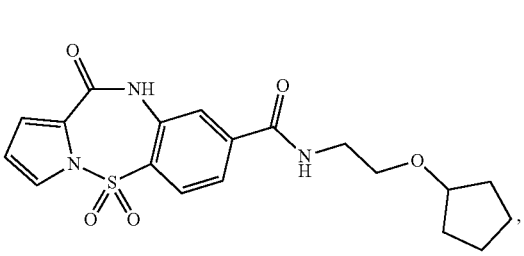
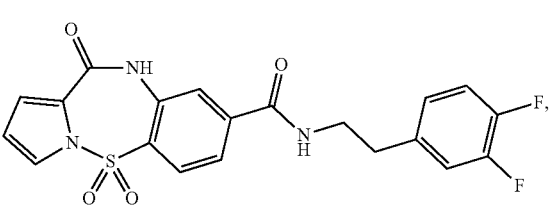
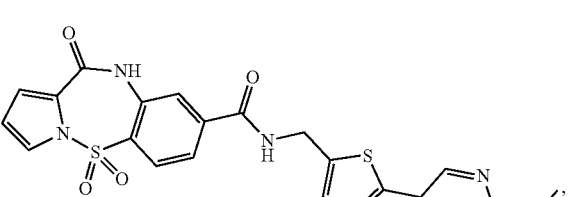
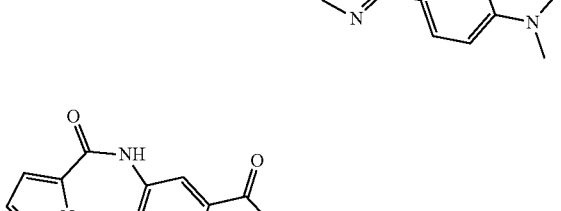
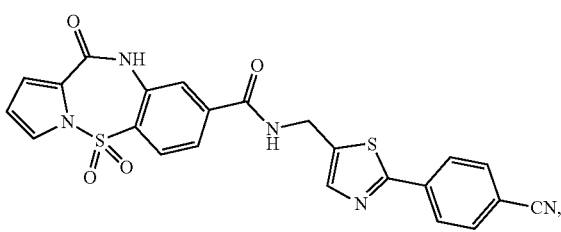

-continued
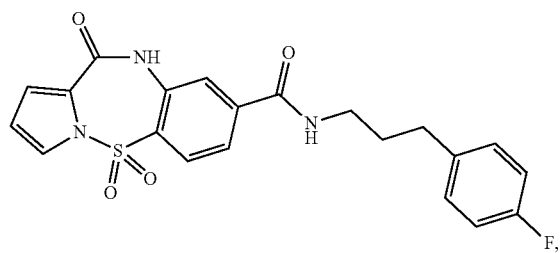
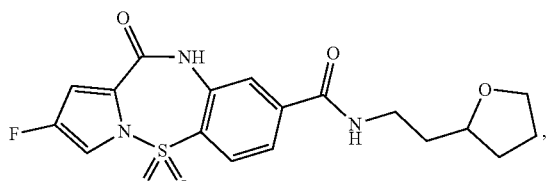
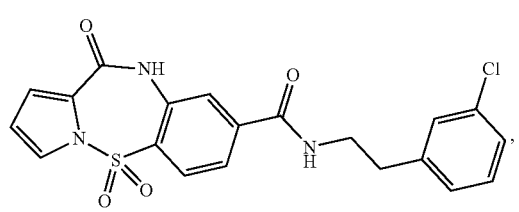
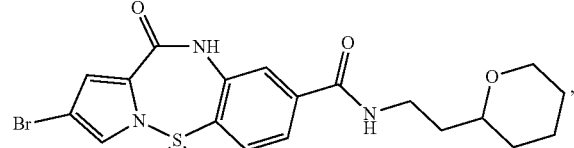
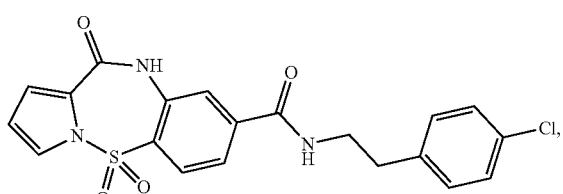
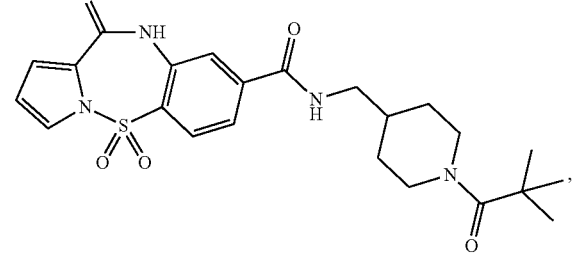
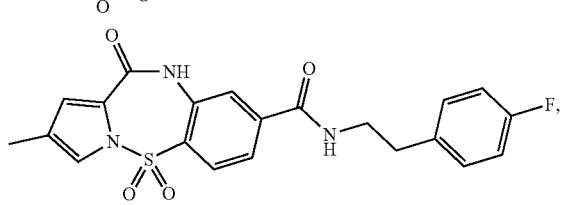
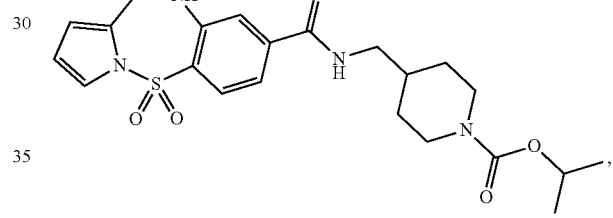
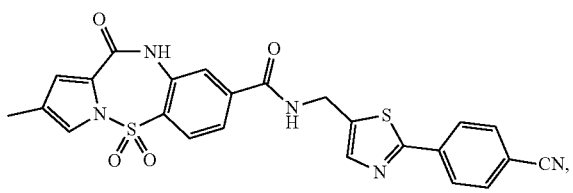
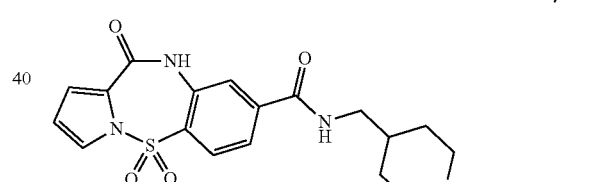
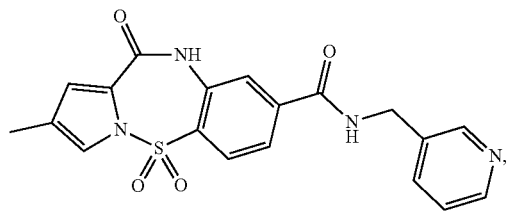
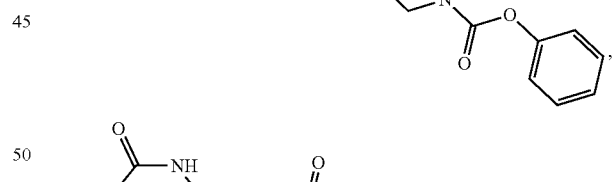
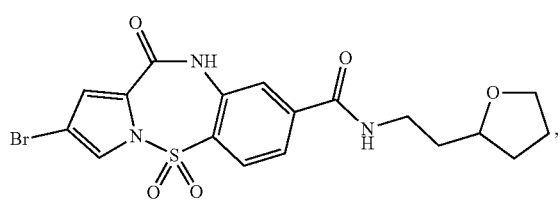
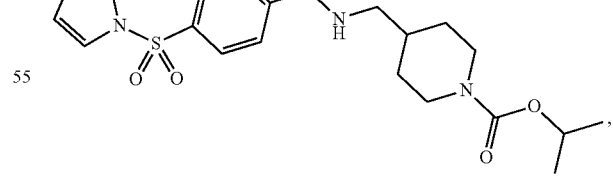
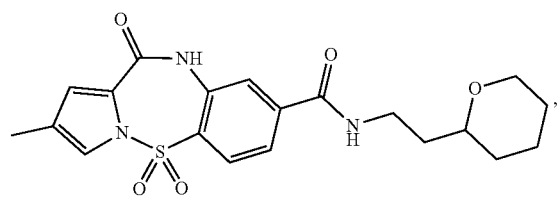
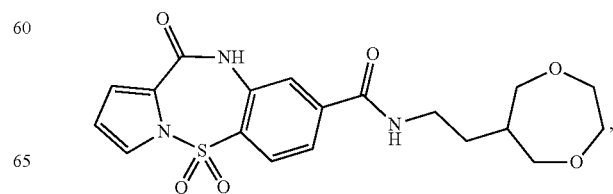

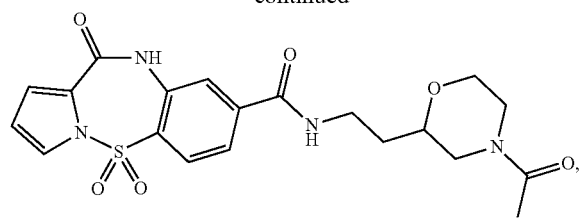
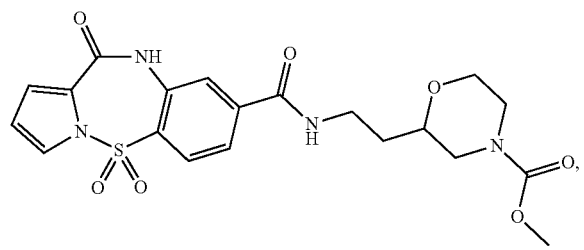
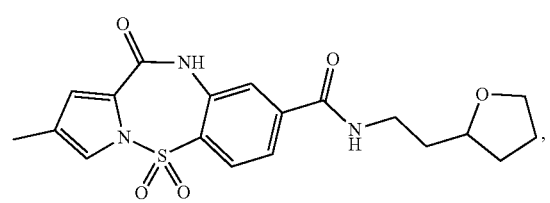
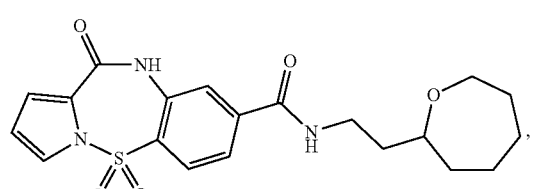
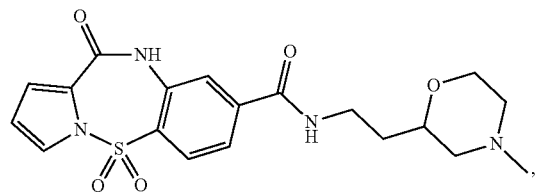
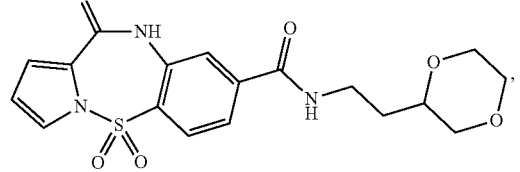
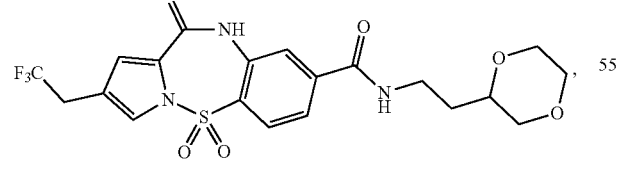
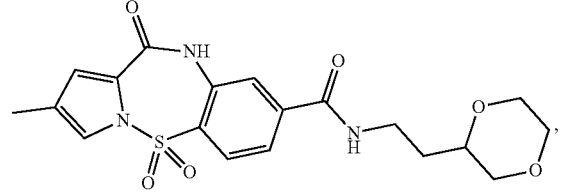
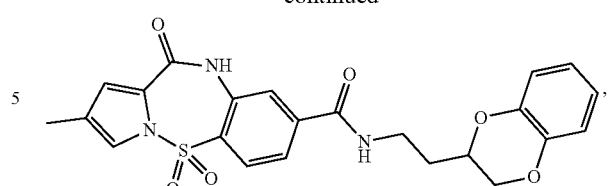
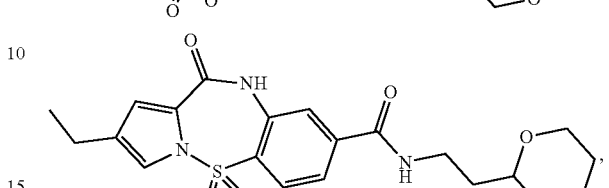
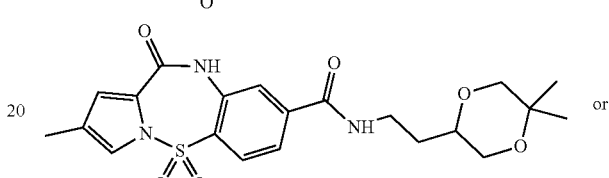
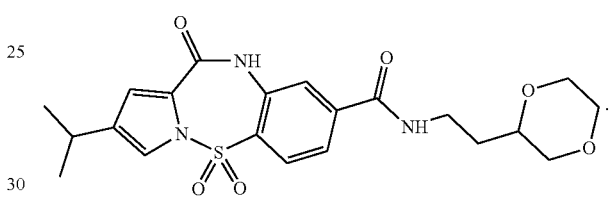
In some embodiments of the invention, the compound, the isomer thereof or the pharmaceutically acceptable salt thereof is selected from the group consisting of:
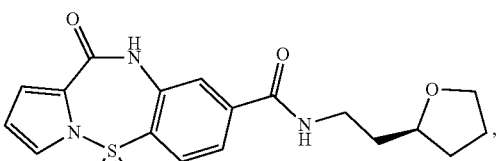
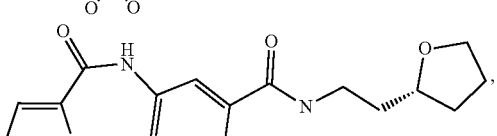
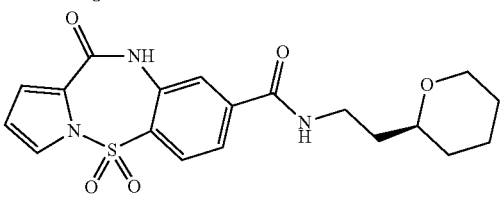
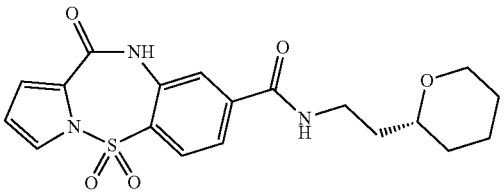

-continued

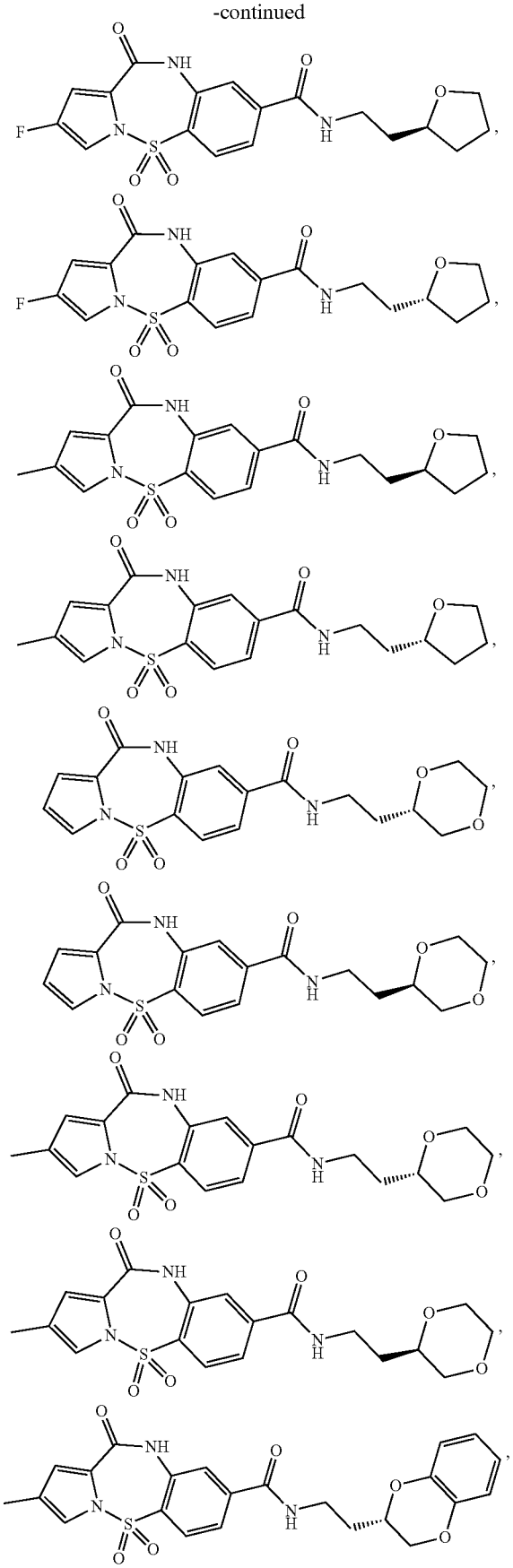

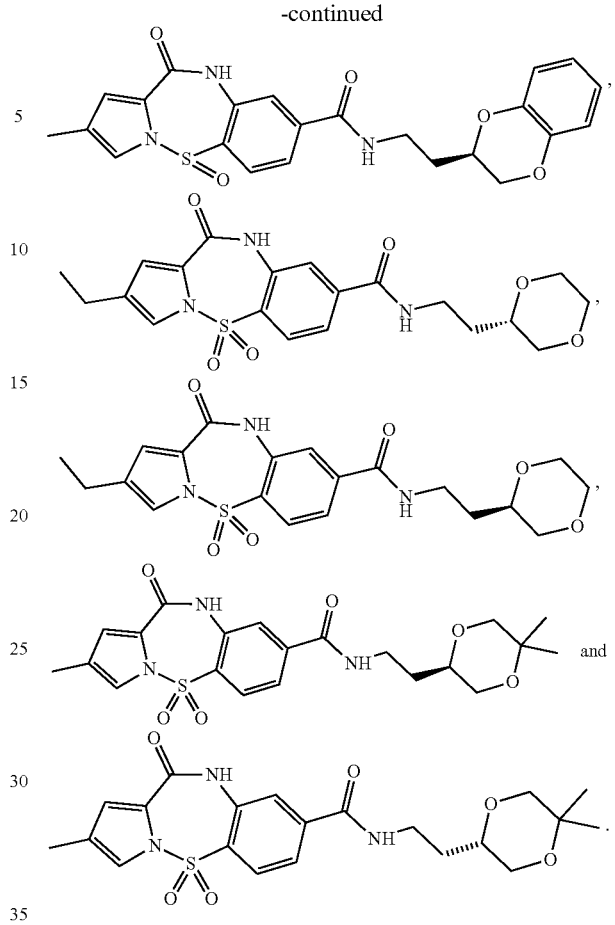

The invention also provides a pharmaceutical composition comprising a therapeutically effective amount of the compound, the isomer thereof or the pharmaceutically acceptable salt thereof, and a pharmaceutically acceptable carrier.

The invention also provides a use of the compound, the isomer thereof or the pharmaceutically acceptable salt thereof in manufacturing a medicament for treating a disease associated with HBV.

The invention also provides a use of the pharmaceutical composition in manufacturing a medicament for treating a disease associated with HBV.

Technical Effect

As a new type of anti-hepatitis B drug, the compound of the invention has a significant inhibitory effect on HBV, a good pharmacokinetic property in one or partial parameter on canine, and a good in vivo efficacy, and shows a dose-dependent effect.

Definition and Description

Unless otherwise indicated, the following terms when used in the descriptions and the claims of the invention have the following meanings. A specific term or phrase should not be considered indefinite or unclear in the absence of a particular definition, but should be understood in the ordinary sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the invention that is prepared by reacting the compound having a specific substituent of the invention with a relatively non-toxic acid or base. When the compound of the invention contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the invention contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds of the invention that contain both basic and acidic functional groups can be converted to any base or acid addition salt.

The pharmaceutically acceptable salt of the invention can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

In addition to the salt form, the compound provided by the invention also exists in prodrug form. The prodrug of the compound described herein is the compound that readily undergoes chemical change under physiological condition to be converted into the compound of the invention. Additionally, the prodrug can be converted to the compound of the invention by a chemical or biochemical method in vivo environment.

Certain compounds of the invention can exist in a non-solvated form or a solvated form, including hydrated form. Generally, the solvated form is equivalent to the nonsolvated form, and both are encompassed within the scope of the invention.

The compound of the invention may have a specific geometric or stereoisomeric form. The invention contemplates all such compounds, including cis and trans isomer, (−)- and (+)-enantiomer, (R)- and (S)-enantiomer, diastereoisomer, (D)-isomer, (L)-isomer, and racemic mixture and other mixtures, for example, an enantiomer or diastereoisomer enriched mixture, all of which are encompassed within the scope of the invention. The substituent such as alkyl may have an additional asymmetric carbon atom. All these isomers and mixtures thereof are encompassed within the scope of the invention.

Unless otherwise specified, the term "enantiomer" or "optical isomer" refers to stereoisomers that are mirror images of each other.

Unless otherwise specified, the term "cis-trans isomer" or "geometric isomer" is caused by the inability of a double bond or a single bond of carbon atoms on the ring to freely rotate.

Unless otherwise specified, the term "diastereomer" refers to stereoisomers in which the molecules have two or more chiral centers and are not mirror images of each other.

Unless otherwise specified, "(D)" or "(+)" refers to dextrorotation, "(L)" or "(−)" refers to levorotation, "(DL)" or "(±)" refers to racemization.

Unless otherwise specified, the absolute configuration of a stereogenic center is represented by a wedged solid bond ( ◢ ) and a wedged dashed bond ( ◣ ), and the relative configuration of a stereogenic center is represented by a straight solid bond ( ◢ ) and a straight dashed bond ( ◣ ). A wave line ( ∿ ) represents a wedged solid bond ( ◢ ) or a wedged dashed bond ( ◣ ), or represents a straight solid bond ( ◢ ) or a straight dashed bond ( ◣ ).

The compounds of the invention may be present in particular. Unless otherwise indicated, the terms "tautomer" or "tautomeric form" refer to the fact that the different functional isomers are in dynamic equilibrium at room temperature and can be rapidly converted into each other. If tautomers are possible (e.g., in solution), the chemical equilibrium of the tautomers can be achieved. For example, proton tautomers (also known as prototropic tautomers) include interconversions by proton transfer, such as keto-enol isomerization and imine-enamine isomerization. The valence tautomer includes the mutual transformation of some bonding electrons. A specific example of keto-enol tautomerization is the interconversion between two tautomers of pentane-2,4-dione and 4-hydroxypent-3-en-2-one.

Unless otherwise specified, the terms "enriched in one isomer", "isomer enriched", "enriched in one enantiomer" or "enantiomer enriched" refer to the content of one of the isomers or enantiomers is less than 100%, and the content of the isomer or enantiomer is 60% or more, or 70% or more, or 80% or more, or 90% or more, or 95% or more, or 96% or more, or 97% or more, or 98% or more, or 99% or more, or 99.5% or more, or 99.6% or more, or 99.7% or more, or 99.8% or more, or 99.9% or more.

Unless otherwise specified, the terms "excess of isomer" or "excess of enantiomer" refers to the difference between the relative percentages of the two isomers or enantiomers. For example, wherein, the content of one of the isomers or enantiomers is 90%, and the other one is 10%, then the excess of isomer or enantiomer (ee value) is 80%.

Optically active (R)- and (S)-isomer, or D and L isomer can be prepared using chiral synthesis or chiral reagents or other conventional techniques. If one kind of enantiomer of certain compound of the invention is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine). The compound of the invention may contain an unnatural proportion of atomic isotope at one or more than one atom(s) that constitute the compound. For example, the compound can be radiolabeled with a radioactive isotope, such as tritium ($^3H$), iodine-125 ($^{125}I$) or C-14 ($^{14}C$). For another example, hydrogen can be replaced by heavy hydrogen to form a deuterated drug, and the bond composed of barium and carbon is stronger than the bond composed of common hydrogen and carbon. Compared with undeuterated drugs, deuterated drugs have reduced side effects and increased drug stability, enhanced the efficacy and prolonged the biological half-life of the drug. All isotopic variations of the compound of the invention, whether radioactive or not, are encompassed within the scope of the invention.

"Optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variants, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When a bond of a substituent can be cross-linked to more than one atom on a ring, such substituent can be bonded to any atom of the ring. For example, the structural unit

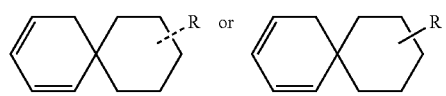

means that the substituent R can be located at any position on cyclohexyl or cyclohexadiene. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring. When the enumerative linking group does not indicate the direction for linking, the direction for linking is arbitrary, for example, the linking group L contained in

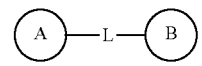

is -MW-, then -MW- can link ring A and ring B to form

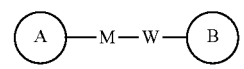

in the direction same as left-to-right reading order, and form

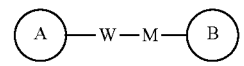

in the direction contrary to left-to-right reading order. A combination of substituents and/or variants thereof is allowed only when such combination can result in a stable compound.

Unless otherwise specified, the term "hetero" represents a heteroatom or a heteroatomic group (e.g., an atomic group containing a heteroatom), including the atom except carbon (C) and hydrogen (H) and the atomic group containing the above heteroatom, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and the group consisting of —C(=O)N(H)—, —N(H)—, —C(=NH)—, —S(=O)$_2$N(H)— and —S(=O)N(H)—, each of which is optionally substituted.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so-called ring includes a single ring, a double ring, a spiral ring, a fused ring or a bridged ring. The number of the atom on the ring is usually defined as the member number of the ring, for example, a "5-7 membered ring" means that 5 to 7 atoms are arranged on a ring. Unless otherwise specified, the ring optionally contains 1 to 3 heteroatoms. Therefore, a "5-7 membered ring" includes, for example, phenyl, pyridinyl and piperidinyl; on the other hand, the term "5-7 membered heterocycloalkyl ring" includes pyridyl and piperidinyl, but excluding phenyl. The term "ring" also includes a ring system containing at least one ring, wherein each ring independently meets the above definition.

Unless otherwise specified, the term "heterocycle" or "heterocycle" refers to a stable monocyclic, bicyclic or tricyclic ring containing a heteroatom or a heteroatom group, which can be saturated, partially unsaturated or unsaturated (aromatic) and can contain carbon atoms and 1, 2, 3 or 4 ring heteroatoms independently selected from N, O and S, wherein any of the above heterocycle can be fused to a benzene ring to form a bicyclic ring. Nitrogen and sulfur heteroatoms can optionally be oxidized (i.e., NO and S(O)p, p is 1 or 2). Nitrogen atom can be substituted or unsubstituted (i.e., N or NR, wherein R is H or other substituents already defined herein). The heterocycle can be attached to the pendant group of any heteroatom or carbon atom to form a stable structure. If the resulting compound is stable, the heterocycle described herein may have a substitution at a carbon or nitrogen position. Nitrogen atom on the heterocycle is optionally quaternized. In a preferred embodiment, when the total number of S and O atom of the heterocycle is more than 1, the heteroatom is not adjacent to each other. In another preferred embodiment, the total number of S and O atom of the heterocycle is not more than 1. As used herein, the term "aromatic heterocyclic group" or "heteroaryl" refers to a stable 5-, 6- or 7-membered monocyclic or bicyclic or 7-, 8-, 9- or 10-membered bicyclic heterocyclic aromatic ring which contains carbon atoms and 1, 2, 3 or 4 ring heteroatoms independently selected from N, O and S. Nitrogen atom can be substituted or unsubstituted (i.e., N or NR, wherein R is H or other substituents already defined herein). Nitrogen and sulfur heteroatoms may optionally be oxidized (i.e., NO and S(O)$_p$, p is 1 or 2). It is worth noting that the total number of S and O atom of an aromatic heterocycle is not more than one. The bridged ring is also included in the definition of the heterocycle. A bridged ring is formed when one or more than one atom (i.e, C, O, N or S) link two non-adjacent carbon or nitrogen atoms. A preferred bridged ring includes, but not limited to one carbon atom, two carbon atoms, one nitrogen atom, two nitrogen atoms and one carbon-nitrogen group. It is worth noting that a bridge always converts a monocyclic ring to a tricyclic ring. In a bridged ring, the substituent on the ring may also be present on the bridge.

Examples of the heterocyclic compound include, but are not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxindolyl, pyrimidinyl, phenanthridinyl, phenanthrolinyl, phenazine, phenothiazine, benzoxanthinyl, phenoloxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazolyl, pyrido-imidazolyl, pyrido-thiazolyl, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thieno-oxazolyl, thieno-thiazolyl, thieno-imidazolyl, thienyl, triazinyl, 2H-1, 2,3-triazolyl, 1H-1,2,4-triazolyl, 4H-1,2,4-triazolyl and xanthenyl. Also included are fused-ring compounds and spiro compounds.

Unless otherwise specified, the term "hydrocarbyl" or its hyponyms (e.g., alkyl, alkenyl, alkynyl, and aryl, etc.), by itself or as part of another substituent, refers to a linear, branched chain or cyclic hydrocarbon radical or any combination thereof. They can be fully saturated (e.g., alkyl), mono- or polyunsaturated (e.g., alkenyl, alkynyl, and aryl), can be mono-, di- or poly-substituted, can be monovalent (e.g., methyl), divalent (e.g., methylene) or multivalent (e.g., methenyl), can also include a divalent or multivalent group, have a specified number of carbon atom (for example, $C_1$-$C_{12}$ indicates 1 to 12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$). The term "hydrocarbyl" includes, but is not limited to aliphatic hydrocarbyl and aromatic hydrocarbyl. The aliphatic hydrocarbyl includes linear and cyclic hydrocarbyl, specifically includes but not limited to alkyl, alkenyl, and alkynyl. The aromatic hydrocarbyl includes but is not limited to 6-12 membered aromatic hydrocarbyl such as phenyl, naphthyl and the like. In some embodiments, the term "hydrocarbyl" refers to a linear or branched group or a combination thereof which can be fully saturated, mono- or polyunsaturated, and can include a divalent or multivalent group. Examples of the saturated hydrocarbyl group include, but are not limited to, methyl, ethyl, n-propyl, isopropyl, n-butyl, tert-butyl, isobutyl, sec-butyl, cyclohexyl, (cyclohexyl)methyl, cyclopropylmethyl, and the homolog or isomer of n-amyl, n-hexyl, n-heptyl, n-octyl and other atom groups. The unsaturated hydrocarbyl has one or more than one double or triple bonds. Examples of the unsaturated alkyl include but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and more higher homologs and isomers.

Unless otherwise specified, the term "heterohydrocarbyl" or its hyponyms (such as heteroalkyl, heteroalkenyl, heteroalkynyl, and heteroaryl, etc.), by itself or as part of another substituent, refers to a stable linear, branched or cyclic hydrocarbon group or any combination thereof, which has a specified number of carbon atoms and at least one heteroatom. In some embodiments, the term "heteroalkyl" by itself or in combination with another term refers to a stable linear chain, branched hydrocarbon radical or a combination thereof which has a specified number of carbon atoms and at least one heteroatom. In a specific embodiment, a heteroatom is selected from B, O, N and S, wherein nitrogen and sulfur atoms are optionally oxidized and the nitrogen atom is optionally quaternized. The heteroatom or heteroatom group can be located at any interior position of a heterohydrocarbyl, including the position where the hydrocarbyl attaches to the rest part of the molecule. But the terms "alkoxy", "alkylamino" and "alkylthio" (or thioalkyl) are used by the conventional meaning and refer to an alkyl group connected to the rest part of the molecule via an oxygen atom, an amino or a sulfur atom respectively. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —CH$_2$—CH═N—OCH$_3$ and —CH═CH—N(CH$_3$)—CH$_3$. Up to two consecutive heteroatoms can be present, such as, —CH$_2$—NH—OCH$_3$.

Unless otherwise specified, the term "cyclohydrocarbyl", "heterocyclohydrocarbyl" or its hyponyms (such as aryl, heteroaryl, cycloalkyl, heterocycloalkyl, cycloalkenyl, heterocycloalkenyl, cycloalkynyl, heterocycloalkynyl, etc.) by itself or in combination with another term refers to cyclized "hydrocarbyl" or "heterohydrocarbyl". Furthermore, for heterohydrocarbyl or heterocyclohydrocarbyl (e.g., heteroalkyl, and heterocycloalkyl), one heteroatom can occupy the position where the heterocycle attaches to the remainder position of the molecule. Examples of the cycloalkyl include, but are not limited to, cyclopentyl, cyclohexyl, 1-cyclohexenyl, 3-cyclohexenyl, cycloheptyl and the like. Non-limiting examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydro-thiophen-2-yl, tetrahydro-thiophen-3-yl, 1-piperazinyl and 2-piperazinyl.

Unless otherwise specified, the term "heterocycloalkyl", by itself or in conjunction with other terms, refers to a cyclized "heteroalkyl", respectively. In addition, in the case of the "heterocycloalkyl", a heteroatom can occupy the position at which the heterocycle is attached to the remainder of the molecule. In some embodiments, the heterocycloalkyl is a 4-6 membered heterocycloalkyl; in other embodiments, the heterocycloalkyl is a 5-6 membered heterocycloalkyl. Examples of the heterocycloalkyl include, but are not limited to, azetidinyl, oxetanyl, thioheterobutyl, pyrrolidinyl, pyrazolidinyl, imidazolidinyl, tetrahydrothiophenyl, tetrahydrofuranyl, tetrahydropyranyl, piperidinyl, piperazinyl, morpholinyl, dioxoalkyl, dithiaalkyl, isoxazolidinyl, isothiazolidinyl, 1,2-oxazinyl, 1,2-thiazinyl, hexahydropyridazinyl, homopiperazinyl, homopiperidinyl or oxetanyl.

Unless otherwise specified, the term "alkyl" refers to a linear chain or branched saturated hydrocarbon group, can be mono-substituted (e.g., —$CH_2F$) or poly-substituted (e.g., —$CF_3$), can be monovalent (e.g. methyl), divalent (e.g., methylene) or multivalent (e.g., methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, the term "alkenyl" refers to an alkyl group having one or more than one carbon-carbon double bonds at any position on the chain, can be mono-substituted or poly-substituted, and can be monovalent, divalent or multivalent. Examples of alkenyl include ethenyl, propenyl, butenyl, pentenyl, hexenyl, butadienyl, pentadienyl, hexadienyl, and the like.

Unless otherwise specified, the term "alkynyl" refers to an alkyl group having one or more than one carbon-carbon triple bonds at any position on the chain, can be mono-substituted or poly-substituted, and can be monovalent, divalent or multivalent. Examples of alkynyl include ethynyl, propynyl, butynyl, pentynyl, and the like.

Unless otherwise specified, cycloalkyl includes any stable cyclic or polycyclic hydrocarbyl, and any carbon atom is saturated, can be mono-substituted or poly-substituted, and can be monovalent, divalent or multivalent. Examples of cycloalkyl include, but are not limited to, cyclopropyl, norbornanyl, [2.2.2]bicyclooctane, [4.4.0]bicyclodecanyl and the like.

Unless otherwise specified, cycloalkenyl includes any stable cyclic or polycyclic hydrocarbyl having one or more than one unsaturated carbon-carbon single bonds at any position on the ring, can be mono-substituted or poly-substituted, and can be monovalent, divalent or multivalent. Examples of the cycloalkenyl include, but are not limited to, cyclopentenyl, cyclohexenyl and the like.

Unless otherwise specified, cycloalkynyl includes any stable cyclic or polycyclic hydrocarbyl having one or more carbon-carbon triple bonds at any position on the ring, can be mono-substituted or poly-substituted, and can be monovalent, divalent or multivalent.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo($C_1$-$C_4$)alkyl" is meant to include, but not limited to, trifluoromethyl, 2,2,2-trifluoroethyl, 4-chlorobutyl, 3-bromopropyl and the like. Examples of haloalkyl include, but not limited to trifluoromethyl, trichloromethyl, pentafluoroethyl and pentachloroethyl.

The term "alkoxy" represents any alkyl defined above having a specified number of carbon atoms attached by an oxygen bridge. Unless otherwise specified, $C_{1-6}$ alkoxy includes $C_1$, $C_2$, $C_3$, $C_4$, $C_5$ and $C_6$ alkoxy. Examples of alkoxy include, but not limited to methoxy, ethoxy, n-propoxy, isopropoxy, n-butoxy, sec-butoxy, tert-butoxy, n-pentyloxy and S-pentoxy.

Unless otherwise specified, the term "aryl" refers to a polyunsaturated aromatic substituent, can be mono-, di- or poly-substituted, can be a monovalent, divalent or multivalent, can be a single ring or a multiple ring (e.g. one to three rings; wherein at least one ring is aromatic), which are fused together or connected covalently. The term "heteroaryl" refers to an aryl (or ring) containing one to four heteroatoms. In an illustrative example, the heteroatom is selected from B, O, N and S, wherein nitrogen and sulfur atoms are optionally oxidized and nitrogen atom is optionally quaternized. A heteroaryl may attach to the rest part of a molecule via a heteroatom. Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furanyl, thienyl, pyridyl, pyrimidinyl, benzothiazolyl, purinyl, benzimidazolyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of any of the above aryl and heteroaryl ring system is selected from the acceptable substituent described below.

Unless otherwise specified, when aryl combines with other terms (such as aryloxy, arylthio, arylalkyl), the aryl includes the aryl and heteroaryl ring as defined above. Thus, the term "aralkyl" is meant to include the group (e.g., benzyl, phenethyl, pyridylmethyl, etc.) where an aryl is attached to an alkyl, including an alkyl where the carbon atom (e.g, methylene) has been replaced by an atom such as oxygen, for example, phenoxymethyl, 2-pyridyloxy, 3-(1-naphthyloxy)propyl, and the like.

The term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group"

refers to a protecting group suitable for blocking the side reaction on the nitrogen of an amino. Representative amino protecting groups include, but are not limited to: formyl; acyl, such as alkanoyl (e.g, acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g, acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compound of the invention can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The preferred embodiment includes, but is not limited to the embodiment of the invention.

All of the solvents used in the invention are commercially available. The invention adopts the abbreviating words as followed: "Aq" refers to water; "HATU" refers to O-(7-azabenzotriazol-1-yl)-N,N,N',N'-tetramethyluronium hexafluorophosphate; "EDC" refers to N-(3-dimethylaminopropyl)-N'-ethylcarbodiimide hydrochloride; "m-CPBA" refers to 3-chloroperoxybenzoic acid; "eq" refers to equivalent; "CDI" refers to carbonyldiimidazole; "DCM" refers to dichloromethane; "PE" refers to petroleum ether; "DIAD" refers to diisopropyl azodicarboxylate; "DMF" refers to N,N-dimethylformamide; "DMSO" refers to dimethyl sulfoxide; "EtOAc" refers to ethyl acetate; "EtOH" refers to ethanol; "MeOH" refers to methanol; "CBz" refers to benzyloxycarbonyl, which is an amine protecting group; "BOC" refers to tert-butylcarbonyl, which is an amine protecting group; "HOAc" refers to acetic acid; "NaCNBH$_3$" refers to sodium cyanoborohydride; "r.t." refers to room temperature; "O/N" refers to overnight; "THF" refers to tetrahydrofuran; "Boc$_2$O" refers to di-tert-butyldicarbonate; "TFA" refers to trifluoroacetic acid; "DIPEA" refers to diisopropylethylamine; "SOCl$_2$" refers to thionyl chloride; "CS$_2$" refers to carbon disulfide; "TsOH" refers to p-toluenesulfonic acid; "NFSI" refers to N-fluoro-N-(phenylsulfonyl)benzenesulfonamide; "NCS" refers to 1-chloropyrrolidine-2,5-dione; "n-Bu$_4$NF" refers to tetrabutylammonium fluoride; "iPrOH" refers to 2-propanol; "mp" refers to melting point; "LDA" refers to diisopropylamino lithium; "EDCI" refers to carbodiimide; "HOBt" refers to 1-hydroxybenzotriazole; "Pd (dppf)Cl$_2$" refers to [1,1'-bis(diphenylphosphino)ferrocene] palladium dichloride; "MgSO$_4$" refers to magnesium sulfate; "DMAP" refers to 4-dimethylaminopyridine; "EEDQ" refers to 2-ethoxy-1-ethoxycarbonyl-1,2-dihydroquinoline; "LAWESSON'S" refers to 2,4-bis(p-methoxyphenyl)-1,3-dithio-diphosphetane-2,4 sulfide (Lawson's reagent); "TEA" refers to triethanolamine; "TosCl" refers to p-toluenesulfonyl chloride; "Et$_3$N" refers to triethylamine; "BF$_3$.Et$_2$O" refers to boron trifluoride etherate; "Raney-Ni" refers to Raney nickel; "PPh$_3$" refers to triphenylphosphine; "IPA" refers to isopropanol; "DPBS" refers to dulbecco's phosphate buffered saline; "DIEA" refers to N,N-diisopropylethylamine; "Pd(PPh$_3$)$_4$" refers to tetrakis(triphenylphosphine)palladium; "t-BuOK" refers to potassium tert-butoxide.

Compounds are named manually or by ChemDraw® software, the commercially available compounds use their vendor directory names.

DETAILED DESCRIPTION OF THE PREFERRED EMBODIMENT

Figure 1:
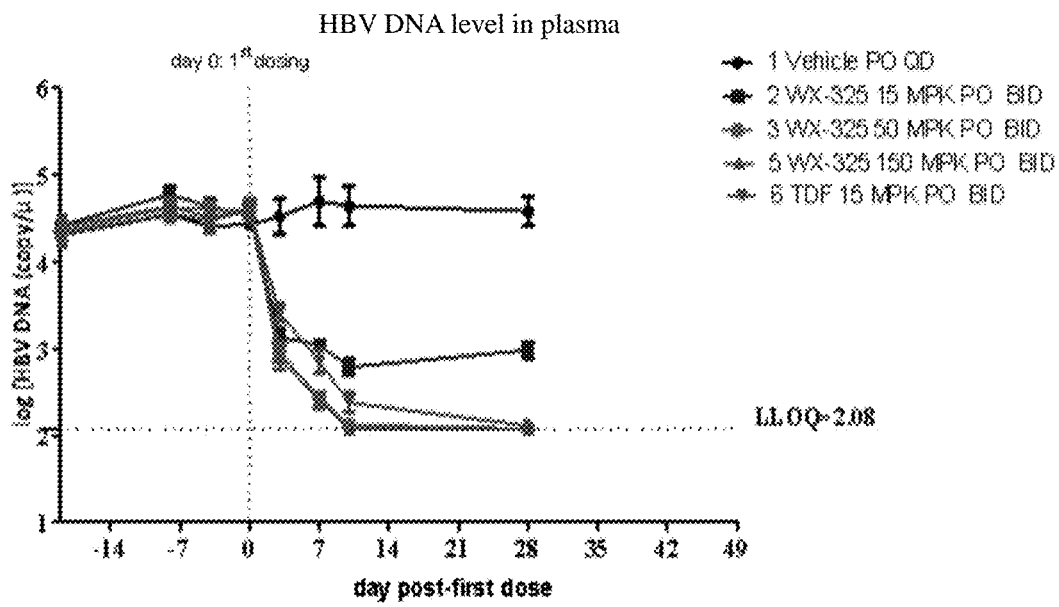
FIG. 1: Hepatitis B virus DNA level in plasma; broken line 1 refers to that 10% Solutol aqueous solution as a blank control was administered once a day (QD) by intragastrical gavage (PO); broken line 2 refers to that the test compound WX325 was administered twice a day (BID) at an interval of 8 hours by intragastricalgavage (PO) at a dose of 15 mg/kg; broken line 3 refers to that the test compound WX325 was administered twice a day (BID) at an interval of 8 hours by intragastrical gavage (PO) at a dose of 50 mg/kg; broken line 5 refers to that the test compound WX325 was administered twice a day (BID) at an interval of 8 hours by intragastrical gavage (PO) at a dose of 150 mg/kg; broken line 6 refers to that Tenofovir (TDF) as a positive compound was administered twice a day (BID) at an interval of 8 hours by intragastricalgavage (PO) at a dose of 15 mg/kg; LLOQ refers to the lower limit of detection; day post-first dose refers to the number of days of administration.

The following examples further illustrate the invention, but the invention is not limited thereto. The invention has been described in detail in the text, and its specific embodiments have also been disclosed, for one skilled in the art, it is obvious to modify and improve the embodiments of the invention within the spirit and scope of the invention.

Reference Embodiment 1: Fraction BB-1

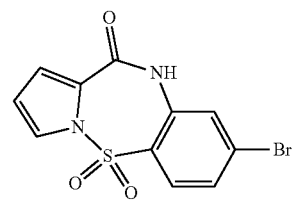 [SMILES: O=C1Nc2cc(Br)ccc2S(=O)(=O)n2cccc21]

Synthetic Route

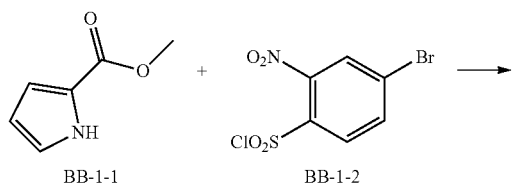

BB-1-1               BB-1-2

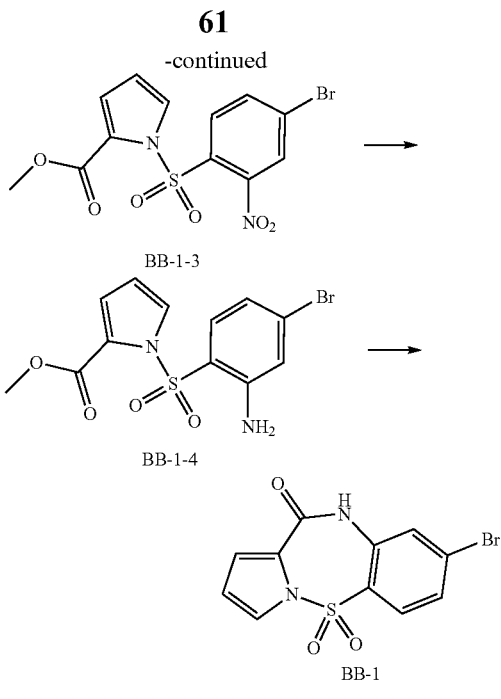

7.01 (dd, J=1.9, 3.6 Hz, 1H), 6.82 (d, J=1.8 Hz, 1H), 6.78 (dd, J=1.8, 8.8 Hz, 1H), 6.23 (t, J=3.4 Hz, 1H), 5.15 (br s, 2H), 3.69 (s, 3H).

Step 3: Synthesis of Compound BB-1

BB-1-4 (57 g, 158.69 mmol) was dissolved in toluene (50 mL), and a solution of trimethylaluminum (2 M, 79.34 mL) in toluene was added thereto. The mixture was heated to 110° C. and stirred for 2 hours. The reaction mixture was cooled to room temperature, poured into 4 L of water, and then extracted with a large amount of ethyl acetate. The organic phases were combined, and dried over anhydrous sodium sulfate, followed by filtration. The solvent was removed by evaporation under reduced pressure to give a crude product. The crude product was purified by column chromatography to give BB-1 (48 g). $^1$H NMR (400 MHz, DMSO-$d_6$) δ=11.16 (s, 1H), 7.91 (d, J=8.5 Hz, 1H), 7.70-7.53 (m, 3H), 7.15 (dd, J=1.6, 3.6 Hz, 1H), 6.53 (t, J=3.4 Hz, 1H).

Reference Embodiment 2: Fraction BB-2

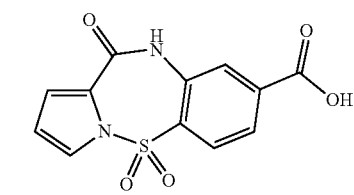 [SMILES: O=C(O)c1ccc2c(c1)NC(=O)c1cccn1S2(=O)=O]

Synthetic Route

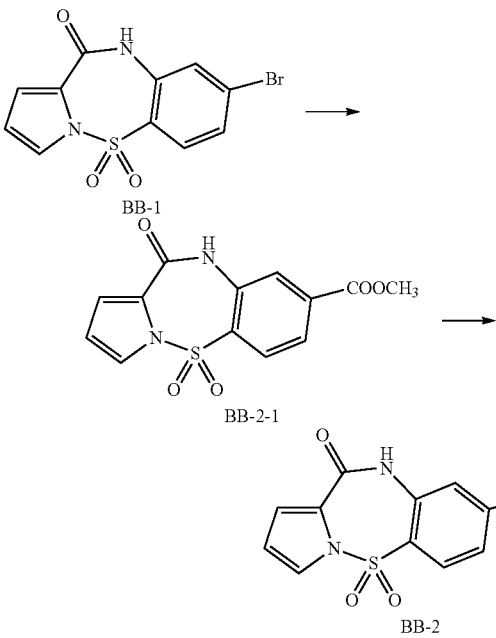

Step 1: Synthesis of Compound BB-1-3

BB-1-1 (40 g, 319.68 mmol) was added into a pre-dried 3 L three-necked flask under nitrogen atmosphere, and then tetrahydrofuran (500 mL) was added thereto. A solution of potassium tert-butoxide in tetrahydrofuran (1 M, 479.52 mL) was added dropwise at 0° C. After completion of the dropwise addition, the reaction solution was stirred at 0° C. for 15 minutes. After 15 minutes, a solution of BB-1-2 (115.28 g, 383.62 mmol) in tetrahydrofuran (500 mL) was slowly added dropwise to the above reaction mixture at 0° C. After completion of the dropwise addition, the reaction mixture was heated to 25° C. and stirred for 4.5 hours. The reaction was quenched with water (600 mL). The reaction mixture was extracted with ethyl acetate (1L*3). The organic phase was dried over anhydrous sodium sulfate, followed by filtration. The solvent was removed by evaporation under reduced pressure to give a crude product of BB-1-3. The crude product was slurried to give BB-1-3. $^1$H NMR (400 MHz, CHLOROFORM-d) δ=8.29 (d, J=8.3 Hz, 1H), 7.97-7.88 (m, 2H), 7.65 (dd, J=2.0, 3.3 Hz, 1H), 7.13 (dd, J=1.9, 3.6 Hz, 1H), 6.36 (t, J=3.5 Hz, 1H), 3.74 (s, 3H).

Step 2: Synthesis of Compound BB-1-4

Iron powder (21.02 g, 376.45 mmol) was added to a solution of BB-1-3 (29.30 g, 75.29 mmol) in acetic acid (200.00 mL) at 18° C. The reaction mixture was then heated to 70° C. and stirred for 2 hours. The solid matter was removed by filtration, and the filter cake was washed with ethyl acetate. The filtrate was collected and the pH value of the filtrate was adjusted to 7-8 with saturated sodium bicarbonate, followed by extraction and separation. The organic phase was washed with saturated sodium chloride solution and dried over anhydrous sodium sulfate, followed by filtration. The solvent was removed by evaporation under reduced pressure to give a crude product of BB-1-4. The crude product was purified by column chromatography to give BB-1-4 (15 g). $^1$H NMR (400 MHz, CHLOROFORM-d) δ=7.61 (dd, J=2.0, 3.3 Hz, 1H), 7.42 (d, J=8.8 Hz, 1H), Step 1: Synthesis of Compound BB-2-1

BB-1 (6 g, 18.34 mmol), triethylamine (1.86 g, 18.34 mmol, 2.54 mL), Pd(dppf)Cl$_2$.CH$_2$Cl$_2$ (1.50 g, 1.83 mmol)

and a solvent of methanol (360 mL), DMF (36.00 mL) were added into a pre-dried hydrogenation flask. After completion of the addition, CO gas was introduced into the reaction system, and stirred at 80° C. for 12 hours under 50 psi. After the reaction system was cooled to room temperature, methanol and DMF were removed by evaporation under reduced pressure to give a crude product. The crude product was dissolved in ethyl acetate (800 mL). The organic phase was washed with water (300 mL*2), and dried over anhydrous sodium sulfate, followed by filtration. The filtrate was concentrated under reduced pressure to remove the solvent to give BB-2-1. $^1$H NMR (400 MHz, DMSO-$d_6$) δ=11.27 (s, 1H), 8.15 (d, J=8.4 Hz, 1H), 8.05 (s, 1H), 7.91 (d, J=8.4 Hz, 1H), 7.67-7.59 (m, 1H), 7.17 (dd, J=1.7, 3.4 Hz, 1H), 6.56 (t, J=3.4 Hz, 1H), 3.97-3.82 (m, 3H).

Step 2: Synthesis of Compound BB-2

Raw material BB-2-1 (1.5 g, 4.90 mmol), lithium hydroxide monohydrate (205 mg, 4.90 mmol), tetrahydrofuran (15 mL) and water (3 mL) were added into a dry single-necked flask. The reaction solution in the flask was then stirred in an oil bath at 60° C. for 4 hours. The reaction solution was evaporated under reduced pressure to remove THF, followed by addition of 20 mL of water. The pH value was adjusted to about 3 with 2 M diluted hydrochloric acid. Solids were precipitated and collected by filtration to give BB-2. $^1$H NMR (400 MHz, DMSO-$d_6$) δ=11.26 (s, 1H), 8.13 (d, J=8.2 Hz, 1H), 8.02 (d, J=1.3 Hz, 1H), 7.90 (dd, J=1.5, 8.2 Hz, 1H), 7.62 (dd, J=1.8, 3.1 Hz, 1H), 7.16 (dd, J=1.7, 3.6 Hz, 1H), 6.55 (t, J=3.4 Hz, 1H).

Reference Embodiment 3: Fraction BB-3

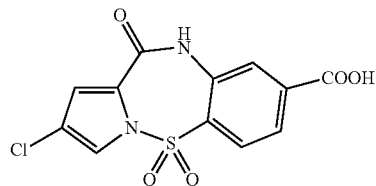 [SMILES: O=C(O)c1ccc2c(c1)NC(=O)c1cc(Cl)cn1S2(=O)=O]

Synthetic Route

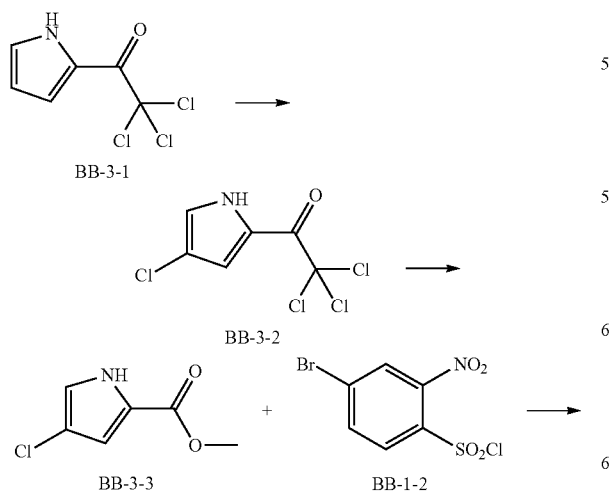

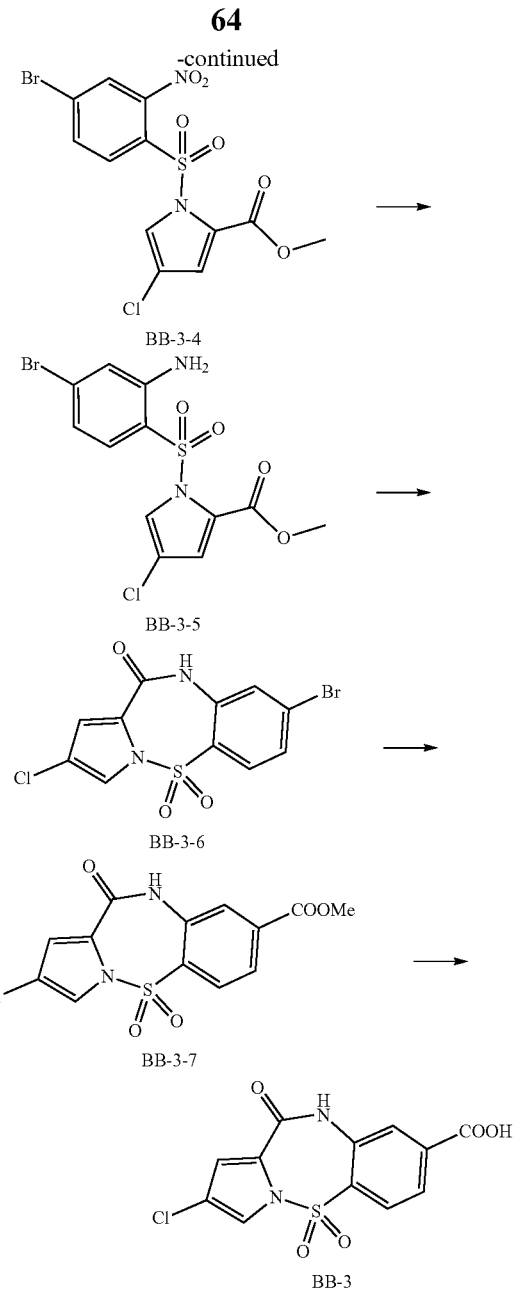

Step 1: Synthesis of Compound BB-3-2

BB-3-1 (10.00 g, 47.07 mmol) and chloroform (50.00 mL) were added into a pre-dried 250 mL flask at 0° C., and then sulfuryl chloride (12.71 g, 94.14 mmol, 9.41 mL) was added dropwise thereto. After completion of the addition, the reaction mixture was stirred at 25° C. for 3 hours. The reaction mixture was poured into ice water (100 mL), and the aqueous phase was extracted with dichloromethane (100 mL*3). The organic phases were combined, washed to neutral with water, dried over anhydrous sodium sulfate, filtered and concentrated under reduced pressure to give BB-3-2, which was directly used in the next step.

Step 2: Synthesis of Compound BB-3-3

BB-3-2 (10.00 g, 40.50 mmol) and methanol (100 mL) were added into a pre-dried 250 mL flask, and then sodium methoxide (2.63 g, 48.60 mmol) was added thereto. After completion of the addition, the reaction mixture was stirred at 25° C. for 1 hour under nitrogen atmosphere. After removal of the methanol by evaporation under reduced pressure, the mixture was diluted with dichloromethane (100 mL). The organic phase was sequentially washed with water (40 mL) and saturated brine (30 mL), dried over anhydrous sodium sulfate, and concentrated under reduced pressure to give a crude product. The crude product was purified by flash column chromatography to give BB-3-3. $^1$H NMR (400 MHz, CHLOROFORM-d) δ=9.17 (br s, 1H), 6.93-6.90 (m, 1H), 6.82 (dd, J=1.8, 2.6 Hz, 1H), 3.88 (s, 3H).

Step 3: Synthesis of Compound BB-3-4

Potassium tert-butoxide (1 M, 62.68 mL) and tetrahydrofuran (30 mL) were added into a 250 mL pre-dried three-necked flask under nitrogen atmosphere, and then a solution of BB-3-3 (4.00 g, 25.07 mmol, 1.00 eq) in tetrahydrofuran (40 mL) was slowly added dropwise thereto at 0° C. After the reaction system was heated to 25° C. and stirred for 15 minutes, a solution of BB-1-2 (15.07 g, 50.14 mmol) in tetrahydrofuran (10.00 mL) was slowly added dropwise at 0° C. After completion of the addition, the reaction mixture was stirred at 25° C. for 4.5 hours under nitrogen atmosphere. The reaction was quenched by addition of water (150 mL). After the reaction mixture was concentrated under reduced pressure to remove tetrahydrofuran, the aqueous phase was extracted with ethyl acetate (100 mL*3), dried over anhydrous sodium sulfate, followed by filtration. The filtrate was concentrated under reduced pressure to give a crude product. The crude product was purified by flash column chromatography to give BB-3-4. $^1$H NMR (400 MHz, DMSO-d$_6$) δ=8.53 (d, J=2.0 Hz, 1H), 8.17 (dd, J=1.9, 8.6 Hz, 1H), 7.96 (d, J=2.0 Hz, 1H), 7.89 (d, J=8.7 Hz, 1H), 7.36 (d, J=2.0 Hz, 1H), 3.65 (s, 3H).

Step 4: Synthesis of Compound BB-3-5

BB-3-4 (300.00 mg, 708.18 μmol) and acetic acid (3.00 mL) were added into a pre-dried vial, and then iron powder (197.76 mg, 3.54 mmol) was added thereto. After completion of the addition, the reaction mixture was stirred at 70° C. for 40 minutes under nitrogen atmosphere. After the reaction system was cooled to room temperature, a saturated aqueous solution of sodium bicarbonate was added dropwise to the reaction system until the pH value was equal to 6. The reaction mixture was extracted with ethyl acetate (15 mL*3), washed with saturated brine (20 mL*2), and dried over anhydrous sodium sulfate, followed by filtration. The filtrate was concentrated under reduced pressure to give product BB-3-5. $^1$H NMR (400 MHz, DMSO-d$_6$) δ=8.23 (d, J=2.0 Hz, 1H), 7.67 (d, J=8.8 Hz, 1H), 7.16 (d, J=2.0 Hz, 1H), 7.09 (d, J=1.9 Hz, 1H), 6.87 (dd, J=1.9, 8.8 Hz, 1H), 6.50 (s, 2H), 3.71 (s, 3H).

Step 5: Synthesis of Compound BB-3-6

BB-3-5 (1.00 g, 2.54 mmol) and toluene (10 mL) were added into a pre-dried 50 mL flask, and then a solution of trimethylaluminum (2.5 M, 1.52 mL) in toluene was added thereto. After completion of the addition, the reaction mixture was stirred at 80° C. for 1.5 hours under nitrogen atmosphere. After the reaction system was cooled to room temperature, water (30 mL) was added to the reaction mixture to quench the reaction, and a pale yellow solid was precipitated. 2 M hydrochloric acid was added dropwise until the solid was completely dissolved. The aqueous phase was extracted with ethyl acetate (75 mL*2), and the organic phase was dried over anhydrous sodium sulfate, followed by filtration. The filtrate was concentrated under reduced pressure to give product BB-3-6. $^1$H NMR (400 MHz, DMSO-d$_6$) δ=11.33 (s, 1H), 7.93 (d, J=8.3 Hz, 1H), 7.85 (d, J=1.8 Hz, 1H), 7.68-7.64 (m, 2H), 7.21 (d, J=1.8 Hz, 1H).

Step 6: Synthesis of Compound BB-3-7

BB-3-6 (170.00 mg, 470.13 μmol), triethylamine (71.36 mg, 705.20 μmol, 97.75 μL), Pd(dppf)Cl$_2$.CH$_2$Cl$_2$ (38.39 mg, 47.01 μmol) and methanol (10 mL), DMF (1.00 mL) were added into a pre-dried hydrogenation flask. After completion of the addition, carbon monoxide gas was introduced to the reaction system and the reaction solution was stirred at 80° C. for 12 hours under 50 psi. The reaction system was cooled to room temperature, then concentrated under reduced pressure to remove methanol and DMF to give a crude product. The crude product was isolated by flash column chromatography to give BB-3-7. $^1$H NMR (400 MHz, DMSO-d$_6$) δ=13.78 (s, 1H), 11.45 (s, 1H), 11.53-11.36 (m, 1H), 8.16 (d, J=8.4 Hz, 1H), 8.04 (d, J=1.1 Hz, 1H), 7.94 (dd, J=1.4, 8.3 Hz, 1H), 7.89 (d, J=2.0 Hz, 1H), 7.26-7.18 (m, 1H), 3.91 (s, 3H).

Step 7: Synthesis of Compound BB-3

BB-3-7 (50.00 mg, 146.74 μmol), diluted hydrochloric acid (6 M, 300.00 μL) and dioxane (600.00 μL) were added into a pre-dried vial. After completion of the addition, the reaction mixture was stirred at 50° C. for 58 hours under nitrogen atmosphere, followed by filtration to give product BB-3. $^1$H NMR (400 MHz, DMSO-d$_6$) δ=13.79 (s, 1H), 11.45 (s, 1H), 8.13 (d, J=8.3 Hz, 1H), 8.01 (s, 1H), 7.94-7.87 (m, 2H), 7.24-7.20 (m, 1H).

Reference Embodiment 4: Fraction BB-4

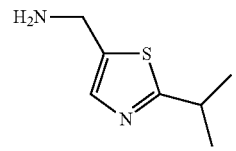

Synthetic Route

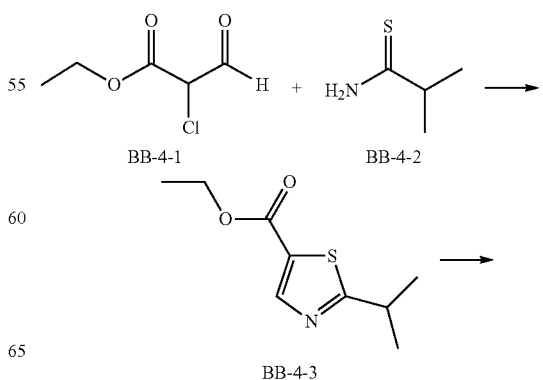

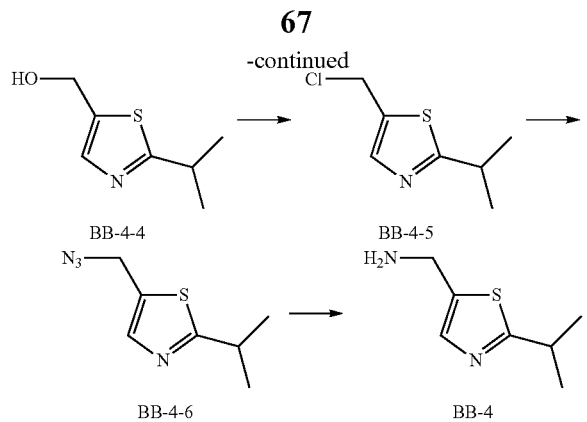

Step 1: Synthesis of Compound BB-4-3

Compound BB-4-1 (2.90 g, 19.26 mmol), BB-4-2 (1.45 g, 14.06 mmol) and MgSO$_4$ (4.82 g, 40.06 mmol) were dissolved in ethanol (30 mL). The reaction mixture was heated to 85° C. and stirred for 12 hours. The reaction was quenched with saturated aqueous solution of sodium carbonate (30 mL), then the mixture was extracted with ethyl acetate (20 mL*3). The organic phases were combined, washed with saturated aqueous solution of sodium chloride (10 mL*2), and dried over anhydrous sodium sulfate, followed by filtration and removal of the solvent by evaporation under reduced pressure. The crude product was isolated by column chromatography to give BB-4-3. $^1$H NMR (400 MHz, DMSO-d$_6$) δ=8.30 (s, 1H), 4.29 (q, J=7.2 Hz, 2H), 3.32-3.26 (m, 1H), 1.34 (d, J=6.9 Hz, 6H), 1.28 (t, J=7.1 Hz, 3H).

Step 2: Synthesis of Compound BB-4-4

A solution of BB-4-3 (1.7 g, 8.53 mmol) in tetrahydrofuran (5.00 mL) was added dropwise to a solution of lithium tetrahydroaluminum (809.39 mg, 21.33 mmol) in tetrahydrofuran (5.00 mL). The reaction solution was stirred at 5° C. for 2 hours, then heated to 25° C. and stirred for another 12 hours. Sodium sulfate containing crystal water was added to the reaction mixture to quench the reaction, followed by filtration. The filter cake was washed with a large amount of ethyl acetate, and the filtrate was collected. The filtrate was dried over anhydrous sodium sulfate, followed by filtration and removal of the solvent by evaporation under reduced pressure to give BB-4-4, which was directed used in the next step. $^1$H NMR (400 MHz, METHANOL-d$_4$) δ=7.47 (s, 1H), 4.61 (d, J=5.6 Hz, 2H), 3.29-3.16 (m, 1H), 1.30 (d, J=6.9 Hz, 6H).

Step 3: Synthesis of Compound BB-4-5

DMAP (15.52 mg, 127.00 μmol) and triethylamine (385.53 mg, 3.81 mmol, 528.12 μL) were added to a solution of BB-4-4 (200.00 mg, 1.27 mmol) in dichloromethane (3.00 mL) at 0° C., and then methanesulfonyl chloride (218.22 mg, 1.91 mmol, 147.45 μL) was added dropwise thereto. The reaction mixture was gradually heated to 25° C. and stirred at this temperature for 3 hours. The reaction was quenched with water (5 mL), followed by extraction with dichloromethane (10 mL*3). The organic phases were combined and dried over anhydrous sodium sulfate, followed by filtration and removal of the solvent by evaporation under reduced pressure to give BB-4-5, which was directed used in the next step.

Step 4: Synthesis of Compound BB-4-6

Sodium azide (148.22 mg, 2.28 mmol) was added to a solution of BB-4-5 (200.00 mg, 1.14 mmol) in DMF (2.00 mL) at 25° C. The reaction mixture was heated to 80° C. and stirred for 16 hours. The reaction was quenched with saturated aqueous solution of sodium carbonate (2.0 mL), followed by extraction with ethyl acetate (5 mL*3). The organic phases were combined and washed with saturated sodium chloride, and dried over anhydrous sodium sulfate, followed by filtration and removal of the solvent by evaporation under reduced pressure. The crude product was isolated by thin layer chromatography to give BB-4-6. $^1$H NMR (400 MHz, DMSO-d$_6$) δ=7.76-7.59 (m, 1H), 4.69 (s, 2H), 3.26 (td, J=6.8, 13.7 Hz, 1H), 1.32 (d, J=6.8 Hz, 6H).

Step 5: Synthesis of Compound BB-4

Triphenylphosphine (259.05 mg, 987.66 μmol) was added to a solution of compound BB-4-6 (90.00 mg, 493.83 μmol) in tetrahydrofuran (2.00 mL) and water (400.00 μL). The reaction mixture was stirred at 25° C. for 2 hours. The solvent was removed by evaporation under reduced pressure to give a crude product. The crude product was purified by thin layer chromatography to give BB-4, which was directed used in the next step.

Reference Embodiment 5: Fraction BB-5

Synthetic Route

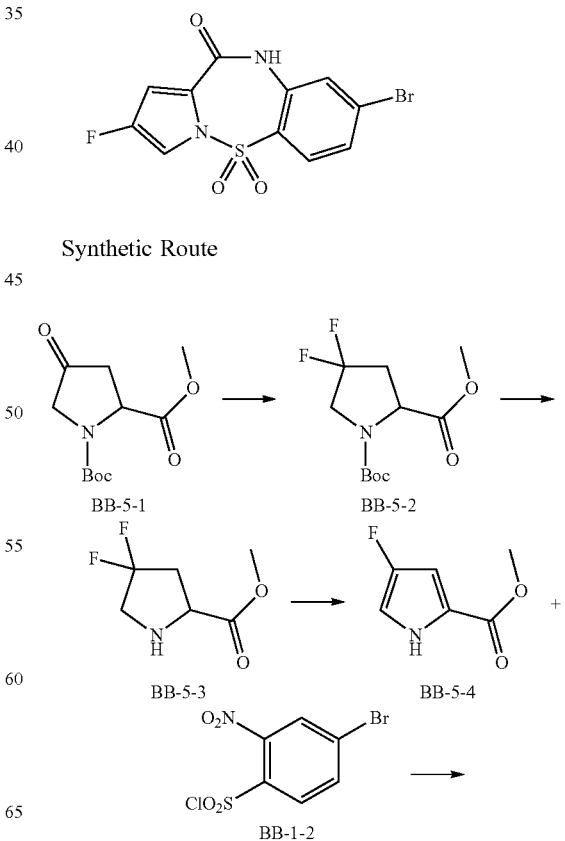

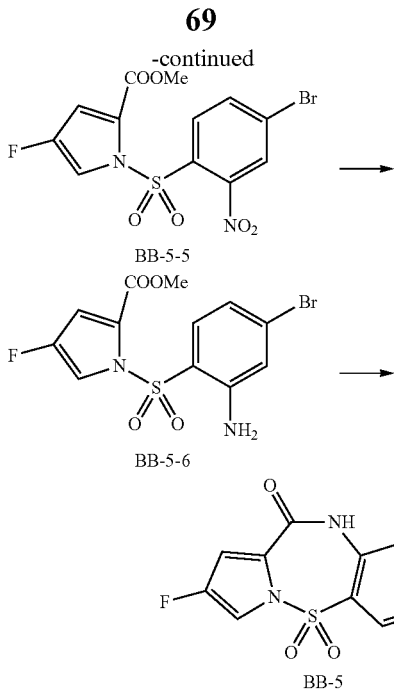

Step 1: Synthesis of Compound BB-5-2

Compound BB-5-1 (9.70 g, 39.88 mmol) and dichloromethane (100.00 mL) were added to a dry 500 mL three-necked flask, and the system was cooled to −78° C., followed by dropwise addition of DAST (25.71 g, 159.52 mmol, 21.07 mL). After completion of the dropwise addition, the three-necked flask was placed in an oil bath at 25° C. and the reaction mixture was stirred for 4 hours. The reaction system was cooled to 0° C., and a saturated aqueous solution of sodium bicarbonate was added dropwise thereto to adjust the pH value to about 10. The dichloromethane phase was collected, and the aqueous phase was extracted with dichloromethane (50 mL*2). The organic phases were combined, and dried over anhydrous sodium sulfate, followed by filtration. The filtrate was concentrated under reduced pressure to give BB-5-2.

Step 2: Synthesis of Compound BB-5-3

Compound BB-5-2 (9.05 g, 34.12 mmol) and a solution of 4 M hydrogen chloride in ethyl acetate (100.00 mL) were added into a dry 500 mL single-necked flask. The single-necked flask was then placed in an oil bath at 25° C. and the reaction mixture was stirred for 1 hour. The reaction mixture was concentrated under reduced pressure to give BB-5-3, which was directly used in the next step.

Step 3: Synthesis of Compound BB-5-4

Compound BB-5-3 (6.88 g, 34.13 mmol), manganese dioxide (11.87 g, 136.51 mmol) and tetrahydrofuran (100 mL) were added into a dry single-necked flask, and purged with nitrogen gas for three times. The single-necked flask was placed in an oil bath at 70° C. and the reaction mixture was stirred for 4 hours. The reaction mixture was filtered, and the filtrate was concentrated under reduced pressure to give a crude product as a brown solid. The crude product was subjected to silica gel column chromatography to give BB-5-4.

Step 4: Synthesis of Compound BB-5-5

A solution of potassium tert-butoxide in tetrahydrofuran (1 M, 64.63 mL) was added into a dry 500 mL three-necked flask, and a solution of compound BB-5-4 (3.7 g, 25.85 mmol) in tetrahydrofuran (60 mL) was added dropwise to the system at 0° C. The system was stirred at 25° C. for 15 minutes, followed by dropwise addition of a solution of compound BB-1-2 (15.54 g, 51.71 mmol) in tetrahydrofuran (40 mL) at 0° C. Finally, the three-necked flask was placed in an oil bath at 25° C. for 5 hours. The reaction mixture was filtered, and the filter cake was washed with ethyl acetate (100 mL). The filtrate was concentrated to give a crude product, which was subjected to silica gel column chromatography to give BB-5-5. $^1$H NMR (400 MHz, CHLOROFORM-d) δ=8.29 (d, J=8.6 Hz, 1H), 7.98-7.91 (m, 2H), 7.44 (dd, J=2.3, 3.2 Hz, 1H), 6.90 (d, J=2.2 Hz, 1H), 3.75 (s, 3H).

Step 5: Synthesis of Compound BB-5-6

Compound BB-5-5 (900 mg, 2.21 mmol), iron powder (493.76 mg, 8.84 mmol) and acetic acid (5 mL) were added into a dry single-necked flask, and purged with nitrogen gas for three times. The reaction was then carried out in an oil bath at 70° C. while stirring for 1 hour. The reaction mixture was hot filtered through a five-hole funnel padded with diatomite. The filter cake was washed with dichloromethane (10 mL), and the filtrate was concentrated under reduced pressure to give BB-5-6.

Step 6: Synthesis of Compound BB-5

Compound BB-5-6 (1.1 g, 2.92 mmol) and toluene (10 mL) were added into a dry single-necked flask, and purged with nitrogen gas for three times, followed by addition of a solution of trimethylaluminum in toluene (2.5 M, 1.75 mL). The reaction was then carried out in an oil bath at 110° C. while stirring for 2 hours. 10 mL of water was added to the reaction system, followed by extraction with ethyl acetate (30 mL*3). The organic phases were combined, and dried over anhydrous sodium sulfate, followed by filtration. The filtrate was concentrated under reduced pressure to give BB-5.

Reference Embodiment 6: Fraction BB-6

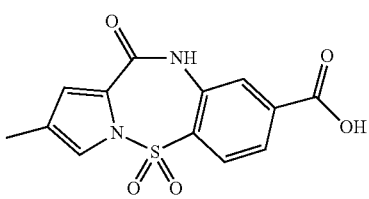 [SMILES: Cc1cc2n(c1)S(=O)(=O)c1ccc(C(=O)O)cc1NC2=O]

Synthetic Route

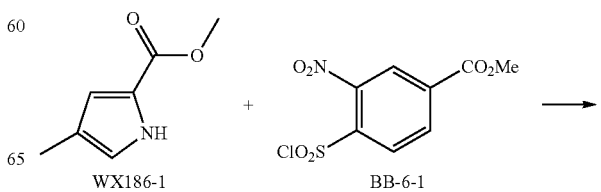

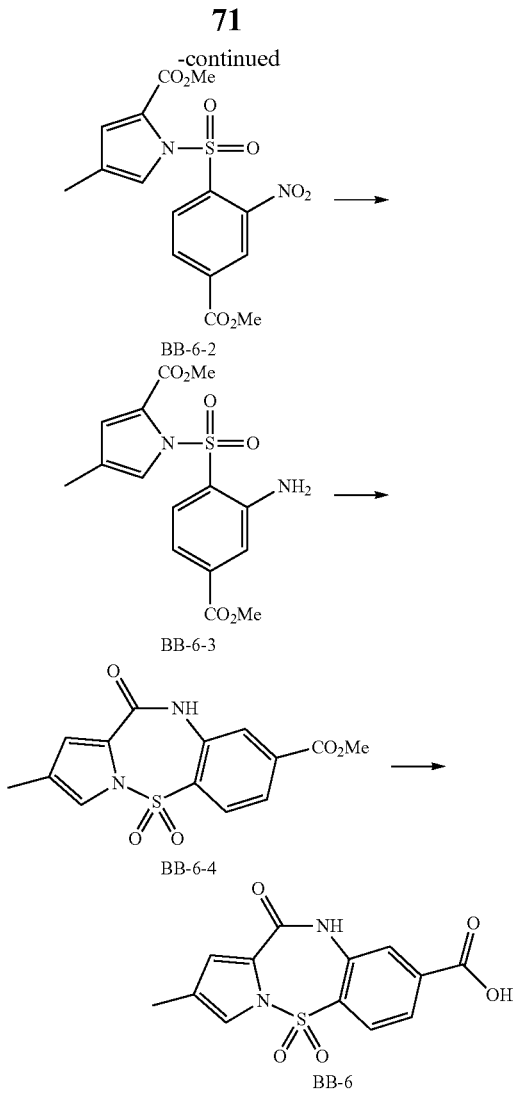

necked flask. After the solid was completely dissolved, iron powder (7.05 g, 126.14 mmol) was added. The reaction was carried out at 70° C. for 5 hours. The reaction mixture was hot filtered through diatomite, and the filtrate was washed with 500 mL EtOAc. The filtrate was collected, and evaporated under reduced pressure to remove the solvent to give a crude product of BB-6-3, which was directly used in the next step.

Step 3: Synthesis of Compound BB-6-4

The raw material BB-6-3 (14 g, 38.21 mmol) and toluene (150 mL) were added into a pre-dried 250 mL single-necked flask, followed by slow addition of trimethylaluminum (2 M, 28.66 mL). After completion of the addition, the reaction mixture was stirred at 110° C. for 5 hours. 300 mL of saturated aqueous solution of sodium dihydrogen phosphate was added to quench the reaction, followed by addition of 500 mL of EtOAc. The mixture was stirred thoroughly, followed by filtration through diatomite. The filtrate was partitioned, and the aqueous phase was extracted with EtOAc (2*300 mL). The organic phases were combined, washed with 250 mL of saturated brine, and dried over anhydrous sodium sulfate, followed by filtration. The filtrate was collected, and evaporated under reduced pressure to remove the solvent to give BB-6-4.

Step 4: Synthesis of Compound BB-6

The raw material BB-6-4 (9 g, 28.10 mmol) and THF (90 mL) were added into a pre-dried 250 mL single-necked flask, followed by addition of a solution of LiOH.H$_2$O (2.36 g, 56.20 mmol) in water (25 mL), and the color of the solution turned dark red. The reaction was carried out at 25° C. for 2 hours. 1 M HCl was added to the solution until the pH value was equal to 2-3, then the mixture was cooled down under an ice bath. Then a solid was precipitated, and the mixture was stirred for a while, followed by filtration. The filter cake was washed with 50 mL of ice water, the obtained solid was dried with an oil pump to give BB-6.

Embodiment 1: WX143

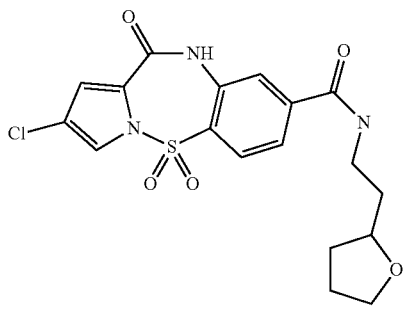 [SMILES: O=C(NCCC1CCCO1)c1ccc2c(c1)NC(=O)c1cc(Cl)cn1S2(=O)=O]

Synthetic Route

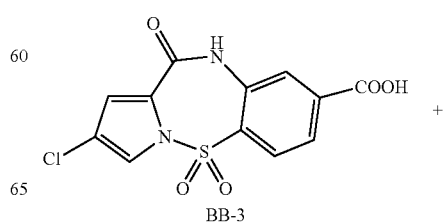

Step 1: Synthesis of Compound BB-6-2

Potassium tert-butoxide (1 M, 39.17 mL) and THF (50 mL) were added into a pre-dried 500 mL three-necked flask, and then vacuumized and purged with nitrogen gas for three times. After the mixture was cooled to 0° C., a solution of WX186-1 (5 g, 32.64 mmol) in THF (50 mL) was added dropwise at a temperature of 0-5° C. After completion of the addition, the solution was heated to 25° C. and stirred for 20 minutes, and the mixture became a white suspension. After cooling down to 0° C., a solution of BB-6-1 (10.95 g, 39.17 mmol) in THF (100 mL) was slowly added dropwise below 5° C. The color of the solution turned deep red. After completion of the addition, the solution was heated to 25° C. and stirred for 12 hours, and the color of the solution turned yellow. The reaction mixture was poured into 300 mL of water to quench the reaction, extracted with ethyl acetate (300 mL). The combined organic phase was washed with 250 mL saturated brine and dried over anhydrous sodium sulfate, followed by filtration. The filtrate was collected, and evaporated under reduced pressure to remove the solvent to give BB-6-2.

Step 2: Synthesis of Compound BB-6-3

The raw material BB-6-2 (12.5 g, 31.54 mmol) and acetic acid (250 mL) were added into a pre-dried 500 mL three-

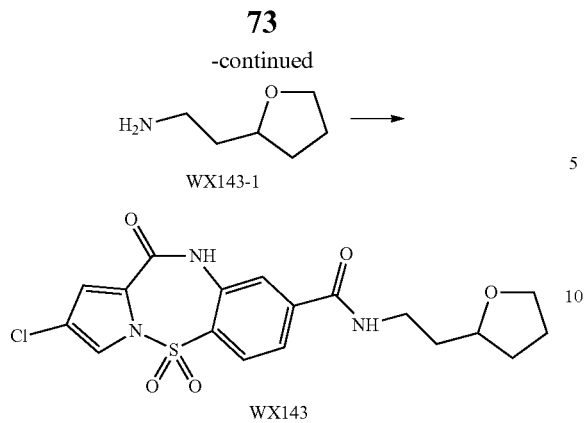

Step 1: Synthesis of Compound WX143

BB-3 (15.00 mg, 45.91 µmol), EDCI (13.20 mg, 68.86 µmol), HOBt (9.31 mg, 68.86 µmol), DIPEA (10.68 mg, 82.64 µmol) and DMF (1.00 mL) were added into a pre-dried vial, then WX143-1 (6.96 mg, 45.91 µmol, 1.00 eq) was added thereto at 0° C. After completion of the addition, the reaction mixture was stirred at 25° C. for 12 hours under nitrogen atmosphere. The reaction mixture was filtered to give a crude product. The crude product was isolated by HPLC to give WX143.

Embodiment 2: WX145

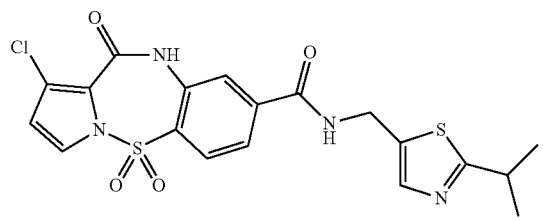 [SMILES: CC(C)c1ncc(CNC(=O)c2ccc3c(c2)NC(=O)c2c(Cl)ccn2S3(=O)=O)s1]

Synthetic Route

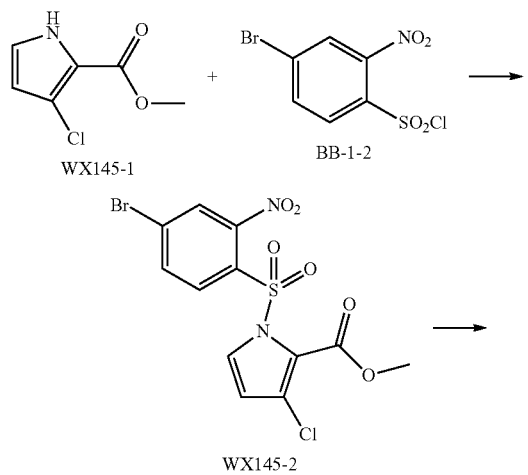

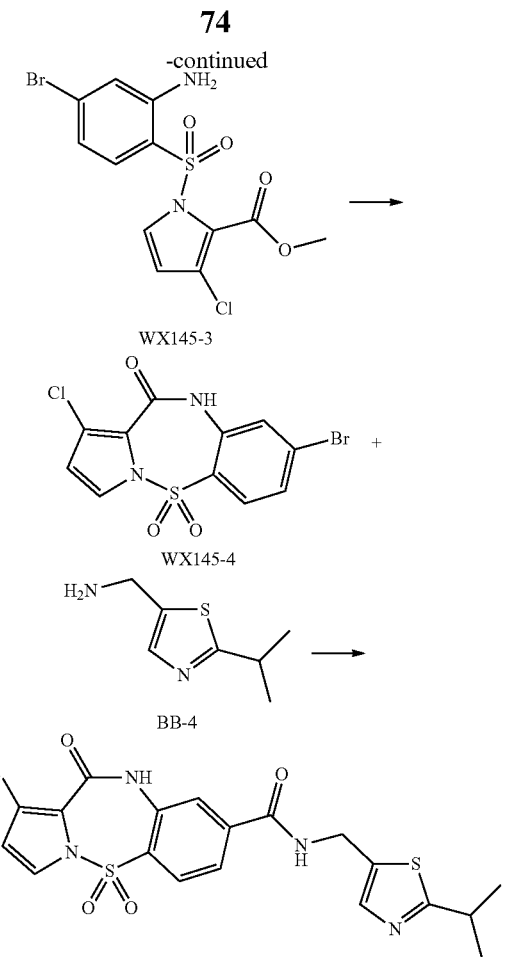

Step 1: Synthesis of Compound WX145-2

Potassium tert-butoxide (1 M, 15.67 mL) was added into a pre-dried 100 mL flask, followed by addition of tetrahydrofuran (15 mL). A solution of WX145-1 (1.00 g, 6.27 mmol) in tetrahydrofuran (15 mL) was slowly added dropwise to the reaction mixture at 0° C. The reaction mixture was stirred at 20° C. for 15 minutes, followed by slow dropwise addition of a solution of BB-1-2 (3.77 g, 12.54 mmol, 2.00 eq) in tetrahydrofuran (20 mL) at 0° C. The system was returned to 20° C. and stirred for 4.5 hours. The reaction mixture was diluted with ethyl acetate and water (1:1, 100 mL), and the aqueous phase was washed with ethyl acetate (100 mL*2). The organic phases were combined, dried over anhydrous sodium sulfate, filtered, concentrated and isolated by column chromatography to give WX145-2. $^1$H NMR (400 MHz, DMSO-$d_6$) δ=8.54 (d, J=2.0 Hz, 1H), 8.18 (dd, J=2.0, 8.6 Hz, 1H), 7.85-7.79 (m, 2H), 6.76 (d, J=3.7 Hz, 1H), 3.66 (s, 3H).

Step 2: Synthesis of Compound WX145-3

The raw material WX145-2 (450.00 mg, 1.06 mmol) and acetic acid (2.00 mL) were added into a dry vial and stirred for dissolution, followed by addition of iron powder (296.01 mg, 5.30 mmol). The reaction system was purged with nitrogen gas for three times, then stirred at 70° C. for 2 hours. The reaction mixture was concentrated under reduced pressure to give a crude product. The crude product was subjected to column chromatography to give WX145-3. $^1$H NMR (400 MHz, METHANOL-$d_4$) δ=7.55 (d, J=3.5 Hz, 1H), 7.48 (d, J=8.8 Hz, 1H), 6.96-6.84 (m, 2H), 6.32 (d, J=3.5 Hz, 1H), 5.20 (br s, 2H), 3.85 (s, 3H).

Step 3: Synthesis of Compound WX145-4

WX145-3 (410.00 mg, 1.04 mmol) and toluene (1.00 mL) were added into a dry 100 mL vial and stirred for dissolution, followed by addition of a solution of trimethylaluminum (2.5 M, 624.94 μL) in toluene. The reaction system was purged with nitrogen gas for three times and then stirred at 110° C. for 1.5 hours, followed by addition of water and ethyl acetate (1:1, 10 mL). The aqueous phase was extracted with ethyl acetate (5 mL*3). The organic phases were combined, dried over anhydrous sodium sulfate, and concentrated under reduced pressure to give a crude product. The crude product was subjected to column chromatography to give WX145-4. $^1$H NMR (400 MHz, DMSO-$d_6$) δ=11.30 (s, 1H), 7.91 (d, J=8.6 Hz, 1H), 7.67-7.62 (m, 3H), 6.68 (d, J=3.5 Hz, 1H).

Step 4: Synthesis of Compound WX145

WX145-4 (50.00 mg, 138.27 μmol) and BB-4 (23.77 mg, 152.10 μmol) were dissolved in DMF (3.00 mL), followed by addition of triethylamine (13.99 mg, 138.27 μmol, 19.16 μL) and Pd(dppf)Cl$_2$ (10.12 mg, 13.83 μmol). The reaction system was purged with argon gas for three times, then purged with carbon monoxide gas three times and pressurized to 50 psi. The reaction mixture was heated to 80° C. and stirred for 16 hours. The reaction mixture was cooled to room temperature and concentrated directly to give a crude product. The crude product was isolated by HPLC to give WX145. $^1$H NMR (400 MHz, DMSO-$d_6$) δ=11.36 (s, 1H), 9.49-9.43 (m, 1H), 8.10 (d, J=8.2 Hz, 1H), 7.88 (s, 1H), 7.82 (d, J=8.4 Hz, 1H), 7.64 (d, J=3.3 Hz, 1H), 7.56 (s, 1H), 6.68 (d, J=3.3 Hz, 1H), 4.62 (d, J=5.7 Hz, 2H), 3.21 (td, J=7.0, 13.8 Hz, 1H), 1.28 (d, J=6.8 Hz, 6H).

Embodiment 3: WX146

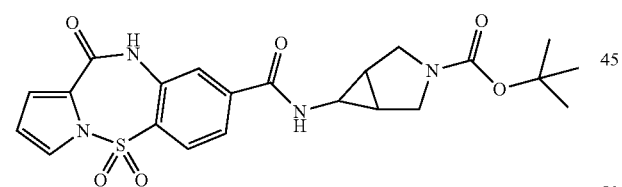

Synthetic Route

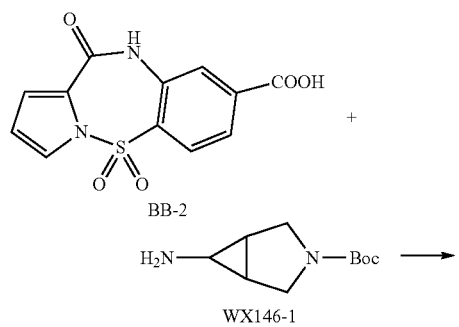

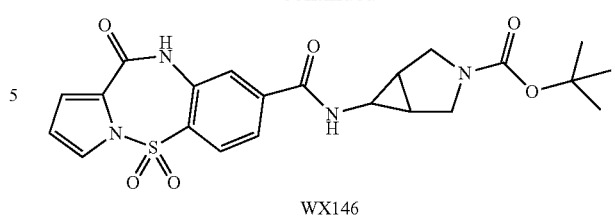

WX146

Step 1: Synthesis of Compound WX146

The synthesis of compound WX146 was referred to the synthesis of WX143 in Embodiment 1. $^1$H NMR (400 MHz, DMSO-$d_6$) δ=11.22 (s, 1H), 8.85 (d, J=4.2 Hz, 1H), 8.10 (d, J=8.4 Hz, 1H), 7.86 (s, 1H), 7.77 (d, J=8.4 Hz, 1H), 7.61 (d, J=1.1 Hz, 1H), 7.18-7.11 (m, 1H), 6.54 (t, J=3.3 Hz, 1H), 3.53 (d, J=11.0 Hz, 2H), 3.40-3.32 (m, 3H), 1.79 (br s, 2H), 1.39 (s, 9H).

Embodiment 4: WX170 and WX171

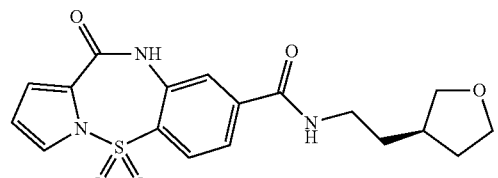

WX170 or WX171

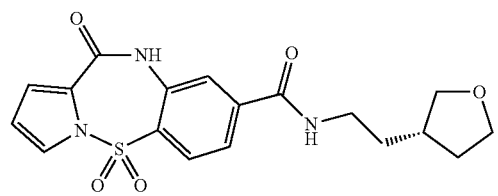

WX171 or WX170

Synthetic Route

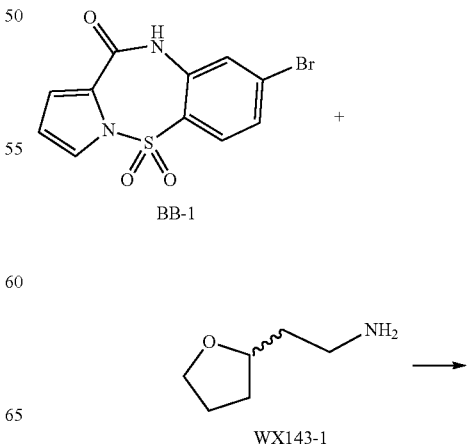

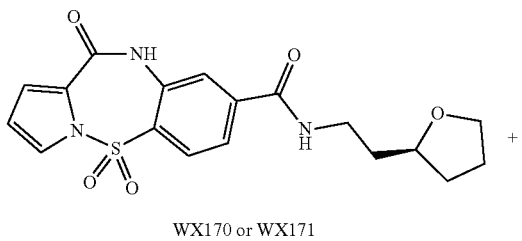

WX170 or WX171

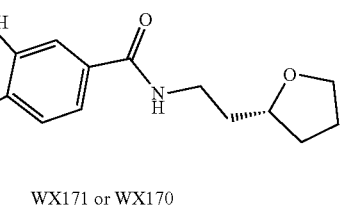

WX171 or WX170

Step 1: Synthesis of Compound WX170 and WX171

The synthesis of the compounds WX170 and WX171 was referred to the step 4 of the synthesis of WX145 in Embodiment 2.

Compound WX170: $^1$H NMR (400 MHz, DMSO-d$_6$) δ=11.22 (s, 1H), 8.77 (br t, J=5.5 Hz, 1H), 8.10 (d, J=8.5 Hz, 1H), 7.86 (d, J=1.5 Hz, 1H), 7.78 (dd, J=1.5, 8.0 Hz, 1H), 7.61 (dd, J=2.0, 3.0 Hz, 1H), 7.15 (dd, J=1.5, 3.5 Hz, 1H), 6.54 (t, J=3.3 Hz, 1H), 3.82-3.69 (m, 2H), 3.63-3.53 (m, 1H), 3.33-3.25 (m, 2H), 2.01-1.89 (m, 1H), 1.88-1.74 (m, 2H), 1.73-1.65 (m, 2H), 1.49-1.28 (m, 1H);

Compound WX171: $^1$H NMR (400 MHz, DMSO-d$_6$) δ=11.22 (s, 1H), 8.77 (br t, J=5.4 Hz, 1H), 8.10 (d, J=8.3 Hz, 1H), 7.86 (d, J=1.3 Hz, 1H), 7.78 (dd, J=1.3, 8.3 Hz, 1H), 7.61 (dd, J=1.8, 3.0 Hz, 1H), 7.15 (dd, J=1.8, 3.5 Hz, 1H), 6.54 (t, J=3.4 Hz, 1H), 3.90-3.68 (m, 2H), 3.65-3.53 (m, 1H), 3.33-3.25 (m, 2H), 1.99-1.91 (m, 1H), 1.86-1.75 (m, 2H), 1.69 (q, J=6.9 Hz, 2H), 1.47-1.34 (m, 1H).

Chiral resolution conditions: chiral column: OJ (250 mm*30 mm, 5 μm); mobile phase: 0.1% ammonia solution/ethanol; flow rate: 60 mL/min; column temperature: 40° C.

Retention time of compound WX171: 3.949 min (peak 2); retention time of compound WX170: 3.658 min (peak 1).

Embodiment 5: WX175

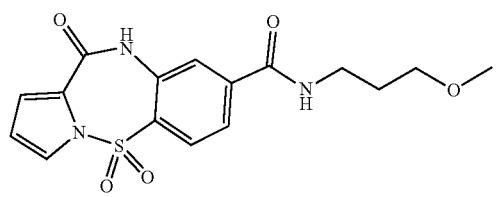 [SMILES: COCCCNC(=O)c1ccc2c(c1)NC(=O)c1cccn1S2(=O)=O]

Synthetic Route

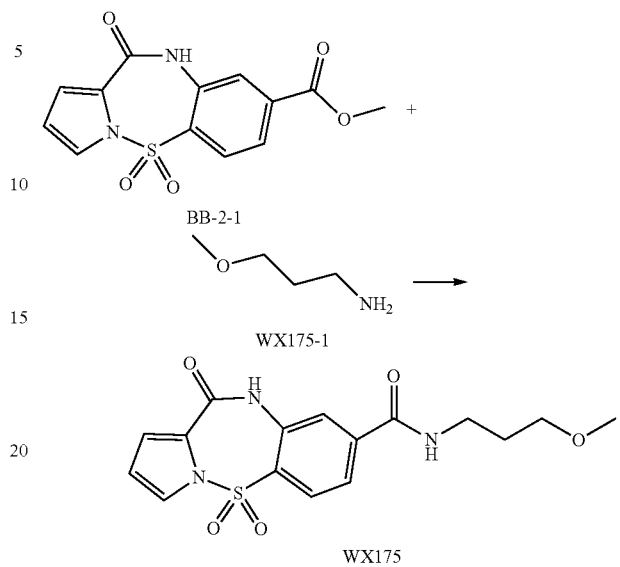

Step 1: Synthesis of Compound WX175

BB-2-1 (85.00 mg, 277.51 μmol) and compound WX175-1 (24.74 mg, 277.51 μmol, 28.44 μL) were added into a pre-dried 50 mL flask, followed by addition of toluene (5.00 mL). A solution of trimethylaluminum (2 M, 208.13 μL) in toluene was then slowly added to the reaction mixture at 25° C. The reaction mixture was stirred at 110° C. for 1 hour. The reaction mixture was diluted with ethyl acetate and water (1:1, 20 mL), and the aqueous phase was washed with ethyl acetate (20 mL*2). The organic phases were combined, dried over anhydrous sodium sulfate, filtered and concentrated. The crude product was isolated by pre-HPLC to give WX175. $^1$H NMR (400 MHz, DMSO-d$_6$) δ=8.79 (br t, J=5.4 Hz, 1H), 8.11 (d, J=8.3 Hz, 1H), 7.87 (s, 1H), 7.79 (dd, J=1.5, 8.3 Hz, 1H), 7.62 (dd, J=1.6, 2.9 Hz, 1H), 7.16 (dd, J=1.8, 3.5 Hz, 1H), 6.55 (t, J=3.4 Hz, 1H), 3.37-3.34 (m, 2H), 3.32-3.27 (m, 2H), 3.23 (s, 3H), 1.75 (q, J=6.7 Hz, 2H).

Embodiment 6: WX176

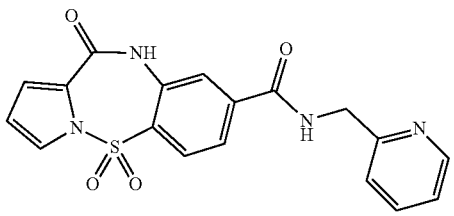 [SMILES: O=C(NCc1ccccn1)c1ccc2c(c1)NC(=O)c1cccn1S2(=O)=O]

Synthetic Route

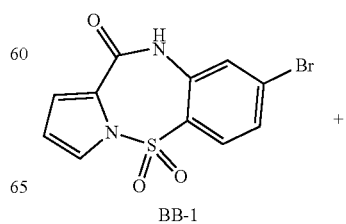

BB-1

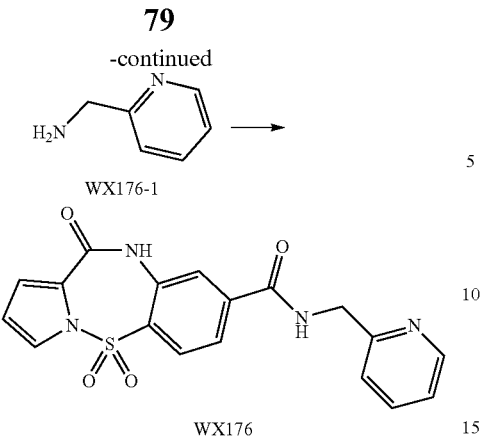

WX176-1

WX176

Step 1: Synthesis of Compound WX176

The synthesis of the compounds WX176 was referred to the step 4 of the synthesis of WX145 in Embodiment 2. $^1$H NMR (400 MHz, METHANOL-$d_4$) δ=8.52 (br d, J=4.3 Hz, 1H), 8.17 (d, J=8.8 Hz, 1H), 7.90-7.80 (m, 3H), 7.55 (dd, J=1.8, 3.0 Hz, 1H), 7.49-7.44 (m, 1H), 7.35 (dd, J=5.3, 7.0 Hz, 1H), 7.19 (dd, J=1.6, 3.6 Hz, 1H), 6.52 (t, J=3.3 Hz, 1H), 4.72 (s, 2H).

Embodiment 7: WX254

Step 1: Synthesis of Compound WX254

The synthesis of compound WX254 was referred to the synthesis of WX143 in Embodiment 1. $^1$H NMR (400 MHz, DMSO-$d_6$) δ=11.21 (s, 1H), 9.44 (t, J=5.7 Hz, 1H), 8.11 (d, J=8.4 Hz, 1H), 7.90 (s, 1H), 7.80 (dd, J=1.2, 8.3 Hz, 1H), 7.61 (dd, J=1.8, 2.9 Hz, 1H), 7.56 (s, 1H), 7.15 (dd, J=1.5, 3.5 Hz, 1H), 6.54 (t, J=3.3 Hz, 1H), 4.61 (d, J=5.7 Hz, 2H), 3.20 (t, J=6.8 Hz, 1H), 1.28 (d, J=6.8 Hz, 6H).

Embodiment 8: WX255

Synthetic Route

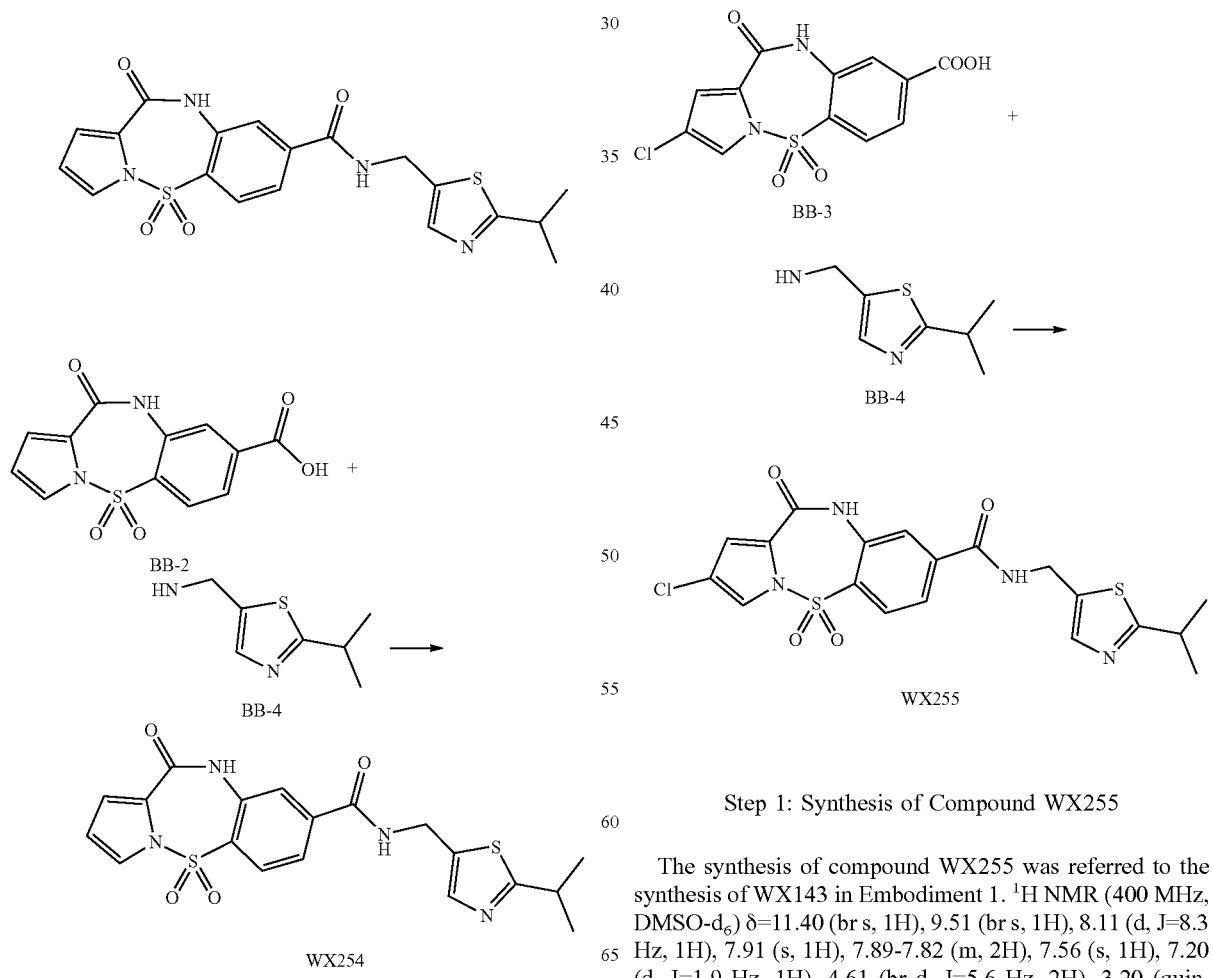

Step 1: Synthesis of Compound WX255

The synthesis of compound WX255 was referred to the synthesis of WX143 in Embodiment 1. $^1$H NMR (400 MHz, DMSO-$d_6$) δ=11.40 (br s, 1H), 9.51 (br s, 1H), 8.11 (d, J=8.3 Hz, 1H), 7.91 (s, 1H), 7.89-7.82 (m, 2H), 7.56 (s, 1H), 7.20 (d, J=1.9 Hz, 1H), 4.61 (br d, J=5.6 Hz, 2H), 3.20 (quin, J=6.8 Hz, 1H), 1.28 (d, J=6.9 Hz, 6H).

Embodiment 9: WX257

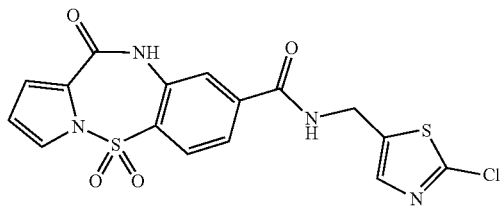 [SMILES: O=C(NCc1cnc(Cl)s1)c1ccc2c(c1)NC(=O)c1cccn1S2(=O)=O]

Synthetic Route

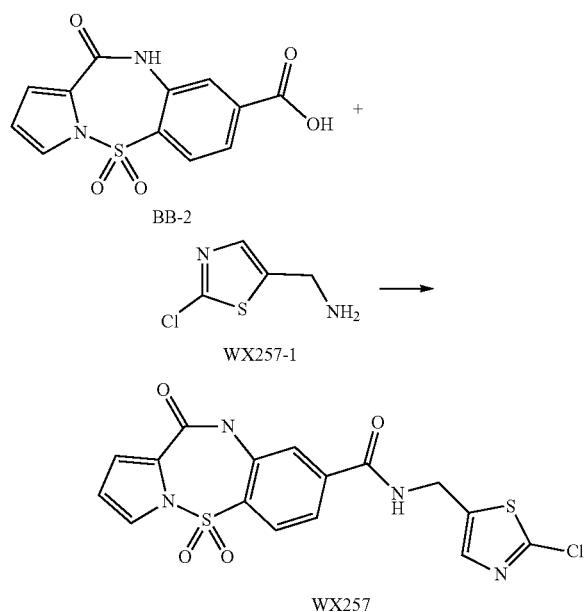

Step 1: Synthesis of Compound WX257

The synthesis of compound WX257 was referred to the synthesis of WX143 in Embodiment 1. $^1$H NMR (400 MHz, DMSO-$d_6$) δ=11.21 (s, 1H), 9.53 (t, J=5.6 Hz, 1H), 8.12 (d, J=8.4 Hz, 1H), 7.90 (d, J=1.5 Hz, 1H), 7.80 (dd, J=1.5, 8.4 Hz, 1H), 7.63-7.58 (m, 2H), 7.15 (dd, J=1.7, 3.6 Hz, 1H), 6.57-6.52 (m, 1H), 4.60 (d, J=5.5 Hz, 2H).

Embodiment 10: WX258

Synthetic Route

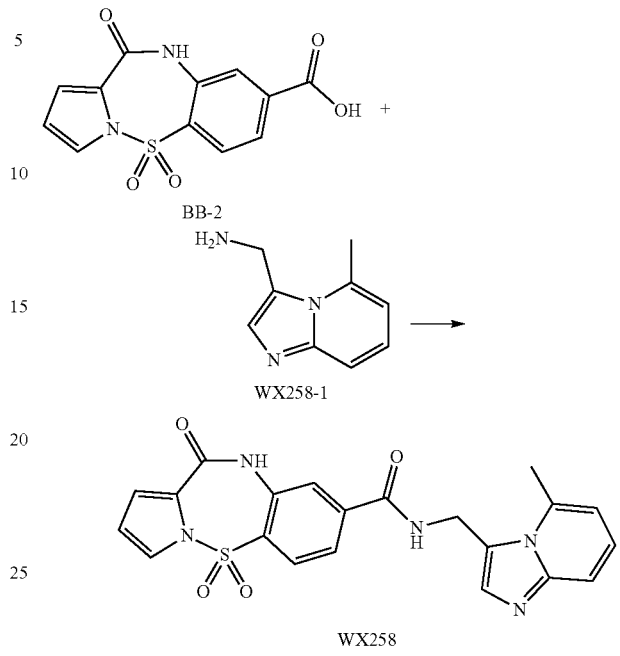

Step 1: Synthesis of Compound WX258

The synthesis of compound WX258 was referred to the synthesis of WX143 in Embodiment 1. $^1$H NMR (400 MHz, DMSO-$d_6$) δ=11.42-11.12 (m, 1H), 9.69-9.28 (m, 1H), 8.19 (s, 1H), 8.11 (d, J=8.4 Hz, 1H), 7.97 (d, J=1.1 Hz, 1H), 7.90 (dd, J=1.1, 8.4 Hz, 1H), 7.85 (br d, J=3.7 Hz, 2H), 7.61 (dd, J=1.7, 3.0 Hz, 1H), 7.31 (br s, 1H), 7.14 (dd, J=1.8, 3.5 Hz, 1H), 6.54 (t, J=3.3 Hz, 1H), 5.07 (d, J=4.4 Hz, 2H), 2.99 (s, 3H).

Embodiment 11: WX259

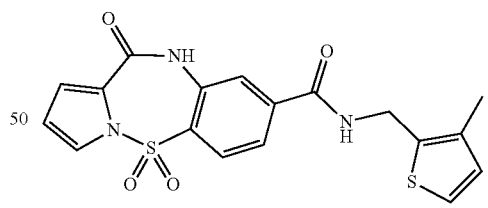

Synthetic Route

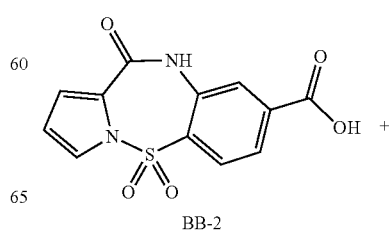

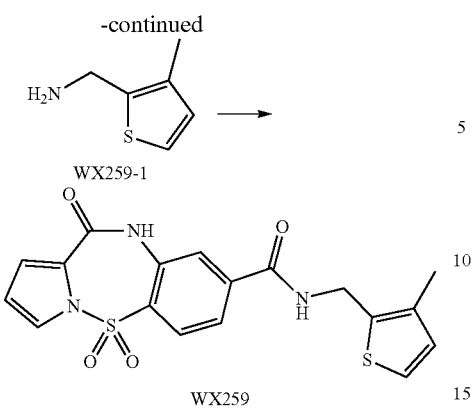

WX259-1

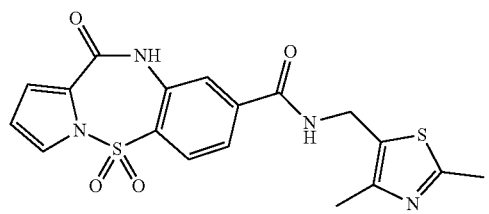 [SMILES: Cc1nc(C)c(CNC(=O)c2ccc3c(c2)NC(=O)c2cccn2S3(=O)=O)s1]

WX259

Step 1: Synthesis of Compound WX259

The synthesis of compound WX259 was referred to the synthesis of WX143 in Embodiment 1. ¹H NMR (400 MHz, DMSO-d$_6$) δ=11.21 (s, 1H), 9.32 (t, J=5.7 Hz, 1H), 8.12 (d, J=8.4 Hz, 1H), 7.90 (d, J=1.5 Hz, 1H), 7.81 (dd, J=1.5, 8.4 Hz, 1H), 7.61 (dd, J=1.8, 3.1 Hz, 1H), 7.29 (d, J=5.1 Hz, 1H), 7.15 (dd, J=1.8, 3.5 Hz, 1H), 6.84 (d, J=5.1 Hz, 1H), 6.54 (t, J=3.3 Hz, 1H), 4.55 (d, J=5.7 Hz, 2H), 2.22 (s, 3H).

Embodiment 12: WX260

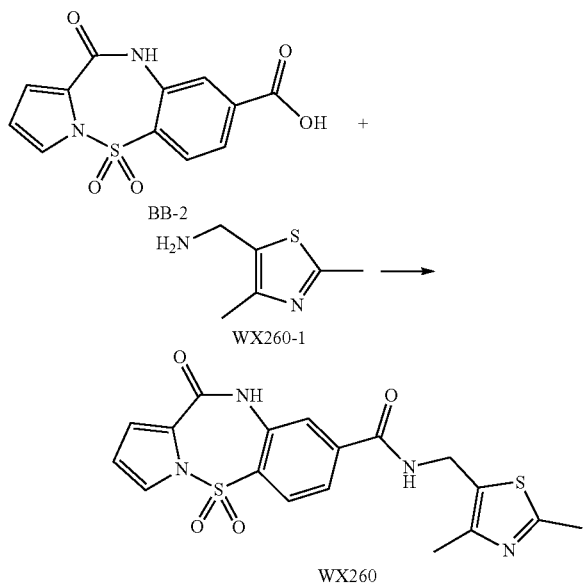

Synthetic Route

WX260

Step 1: Synthesis of Compound WX260

The synthesis of compound WX260 was referred to the synthesis of WX143 in Embodiment 1. ¹H NMR (400 MHz, DMSO-d$_6$) δ=11.23 (s, 1H), 9.54 (t, J=5.6 Hz, 1H), 8.11 (d, J=8.2 Hz, 1H), 7.89 (d, J=1.3 Hz, 1H), 7.80 (dd, J=1.4, 8.3 Hz, 1H), 7.60 (dd, J=1.8, 3.1 Hz, 1H), 7.14 (dd, J=1.8, 3.5 Hz, 1H), 6.53 (t, J=3.4 Hz, 1H), 4.53 (d, J=5.7 Hz, 2H), 2.67-2.62 (m, 3H), 2.38 (s, 3H).

Embodiment 13: WX261

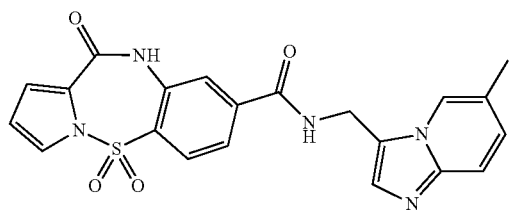 [SMILES: Cc1ccc2ncc(CNC(=O)c3ccc4c(c3)NC(=O)c3cccn3S4(=O)=O)n2c1]

Synthetic Route

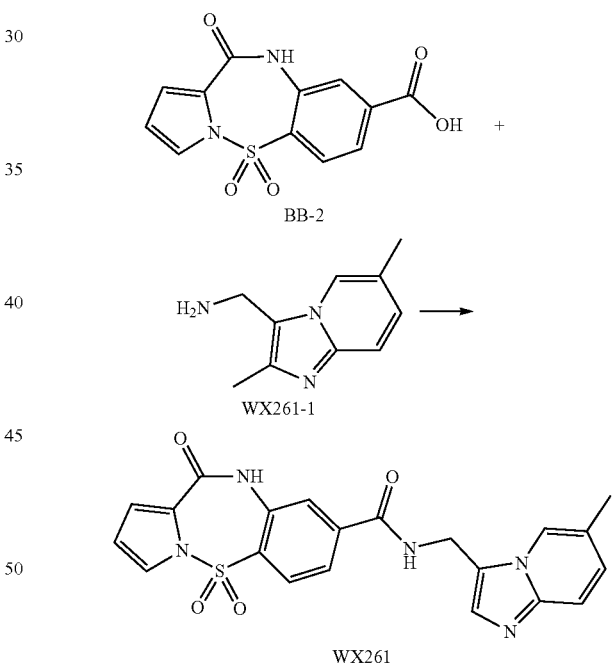

WX261

Step 1: Synthesis of Compound WX261

The synthesis of compound WX261 was referred to the synthesis of WX143 in Embodiment 1. ¹H NMR (400 MHz, DMSO-d$_6$) δ=11.25 (s, 1H), 9.69 (t, J=5.2 Hz, 1H), 8.92 (s, 1H), 8.18 (s, 1H), 8.20-8.16 (m, 1H), 8.20-8.16 (m, 1H), 8.20-8.16 (m, 1H), 8.11 (d, J=8.2 Hz, 1H), 7.95-7.82 (m, 4H), 7.60 (dd, J=1.8, 3.1 Hz, 1H), 7.14 (dd, J=1.7, 3.6 Hz, 1H), 6.53 (t, J=3.3 Hz, 1H), 4.88 (d, J=5.3 Hz, 2H), 2.44 (s, 3H).

85

Embodiment 14: WX262

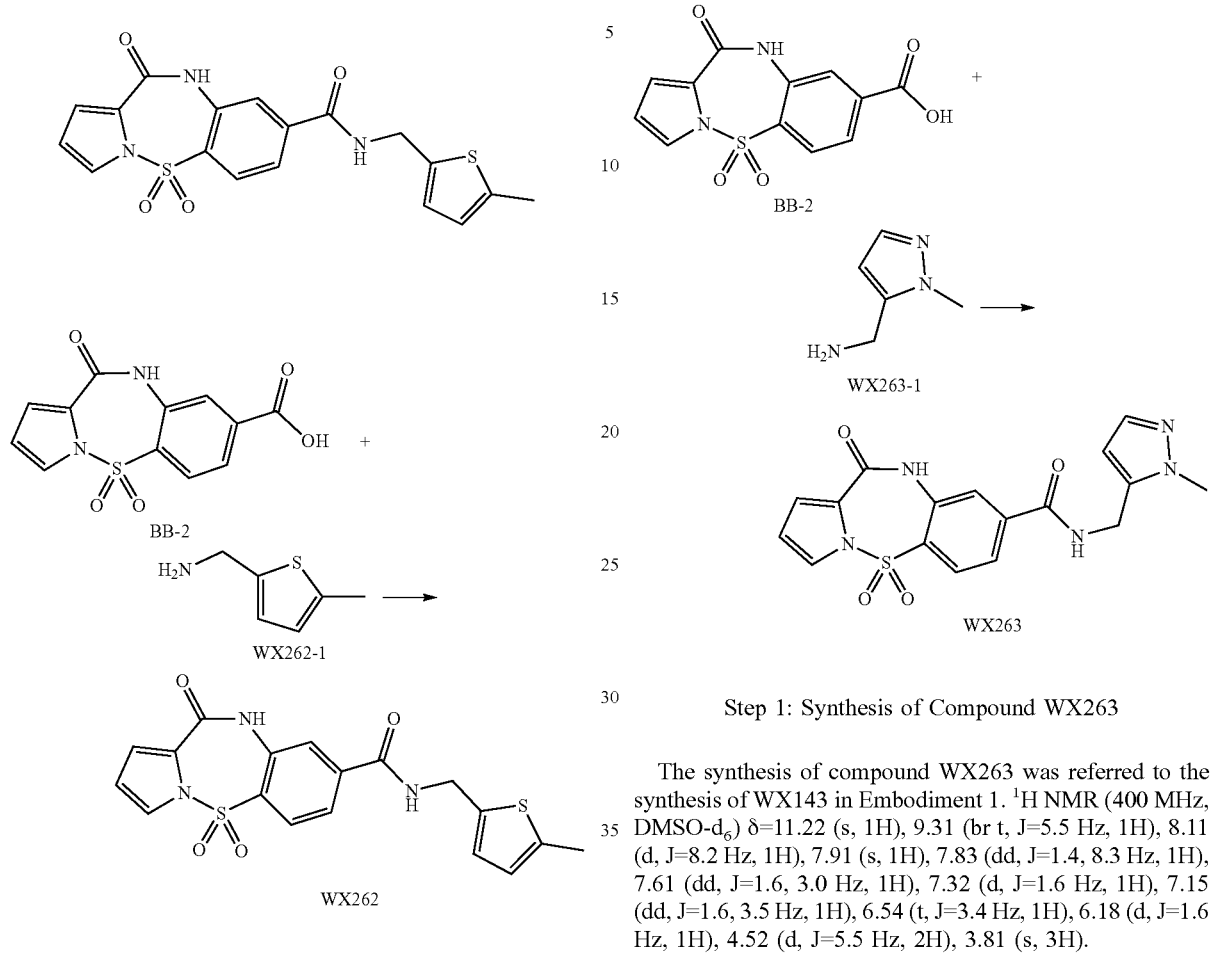

Step 1: Synthesis of Compound WX262

The synthesis of compound WX262 was referred to the synthesis of WX143 in Embodiment 1. $^1$H NMR (400 MHz, DMSO-d$_6$) δ=11.21 (s, 1H), 9.37 (t, J=5.8 Hz, 1H), 8.11 (d, J=8.2 Hz, 1H), 7.90 (d, J=1.3 Hz, 1H), 7.80 (dd, J=1.4, 8.3 Hz, 1H), 7.61 (dd, J=1.5, 3.1 Hz, 1H), 7.15 (dd, J=1.7, 3.6 Hz, 1H), 6.79 (d, J=3.3 Hz, 1H), 6.62 (dd, J=1.1, 3.3 Hz, 1H), 6.54 (t, J=3.3 Hz, 1H), 4.53 (d, J=5.7 Hz, 2H), 2.38 (s, 3H).

Embodiment 15: WX263

86

Synthetic Route

Step 1: Synthesis of Compound WX263

The synthesis of compound WX263 was referred to the synthesis of WX143 in Embodiment 1. $^1$H NMR (400 MHz, DMSO-d$_6$) δ=11.22 (s, 1H), 9.31 (br t, J=5.5 Hz, 1H), 8.11 (d, J=8.2 Hz, 1H), 7.91 (s, 1H), 7.83 (dd, J=1.4, 8.3 Hz, 1H), 7.61 (dd, J=1.6, 3.0 Hz, 1H), 7.32 (d, J=1.6 Hz, 1H), 7.15 (dd, J=1.6, 3.5 Hz, 1H), 6.54 (t, J=3.4 Hz, 1H), 6.18 (d, J=1.6 Hz, 1H), 4.52 (d, J=5.5 Hz, 2H), 3.81 (s, 3H).

Embodiment 16: WX265

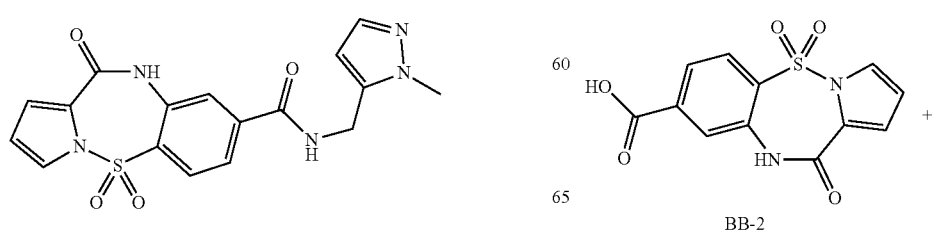

Synthetic Route

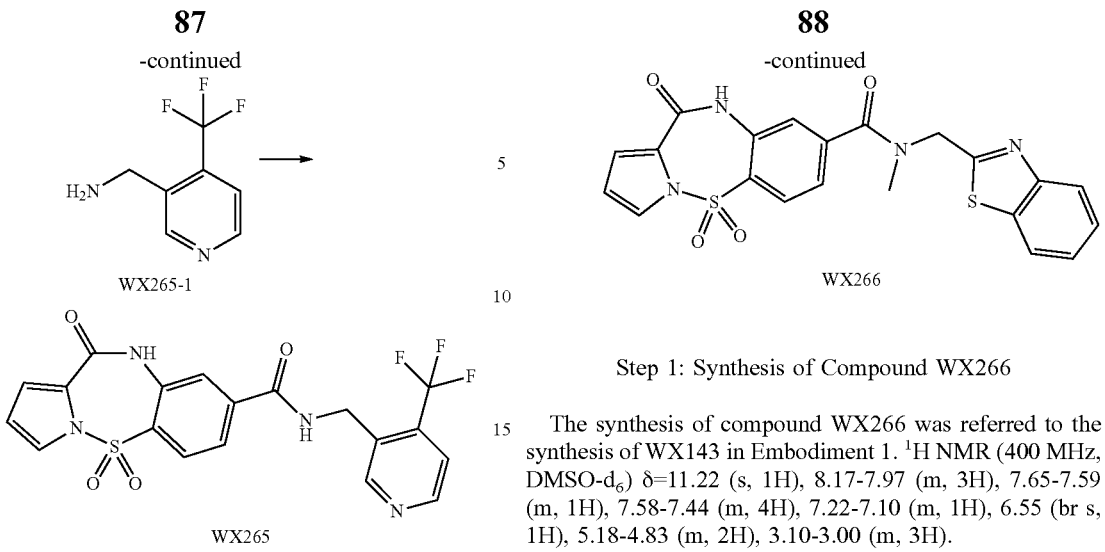

Step 1: Synthesis of Compound WX265

The synthesis of compound WX265 was referred to the synthesis of WX143 in Embodiment 1. $^1$H NMR (400 MHz, DMSO-$d_6$) δ=11.24 (s, 1H), 9.48-9.40 (m, 1H), 8.86-8.75 (m, 2H), 8.14 (d, J=8.3 Hz, 1H), 7.93 (s, 1H), 7.86 (br d, J=8.3 Hz, 1H), 7.76 (d, J=5.0 Hz, 1H), 7.62 (br d, J=1.3 Hz, 1H), 7.21-7.10 (m, 1H), 6.54 (t, J=3.3 Hz, 1H), 4.69 (br d, J=4.6 Hz, 2H).

Embodiment 17: WX266

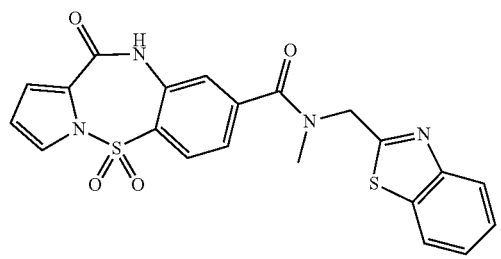 [SMILES: CN(Cc1nc2ccccc2s1)C(=O)c1ccc2c(c1)NC(=O)c1cccn1S2(=O)=O]

Synthetic Route

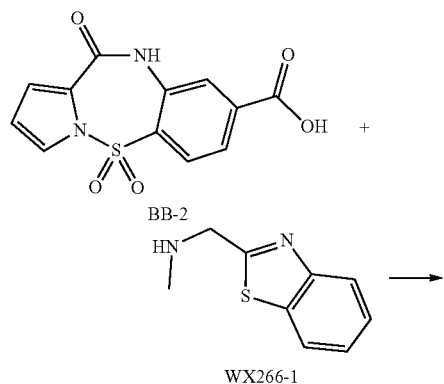

Step 1: Synthesis of Compound WX266

The synthesis of compound WX266 was referred to the synthesis of WX143 in Embodiment 1. $^1$H NMR (400 MHz, DMSO-$d_6$) δ=11.22 (s, 1H), 8.17-7.97 (m, 3H), 7.65-7.59 (m, 1H), 7.58-7.44 (m, 4H), 7.22-7.10 (m, 1H), 6.55 (br s, 1H), 5.18-4.83 (m, 2H), 3.10-3.00 (m, 3H).

Embodiment 18: WX267

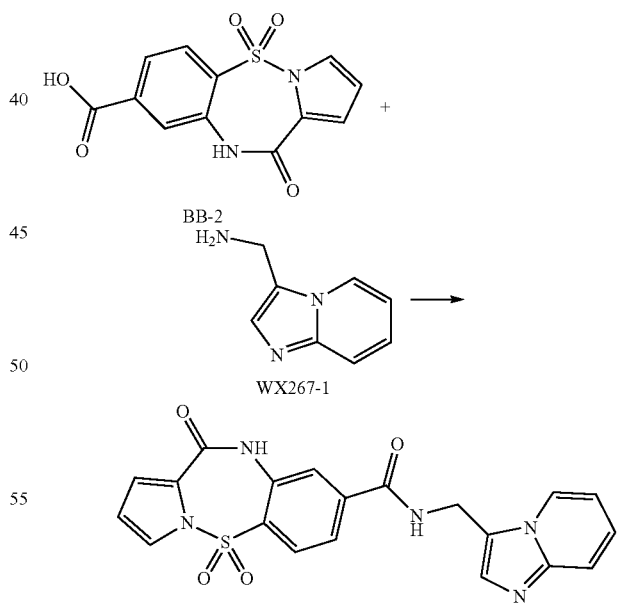

Step 1: Synthesis of Compound WX267

The synthesis of compound WX267 was referred to the synthesis of WX143 in Embodiment 1. $^1$H NMR (400 MHz, DMSO-$d_6$) δ=11.25 (s, 1H), 9.60 (br s, 1H), 8.98 (br d, J=6.8

Hz, 1H), 8.24 (s, 1H), 8.12 (d, J=8.3 Hz, 1H), 8.03-7.96 (m, 2H), 7.92 (s, 1H), 7.85 (br d, J=8.2 Hz, 1H), 7.64-7.54 (m, 2H), 7.14 (br d, J=1.8 Hz, 1H), 6.58-6.49 (m, 1H), 4.93 (br d, J=4.9 Hz, 2H).
Embodiment 19: WX270
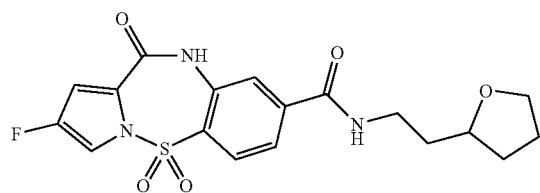 [SMILES: O=C(NCCC1CCCO1)c1ccc2c(c1)NC(=O)c1cc(F)cn1S2(=O)=O]
Synthetic Route
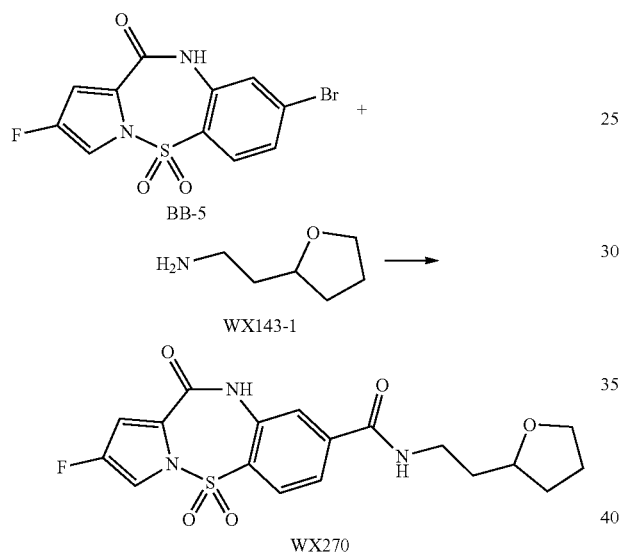
Step 1: Synthesis of Compound WX270
The synthesis of compound WX270 was referred to the step 4 of the synthesis of WX145 in Embodiment 2. $^1$H NMR (400 MHz, DMSO-d$_6$) δ=11.39 (s, 1H), 8.82 (br t, J=5.2 Hz, 1H), 8.09 (d, J=8.2 Hz, 1H), 7.89 (s, 1H), 7.82 (d, J=9.0 Hz, 1H), 7.74-7.68 (m, 1H), 7.14 (d, J=1.8 Hz, 1H), 3.83-3.70 (m, 2H), 3.63-3.54 (m, 1H), 3.31-3.25 (m, 2H), 2.02-1.90 (m, 1H), 1.86-1.74 (m, 2H), 1.69 (m, 2H), 1.48-1.33 (m, 1H).
Embodiment 20: WX185
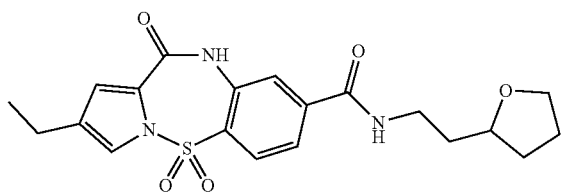 [SMILES: CCc1cc2n(c1)S(=O)(=O)c1ccc(C(=O)NCCC3CCCO3)cc1NC2=O]
Synthetic Route
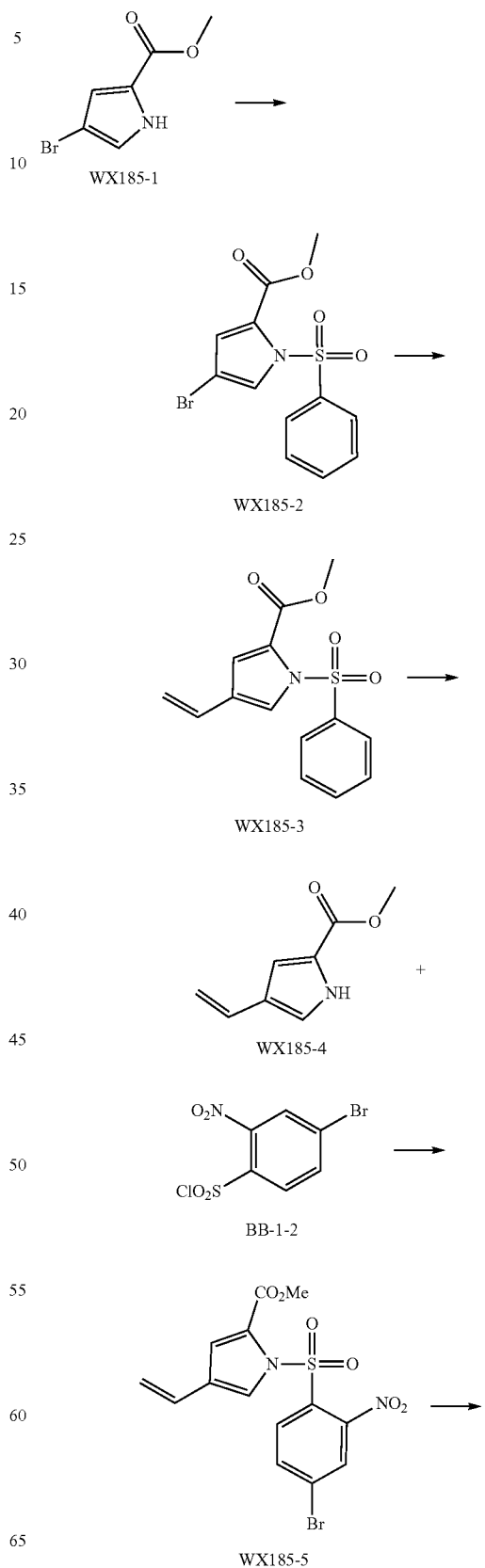

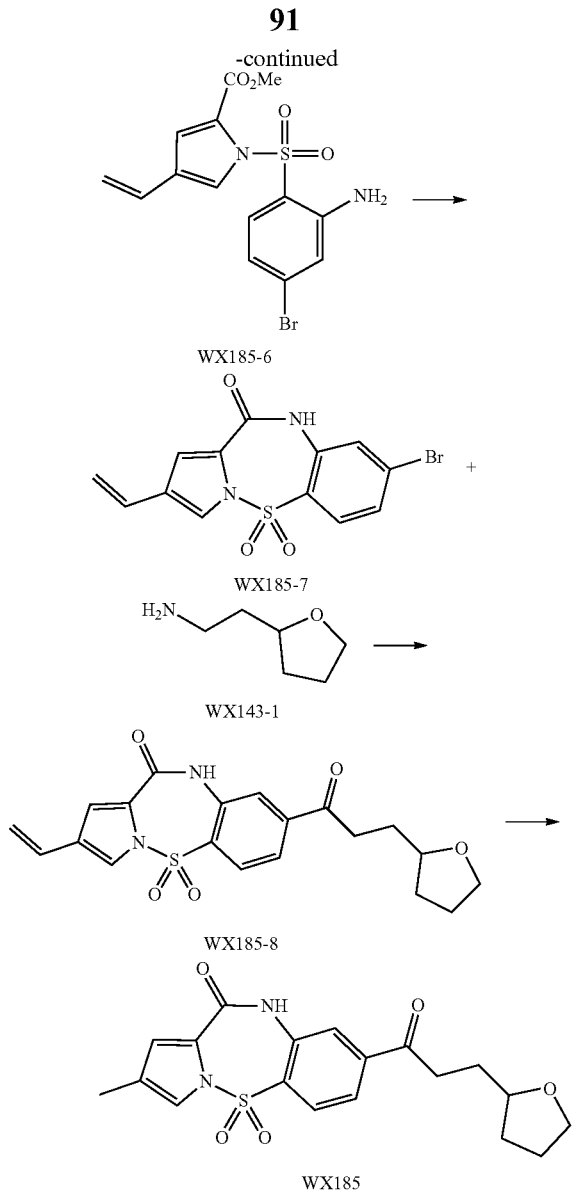

Step 1: Synthesis of Compound WX185-2

WX185-1 (5 g, 24.51 mmol) was dissolved in dichloromethane (60 mL), and triethylamine (5.46 g, 53.92 mmol, 7.50 mL) and DMAP (299.40 mg, 2.45 mmol) were added, followed by dropwise addition of benzylsulfonyl chloride (4.76 g, 26.96 mmol, 3.45 mL). The reaction was carried out at 30° C. while stirring for 5 hours. Dichloromethane (100 mL) was added to the reaction mixture, and the reaction mixture was washed with 2 M dilute hydrochloric acid (30 mL*2). The dichloromethane phase was dried over anhydrous sodium sulfate, and evaporated under reduced pressure to remove the solvent. The crude product was subjected to silica gel column chromatography to give WX185-2. $^1$H NMR (400 MHz, DMSO-d$_6$) δ=8.06 (td, J=2.2, 4.4 Hz, 2H), 7.79 (d, J=7.5 Hz, 1H), 7.72-7.65 (m, 2H), 7.19 (d, J=2.0 Hz, 1H), 3.69 (s, 3H).

Step 2: Synthesis of Compound WX185-3

WX185-3 (9 g, 26.15 mmol) was dissolved in DMF (60 mL), followed by addition of tetrakis(triphenylphosphine) palladium (1.51 g, 1.31 mmol) and tri-tert-butyl(vinyl)tin (10.78 g, 33.99 mmol, 9.89 mL). The reaction system was purged with nitrogen gas for three times and the reaction was carried out at 100° C. while stirring for 24 hours. A solution of cesium fluoride (8 g dissolved in 50 mL of water) was added to the reaction mixture, and the reaction mixture was stirred for 6 hours, followed by addition of ethyl acetate (100 mL) and washing with water (50 mL*2). The ethyl acetate phase was filtered (some solid organic material was contained in EA phase), and the filtrate was dried over anhydrous sodium sulfate, and concentrated under reduced pressure. The crude product was purified by silica gel column chromatography to give WX185-3. $^1$H NMR (400 MHz, DMSO-d$_6$) δ=8.03-7.98 (m, 2H), 7.94 (d, J=1.9 Hz, 1H), 7.76 (d, J=7.5 Hz, 1H), 7.68 (d, J=8.2 Hz, 2H), 7.37 (d, J=1.9 Hz, 1H), 6.66-6.56 (m, 1H), 5.72 (dd, J=1.0, 17.7 Hz, 1H), 5.21 (dd, J=1.1, 11.0 Hz, 1H), 3.68 (s, 3H).

Step 3: Synthesis of Compound WX185-4

WX185-3 (5.7 g, 19.57 mmol) was dissolved in methanol (60 mL), followed by addition of sodium methoxide (1.37 g, 25.44 mmol). The reaction was carried out at 50° C. while stirring for 12 hours. The reaction mixture was concentrated under reduced pressure. The crude product was subjected to silica gel column chromatography to give WX185-4. $^1$H NMR (400 MHz, DMSO-d$_6$) δ=11.88 (br s, 1H), 7.11 (dd, J=1.6, 2.9 Hz, 1H), 6.94 (s, 1H), 6.53 (dd, J=10.9, 17.7 Hz, 1H), 5.46 (dd, J=1.5, 17.7 Hz, 1H), 4.94 (dd, J=1.6, 10.9 Hz, 1H), 3.75 (s, 3H).

Step 4: Synthesis of Compound WX185-5

A solution of WX185-4 (1.79 g, 11.84 mmol) in tetrahydrofuran (30 mL) was added dropwise to a solution of potassium tert-butoxide in tetrahydrofuran (1 M, 29.60 mL, 2.5 eq) at 0° C. The system was stirred at 30° C. for 30 minutes, and the temperature of the system was then lowered to 0° C., followed by addition of a solution of BB-1-2 (7.12 g, 23.68 mmol, 2 eq) in tetrahydrofuran (30 mL). Afterwards, the reaction mixture was warmed to 30° C. and stirred for 3 hours. The solvent was removed under reduced pressure. The crude product was purified by silica gel column chromatography to give WX185-5. $^1$H NMR (400 MHz, DMSO-d$_6$) δ=8.51 (d, J=2.0 Hz, 1H), 8.16 (dd, J=1.9, 8.7 Hz, 1H), 7.90-7.80 (m, 2H), 7.55 (d, J=1.6 Hz, 1H), 6.65 (dd, J=11.0, 17.7 Hz, 1H), 5.79 (br d, J=17.6 Hz, 1H), 5.26 (d, J=10.9 Hz, 1H), 3.65 (s, 3H).

Step 5: Synthesis of Compound WX185-6

WX185-5 (0.8 g, 1.93 mmol) was dissolved in acetic acid (10 mL), followed by addition of iron powder (430.39 mg, 7.71 mmol), and the reaction was carried out at 65° C. while stirring for 2 hours. The reaction mixture was filtered, and the filtrate was concentrated under reduced pressure. The crude product was subjected to silica gel column chromatography to give WX185-6. $^1$H NMR (400 MHz, DMSO-d$_6$) δ=8.09 (d, J=1.9 Hz, 1H), 7.62 (d, J=8.8 Hz, 1H), 7.36 (d, J=1.8 Hz, 1H), 7.08 (d, J=1.9 Hz, 1H), 6.89-6.82 (m, 1H), 6.60-6.48 (m, 1H), 6.42 (s, 2H), 5.70 (dd, J=1.0, 17.7 Hz, 1H), 5.23-5.11 (m, 1H), 3.70 (s, 3H), 1.99 (s, 1H).

Step 6: Synthesis of Compound WX185-7

WX185-6 (1.8 g, 4.67 mmol) was dissolved in DMSO (10 mL), followed by addition of potassium tert-butoxide (786.47 mg, 7.01 mmol), and the reaction mixture was stirred at 80° C. for 2 hours. Ethyl acetate (50 mL) was added to the reaction mixture, and the reaction mixture was washed with 1 M diluted hydrochloric acid (30 mL*2) and water (30 mL). The organic phase was dried over anhydrous sodium sulfate and concentrated under reduced pressure. The crude product was purified by silica gel column chromatography to give WX185-7. $^1$H NMR (400 MHz, DMSO-$d_6$) δ=11.20 (s, 1H), 7.92 (d, J=8.4 Hz, 1H), 7.69 (dd, J=1.7, 9.6 Hz, 2H), 7.64 (dd, J=1.5, 8.6 Hz, 1H), 7.42 (d, J=1.8 Hz, 1H), 6.58 (dd, J=11.0, 17.6 Hz, 1H), 5.79-5.72 (m, 1H), 5.21 (d, J=11.2 Hz, 1H).

Step 7: Synthesis of Compound WX185-8

WX185-7 (80 mg, 226.51 μmol) and WX173-1 (37.78 mg, 249.16 μmol) were dissolved in DMF (5 mL), followed by addition of triethylamine (45.84 mg, 453.01 μmol, 63.05 μL) and Pd(dppf)Cl$_2$ (16.57 mg, 22.65 μmol). Carbon monoxide gas was introduced to the reaction, and the reaction was carried out at 80° C. at 50 psi for 16 hours. The solvent was removed under reduced pressure and the crude product was purified by column chromatography to give WX185-8.

Step 8: Synthesis of Compound WX185

WX185-8 (40 mg, 96.28 μmol) was dissolved in methanol (10 mL), followed by addition of Pd/C (40 mg, 377.36 μmol) and introduction of hydrogen gas. The reaction mixture was stirred at 30° C. at 15 psi for 12 hours. The solvent was removed under reduced pressure. The crude product was purified by HPLC to give WX185. $^1$H NMR (400 MHz, DMSO-$d_6$) δ=11.17 (br s, 1H), 8.83 (br s, 1H), 8.06 (d, J=8.2 Hz, 1H), 7.88 (s, 1H), 7.80 (br d, J=8.4 Hz, 1H), 7.38 (s, 1H), 7.06 (s, 1H), 3.83-3.69 (m, 2H), 3.58 (br d, J=6.4 Hz, 1H), 2.46-2.40 (m, 4H), 1.96 (br d, J=7.3 Hz, 1H), 1.80 (br dd, J=7.1, 14.1 Hz, 2H), 1.73-1.64 (m, 2H), 1.47-1.36 (m, 1H), 1.12 (t, J=7.5 Hz, 3H).

Embodiment 21: WX186

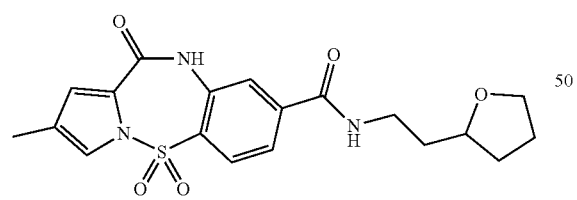

Synthetic Route

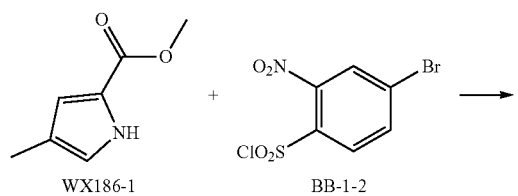

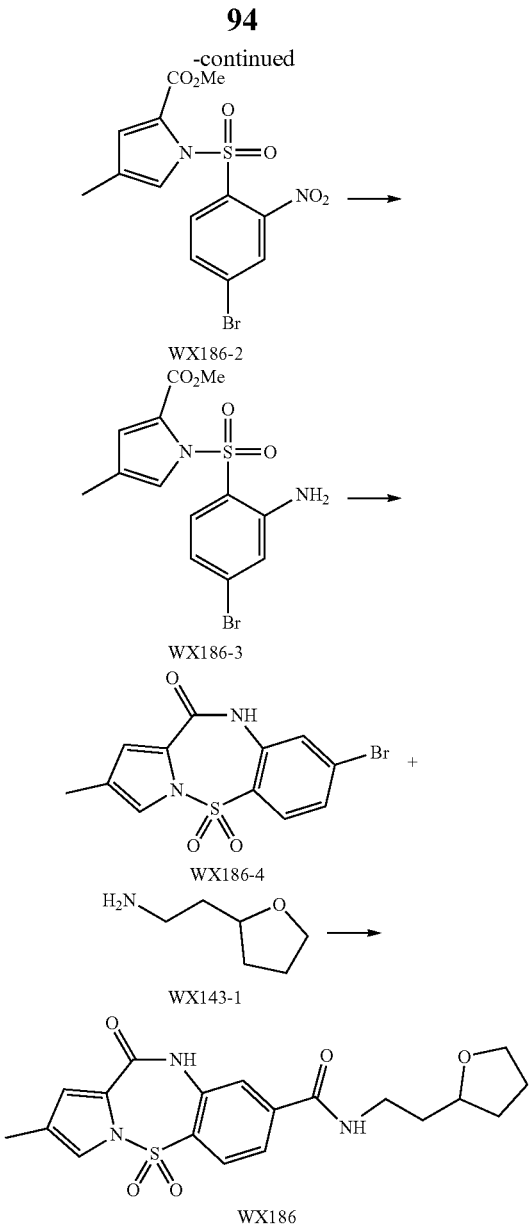

Step 1: Synthesis of Compound WX186-2

The synthesis of compound WX186-2 was referred to the step 4 of the synthesis of WX185-5 in Embodiment 20. $^1$H NMR (400 MHz, DMSO-$d_6$) δ=8.53 (d, J=2.0 Hz, 1H), 8.18 (dd, J=1.9, 8.7 Hz, 1H), 7.88-7.80 (m, 1H), 7.53 (d, J=1.6 Hz, 1H), 6.62 (dd, J=11.0, 17.7 Hz, 1H), 3.89 (s, 3H), 2.04 (s, 3H).

Step 2: Synthesis of Compound WX186-3

The synthesis of compound WX186-3 was referred to the step 5 of the synthesis of WX185-6 in Embodiment 20.

Step 3: Synthesis of Compound WX186-4

The synthesis of compound WX186-4 was referred to the step 6 of the synthesis of WX185-7 in Embodiment 20.

Step 4: Synthesis of Compound WX186

The synthesis of compound WX186 was referred to the step 4 of the synthesis of WX145 in Embodiment 2. ¹H NMR (400 MHz, DMSO-d$_6$) δ=11.36 (s, 1H), 8.80 (br t, J=5.2 Hz, 1H), 8.07 (d, J=8.2 Hz, 1H), 7.87 (s, 1H), 7.80 (d, J=9.0 Hz, 1H), 7.72-7.69 (m, 1H), 7.13 (d, J=1.8 Hz, 1H), 3.81-3.70 (m, 2H), 3.61-3.53 (m, 1H), 3.30-3.23 (m, 2H), 2.04 (s, 3H), 2.00-1.90 (m, 1H), 1.86-1.74 (m, 2H), 1.69 (m, 2H), 1.48-1.33 (m, 1H).

Embodiment 22: WX184

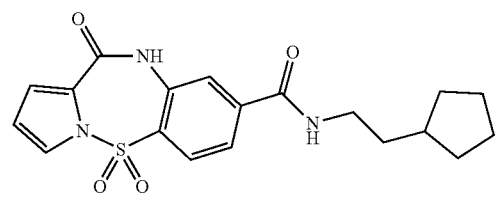 [SMILES: O=C(NCCC1CCCC1)c1ccc2c(c1)NC(=O)c1cccn1S2(=O)=O]

Synthetic Route

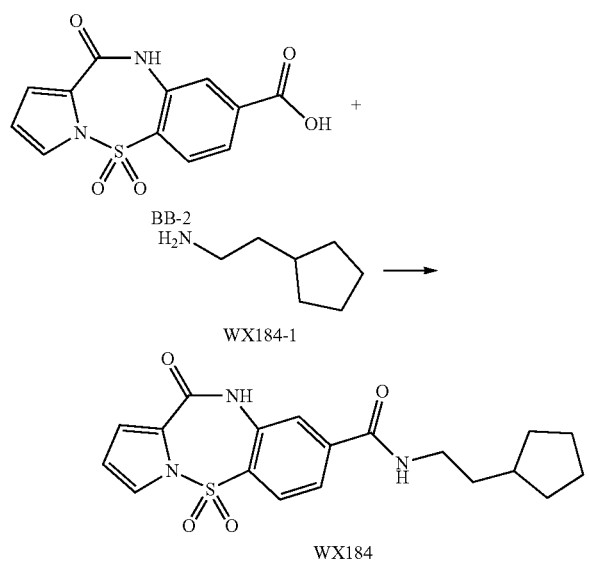

Step 1: Synthesis of Compound WX184

BB-2 (38.7 mg, 342.15 μmol), EDCI (98.4 mg, 513.23 μmol), DIPEA (88.4 mg, 684.31 μmol) and DMF (1 mL) were added into a pre-dried vial, and WX184-1 (100 mg, 342.15 μmol) was added thereto at 0° C. The reaction mixture was stirred at 25° C. for 12 hours under nitrogen atmosphere. The reaction mixture was filtered to give a crude product. The crude product was purified by HPLC to give WX184. ¹H NMR (400 MHz, CHLOROFORM-d) δ 8.94 (br s, 1H), 8.09 (d, J=8.16 Hz, 1H), 7.79 (br s, 1H), 7.63 (br d, J=7.72 Hz, 1H), 7.45 (br s, 1H), 6.43 (t, J=3.20 Hz, 1H), 6.20 (br s, 1H), 3.54-3.49 (m, 2H), 1.87-1.74 (m, 3H), 1.49-1.67 (m, 5H), 1.25 (s, 1H), 1.14 (br s, 2H).

Embodiment 23: WX187

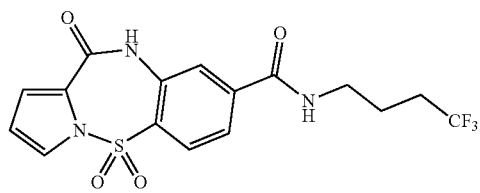 [SMILES: O=C(NCCCC(F)(F)F)c1ccc2c(c1)NC(=O)c1cccn1S2(=O)=O]

Synthetic Route

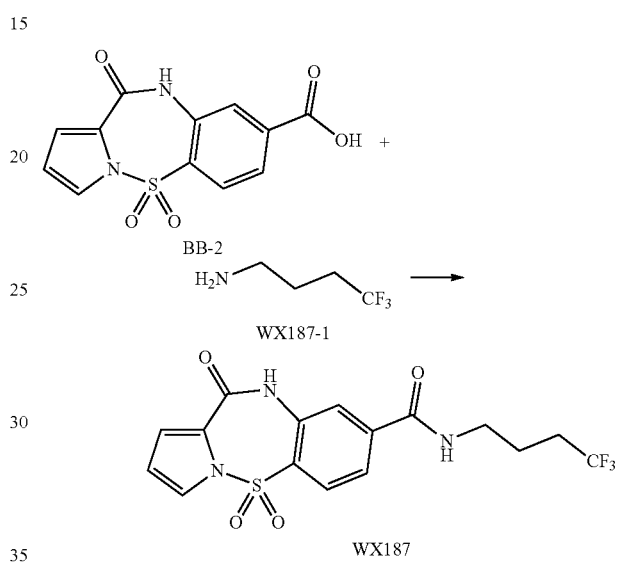

Step 1: Synthesis of Compound WX187

BB-2 (0.1 g, 342.15 μmol) and DMF (1 mL) were added into a dry vial, followed by addition of HOBt (69.3 mg, 513.22 μmol), EDCI (98.4 mg, 513.22 μmol), DIPEA (88.4 mg, 684.30 μmol) and WX187-1 (43.5 mg, 342.15 μmol). The reaction system was purged with nitrogen gas for three times and the reaction was carried out at 20° C. while stirring for 12 hours. The reaction mixture was filtered through an organic phase needle filter to give a crude product. The crude product was isolated by HPLC to give WX187. ¹H NMR (400 MHz, DMSO-d$_6$) δ=11.21 (s, 1H), 8.82 (t, J=5.6 Hz, 1H), 8.11 (d, J=8.2 Hz, 1H), 7.88 (s, 1H), 7.80 (d, J=8.2 Hz, 1H), 7.61 (dd, J=1.7, 3.0 Hz, 1H), 7.15 (dd, J=1.7, 3.6 Hz, 1H), 6.54 (t, J=3.3 Hz, 1H), 3.35-3.30 (m, 2H), 2.37-2.24 (m, 2H), 1.78-1.70 (m, 2H).

Embodiment 24: WX189

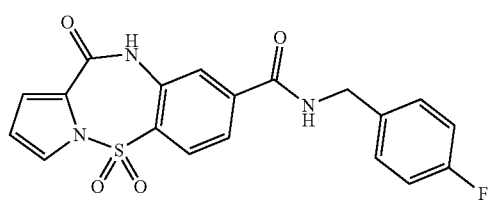 [SMILES: O=C(NCc1ccc(F)cc1)c1ccc2c(c1)NC(=O)c1cccn1S2(=O)=O]

Synthetic Route

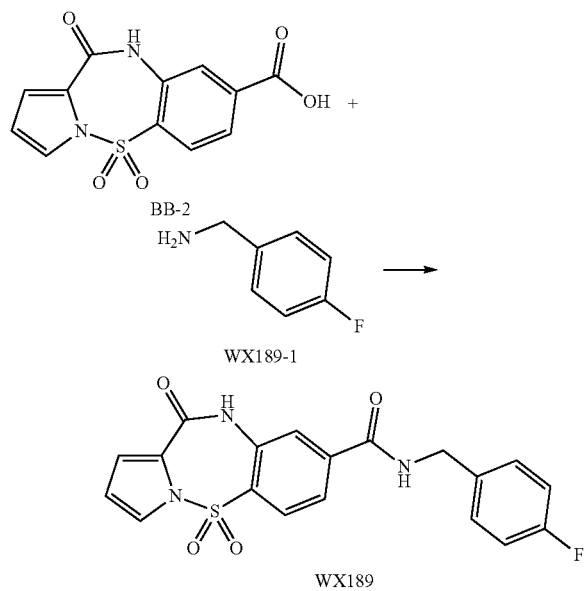

Step 1: Synthesis of Compound WX189

BB-2 (0.1 g, 342.15 μmol) and DMF (1 mL) were added to a dry vial, followed by addition of HOBt (69.3 mg, 513.22 μmol), EDCI (98.4 mg, 513.22 μmol), DIPEA (88.4 mg, 684.30 μmol, 119.19 μL, 2 eq) and WX189-1 (42.8 mg, 342.15 μmol). The reaction system was purged with nitrogen gas for three times and the reaction was carried out at 20° C. while stirring for 12 hours. The reaction mixture was filtered through an organic phase needle filter to give a crude product. The crude product was isolated by HPLC to give WX189. $^1$H NMR (400 MHz, DMSO-d$_6$) δ=11.21 (s, 1H), 9.33 (br t, J=6.0 Hz, 1H), 8.12 (d, J=8.2 Hz, 1H), 7.92 (s, 1H), 7.84 (d, J=8.2 Hz, 1H), 7.61 (dd, J=1.8, 3.1 Hz, 1H), 7.35 (dd, J=5.6, 8.5 Hz, 2H), 7.21-7.10 (m, 3H), 6.54 (t, J=3.3 Hz, 1H), 4.46 (d, J=5.7 Hz, 2H).

Embodiment 25: WX190

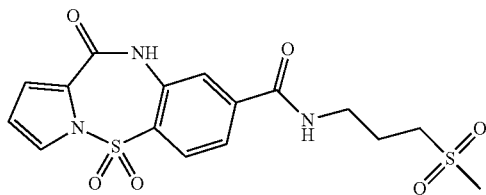 [SMILES: CS(=O)(=O)CCCNC(=O)c1ccc2c(c1)NC(=O)c1cccn1S2(=O)=O]

Synthetic Route

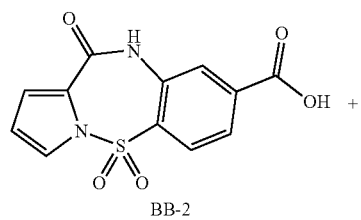

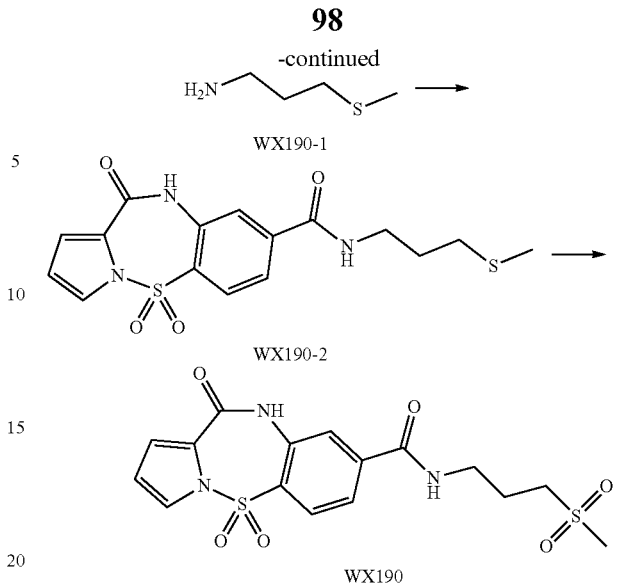

Step 1: Synthesis of Compound WX190-2

BB-2 (0.2 g, 684.31 μmol) and DMF (1 mL) were added into a dry vial, followed by addition of HOBt (138.7 mg, 1.03 mmol), EDCI (196.8 mg, 1.03 mmol), DIPEA (176.9 mg, 1.37 mmol) and WX190-1 (71.99 mg, 684.31 μmol). The reaction system was purged with nitrogen gas for three times and the reaction was carried out at 20° C. while stirring for 12 hours. The reaction mixture was concentrated under reduced pressure to give a crude product. The crude product was purified by column chromatography to give WX190-2. $^1$H NMR (400 MHz, DMSO-d$_6$) δ=11.19 (br s, 1H), 8.77 (t, J=5.3 Hz, 1H), 8.10 (d, J=8.2 Hz, 1H), 7.88 (s, 1H), 7.79 (d, J=8.4 Hz, 1H), 7.61 (d, J=1.5 Hz, 1H), 7.18-7.13 (m, 1H), 6.54 (q, J=3.4 Hz, 1H), 3.38-3.32 (m, 2H), 2.52 (br s, 2H), 2.04 (s, 3H), 1.78 (q, J=7.0 Hz, 2H).

Step 2: Synthesis of Compound WX190

WX190-2 (0.2 g, 527.07 μmol), saturated sodium bicarbonate solution (4.32 g, 51.42 mmol, 2 mL) and EtOAc (3 mL) were added into a dry single-necked flask, followed by addition of m-chloroperoxybenzoic acid (374.52 mg, 1.84 mmol, 85% purity). The reaction system was purged with nitrogen gas for three times and the reaction was carried out at 20° C. while stirring for 2 hours. The reaction mixture was filtered through an organic phase needle filter to give a crude product. The crude product was purified by HPLC to give WX190. $^1$H NMR (400 MHz, DMSO-d$_6$)$^6$=11.22 (s, 1H), 8.85 (t, J=5.5 Hz, 1H), 8.12 (d, J=8.4 Hz, 1H), 7.89 (s, 1H), 7.81 (d, J=8.2 Hz, 1H), 7.61 (br s, 1H), 7.15 (dd, J=1.5, 3.5 Hz, 1H), 6.54 (t, J=3.3 Hz, 1H), 3.39 (q, J=6.6 Hz, 2H), 3.22-3.10 (m, 2H), 2.97 (s, 3H), 1.94 (q, J=7.3 Hz, 2H).

Embodiment 26: WX195

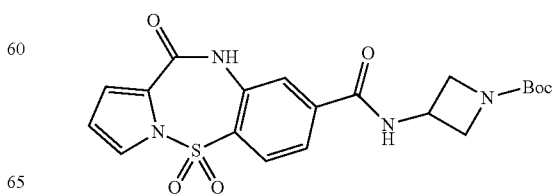

Synthetic Route

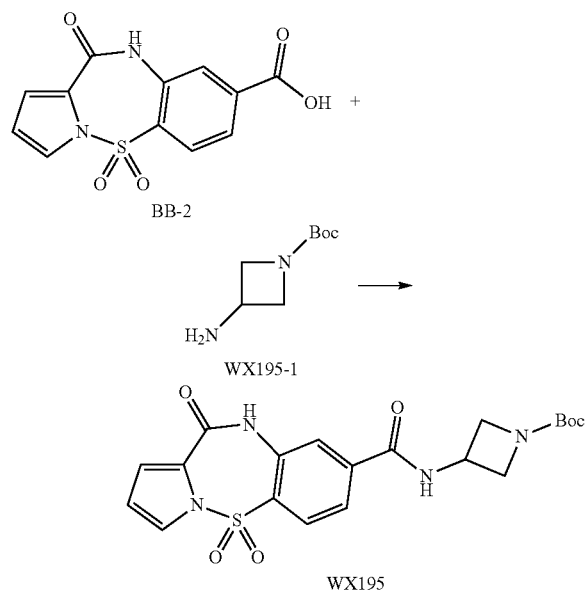

Step 1: Synthesis of Compound WX195

The synthesis of compound WX195 was referred to the step 1 of the synthesis of WX189 in Embodiment 24. ¹H NMR (400 MHz, DMSO-d$_6$) δ=11.22 (br s, 1H), 9.30 (br d, J=6.9 Hz, 1H), 8.14 (d, J=8.3 Hz, 1H), 7.93-7.80 (m, 2H), 7.61 (d, J=1.6 Hz, 1H), 7.15 (d, J=1.9 Hz, 1H), 6.59-6.49 (m, 1H), 4.64 (d, J=6.4 Hz, 1H), 4.12 (br s, 2H), 3.84 (br s, 2H), 1.44-1.34 (m, 9H).

Embodiment 27: WX196

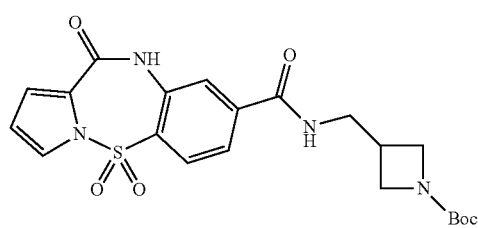 [SMILES: CC(C)(C)OC(=O)N1CC(CNC(=O)c2ccc3c(c2)NC(=O)c2cccn2S3(=O)=O)C1]

Synthetic Route

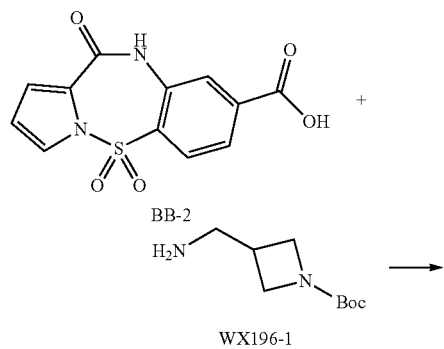

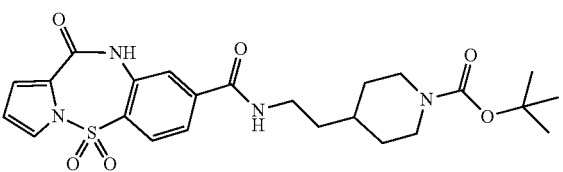 [SMILES: CC(C)(C)OC(=O)N1CCC(CCNC(=O)c2ccc3c(c2)NC(=O)c2cccn2S3(=O)=O)CC1]

Step 1: Synthesis of Compound WX196

The synthesis of compound WX196 was referred to the step 1 of the synthesis of WX189 in Embodiment 24. ¹H NMR (400 MHz, DMSO-d$_6$) δ=11.34-11.10 (m, 1H), 8.89 (t, J=5.5 Hz, 1H), 8.12 (d, J=8.3 Hz, 1H), 7.88 (d, J=1.4 Hz, 1H), 7.78 (dd, J=1.5, 8.3 Hz, 1H), 7.61 (dd, J=1.7, 3.1 Hz, 1H), 7.15 (dd, J=1.7, 3.6 Hz, 1H), 6.54 (t, J=3.3 Hz, 1H), 3.87 (br s, 3H), 3.58 (br s, 2H), 3.45 (br t, J=6.3 Hz, 2H), 1.34 (s, 9H).

Embodiment 28: WX197

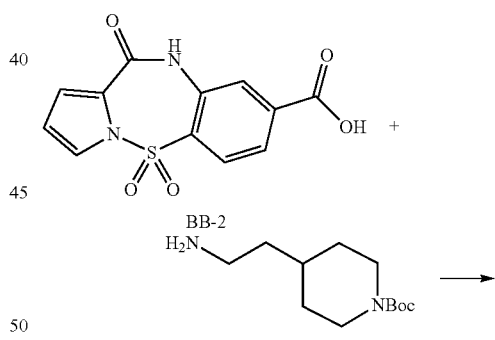

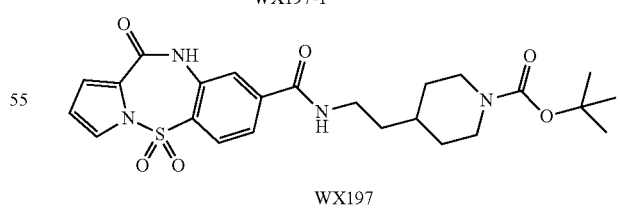

Step 1: Synthesis of Compound WX197

The synthesis of compound WX197 was referred to the step 1 of the synthesis of WX189 in Embodiment 24. ¹H NMR (400 MHz, DMSO-d$_6$) δ=11.22 (s, 1H), 8.76 (br s, 1H), 8.10 (d, J=8.3 Hz, 1H), 7.87 (s, 1H), 7.80 (s, 1H), 7.61

(br s, 1H), 7.15 (d, J=1.9 Hz, 1H), 6.54 (t, J=3.2 Hz, 1H), 4.00-3.80 (m, 2H), 3.30 (br d, J=5.6 Hz, 2H), 2.65 (m, 2H), 1.71-1.60 (m, 2H), 1.48-1.43 (m, 3H), 1.38 (s, 9H), 1.05-0.90 (m, 2H).

Embodiment 29: WX198

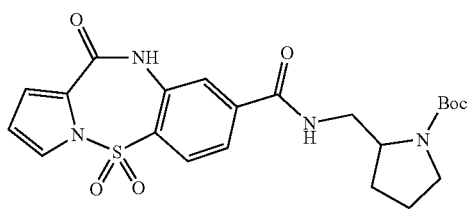 [SMILES: CC(C)(C)OC(=O)N1CCCC1CNC(=O)c1ccc2c(c1)NC(=O)c1cccn1S2(=O)=O]

Synthetic Route

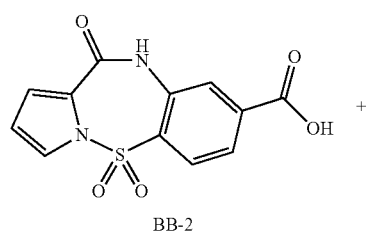

BB-2

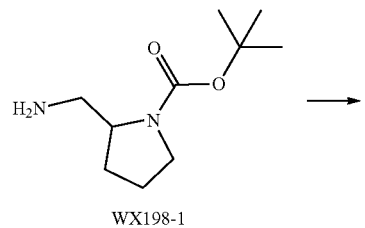

WX198-1

WX198

Step 1: Synthesis of Compound WX198

The synthesis of compound WX198 was referred to the step 1 of the synthesis of WX189 in Embodiment 24. $^1$H NMR (400 MHz, DMSO-$d_6$) δ 11.07-11.36 (m, 1H), 8.81 (br t, J=5.77 Hz, 1H), 8.12 (br d, J=5.40 Hz, 1H), 7.89 (s, 1H), 7.80 (br s, 1H), 7.62 (dd, J=1.76, 3.01 Hz, 1H), 7.16 (dd, J=1.69, 3.58 Hz, 1H), 6.55 (t, J=3.39 Hz, 1H), 3.93 (m, 2H), 3.25 (br s, 3H), 1.82 (br s, 4H), 1.40 (s, 9H).

Embodiment 30: WX200

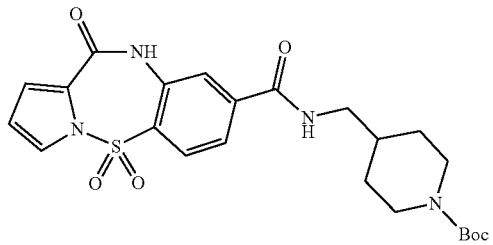 [SMILES: CC(C)(C)OC(=O)N1CCC(CNC(=O)c2ccc3c(c2)NC(=O)c2cccn2S3(=O)=O)CC1]

Synthetic Route

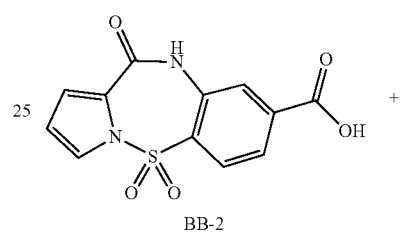

BB-2

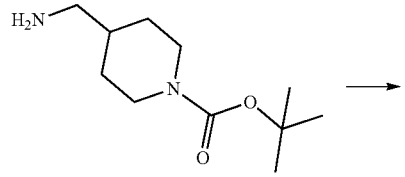

WX200-1

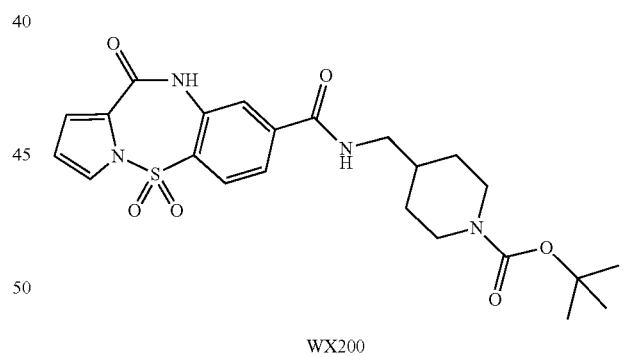

WX200

Step 1: Synthesis of Compound WX200

The synthesis of compound WX200 was referred to the step 1 of the synthesis of WX189 in Embodiment 24. $^1$H NMR (400 MHz, DMSO-$d_6$) δ 11.16 (s, 1H), 8.75 (br t, J=5.62 Hz, 1H), 8.07 (d, J=8.16 Hz, 1H), 7.85 (s, 1H), 7.77 (d, J=8.16 Hz, 1H), 7.58 (dd, J=1.65, 2.98 Hz, 1H), 7.12 (dd, J=1.54, 3.53 Hz, 1H), 6.51 (t, J=3.31 Hz, 1H), 3.89 (br d, J=12.35 Hz, 2H), 3.13 (br t, J=5.95 Hz, 2H), 2.64 (br s, 2H), 1.56-1.75 (m, 3H), 1.35 (s, 9H), 0.99 (dq, J=3.86, 12.09 Hz, 2H).

Embodiment 31: WX201

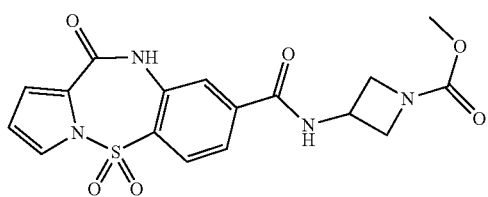 [SMILES: COC(=O)N1CC(NC(=O)c2ccc3c(c2)NC(=O)c2cccn2S3(=O)=O)C1]

Synthetic Route

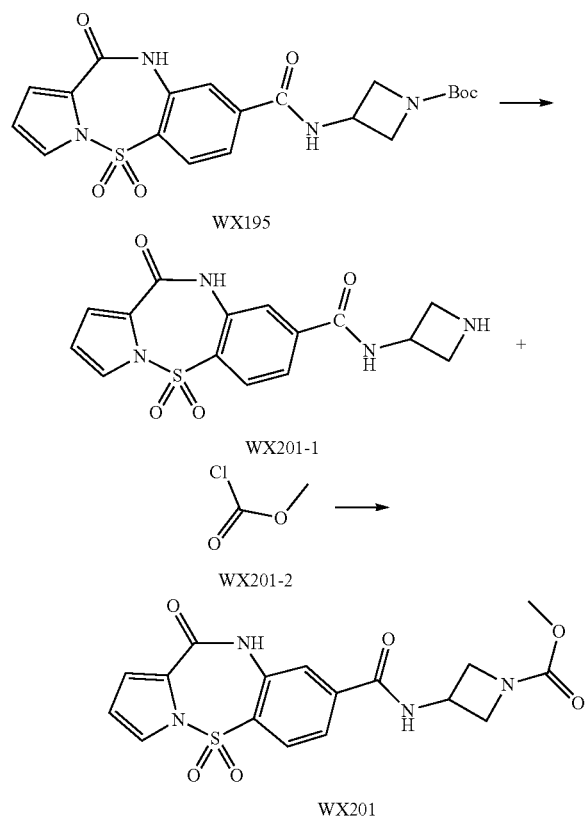

Step 1: Synthesis of Compound WX201-1

WX195 (400 mg, 895.90 μmol) and a solution of hydrogen chloride in ethyl acetate (15 mL) were added into a pre-dried 50 mL single-necked flask, and the reaction was carried out at 25° C. while stirring for 2 hours. The reaction mixture was concentrated under reduced pressure to remove the solvent to give WX201-1, which was directly used in the next step.

Step 2: Synthesis of Compound WX201

WX201-1 (200 mg, 577.43 μmol), DIPEA (149.26 mg, 1.15 mmol, 201.16 μL) and dichloromethane (5 mL) were added into a pre-dried 50 mL three-necked flask. After the reaction mixture was cooled to 0° C. under nitrogen atmosphere, WX201-2 (54.57 mg, 577.43 μmol, 44.73 μL) was slowly added dropwise, and the reaction was carried out at 25° C. while stirring for 3 hours. The reaction mixture was quenched with water (10 mL), extracted with dichloromethane (10 mL*3). The organic phase was dried over anhydrous sodium sulfate, followed by filtration. The filtrate was concentrated under reduced pressure to give the product. The crude product was purified by HPLC to give WX201. $^1$H NMR (400 MHz, DMSO-$d_6$) δ=11.24 (s, 1H), 9.35 (br d, J=7.2 Hz, 1H), 8.14 (br d, J=8.3 Hz, 1H), 7.92-7.88 (m, 1H), 7.88-7.80 (m, 1H), 7.65-7.59 (m, 1H), 7.18-7.12 (m, 1H), 6.54 (t, J=3.3 Hz, 1H), 4.81-4.63 (m, 1H), 4.20 (br s, 2H), 3.92 (d, J=5.3 Hz, 1H), 3.57 (s, 3H), 1.98-1.74 (m, 1H).

Embodiment 32: WX206

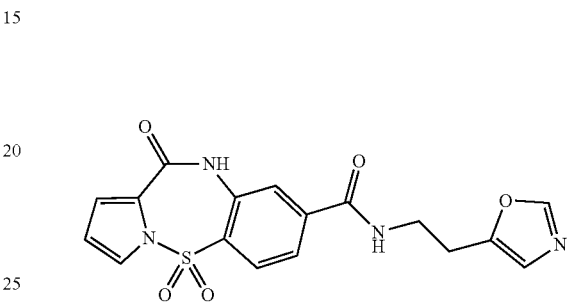

Synthetic Route

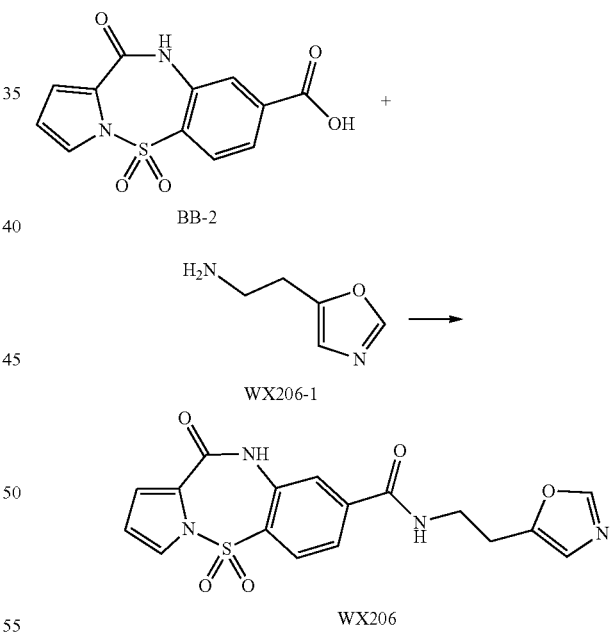

Step 1: Synthesis of Compound WX206

The synthesis of compound WX206 was referred to the step 1 of the synthesis of WX189 in Embodiment 24. $^1$H NMR (400 MHz, DMSO-$d_6$) δ=11.24 (s, 1H), 8.99 (br t, J=5.5 Hz, 1H), 8.24 (s, 1H), 8.10 (d, J=8.4 Hz, 1H), 7.87 (s, 1H), 7.78 (d, J=8.2 Hz, 1H), 7.63-7.56 (m, 1H), 7.14 (dd, J=1.5, 3.5 Hz, 1H), 6.95 (s, 1H), 6.53 (t, J=3.3 Hz, 1H), 3.52 (q, J=6.5 Hz, 2H), 2.98-2.90 (m, 2H).

Embodiment 33: WX208

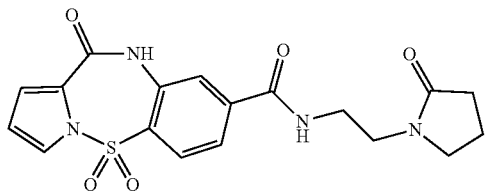 [SMILES: O=C(NCCN1CCCC1=O)c1ccc2c(c1)NC(=O)c1cccn1S2(=O)=O]

Synthetic Route

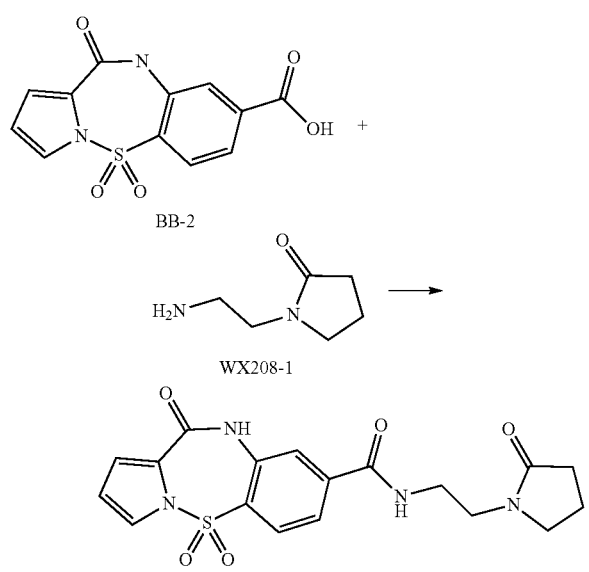

Step 1: Synthesis of Compound WX208

The synthesis of compound WX208 was referred to the step 1 of the synthesis of WX189 in Embodiment 24. $^1$H NMR (400 MHz, DMSO-$d_6$) δ=11.25 (s, 1H), 8.83 (s, 1H), 8.11 (d, J=8.3 Hz, 1H), 7.84 (d, J=1.4 Hz, 1H), 7.73 (dd, J=1.4, 8.3 Hz, 1H), 7.61 (dd, J=1.7, 3.1 Hz, 1H), 7.15 (dd, J=1.7, 3.6 Hz, 1H), 6.54 (t, J=3.3 Hz, 1H), 3.41 (br s, 1H), 3.38-3.31 (m, 3H), 2.56 (m, 2H), 2.16 (t, J=8.1 Hz, 2H), 1.95-1.82 (m, 2H).

Embodiment 34: WX289 and 290

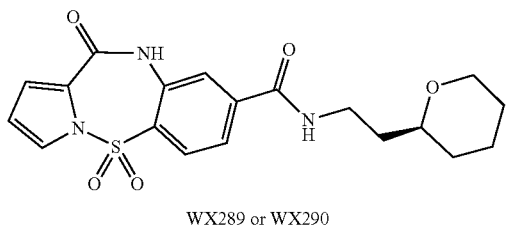

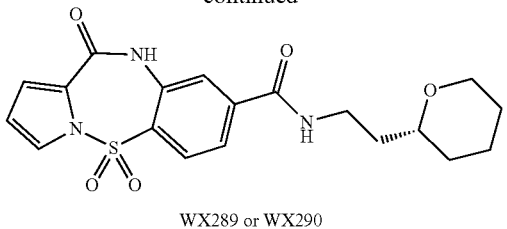

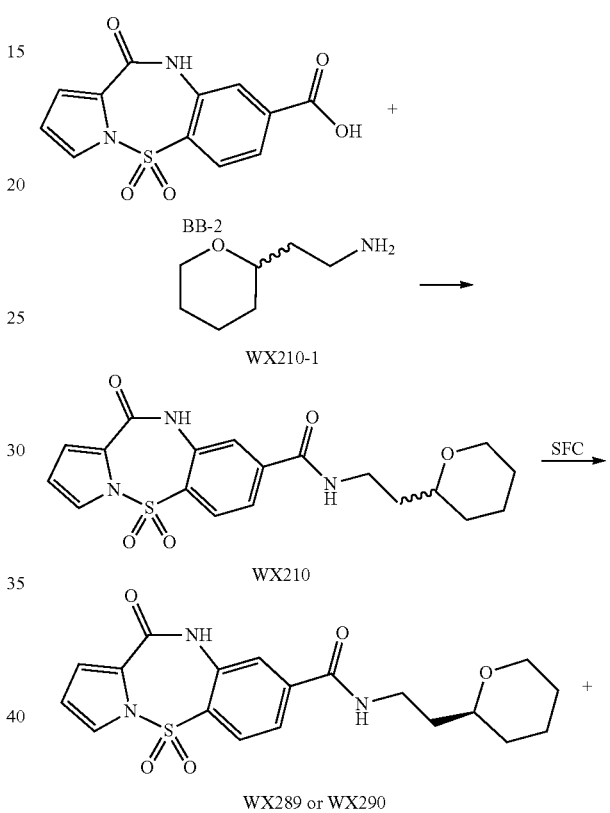

Step 1: Synthesis of Compound WX289 and WX290

The synthesis of compound WX289 and WX290 was referred to the step 1 of the synthesis of WX189 in Embodiment 24.

Compound WX289: $^1$H NMR (400 MHz, DMSO-$d_6$) δ=11.19 (br s, 1H), 8.70 (br t, J=5.51 Hz, 1H), 8.09 (d, J=8.16 Hz, 1H), 7.85 (s, 1H), 7.77 (d, J=8.38 Hz, 1H), 7.60 (d, J=1.76 Hz, 1H), 7.14 (dd, J=1.43, 3.42 Hz, 1H), 6.53 (t, J=3.31 Hz, 1H), 3.85 (br d, J=10.14 Hz, 1H), 3.22-3.29 (m, 4H), 1.74 (br s, 1H), 1.61 (q, J=6.98 Hz, 3H), 1.43 (br s, 3H), 1.13-1.23 (m, 1H);

Compound WX289: ¹H NMR (400 MHz, DMSO-d₆) δ 11.17 (s, 1H), 8.68 (br t, J=5.18 Hz, 1H), 8.07 (d, J=8.38 Hz, 1H), 7.83 (s, 1H), 7.75 (d, J=8.38 Hz, 1H), 7.58 (dd, J=1.76, 2.87 Hz, 1H), 7.12 (dd, J=1.54, 3.53 Hz, 1H), 6.51 (t, J=3.31 Hz, 1H), 3.83 (br d, J=10.36 Hz, 1H), 3.30-3.37 (m, 1H), 3.19-3.28 (m, 3H), 1.71 (br s, 1H), 1.49-1.62 (m, 3H), 1.40 (br s, 3H), 1.13-1.22 (m, 1H).

Chiral resolution conditions: chiral column: AD (250 mm*30 mm, 5 μm); mobile phase: [Neu-MeOH]; B %: 45%-45%, 20 min.

Retention time of compound WX290: 11.13 min (peak 2); retention time of compound WX289: 8.88 min (peak 1).

Embodiment 35: WX211

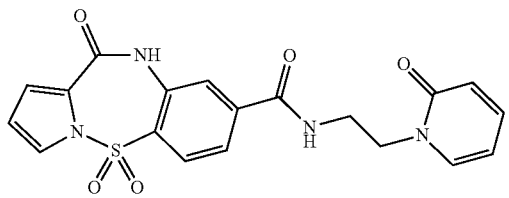 [SMILES: O=C(NCCn1ccccc1=O)c1ccc2c(c1)NC(=O)c1cccn1S2(=O)=O]

Synthetic Route

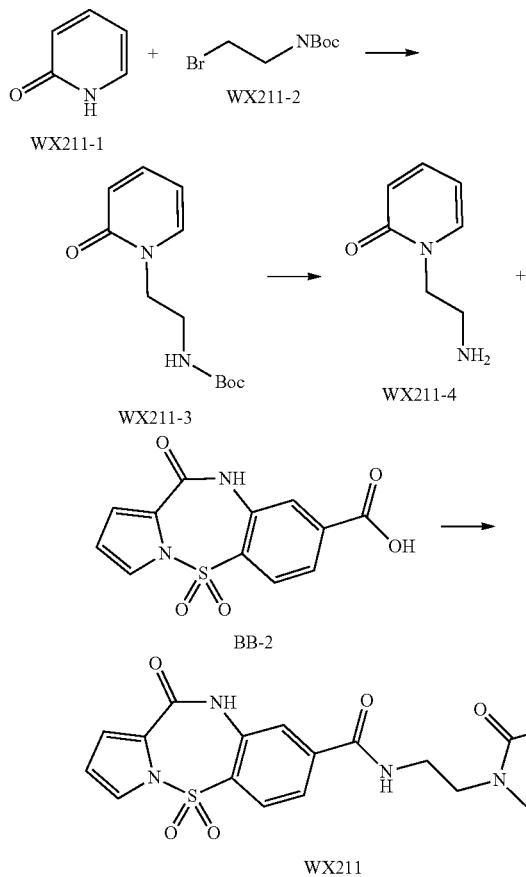

Step 1: Synthesis of Compound WX211-3

WX211-2 (3.13 g, 13.99 mmol), KOH (660.76 mg, 11.78 mmol) and EtOH (10 mL) were added into a pre-dried 100 mL vial, followed by addition of WX211-1 (1 g, 10.52 mmol, 1 eq). The reaction mixture was stirred under reflux at 80° C. for 5 hours under nitrogen atmosphere. The reaction solution was directly evaporated under reduced pressure to give a crude product. The crude product was subjected to column chromatography to give compound WX211-3.

Step 2: Synthesis of Compound WX211-4

WX211-3 (200 mg, 839.34 μmol) and EtOAc (2 mL) were added into a pre-dried single-necked flask, followed by addition of a solution of hydrogen chloride in ethyl acetate (4 M, 3 mL) under nitrogen atmosphere. The reaction mixture was stirred at 25° C. for 0.5 hour. The reaction solution was directly evaporated and the crude product was directly used in the next step.

Step 3: Synthesis of Compound WX211

The synthesis of compound WX211 was referred to the step 1 of the synthesis of WX189 in Embodiment 24. ¹H NMR (400 MHz, DMSO-d₆) δ=11.23 (s, 1H), 8.88 (br t, J=5.63 Hz, 1H), 8.09 (d, J=8.25 Hz, 1H), 7.82 (s, 1H), 7.71 (dd, J=1.50, 8.34 Hz, 1H), 7.59 (dd, J=1.67, 3.03 Hz, 1H), 7.49 (dd, J=2.03, 6.73 Hz, 1H), 7.36 (ddd, J=2.02, 6.74, 8.98 Hz, 1H), 7.13 (dd, J=1.70, 3.57 Hz, 1H), 6.52 (t, J=3.31 Hz, 1H), 6.35 (d, J=9.04 Hz, 1H), 6.12 (t, J=6.17 Hz, 1H), 4.03 (br t, J=5.73 Hz, 2H), 3.56 (q, J=5.73 Hz, 2H).

Embodiment 36: WX215

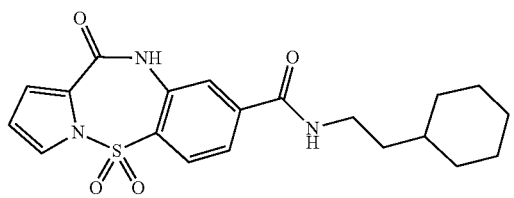 [SMILES: O=C(NCCC1CCCCC1)c1ccc2c(c1)NC(=O)c1cccn1S2(=O)=O]

Synthetic Route

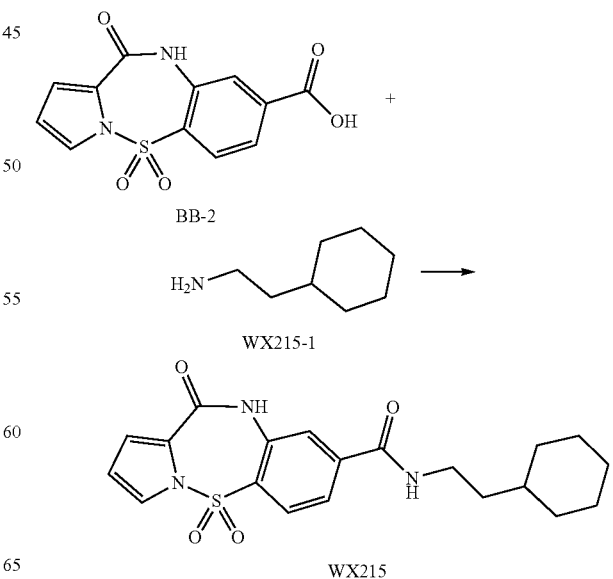

Step 1: Synthesis of Compound WX215

The synthesis of compound WX215 was referred to the step 1 of the synthesis of WX189 in Embodiment 24. $^1$H NMR (400 MHz, DMSO-d$_6$) δ=11.21 (s, 1H), 8.70 (t, J=5.5 Hz, 1H), 8.10 (d, J=8.3 Hz, 1H), 7.86 (s, 1H), 7.78 (dd, J=1.4, 8.3 Hz, 1H), 7.61 (dd, J=1.7, 3.1 Hz, 1H), 7.15 (dd, J=1.7, 3.6 Hz, 1H), 6.54 (t, J=3.3 Hz, 1H), 3.31-3.24 (m, 2H), 1.75-1.56 (m, 6H), 1.41 (q, J=7.0 Hz, 2H), 1.23-1.12 (m, 3H), 0.94-0.85 (m, 2H).

Embodiment 37: WX216

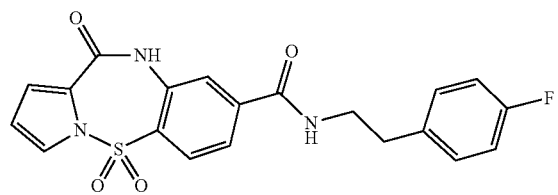 [SMILES: O=C(NCCc1ccc(F)cc1)c1ccc2c(c1)NC(=O)c1cccn1S2(=O)=O]

Synthetic Route

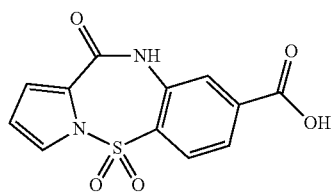

BB-2

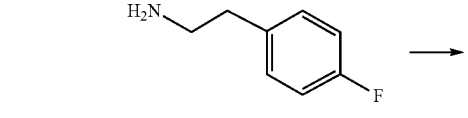

WX216-1

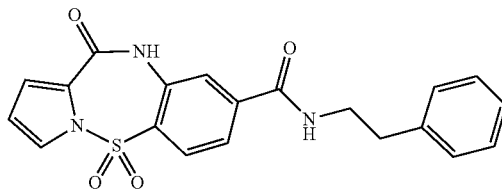

WX216

Step 1: Synthesis of Compound WX216

The synthesis of compound WX216 was referred to the step 1 of the synthesis of WX189 in Embodiment 24. $^1$H NMR (400 MHz, DMSO-d$_6$) δ=11.23 (s, 1H), 8.84 (br t, J=5.4 Hz, 1H), 8.10 (d, J=8.3 Hz, 1H), 7.89-7.82 (m, 1H), 7.75 (dd, J=1.4, 8.3 Hz, 1H), 7.61 (dd, J=1.8, 3.0 Hz, 1H), 7.26 (dd, J=5.7, 8.3 Hz, 2H), 7.18-7.06 (m, 3H), 6.54 (t, J=3.4 Hz, 1H), 3.52-3.44 (m, 2H), 2.83 (br t, J=7.2 Hz, 2H).

Embodiment 38: WX217

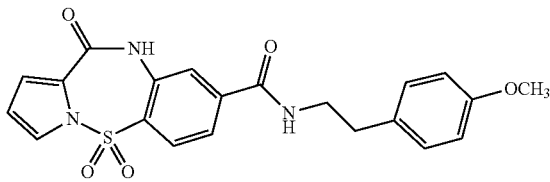 [SMILES: COc1ccc(CCNC(=O)c2ccc3c(c2)NC(=O)c2cccn2S3(=O)=O)cc1]

Synthetic Route

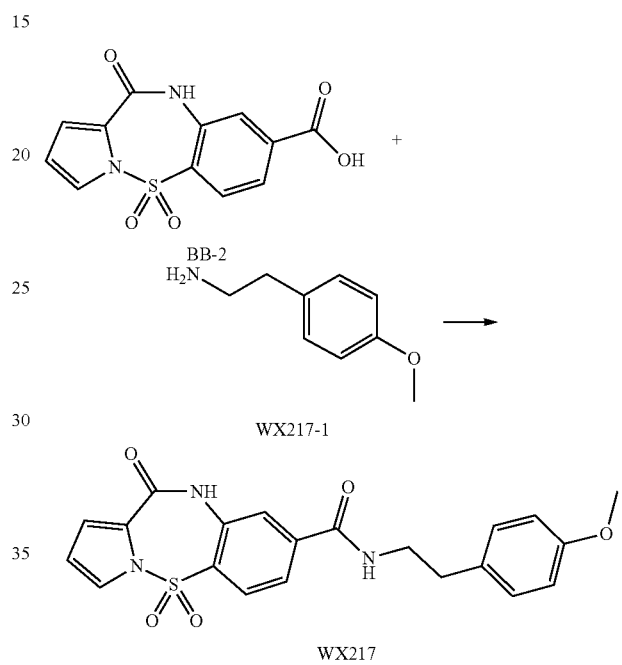

Step 1: Synthesis of Compound WX217

The synthesis of compound WX217 was referred to the step 1 of the synthesis of WX189 in Embodiment 24. $^1$H NMR (400 MHz, DMSO-d$_6$) δ=11.23 (s, 1H), 8.83 (t, J=5.5 Hz, 1H), 8.11 (d, J=8.3 Hz, 1H), 7.86 (d, J=1.4 Hz, 1H), 7.76 (dd, J=1.5, 8.3 Hz, 1H), 7.61 (dd, J=1.8, 3.0 Hz, 1H), 7.17-7.11 (m, 3H), 6.85 (d, J=8.7 Hz, 2H), 6.54 (t, J=3.4 Hz, 1H), 3.71 (s, 3H), 3.48-3.40 (m, 2H), 2.76 (br t, J=7.3 Hz, 2H).

Embodiment 39: WX218

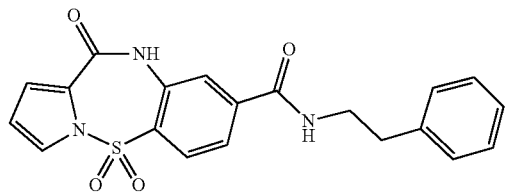 [SMILES: O=C(NCCc1ccccc1)c1ccc2c(c1)NC(=O)c1cccn1S2(=O)=O]

Synthetic Route

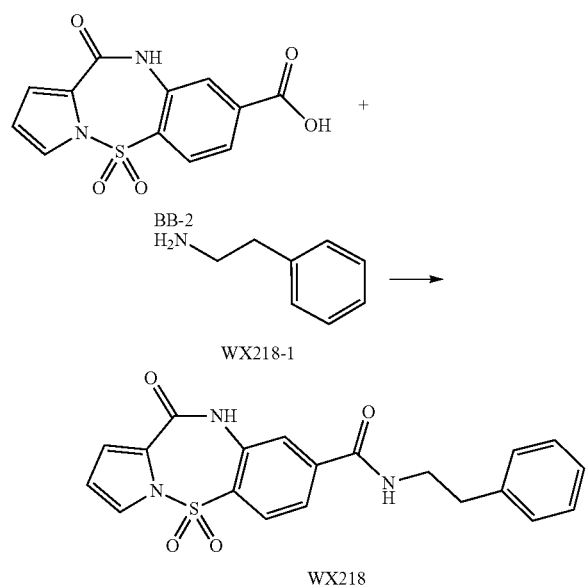

Step 1: Synthesis of Compound WX218

The synthesis of compound WX218 was referred to the step 1 of the synthesis of WX189 in Embodiment 24. ¹H NMR (400 MHz, DMSO-d₆) δ=11.24 (s, 1H), 8.87 (br t, J=5.4 Hz, 1H), 8.11 (d, J=8.3 Hz, 1H), 7.86 (d, J=1.4 Hz, 1H), 7.76 (dd, J=1.5, 8.3 Hz, 1H), 7.61 (dd, J=1.8, 3.1 Hz, 1H), 7.33-7.19 (m, 5H), 7.15 (dd, J=1.8, 3.6 Hz, 1H), 6.54 (t, J=3.4 Hz, 1H), 3.55-3.45 (m, 2H), 2.84 (t, J=7.3 Hz, 2H).

Embodiment 40: WX219

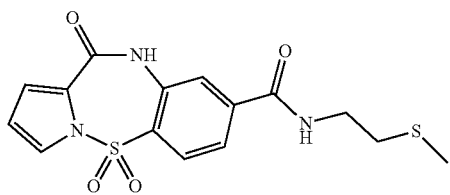 [SMILES: CSCCNC(=O)c1ccc2c(c1)NC(=O)c1cccn1S2(=O)=O]

Synthetic Route

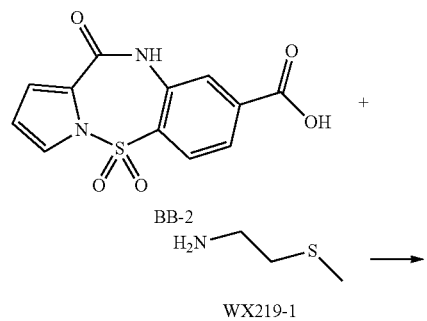

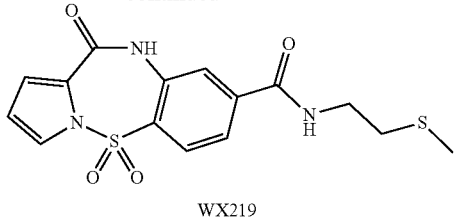

Step 1: Synthesis of Compound WX219

The synthesis of compound WX219 was referred to the step 1 of the synthesis of WX189 in Embodiment 24. ¹H NMR (400 MHz, DMSO-d₆) δ=11.23 (s, 1H), 8.90 (br t, J=5.5 Hz, 1H), 8.12 (d, J=8.3 Hz, 1H), 7.88 (d, J=1.3 Hz, 1H), 7.79 (dd, J=1.5, 8.3 Hz, 1H), 7.61 (dd, J=1.7, 3.1 Hz, 1H), 7.15 (dd, J=1.7, 3.6 Hz, 1H), 6.54 (t, J=3.3 Hz, 1H), 3.46 (q, J=6.4 Hz, 2H), 2.65 (t, J=7.0 Hz, 2H), 2.09 (s, 3H).

Embodiment 41: WX220

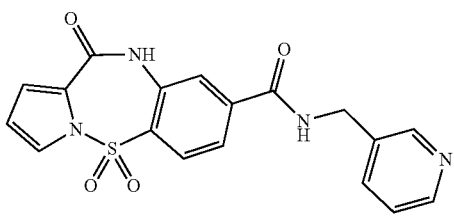 [SMILES: O=C(NCc1cccnc1)c1ccc2c(c1)NC(=O)c1cccn1S2(=O)=O]

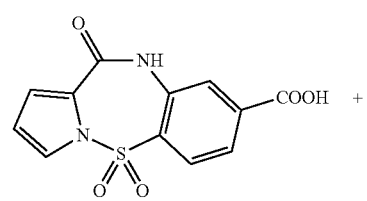

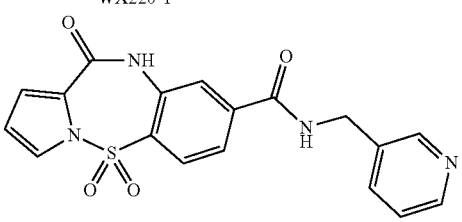

Step 1: Synthesis of Compound WX220

The synthesis of compound WX220 was referred to the step 1 of the synthesis of WX189 in Embodiment 24. ¹H NMR (400 MHz, DMSO-d₆) δ=11.26 (s, 1H), 9.65 (br t, J=5.8 Hz, 1H), 8.88 (s, 1H), 8.80 (d, J=5.1 Hz, 1H), 8.46 (br d, J=8.0 Hz, 1H), 8.14 (d, J=8.3 Hz, 1H), 8.00-7.89 (m, 3H), 7.62 (dd, J=1.8, 3.0 Hz, 1H), 7.15 (dd, J=1.7, 3.6 Hz, 1H), 6.54 (t, J=3.3 Hz, 1H), 4.66 (d, J=5.6 Hz, 2H).

Embodiment 42: WX223

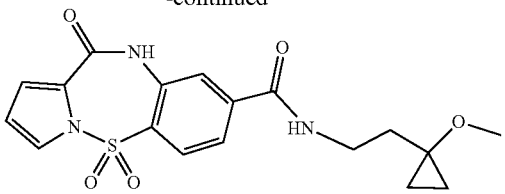

WX223

Synthetic Route

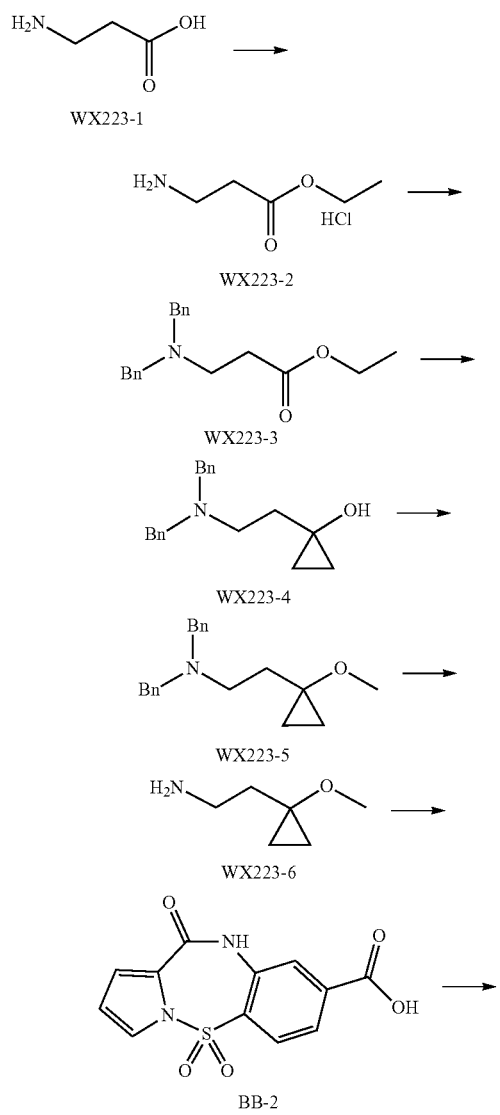

Step 1: Synthesis of Compound WX223-2

EtOH (50 mL) was added into a dry 100 mL three-necked flask, and the solution was purged with nitrogen gas for three times. The system was cooled to −10° C. under cooled methanol bath, followed by addition of SOCl$_2$ (50 mL). The mixture was stirred at −10° C. for 30 minutes. A solution of WX223-1 (10 g, 112.24 mmol) in EtOH (50 mL) was added dropwise to the above reaction system. After completion of the dropwise addition, the reaction mixture was stirred under reflux at 80° C. for 2 hours. The reaction system was cooled to room temperature, followed by addition of 100 mL of methyl tert-butyl ether. The reaction mixture was stirred for 20 minutes, followed by suction filtration under reduced pressure. The filter cake was collected and dried under reduced pressure to give compound WX223-2. $^1$H NMR (400 MHz, DMSO-d$_6$) δ=7.95 (br s, 2H), 4.10 (q, J=7.3 Hz, 2H), 3.07-2.93 (m, 2H), 2.74-2.61 (m, 2H), 1.20 (t, J=7.2 Hz, 3H).

Step 2: Synthesis of Compound WX223-3

WX223-2 (16 g, 104.16 mmol) dissolved in MeCN (200 mL) was added into a dry single-necked flask, followed by addition of K$_2$CO$_3$ (35.99 g, 260.40 mmol) and BnBr (35.63 g, 208.32 mmol, 24.74 mL). The reaction mixture was purged with nitrogen gas for three times. The reaction was carried out at 40° C. while stirring for 16 hours. The reaction was quenched by the addition of 200 mL of water and extracted with ethyl acetate (400 mL*3). The organic phases were combined, washed with saturated brine (200 mL*3), dried over anhydrous sodium sulfate, and concentrated under reduced pressure to give a crude product. The crude product was purified by column chromatography to give WX223-3. $^1$H NMR (400 MHz, CHLOROFORM-d) δ=7.27 (s, 7H), 7.25-7.18 (m, 2H), 4.07 (q, J=7.2 Hz, 2H), 3.57 (s, 4H), 3.62-3.53 (m, 1H), 3.62-3.53 (m, 1H), 2.80 (t, J=7.2 Hz, 2H), 2.48 (t, J=7.2 Hz, 2H), 1.19 (t, J=7.2 Hz, 3H).

Step 3: Synthesis of Compound WX223-4

WX223-3 (5.5 g, 18.49 mmol) and Et$_2$O (50 mL) were added into a dry three-necked flask, followed by addition of tetraisopropyl titanate (525.63 mg, 1.85 mmol, 545.83 μL). The system was cooled to 0° C., and bromoethyl Grignard reagent (3 M, 18.49 mL) was added dropwise to the system. The temperature of the system was maintained at 0-4° C. After completion of the dropwise addition, the reaction was carried out at 20° C. while stirring for 12 hours. 50 mL of saturated ammonium chloride solution was added and the mixture was stirred for 15 minutes, followed by addition of saturated sodium bicarbonate solution to adjust the pH value to 9, and extraction with ethyl acetate (100 mL*3). The organic phases were combined, washed with saturated brine (50 mL*2), dried over anhydrous sodium sulfate, and concentrated under reduced pressure to give a crude product. The crude product was isolated by column chromatography to give WX223-4. ¹H NMR (400 MHz, CHLOROFORM-d) δ=7.31-7.27 (m, 5H), 7.26-7.19 (m, 5H), 3.56 (s, 4H), 2.74-2.70 (m, 2H), 2.07-1.93 (m, 1H), 1.72-1.67 (m, 2H), 0.49-0.45 (m, 2H), 0.16-0.12 (m, 2H).

Step 4: Synthesis of Compound WX223-5

WX223-4 (1.3 g, 4.62 mmol) and THF (5 mL) were added into a pre-dried three-necked flask. After the reaction system was purged with nitrogen gas for three times, the reactor was placed under an ice bath and cooled to 0° C., followed by addition of NaH (369.59 mg, 9.24 mmol, 60%) under nitrogen atmosphere, and the temperature of the system was maintained at 0-5° C. After completion of the addition, the mixture was stirred at 0° C. for 30 minutes, and then methyl iodide (721.32 mg, 5.08 mmol, 316.37 μL) was slowly added dropwise to the system. After completion of the dropwise addition, the mixture was stirred at 20° C. for 3 hours. The reaction system was cooled to 0° C., and 30 mL of water was slowly added to quench the reaction. The aqueous phase was extracted with ethyl acetate (50 mL*3). The organic phases were combined, washed with saturated brine (50 mL*2), dried over anhydrous sodium sulfate, filtered and concentrated under reduced pressure to give a crude product. The crude product column was subjected to column chromatography to give WX223-5. ¹H NMR (400 MHz, CHLOROFORM-d) δ=7.42-7.36 (m, 4H), 7.32 (t, J=7.4 Hz, 4H), 7.26-7.21 (m, 2H), 3.61 (s, 4H), 3.13 (s, 3H), 2.71-2.62 (m, 2H), 1.81-1.72 (m, 2H), 0.71-0.65 (m, 2H), 0.36-0.30 (m, 2H).

Step 5: Synthesis of Compound WX223-6

The raw material WX223-5 (300 mg, 1.02 mmol) was added to a pre-dried hydrogenation flask, followed by addition of EtOH (5 mL), water (0.5 mL), Pd(OH)₂ (28.52 mg, 101.55 μmol, 50% purity). The reaction system was purged with H₂. The mixture was stirred at 20° C., 40 psi for 12 hours, followed by filtration through diatomite. The filtrate was concentrated under reduced pressure to give a crude product. The crude product was used directly in the next step.

Step 6: Synthesis of Compound WX223

The synthesis of compound WX223 was referred to the step 1 of the synthesis of WX189 in Embodiment 24. ¹H NMR (400 MHz, DMSO-d₆) δ=11.24 (s, 1H), 8.78 (t, J=5.3 Hz, 1H), 8.11 (d, J=8.3 Hz, 1H), 7.86 (d, J=1.3 Hz, 1H), 7.78 (dd, J=1.4, 8.3 Hz, 1H), 7.61 (dd, J=1.7, 3.1 Hz, 1H), 7.15 (dd, J=1.7, 3.6 Hz, 1H), 6.54 (t, J=3.3 Hz, 1H), 3.41-3.36 (m, 2H), 3.18 (s, 3H), 1.81-1.76 (m, 2H), 0.69-0.64 (m, 2H), 0.44-0.39 (m, 2H).

Embodiment 43: WX225

Synthetic Route

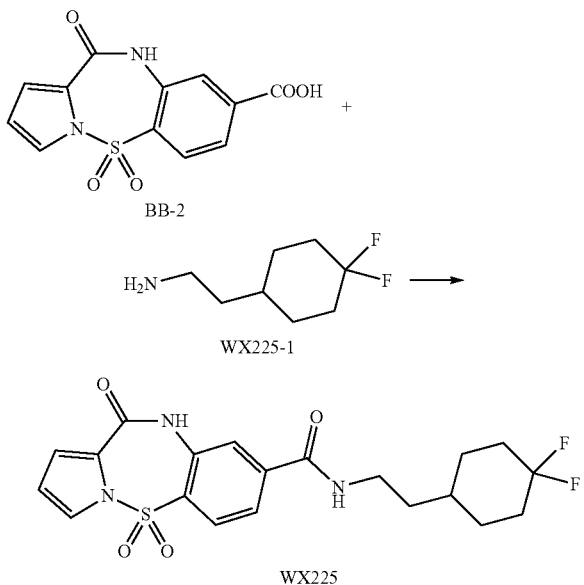

Step 1: Synthesis of Compound WX225

The synthesis of compound WX225 was referred to the step 1 of the synthesis of WX189 in Embodiment 24. ¹H NMR (400 MHz, DMSO-d₆) δ=11.23 (br s, 1H), 8.75 (br s, 1H), 8.10 (d, J=8.3 Hz, 1H), 7.86 (s, 1H), 7.78 (br d, J=8.3 Hz, 1H), 7.61 (dd, J=1.7, 2.9 Hz, 1H), 7.15 (dd, J=1.6, 3.5 Hz, 1H), 6.54 (t, J=3.4 Hz, 1H), 3.29 (br d, J=6.3 Hz, 2H), 1.98 (br d, J=7.3 Hz, 2H), 1.82-1.65 (m, 4H), 1.47 (br d, J=6.1 Hz, 3H), 1.15 (br d, J=10.5 Hz, 2H).

Embodiment 44: WX226

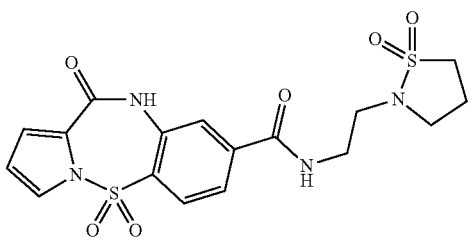 [SMILES: O=C(NCCN1CCCS1(=O)=O)c1ccc2c(c1)NC(=O)c1cccn1S2(=O)=O]

Synthetic Route

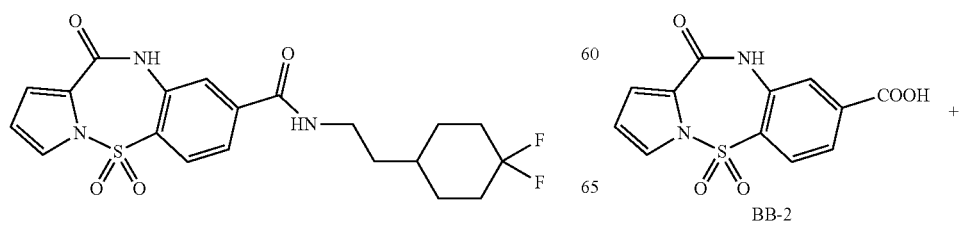

-continued

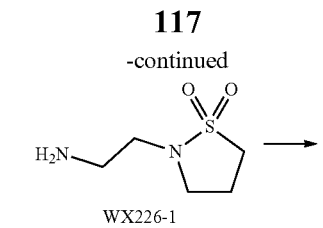
WX226-1

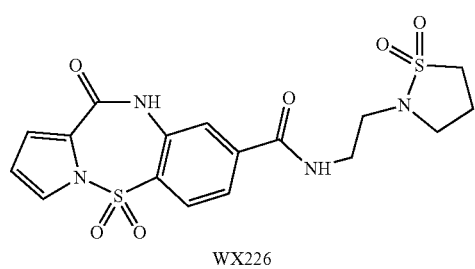
WX226

Step 1: Synthesis of Compound WX226

The synthesis of compound WX226 was referred to the step 1 of the synthesis of WX189 in Embodiment 24. $^1$H NMR (400 MHz, DMSO-d$_6$) δ=11.25 (s, 1H), 8.84 (br t, J=5.4 Hz, 1H), 8.12 (d, J=8.3 Hz, 1H), 7.87 (d, J=1.4 Hz, 1H), 7.79 (dd, J=1.5, 8.3 Hz, 1H), 7.62 (dd, J=1.8, 3.1 Hz, 1H), 7.15 (dd, J=1.7, 3.6 Hz, 1H), 6.54 (t, J=3.3 Hz, 1H), 3.44 (q, J=6.3 Hz, 2H), 3.27 (t, J=6.7 Hz, 2H), 3.15 (t, J=7.6 Hz, 2H), 3.09 (t, J=6.3 Hz, 2H), 2.26-2.15 (m, 2H).

Embodiment 45: WX227

Synthetic Route

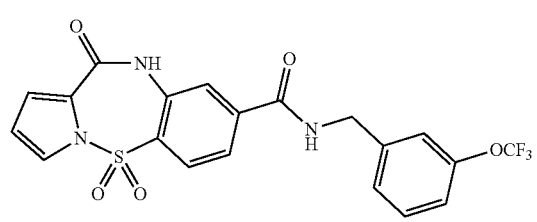 [SMILES: O=C(NCc1cccc(OC(F)(F)F)c1)c1ccc2c(c1)NC(=O)c1cccn1S2(=O)=O]
BB-2

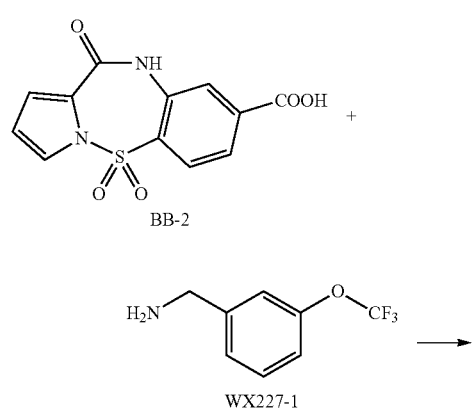
WX227-1

-continued

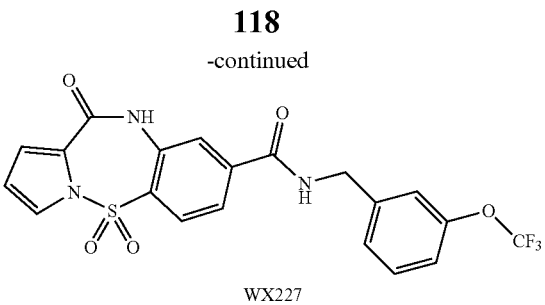
WX227

Step 1: Synthesis of Compound WX227

The synthesis of compound WX227 was referred to the step 1 of the synthesis of WX189 in Embodiment 24. $^1$H NMR (400 MHz, DMSO-d$_6$) δ=11.24 (s, 1H), 9.41 (br s, 1H), 8.13 (br d, J=8.3 Hz, 1H), 7.92 (s, 1H), 7.85 (br d, J=8.2 Hz, 1H), 7.62 (br s, 1H), 7.52-7.43 (m, 1H), 7.40-7.21 (m, 3H), 7.15 (br s, 1H), 6.54 (br s, 1H), 4.53 (br d, J=6.0 Hz, 2H).

Embodiment 46: WX228

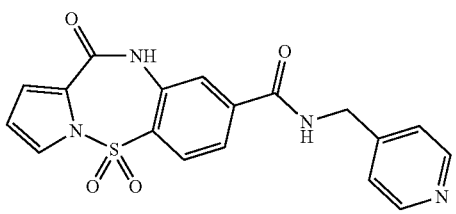 [SMILES: O=C(NCc1ccncc1)c1ccc2c(c1)NC(=O)c1cccn1S2(=O)=O]

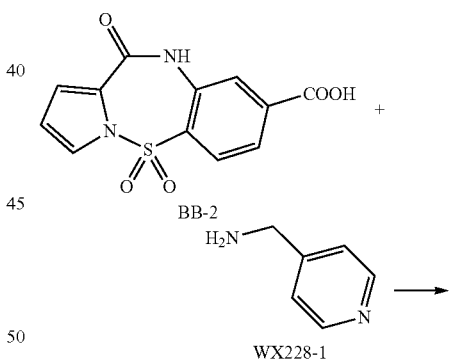
BB-2

WX228-1

WX228

Step 1: Synthesis of Compound WX228

The synthesis of compound WX228 was referred to the step 1 of the synthesis of WX189 in Embodiment 24. $^1$H NMR (400 MHz, DMSO-d$_6$) δ=11.29 (s, 1H), 9.77 (br t, J=5.7 Hz, 1H), 8.84 (d, J=6.7 Hz, 2H), 8.17 (d, J=8.2 Hz, 1H), 7.98-7.91 (m, 4H), 7.63 (dd, J=1.7, 3.1 Hz, 1H), 7.16 (dd, J=1.7, 3.6 Hz, 1H), 6.55 (t, J=3.4 Hz, 1H), 4.75 (br d, J=5.5 Hz, 2H).

Embodiment 47: WX229

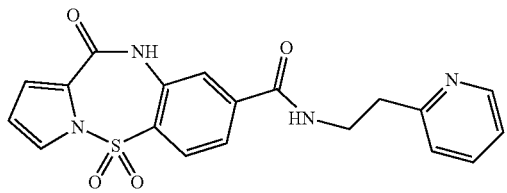 [SMILES: O=C(NCCc1ccccn1)c1ccc2c(c1)NC(=O)c1cccn1S2(=O)=O]

Synthetic Route

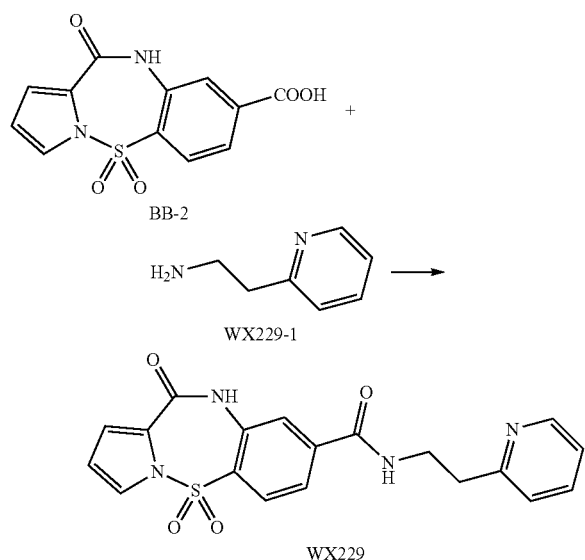

Step 1: Synthesis of Compound WX229

The synthesis of compound WX229 was referred to the step 1 of the synthesis of WX189 in Embodiment 24. $^1$H NMR (400 MHz, DMSO-d$_6$) δ=11.25 (s, 1H), 9.03 (br t, J=5.5 Hz, 1H), 8.79 (br d, J=4.8 Hz, 1H), 8.42 (br t, J=7.8 Hz, 1H), 8.09 (d, J=8.3 Hz, 1H), 7.91-7.84 (m, 2H), 7.81 (d, J=1.4 Hz, 1H), 7.75 (dd, J=1.4, 8.3 Hz, 1H), 7.61 (dd, J=1.7, 3.1 Hz, 1H), 7.15 (dd, J=1.7, 3.6 Hz, 1H), 6.54 (t, J=3.4 Hz, 1H), 3.72 (q, J=6.1 Hz, 2H), 3.28 (br t, J=6.3 Hz, 2H).

Embodiment 48: WX230

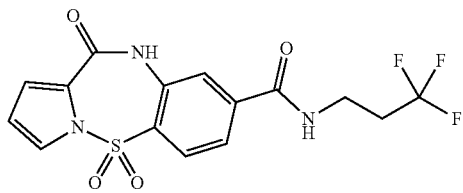 [SMILES: O=C(NCCC(F)(F)F)c1ccc2c(c1)NC(=O)c1cccn1S2(=O)=O]

Synthetic Route

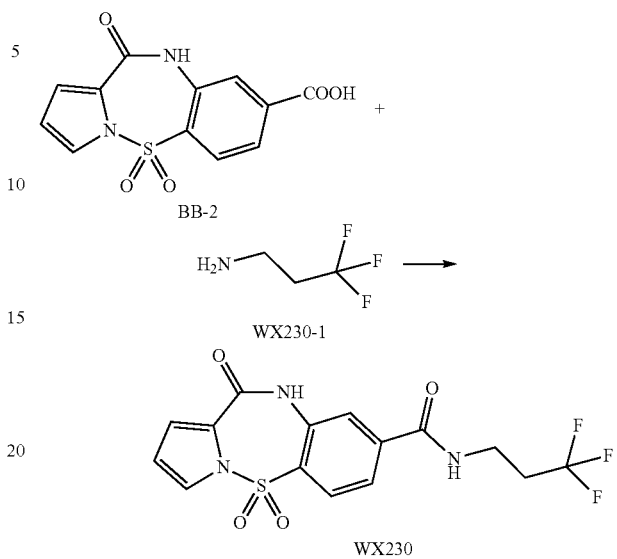

Step 1: Synthesis of Compound WX230

The synthesis of compound WX230 was referred to the step 1 of the synthesis of WX189 in Embodiment 24. $^1$H NMR (400 MHz, DMSO-d$_6$) δ=11.26 (br s, 1H), 9.01 (br t, J=5.5 Hz, 1H), 8.14 (d, J=8.3 Hz, 1H), 7.88 (d, J=1.3 Hz, 1H), 7.78 (dd, J=1.4, 8.3 Hz, 1H), 7.62 (dd, J=1.7, 3.1 Hz, 1H), 7.15 (dd, J=1.7, 3.6 Hz, 1H), 6.54 (t, J=3.3 Hz, 1H), 3.56-3.45 (m, 2H), 2.60-2.53 (m, 2H).

Embodiment 49: WX231

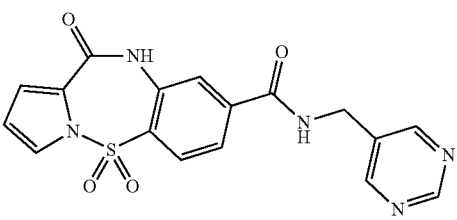 [SMILES: O=C(NCc1cncnc1)c1ccc2c(c1)NC(=O)c1cccn1S2(=O)=O]

Synthetic Route

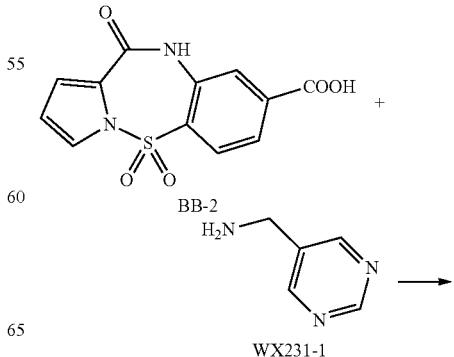

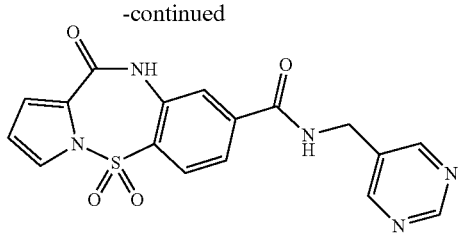

WX231

Step 1: Synthesis of Compound WX231

The synthesis of compound WX231 was referred to the step 1 of the synthesis of WX189 in Embodiment 24. $^1$H NMR (400 MHz, DMSO-$d_6$) δ=11.22 (s, 1H), 9.46 (br t, J=5.5 Hz, 1H), 9.10 (s, 1H), 8.79 (s, 2H), 8.12 (d, J=8.2 Hz, 1H), 7.92 (s, 1H), 7.85 (d, J=8.4 Hz, 1H), 7.61 (dd, J=1.8, 2.9 Hz, 1H), 7.15 (dd, J=1.5, 3.5 Hz, 1H), 6.54 (t, J=3.3 Hz, 1H), 4.52 (d, J=5.5 Hz, 2H).

Embodiment 50: WX232

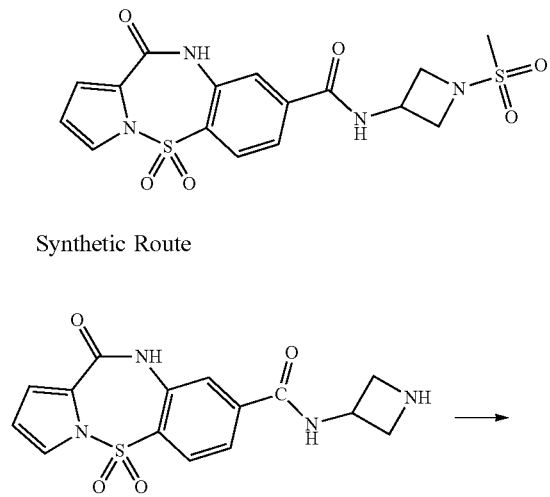

WX232

Step 1: Synthesis of Compound WX232

WX201-1 (120 mg, 346.46 μmol), triethylamine (70.12 mg, 692.92 μmol, 96.45 μL) and dichloromethane (3 mL) were added into a pre-dried vial under nitrogen atmosphere, and methylsulfonyl chloride (39.69 mg, 346.46 μmol, 26.82 μL) was added thereto. The reaction mixture was stirred at 25° C. for 5 hours. The reaction mixture was quenched with water (5 mL) and extracted with dichloromethane (10 mL*3). The organic phase was dried over anhydrous sodium sulfate, followed by filtration. The filtrate was concentrated under reduced pressure to give a crude product. The crude product was isolated by HPLC to give WX232.

$^1$H NMR (400 MHz, DMSO-$d_6$) δ=11.26 (s, 1H), 9.36 (br d, J=6.8 Hz, 1H), 8.15 (d, J=8.3 Hz, 1H), 7.91-7.81 (m, 2H), 7.63 (dd, J=1.6, 3.0 Hz, 1H), 7.16 (dd, J=1.6, 3.5 Hz, 1H), 6.55 (t, J=3.4 Hz, 1H), 4.69 (sxt, J=7.0 Hz, 1H), 4.13 (t, J=8.2 Hz, 2H), 4.01-3.84 (m, 2H), 3.04 (s, 3H).

Embodiment 51: WX233

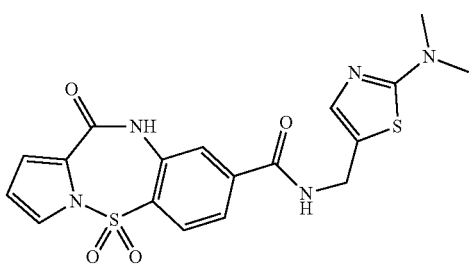 [SMILES: CN(C)c1ncc(CNC(=O)c2ccc3c(c2)NC(=O)c2cccn2S3(=O)=O)s1]

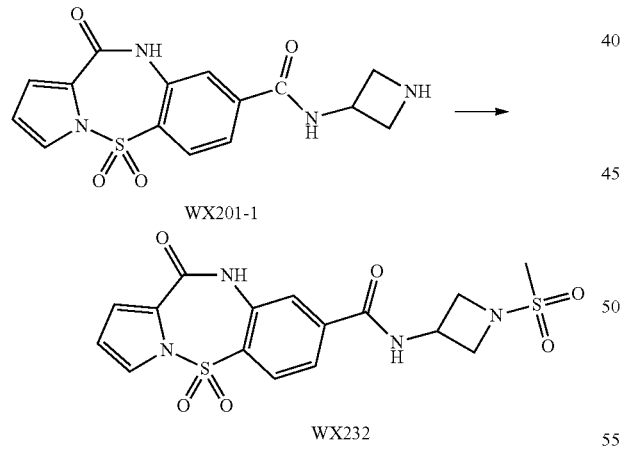

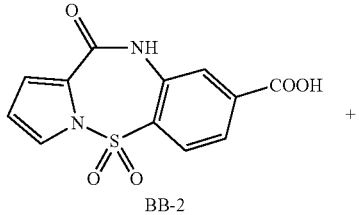

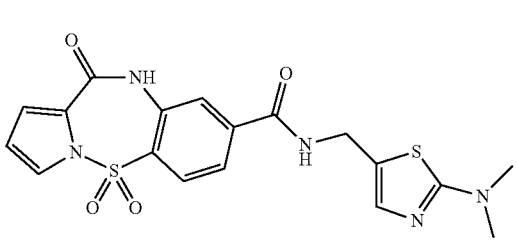

WX233

Step 1: Synthesis of Compound WX233

The synthesis of compound WX233 was referred to the step 1 of the synthesis of WX189 in Embodiment 24. $^1$H NMR (400 MHz, DMSO-$d_6$) δ=11.28 (s, 1H), 9.67 (br t, J=5.4 Hz, 1H), 8.13 (d, J=8.3 Hz, 1H), 7.93 (s, 1H), 7.85 (dd, J=1.4, 8.3 Hz, 1H), 7.62 (dd, J=1.7, 3.1 Hz, 1H), 7.42 (s, 1H), 7.16 (dd, J=1.7, 3.6 Hz, 1H), 6.54 (t, J=3.3 Hz, 1H), 4.46 (br d, J=5.4 Hz, 2H), 3.17 (s, 6H).

Embodiment 52: WX235

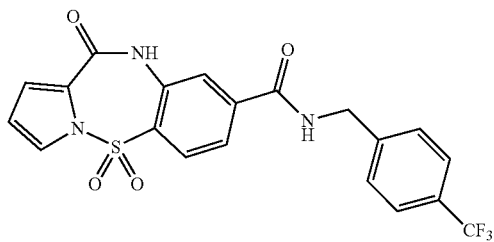 [SMILES: O=C(NCc1ccc(C(F)(F)F)cc1)c1ccc2c(c1)NC(=O)c1cccn1S2(=O)=O]

Synthetic Route

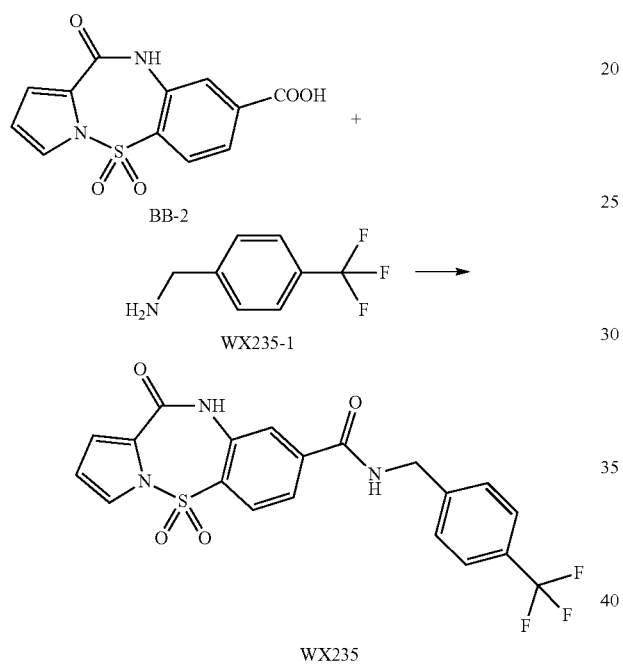

Step 1: Synthesis of Compound WX235

The synthesis of compound WX235 was referred to the step 1 of the synthesis of WX189 in Embodiment 24. $^1$H NMR (400 MHz, DMSO-$d_6$) δ=11.25 (s, 1H), 9.52-9.37 (m, 1H), 8.14 (br d, J=8.2 Hz, 1H), 7.93 (s, 1H), 7.87 (br d, J=8.4 Hz, 1H), 7.70 (br d, J=7.9 Hz, 2H), 7.62 (br s, 1H), 7.53 (br d, J=7.9 Hz, 2H), 7.15 (br s, 1H), 6.54 (br s, 1H), 4.56 (br d, J=5.4 Hz, 2H).

Embodiment 53: WX237

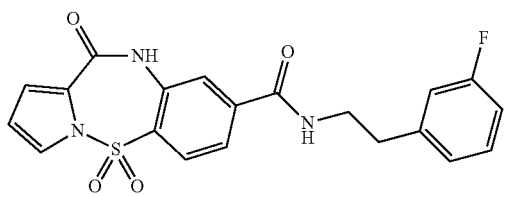 [SMILES: O=C(NCCc1cccc(F)c1)c1ccc2c(c1)NC(=O)c1cccn1S2(=O)=O]

Synthetic Route

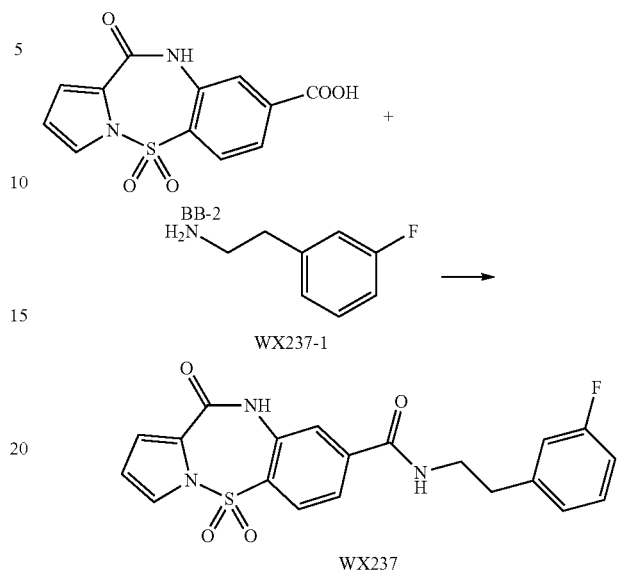

Step 1: Synthesis of Compound WX237

The synthesis of compound WX237 was referred to the step 1 of the synthesis of WX189 in Embodiment 24. $^1$H NMR (400 MHz, DMSO-$d_6$) δ=11.23 (s, 1H), 8.90-8.79 (m, 1H), 8.10 (d, J=8.2 Hz, 1H), 7.85 (s, 1H), 7.79-7.71 (m, 1H), 7.62-7.57 (m, 1H), 7.37-7.26 (m, 1H), 7.18-7.11 (m, 1H), 7.11-7.05 (m, 2H), 7.01 (br t, J=8.6 Hz, 1H), 6.58-6.51 (m, 1H), 3.57-3.46 (m, 2H), 2.87 (s, 2H).

Embodiment 54: WX239

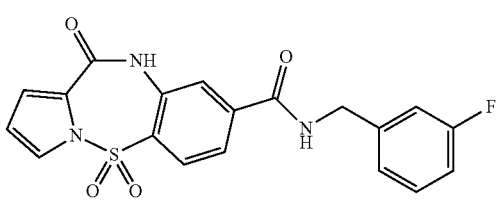 [SMILES: O=C(NCc1cccc(F)c1)c1ccc2c(c1)NC(=O)c1cccn1S2(=O)=O]

Synthetic Route

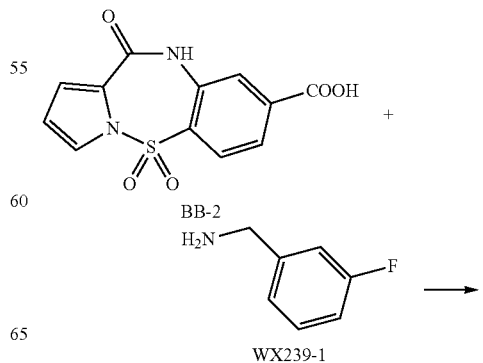

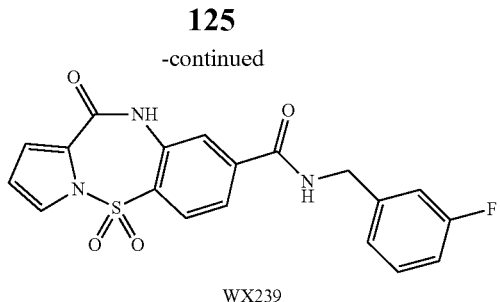

WX239

Step 1: Synthesis of Compound WX239

The synthesis of compound WX239 was referred to the step 1 of the synthesis of WX189 in Embodiment 24. ¹H NMR (400 MHz, DMSO-d$_6$) δ=11.24 (s, 1H), 9.39 (br t, J=5.6 Hz, 1H), 8.13 (d, J=8.3 Hz, 1H), 7.93 (d, J=1.1 Hz, 1H), 7.86 (dd, J=1.3, 8.3 Hz, 1H), 7.62 (dd, J=1.7, 2.9 Hz, 1H), 7.45-7.30 (m, 1H), 7.22-6.99 (m, 4H), 6.54 (t, J=3.3 Hz, 1H), 4.49 (br d, J=5.8 Hz, 2H).

Embodiment 55: WX271

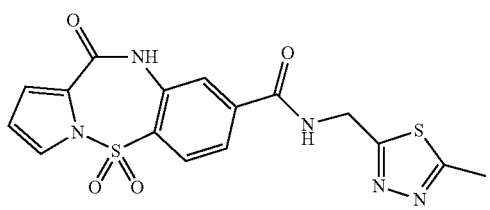 [SMILES: Cc1nnc(CNC(=O)c2ccc3c(c2)NC(=O)c2cccn2S3(=O)=O)s1]

Synthetic Route

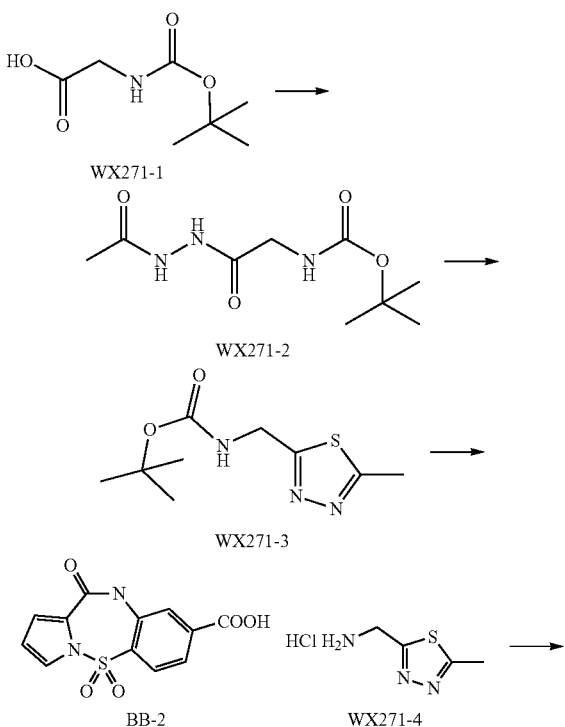

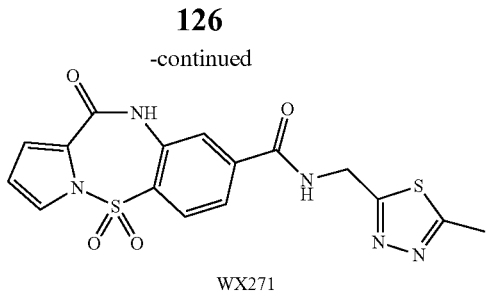

WX271

Step 1: Synthesis of Compound WX271-2

WX271-1 (1 g, 5.71 mmol) was dissolved in DCM (20 mL), followed by addition of EEDQ (1.41 g, 5.71 mmol). The mixture was stirred for 30 minutes, followed by addition of acetyl hydrazine (520.15 mg, 7.02 mmol). The reaction was carried out at 30° C. while stirring for 12 hours. The reaction mixture was filtered to give compound WX271-2. ¹H NMR (400 MHz, CHLOROFORM-d) δ=8.82 (br s, 1H), 8.27-8.18 (m, 1H), 5.23 (br s, 1H), 3.91 (br d, J=6.0 Hz, 2H), 2.07 (s, 3H), 1.47 (s, 9H).

Step 2: Synthesis of Compound WX271-3

WX271-2 (300 mg, 1.30 mmol) was dissolved in THF (25 mL), followed by addition of LAWESSON'S reagent (629.66 mg, 1.56 mmol). The reaction mixture was stirred at 70° C. for 3 hours, and then cooled to 30° C. and stirred for another 12 hours. The reaction mixture was concentrated under reduced pressure, and the crude product was purified by silica gel column chromatography to give WX271-3. ¹H NMR (400 MHz, CHLOROFORM-d) δ=4.73-4.59 (m, 2H), 3.90-3.83 (m, 1H), 2.74 (br s, 3H), 1.45 (s, 9H).

Step 3: Synthesis of Compound WX271-4

WX271-3 (0.25 g, 1.09 mmol) was dissolved in HCl/EtOAc (10 mL). The reaction mixture was stirred at 15° C. for 12 hours. The reaction mixture was filtered, and the filter cake was collected to give WX271-4. ¹H NMR (400 MHz, DMSO-d$_6$) δ=8.89 (br s, 3H), 4.49 (br d, J=5.5 Hz, 2H), 2.74 (s, 3H).

Step 4: Synthesis of Compound WX271

The synthesis of compound WX271 was referred to the step 1 of the synthesis of WX189 in Embodiment 24. ¹H NMR (400 MHz, DMSO-d$_6$) δ=11.27 (s, 1H), 9.77 (s, 1H), 8.14 (d, J=8.3 Hz, 1H), 7.93 (d, J=1.3 Hz, 1H), 7.87-7.79 (m, 1H), 7.62 (dd, J=1.8, 3.0 Hz, 1H), 7.16 (dd, J=1.7, 3.6 Hz, 1H), 6.54 (t, J=3.4 Hz, 1H), 4.81 (d, J=5.8 Hz, 2H), 2.67 (s, 3H).

Embodiment 56: WX272

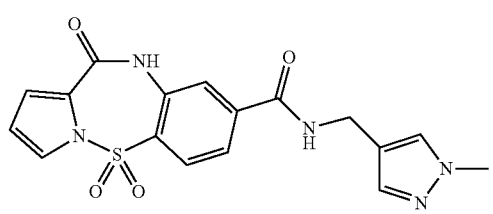 [SMILES: Cn1cc(CNC(=O)c2ccc3c(c2)NC(=O)c2cccn2S3(=O)=O)cn1]

Synthetic Route

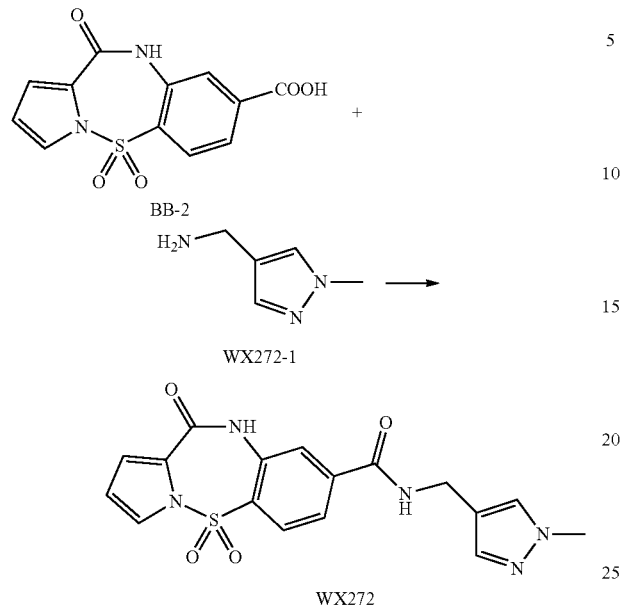

Step 1: Synthesis of Compound WX272

The synthesis of compound WX272 was referred to the step 1 of the synthesis of WX189 in Embodiment 24. $^1$H NMR (400 MHz, DMSO-$d_6$) δ=11.22 (s, 1H), 9.14 (br s, 1H), 8.09 (d, J=8.3 Hz, 1H), 7.89 (d, J=1.4 Hz, 1H), 7.80 (dd, J=1.3, 8.3 Hz, 1H), 7.64-7.58 (m, 2H), 7.36 (s, 1H), 7.15 (dd, J=1.7, 3.6 Hz, 1H), 6.54 (t, J=3.3 Hz, 1H), 4.29 (d, J=5.5 Hz, 2H), 3.78 (s, 3H).

Embodiment 57: WX275

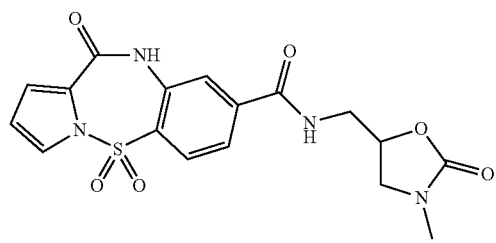 [SMILES: CN1CC(CNC(=O)c2ccc3c(c2)NC(=O)c2cccn2S3(=O)=O)OC1=O]

Synthetic Route

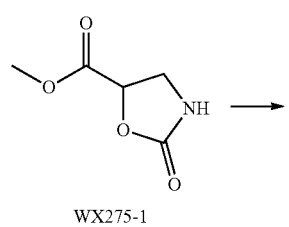

-continued

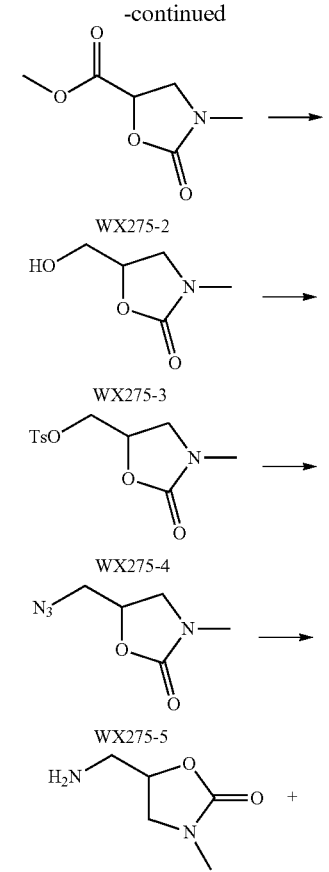

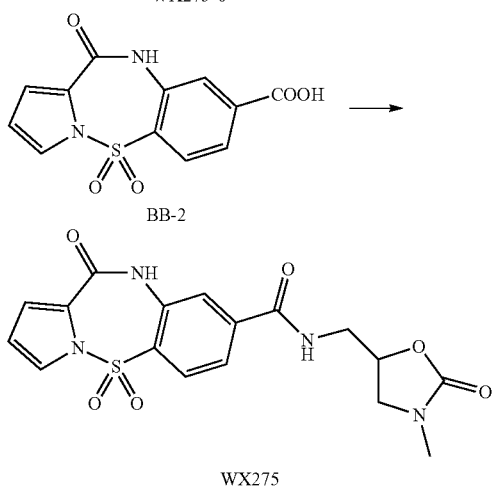

Step 1: Synthesis of Compound WX275-2

WX275-1 (7.9 g, 54.44 mmol) and DMF (80 mL) were added into a dry single-necked flask, followed by addition of Cs$_2$CO$_3$ (35.48 g, 108.88 mmol) and CH$_3$I (9.27 g, 65.33 mmol, 4.07 mL). The reaction mixture was purged with nitrogen gas for three times and stirred at 21° C. for 3 hours. 100 mL of ethyl acetate was added to the reaction system, and a large amount of solid was precipitated from the system. The mixture was filtered through diatomite. The filter cake was washed with 100 mL of ethyl acetate. The filtrate was collected and concentrated under reduced pressure to give WX275-2. ¹H NMR (400 MHz, CHLOROFORM-d) δ=4.88 (dd, J=5.5, 9.7 Hz, 1H), 3.84-3.76 (m, 4H), 3.61 (dd, J=5.5, 9.0 Hz, 1H), 2.86 (s, 3H).

Step 2: Synthesis of Compound WX275-3

WX275-2 (9 g, 56.55 mmol), MeOH (60 mL) and DCM (30 mL) were added into a pre-dried three-necked flask. The reaction mixture was purged with nitrogen gas for three times and then cooled to 0° C., followed by portionwise addition of NaBH₄ (2.78 g, 73.52 mmol, 1.3 eq) under nitrogen atmosphere while maintaining the temperature of the system at 0-5° C. After 30 minutes, the addition was completed and the mixture was stirred at 0° C. for 0.5 hour. The reaction was quenched by addition of 50 mL of saturated ammonium chloride. The reaction mixture was concentrated under reduced pressure to give a crude product. 100 mL of dichloromethane was added and the mixture was stirred for 10 minutes, followed by filtration to remove the insoluble materials. The filtrate was concentrated under reduced pressure to give WX 275-3. ¹H NMR (400 MHz, DMSO-d₆) δ=4.43 (br s, 1H), 3.49 (br dd, J=7.5, 17.4 Hz, 2H), 3.39-3.22 (m, 2H), 2.95 (br s, 1H), 2.72 (br s, 3H).

Step 3: Synthesis of Compound WX275-4

WX275-3 (0.5 g, 3.81 mmol) and DCM (5 mL) were added into a dry three-necked flask. The system was purged with nitrogen gas for three times, and cooled to 0° C., followed by addition of TEA (463.01 mg, 4.58 mmol, 636.87 µL) and TosCl (872.33 mg, 4.58 mmol) while maintaining the reaction temperature at 0-5° C. After completion of the addition, the reaction was carried out at 0° C. while stirring for 1 hour. The reaction was quenched by addition of 10 mL of water, and the mixture was extracted with ethyl acetate (10 mL*3). The organic phases were combined, washed with saturated brine (10 mL*2), dried over anhydrous sodium sulfate, and concentrated under reduced pressure to give a residue. The crude product was subjected to column chromatography to give WX275-4. ¹H NMR (400 MHz, CHLOROFORM-d) δ=7.79 (d, J=8.2 Hz, 2H), 7.38 (d, J=8.2 Hz, 2H), 4.66 (qd, J=4.8, 9.6 Hz, 1H), 4.23-4.07 (m, 2H), 3.64 (t, J=8.9 Hz, 1H), 3.42 (dd, J=6.2, 8.8 Hz, 1H), 2.86 (s, 3H), 2.47 (s, 3H).

Step 4: Synthesis of Compound WX275-5

WX275-4 (0.4 g, 1.40 mmol) and DMF (5 mL) were added into a dry single-necked flask, followed by addition of NaN₃ (546.85 mg, 8.41 mmol). The reaction mixture was purged with nitrogen gas for three times. The reaction was carried out at 65° C. while stirring for 16 hours. The reaction mixture was quenched by addition of 10 mL of water and extracted with ethyl acetate (10 mL*5). The organic phases were combined, dried over anhydrous sodium sulfate and concentrated to 5 mL under reduced pressure, followed by addition of 10 mL of ethanol. Such procedure was repeated 3 times, with 5 mL of ethanol solution left. The reaction mixture was directly used in the next step without further purification.

Step 5: Synthesis of Compound WX275-6

Compound WX275-5 (218 mg, 1.40 mmol) was dissolved in EtOH (5 mL), followed by addition of Pd/C (0.1 g, 5% purity). The reaction mixture was purged with H₂ for three times and pressurized to 15 psi, stirred at 40° C. for 24 hours, followed by filtration through diatomite. The filtrate was concentrated under reduced pressure to give WX275-6. ¹H NMR (400 MHz, CHLOROFORM-d) δ=4.53 (br s, 1H), 3.57 (br t, J=8.7 Hz, 1H), 3.31 (br t, J=7.6 Hz, 1H), 2.97-2.93 (m, 3H), 2.38 (br s, 2H).

Step 6: Synthesis of Compound WX275

The synthesis of compound WX275 was referred to the step 1 of the synthesis of WX189 in Embodiment 24. ¹H NMR (400 MHz, DMSO-d₆) δ=11.23 (s, 1H), 9.06 (br t, J=5.6 Hz, 1H), 8.13 (d, J=8.2 Hz, 1H), 7.89 (s, 1H), 7.81 (d, J=8.4 Hz, 1H), 7.61 (dd, J=1.7, 3.0 Hz, 1H), 7.15 (dd, J=1.8, 3.5 Hz, 1H), 6.54 (t, J=3.3 Hz, 1H), 4.69-4.57 (m, 1H), 3.62 (t, J=8.7 Hz, 1H), 3.53 (t, J=5.6 Hz, 2H), 3.30-3.26 (m, 1H), 2.73 (s, 3H).

Embodiment 58: WX278

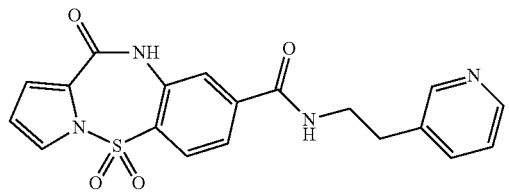 [SMILES: O=C(NCCc1cccnc1)c1ccc2c(c1)NC(=O)c1cccn1S2(=O)=O]

Synthetic Route

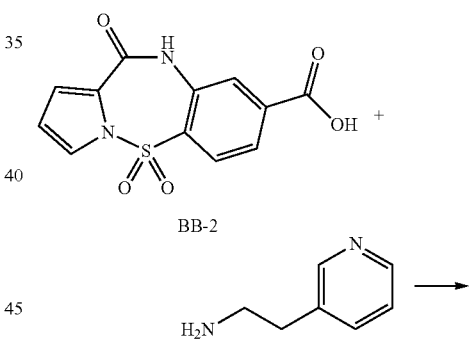

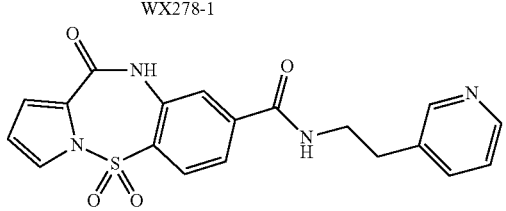

Step 1: Synthesis of Compound WX278

The synthesis of compound WX278 was referred to the step 1 of the synthesis of WX189 in Embodiment 24. ¹H NMR (400 MHz, DMSO-d₆) δ=11.25 (s, 1H), 8.98 (br t, J=5.6 Hz, 1H), 8.87 (s, 1H), 8.77 (br d, J=5.4 Hz, 1H), 8.45 (br d, J=7.9 Hz, 1H), 8.09 (d, J=8.3 Hz, 1H), 7.96 (dd, J=5.9, 7.8 Hz, 1H), 7.82 (s, 1H), 7.75 (br d, J=8.3 Hz, 1H), 7.62 (br d, J=1.6 Hz, 1H), 7.18-7.12 (m, 1H), 6.54 (t, J=3.3 Hz, 1H), 3.62 (br d, J=5.9 Hz, 2H), 3.07 (br t, J=6.3 Hz, 2H).

Embodiment 59: WX280

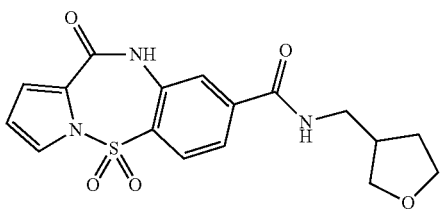 [SMILES: O=C(NCC1CCOC1)c1ccc2c(c1)NC(=O)c1cccn1S2(=O)=O]

Synthetic Route

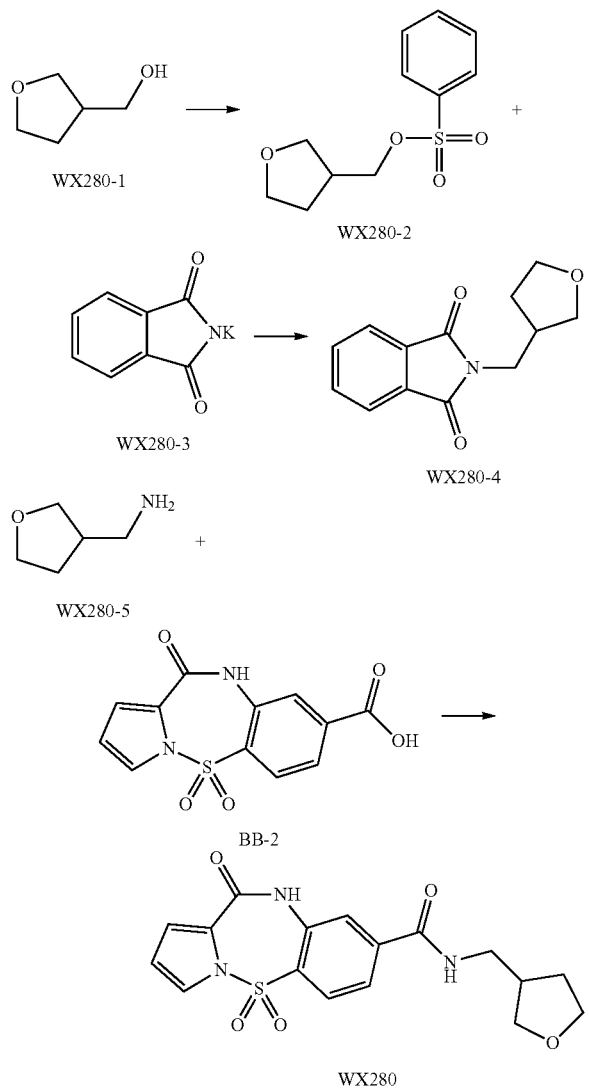

Step 1: Synthesis of Compound WX280-2

WX280-1 (2 g, 19.58 mmol, 1.89 mL) and DCM (10 mL) were added into a pre-dried three-necked flask. The reactor was purged with nitrogen gas for three times and then placed under an ice bath, followed by addition of p-toluenesulfonyl chloride (5.60 g, 29.37 mmol) and pyridine (10 mL) at 0° C. After completion of the addition, the reaction mixture was stirred at 25° C. for 2 hours. The reaction mixture was diluted with water (20 mL) and the aqueous phase was extracted with dichloromethane (3*50 mL). The organic phase was dried over anhydrous sodium sulfate, followed by filtration. The filtrate was concentrated under reduced pressure to remove the solvent to give WX280-2.

Step 2: Synthesis of Compound WX280-4

The raw material WX280-2 (1 g, 3.90 mmol) and DMF (10 mL) were added into a dry 50 mL three-necked flask, and WX280-3 (1.16 g, 6.24 mmol) was added to the reaction mixture. The reaction system was stirred at 100° C. for 12 hours. The reaction mixture was quenched with water (10 mL) and the aqueous phase was extracted with dichloromethane (3*20 mL). The organic phase was dried over anhydrous sodium sulfate, followed by filtration. The filtrate was concentrated under reduced pressure to remove the solvent to give a crude product. The crude product was purified by column chromatography to give WX280-4.

Step 3: Synthesis of Compound WX280-5

WX280-4 (400 mg, 1.71 mmol) and EtOH (5 mL) were added into a pre-dried vial. The mixture was mixed thoroughly, followed by addition of hydrazine hydrate (140.15 mg, 2.74 mmol, 136.07 μL). The reaction mixture was stirred at 70° C. for 0.5 hour. The reaction mixture turned from white to black, and then condensed into a white paste. The reaction system was cooled to room temperature, and then transferred into a 100 mL single-necked flask, followed by addition of 30 mL of ethanol. The mixture was stirred at room temperature for 0.5 hour, and then filtered. The filter cake was discarded, and the filtrate was evaporated to give WX280-5.

Step 4: Synthesis of Compound WX280

The synthesis of compound WX280 was referred to the step 1 of the synthesis of WX189 in Embodiment 24. $^1$H NMR (400 MHz, DMSO-$d_6$) δ 11.20 (s, 1H), 8.85 (br t, J=5.40 Hz, 1H), 8.10 (d, J=8.16 Hz, 1H), 7.87 (s, 1H), 7.79 (d, J=8.16 Hz, 1H), 7.60 (dd, J=1.76, 2.87 Hz, 1H), 7.14 (dd, J=1.54, 3.53 Hz, 1H), 6.53 (t, J=3.31 Hz, 1H), 3.56-3.77 (m, 3H), 3.45 (dd, J=5.29, 8.60 Hz, 1H), 3.20-3.28 (m, 2H), 2.40-2.47 (m, 1H), 1.87-1.98 (m, 1H), 1.53-1.63 (m, 1H).

Embodiment 60: WX288

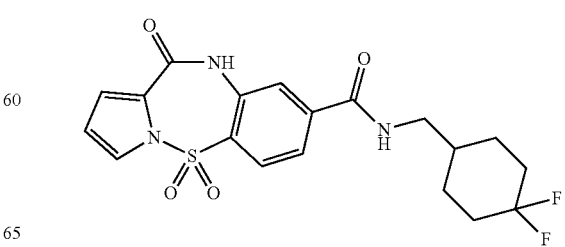

Synthetic Route

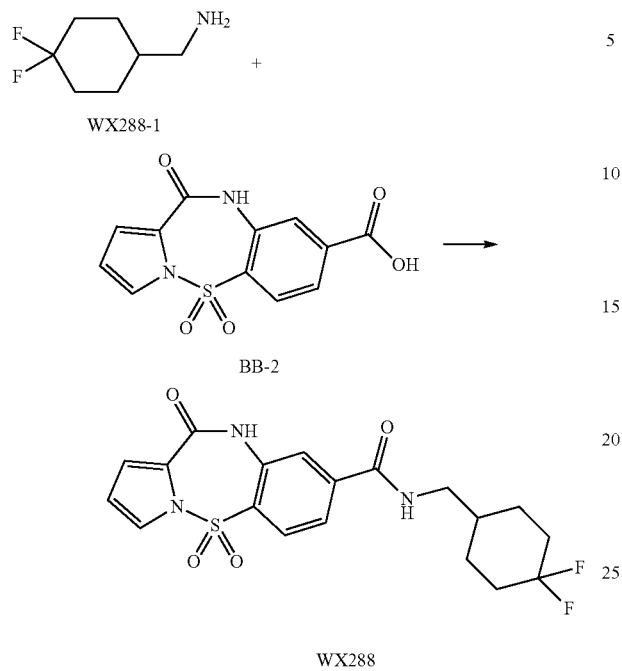

Step 1: Synthesis of Compound WX288

The synthesis of compound WX288 was referred to the step 1 of the synthesis of WX189 in Embodiment 24. $^1$H NMR (400 MHz, DMSO-$d_6$) δ 11.19 (s, 1H), 8.80 (br t, J=5.84 Hz, 1H), 8.10 (d, J=8.38 Hz, 1H), 7.87 (s, 1H), 7.79 (d, J=8.16 Hz, 1H), 7.60 (br s, 1H), 7.14 (dd, J=1.43, 3.42 Hz, 1H), 6.53 (t, J=3.31 Hz, 1H), 3.17 (t, J=6.17 Hz, 2H), 2.00 (br d, J=6.84 Hz, 2H), 1.61-1.86 (m, 5H), 1.12-1.28 (m, 2H).

Embodiment 61: WX292

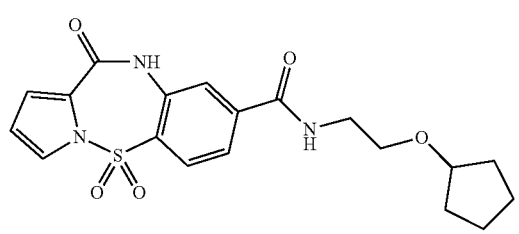 [SMILES: O=C(NCCOC1CCCC1)c1ccc2c(c1)NC(=O)c1cccn1S2(=O)=O]

Synthetic Route

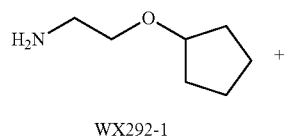

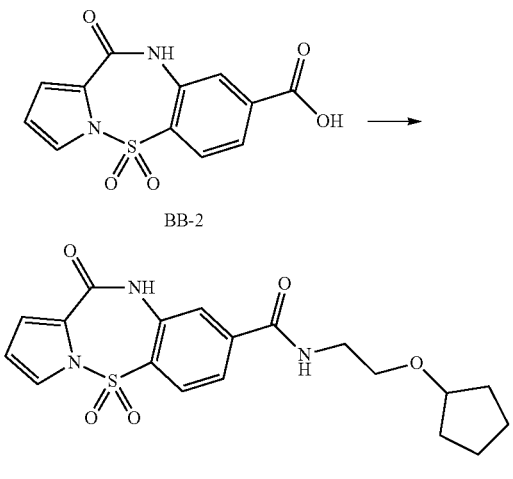

Step 1: Synthesis of Compound WX292

The synthesis of compound WX292 was referred to the step 1 of the synthesis of WX189 in Embodiment 24. $^1$H NMR (400 MHz, DMSO-$d_6$) δ 11.22 (s, 1H), 8.82-8.75 (m, 1H), 8.11 (d, J=8.2 Hz, 1H), 7.87 (s, 1H), 7.79 (d, J=8.2 Hz, 1H), 7.61 (dd, J=1.8, 3.1 Hz, 1H), 7.15 (dd, J=1.5, 3.5 Hz, 1H), 6.54 (t, J=3.4 Hz, 1H), 3.93-3.85 (m, 1H), 3.45 (d, J=5.3 Hz, 2H), 3.38 (br d, J=5.7 Hz, 2H), 1.69-1.51 (m, 6H), 1.49-1.41 (m, 2H).

Embodiment 62: WX293

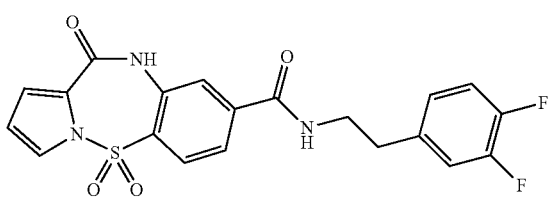 [SMILES: O=C(NCCc1ccc(F)c(F)c1)c1ccc2c(c1)NC(=O)c1cccn1S2(=O)=O]

Synthetic Route

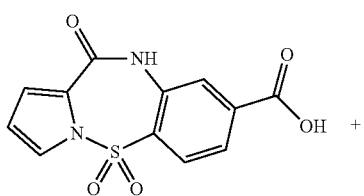

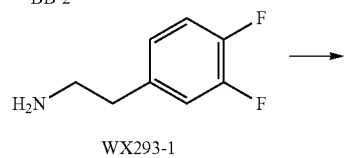

WX293

Step 1: Synthesis of Compound WX293

The synthesis of compound WX293 was referred to the step 1 of the synthesis of WX189 in Embodiment 24. $^1$H NMR (400 MHz, DMSO-d$_6$) δ 11.22 (s, 1H), 8.82 (s, 1H), 8.10 (d, J=8.4 Hz, 1H), 7.84 (s, 1H), 7.74 (d, J=8.4 Hz, 1H), 7.61 (dd, J=1.7, 2.8 Hz, 1H), 7.36-7.27 (m, 2H), 7.15 (dd, J=1.7, 3.4 Hz, 1H), 7.09-7.03 (m, 1H), 6.56-6.52 (m, 1H), 3.50 (br d, J=6.0 Hz, 2H), 2.84 (br t, J=6.8 Hz, 2H).

Embodiment 63: WX295

WX295

Synthetic Route

BB-2

WX295-1

WX295

Step 1: Synthesis of Compound WX295

The synthesis of compound WX295 was referred to the step 1 of the synthesis of WX189 in Embodiment 24. $^1$H NMR (400 MHz, DMSO-d$_6$) δ 11.24 (s, 1H), 9.14 (br t, J=5.4 Hz, 1H), 8.66 (d, J=2.6 Hz, 1H), 8.47 (d, J=5.1 Hz, 1H), 8.14-8.05 (m, 2H), 7.94-7.80 (m, 3H), 7.59 (dd, J=1.5, 2.9 Hz, 1H), 7.13 (dd, J=1.5, 3.5 Hz, 1H), 6.52 (t, J=3.3 Hz, 1H), 4.37 (br t, J=5.4 Hz, 2H), 3.68 (q, J=5.3 Hz, 2H).

Embodiment 64: WX297

WX297-1

WX297-2

WX297-3

WX297-4

WX297-5

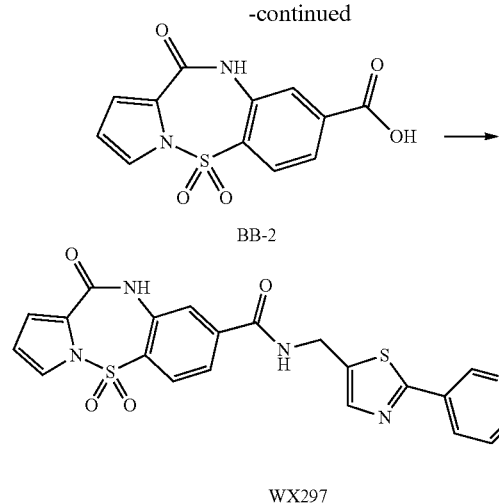

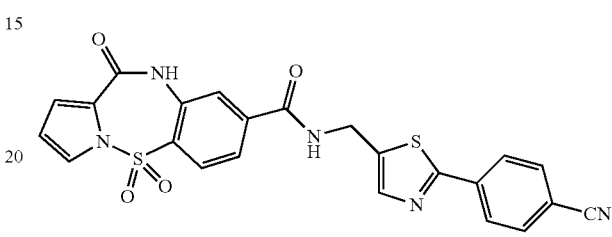

Step 1: Synthesis of Compound WX297-2

WX297-1 (2 g, 13.46 mmol) was dissolved in DCM (20 mL), and then triethylamine (4.09 g, 40.37 mmol, 5.62 mL) and (Boc)$_2$O (3.52 g, 16.15 mmol, 3.71 mL) were added thereto. The reaction mixture was stirred at 30° C. for 12 hours. After the reaction mixture was quenched with water (10 mL), the aqueous phase was extracted with dichloromethane (3*20 mL). The organic phase was dried over anhydrous sodium sulfate, followed by filtration. The filtrate was concentrated under reduced pressure to remove the solvent to give a crude product. The crude product was isolated by column chromatography to give WX297-2.

Step 2: Synthesis of Compound WX297-4

WX297-2 (836.83 mg, 3.36 mmol), dioxane (5 mL) and water (1.5 mL) were added into a pre-dried 50 mL single-necked flask, and then K$_2$CO$_3$ (1.16 g, 8.41 mmol) and WX297-3 (834.81 mg, 3.36 mmol) were added, followed by addition of tetrakis(triphenylphosphine)palladium (388.78 mg, 336.44 μmol) under nitrogen atmosphere. The reaction mixture was stirred at 100° C. for 12 hours. After the reaction mixture was quenched with water (5 mL), the aqueous phase was extracted with ethyl acetate (3*10 mL). The organic phase was dried over anhydrous sodium sulfate, followed by filtration. The filtrate was concentrated under reduced pressure to remove the solvent to give a crude product. The crude product was subjected to column chromatography to give WX297-4.

Step 3: Synthesis of Compound WX297-5

WX297-4 (900 mg, 2.69 mmol) and EtOAc (10 mL) were added into a pre-dried vial, followed by addition of HCl/EtOAc (4 M, 20 mL) under nitrogen atmosphere. The mixture was stirred at 25° C. for 0.5 hour. The reaction mixture was directly evaporated to give WX297-5.

Step 4: Synthesis of Compound WX297

BB-2 (80.17 mg, 342.15 μmol), EDCI (98.39 mg, 513.22 μmol), DIPEA (88.44 mg, 684.30 μmol, 119.19 μL), HOBt (69.35 mg, 513.22 μmol) and DMF (2 mL) were added into a pre-dried vial, followed by addition of WX297-5 (100 mg, 342.15 μmol) at 0° C. The reaction mixture was stirred at 25° C. for 12 hours under nitrogen atmosphere. The reaction mixture was filtered to give a crude product. The crude product was isolated by HPLC to give WX297. $^1$H NMR (400 MHz, DMSO-d$_6$) δ 11.22 (s, 1H), 9.60 (br t, J=5.73 Hz, 1H), 8.41 (d, J=1.98 Hz, 1H), 8.22 (br d, J=8.82 Hz, 1H), 8.11 (d, J=8.38 Hz, 1H), 7.92 (s, 1H), 7.78-7.86 (m, 2H), 7.56-7.62 (m, 1H), 7.13 (dd, J=1.54, 3.53 Hz, 2H), 6.52 (t, J=3.31 Hz, 1H), 4.68 (br d, J=5.51 Hz, 2H), 3.22 (s, 6H).

Embodiment 65: WX298

Synthetic Route

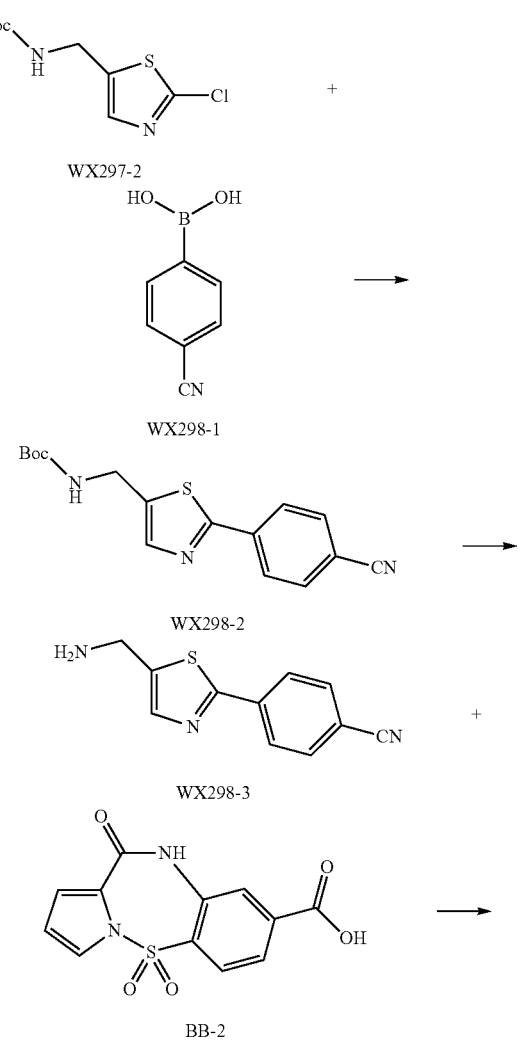

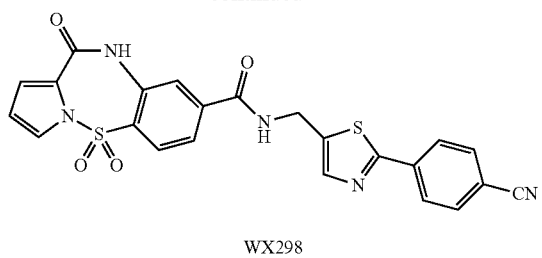

WX298

Step 1: Synthesis of Compound WX298-2

WX297-2 (850.83 mg, 3.42 mmol), water (1.5 mL) and DME (5 mL) were added into a pre-dried 50 mL single-necked flask, and then $K_2CO_3$ (1.18 g, 8.55 mmol) and WX298-1 (502.63 mg, 3.42 mmol) were added, followed by addition of Pd(dppf)Cl$_2$ (250.30 mg, 342.07 μmol) under nitrogen atmosphere. The reaction mixture was stirred at 100° C. for 12 hours. After the reaction mixture was quenched with water (5 mL), the aqueous phase was extracted with ethyl acetate (3*100 mL). The organic phase was dried over anhydrous sodium sulfate, followed by filtration. The filtrate was concentrated under reduced pressure to remove the solvent to give a crude product. The crude product was subjected to column chromatography to give WX298-2 (0.8 g, 2.54 mmol).

Step 2: Synthesis of Compound WX298-3

The synthesis of compound WX298-3 was referred to the step 3 of the synthesis of WX297-5 in Embodiment 64.

Step 3: Synthesis of Compound WX298

The synthesis of compound WX298 was referred to the step 1 of the synthesis of WX189 in Embodiment 24. $^1$H NMR (400 MHz, DMSO-d$_6$) δ 11.21 (s, 1H), 9.55 (br t, J=5.62 Hz, 1H), 8.11 (d, J=8.38 Hz, 1H), 8.06 (d, J=8.38 Hz, 2H), 7.90-7.94 (m, 4H), 7.81 (d, J=8.38 Hz, 1H), 7.59 (dd, J=1.65, 2.98 Hz, 1H), 7.13 (dd, J=1.54, 3.53 Hz, 1H), 6.52 (t, J=3.31 Hz, 1H), 4.72 (d, J=5.73 Hz, 2H).

Embodiment 66: WX299

Synthetic Route

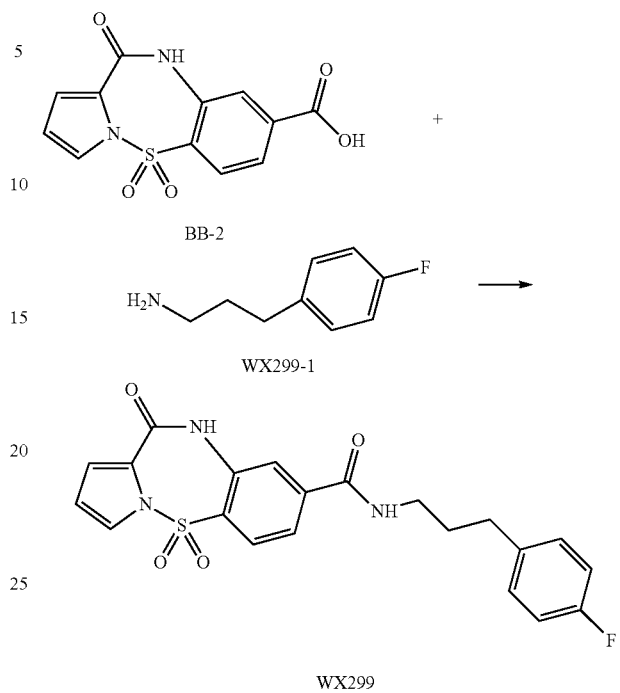

Step 1: Synthesis of Compound WX299

The synthesis of compound WX299 was referred to the step 1 of the synthesis of WX189 in Embodiment 24. $^1$H NMR (400 MHz, DMSO-d$_6$) δ 11.22 (s, 1H), 8.78 (br t, J=5.3 Hz, 1H), 8.10 (d, J=8.3 Hz, 1H), 7.88 (d, J=1.1 Hz, 1H), 7.79 (dd, J=1.4, 8.4 Hz, 1H), 7.61 (dd, J=1.7, 3.1 Hz, 1H), 7.25 (dd, J=5.7, 8.5 Hz, 2H), 7.15 (dd, J=1.7, 3.6 Hz, 1H), 7.13-7.06 (m, 2H), 6.54 (t, J=3.4 Hz, 1H), 3.29-3.23 (m, 2H), 2.61 (br t, J=7.7 Hz, 2H), 1.80 (q, J=7.3 Hz, 2H).

Embodiment 67: WX300

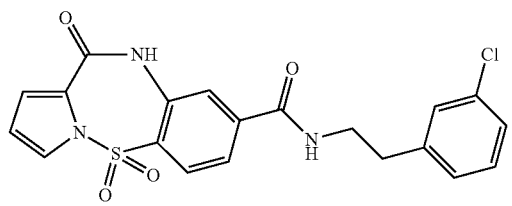 [SMILES: O=C(NCCc1cccc(Cl)c1)c1ccc2c(c1)NC(=O)c1cccn1S2(=O)=O]

Synthetic Route

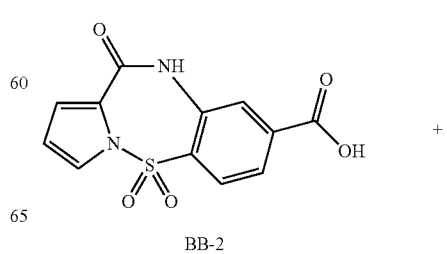

BB-2

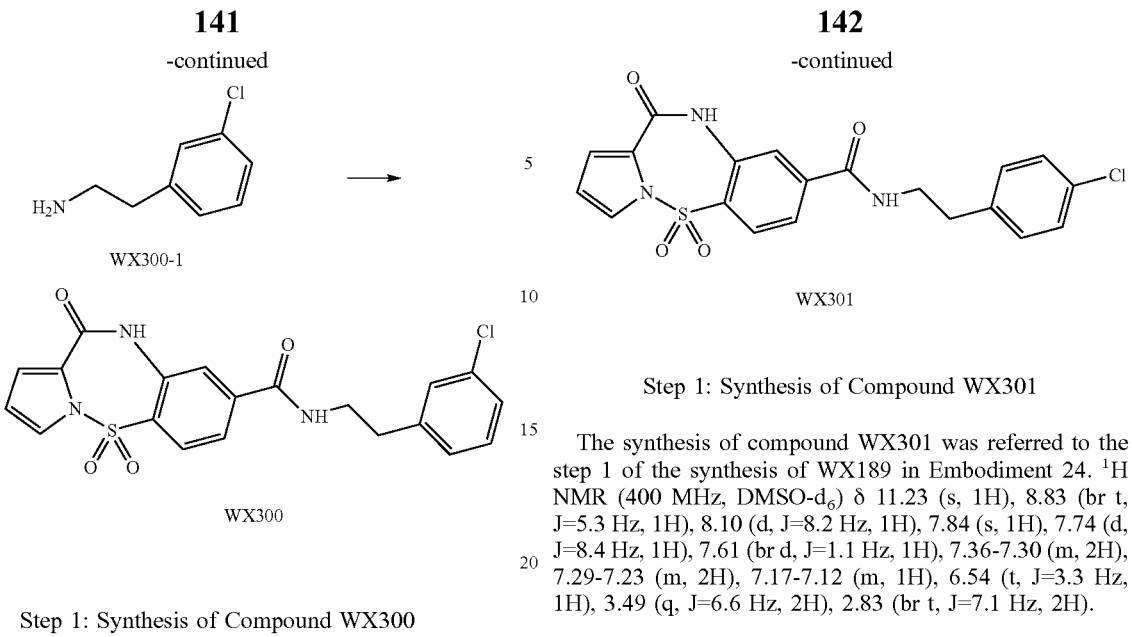

WX300-1

WX300

Step 1: Synthesis of Compound WX300

The synthesis of compound WX300 was referred to the step 1 of the synthesis of WX189 in Embodiment 24. $^1$H NMR (400 MHz, DMSO-$d_6$) δ 11.22 (s, 1H), 8.85 (br t, J=5.4 Hz, 1H), 8.10 (d, J=8.2 Hz, 1H), 7.85 (s, 1H), 7.75 (d, J=8.4 Hz, 1H), 7.61 (dd, J=1.7, 2.8 Hz, 1H), 7.34-7.28 (m, 2H), 7.27-7.23 (m, 1H), 7.19 (d, J=7.3 Hz, 1H), 7.15 (dd, J=1.5, 3.5 Hz, 1H), 6.54 (t, J=3.3 Hz, 1H), 3.55-3.46 (m, 2H), 2.85 (t, J=7.2 Hz, 2H).

Embodiment 68: WX301

Synthetic Route

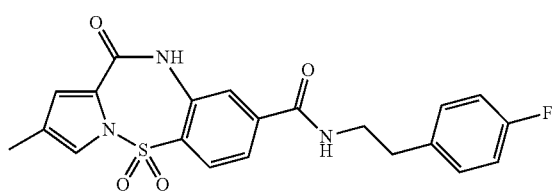 [SMILES: Cc1cc2n(c1)S(=O)(=O)c1ccc(C(=O)NCCc3ccc(F)cc3)cc1NC2=O]

WX301

Step 1: Synthesis of Compound WX301

The synthesis of compound WX301 was referred to the step 1 of the synthesis of WX189 in Embodiment 24. $^1$H NMR (400 MHz, DMSO-$d_6$) δ 11.23 (s, 1H), 8.83 (br t, J=5.3 Hz, 1H), 8.10 (d, J=8.2 Hz, 1H), 7.84 (s, 1H), 7.74 (d, J=8.4 Hz, 1H), 7.61 (br d, J=1.1 Hz, 1H), 7.36-7.30 (m, 2H), 7.29-7.23 (m, 2H), 7.17-7.12 (m, 1H), 6.54 (t, J=3.3 Hz, 1H), 3.49 (q, J=6.6 Hz, 2H), 2.83 (br t, J=7.1 Hz, 2H).

Embodiment 69: WX305

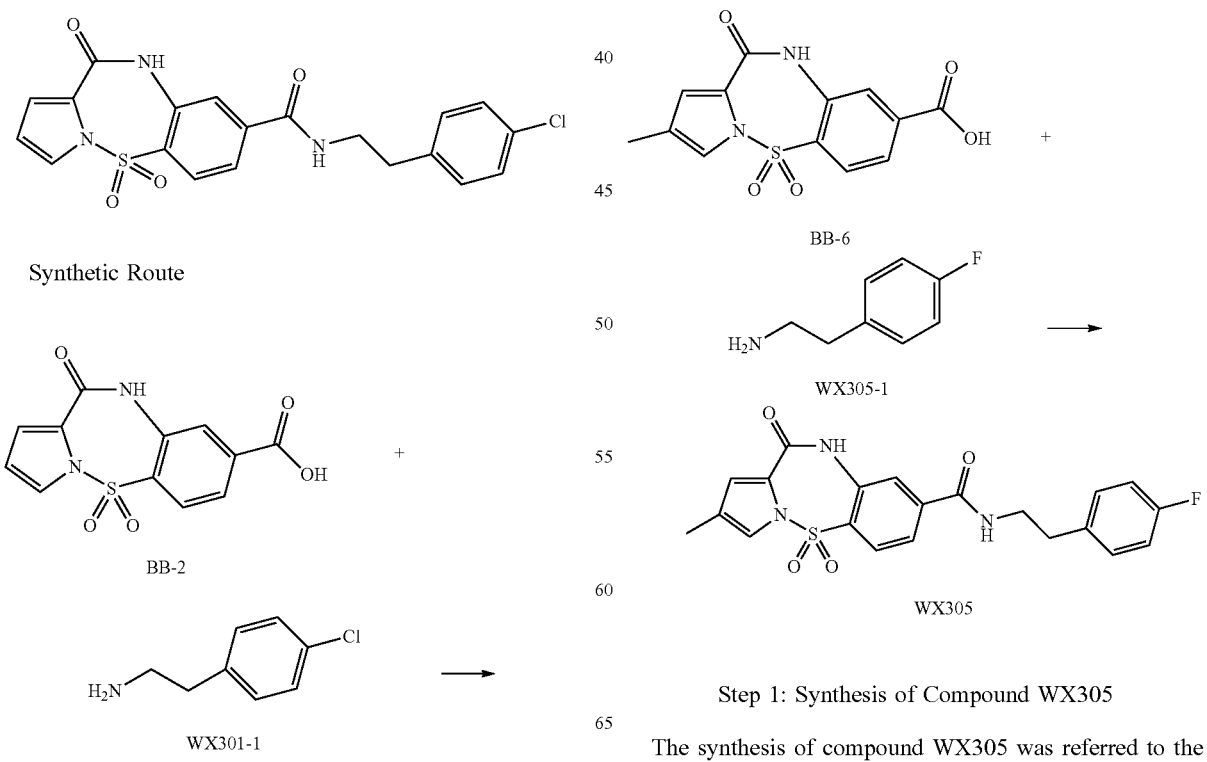

Synthetic Route

Step 1: Synthesis of Compound WX305

The synthesis of compound WX305 was referred to the step 1 of the synthesis of WX189 in Embodiment 24. $^1$H NMR (400 MHz, DMSO-d$_6$) δ 11.12 (s, 1H), 8.79 (t, J=5.4 Hz, 1H), 8.04 (d, J=8.4 Hz, 1H), 7.80 (s, 1H), 7.71 (d, J=8.4 Hz, 1H), 7.36 (s, 1H), 7.23 (dd, J=5.7, 8.6 Hz, 2H), 7.07 (t, J=8.9 Hz, 2H), 6.97 (d, J=1.3 Hz, 1H), 3.45 (q, J=6.8 Hz, 2H), 2.80 (t, J=7.2 Hz, 2H), 2.02 (s, 3H).

Embodiment 70: WX306

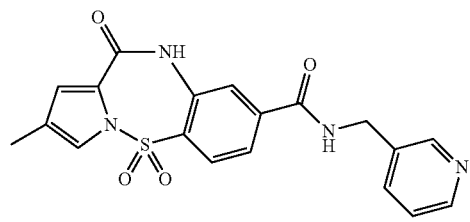 [SMILES: Cc1cc2n(c1)S(=O)(=O)c1ccc(C(=O)NCc3cccnc3)cc1NC2=O]

Synthetic Route

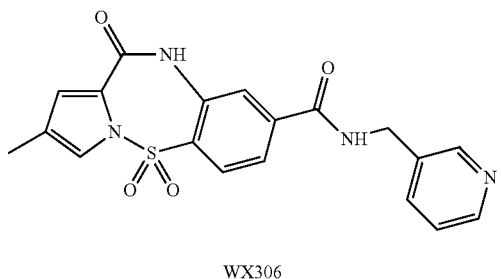

BB-6

WX306-1

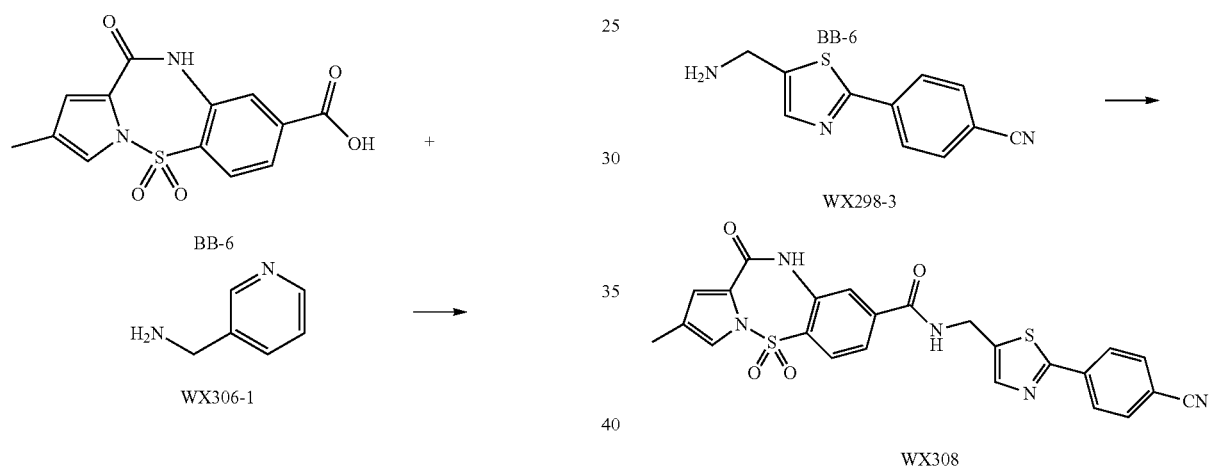

WX306

Step 1: Synthesis of Compound WX306

The synthesis of compound WX306 was referred to the step 1 of the synthesis of WX189 in Embodiment 24. $^1$H NMR (400 MHz, DMSO-d$_6$) δ 11.16 (s, 1H), 9.38 (t, J=5.8 Hz, 1H), 8.56 (d, J=1.8 Hz, 1H), 8.47 (dd, J=1.5, 4.8 Hz, 1H), 8.10 (d, J=8.3 Hz, 1H), 7.91 (d, J=1.4 Hz, 1H), 7.83 (dd, J=1.6, 8.3 Hz, 1H), 7.72 (d, J=7.3 Hz, 1H), 7.43-7.34 (m, 2H), 7.01 (d, J=1.8 Hz, 1H), 4.51 (d, J=5.8 Hz, 2H), 2.5 (s, 3H).

Embodiment 71: WX308

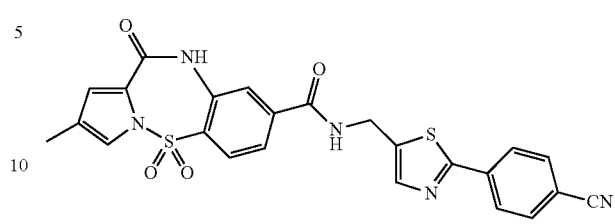

Synthetic Route

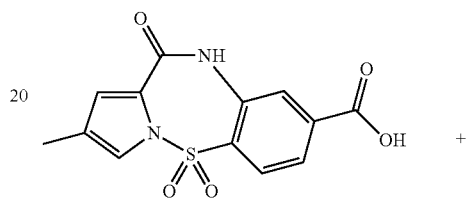

BB-6

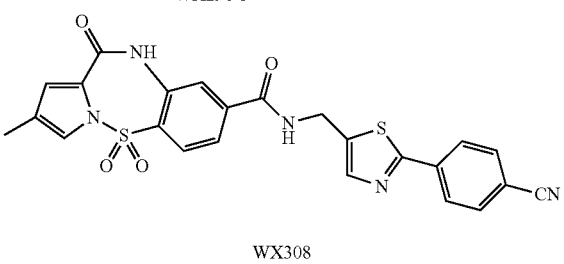

WX298-3

WX308

Step 1: Synthesis of Compound WX308

The synthesis of compound WX308 was referred to the step 1 of the synthesis of WX189 in Embodiment 24. $^1$H NMR (400 MHz, DMSO-d$_6$) δ 11.15 (s, 1H), 9.56 (s, 1H), 8.14-8.03 (m, 3H), 7.97-7.90 (m, 4H), 7.81 (d, J=7.3 Hz, 1H), 7.39 (s, 1H), 7.01 (s, 1H), 4.73 (d, J=5.5 Hz, 2H), 2.05 (s, 3H).

Embodiment 72: WX309

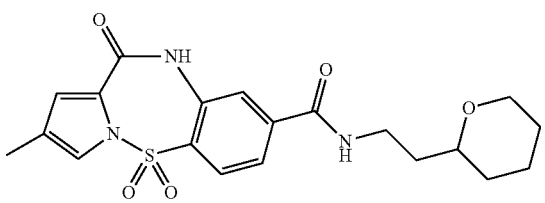 [SMILES: Cc1cc2n(c1)S(=O)(=O)c1ccc(C(=O)NCCC3CCCCO3)cc1NC2=O]

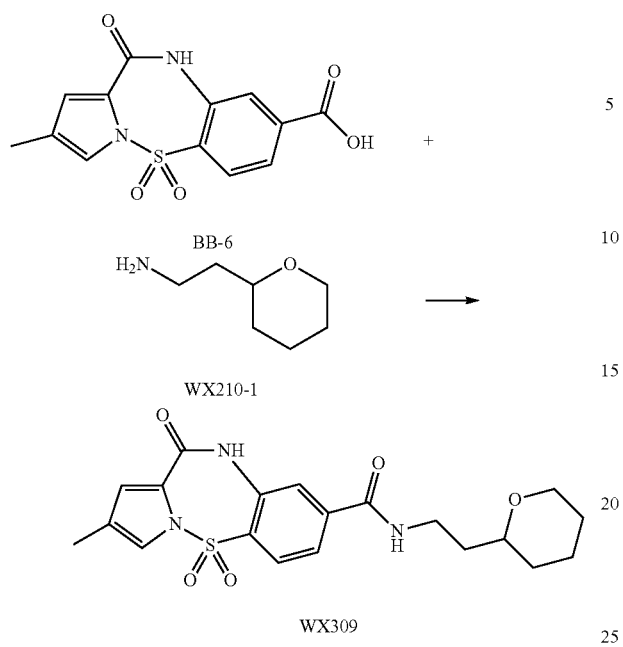

BB-6

WX210-1

WX309

Step 1: Synthesis of Compound WX309

The synthesis of compound WX309 was referred to the step 1 of the synthesis of WX189 in Embodiment 24. $^1$H NMR (400 MHz, DMSO-$d_6$) δ=11.14 (s, 1H), 8.72 (s, 1H), 8.07 (d, J=8.3 Hz, 1H), 7.85 (s, 1H), 7.77 (d, J=8.0 Hz, 1H), 7.39 (s, 1H), 7.00 (s, 1H), 3.86 (d, J=10.3 Hz, 1H), 3.32-3.22 (m, 4H), 2.05 (s, 3H), 1.74 (s, 1H), 1.66-1.53 (m, 3H), 1.43 (s, 3H), 1.24-1.13 (m, 1H).

Embodiment 73: WX311

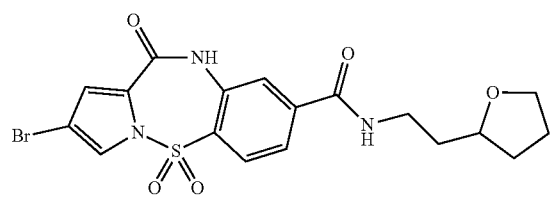 [SMILES: O=C(NCCC1CCCO1)c1ccc2c(c1)NC(=O)c1cc(Br)cn1S2(=O)=O]

Synthetic Route

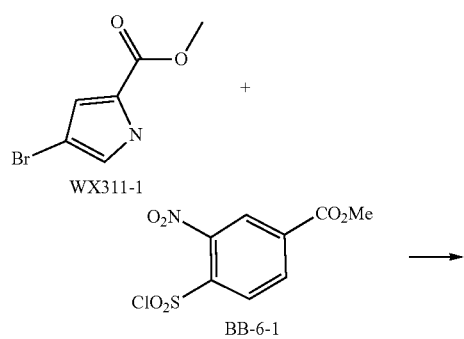

WX311-1

BB-6-1

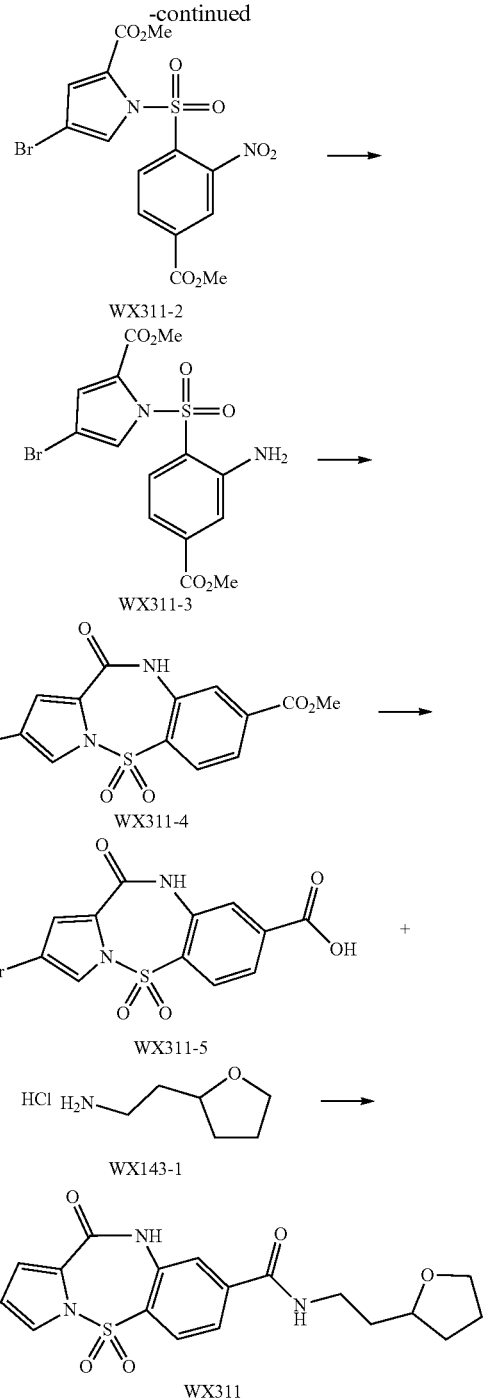

WX311-2

WX311-3

WX311-4

WX311-5

WX143-1

WX311

Step 1: Synthesis of Compound WX311-2

The synthesis of compound WX311-2 was referred to the step 1 of the synthesis of BB-6-2 in Reference fraction 6. $^1$H NMR (400 MHz, CHLOROFORM-d) δ=8.49 (s, 1H), 8.44 (s, 2H), 7.70 (d, J=1.8 Hz, 1H), 7.11 (d, J=1.8 Hz, 1H), 4.03 (s, 3H), 3.75 (s, 3H).

Step 2: Synthesis of Compound WX311-3

The synthesis of compound WX311-3 was referred to the step 1 of the synthesis of BB-6-3 in Reference fraction 6. $^1$H NMR (400 MHz, DMSO-d$_6$) δ=8.28 (d, J=2.0 Hz, 1H), 7.85 (d, J=8.5 Hz, 1H), 7.50 (d, J=1.3 Hz, 1H), 7.19-7.18 (m, 1H), 7.16 (dd, J=1.5, 8.5 Hz, 1H), 6.55 (br s, 2H), 3.83 (s, 3H), 3.67 (s, 3H).

Step 3: Synthesis of Compound WX311-4

The synthesis of compound WX311-4 was referred to the step 1 of the synthesis of BB-6-4 in Reference fraction 6. $^1$H NMR (400 MHz, DMSO-d$_6$) δ=11.44 (s, 1H), 8.16 (d, J=8.3 Hz, 1H), 8.04 (d, J=1.3 Hz, 1H), 7.94 (dd, J=1.5, 8.3 Hz, 1H), 7.88 (d, J=2.0 Hz, 1H), 7.25 (d, J=1.8 Hz, 1H), 3.91 (s, 3H).

Step 4: Synthesis of Compound WX311-5

WX311-4 (300 mg, 778.84 μmol, 1 eq) was dissolved in dioxane (5.0 mL), followed by addition of 6 M diluted hydrochloric acid (5.0 mL). The reaction mixture was stirred at 50° C. for 48 hours, and then concentrated under reduced pressure, followed by extraction. The organic phase was collected, dried over anhydrous sodium sulfate, followed by filtration. The filtrate was concentrated under reduced pressure. The crude product was subjected to column chromatograph to give WX311-5. $^1$H NMR (400 MHz, DMSO-d$_6$) δ=11.47 (s, 1H), 8.33-8.07 (m, 2H), 8.06-7.98 (m, 2H), 7.85 (s, 1H), 7.22 (s, 1H).

Step 5: Synthesis of Compound WX311

The synthesis of compound WX311 was referred to the step 1 of the synthesis of WX189 in Embodiment 24. $^1$H NMR (400 MHz, DMSO-d$_6$) δ=11.34 (s, 1H), 8.76 (t, J=5.5 Hz, 1H), 8.07 (d, J=8.2 Hz, 1H), 7.83 (dd, J=1.7, 6.5 Hz, 2H), 7.77 (dd, J=1.5, 8.4 Hz, 1H), 7.19 (d, J=1.8 Hz, 1H), 3.78-3.68 (m, 2H), 3.55 (dt, J=6.4, 7.9 Hz, 1H), 3.29-3.23 (m, 2H), 1.97-1.88 (m, 1H), 1.82-1.73 (m, 2H), 1.66 (q, J=7.1 Hz, 2H), 1.45-1.30 (m, 1H).

Embodiment 74: WX312

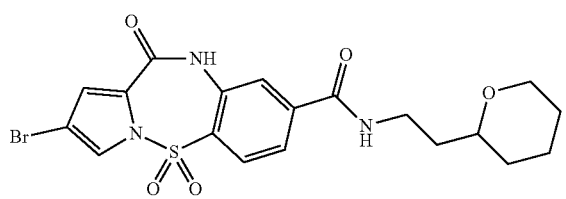 [SMILES: O=C(NCCC1CCCCO1)c1ccc2c(c1)NC(=O)c1cc(Br)cn1S2(=O)=O]

Synthetic Route

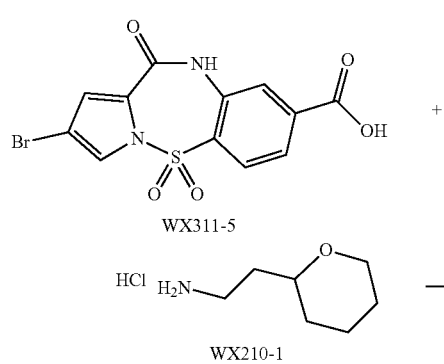

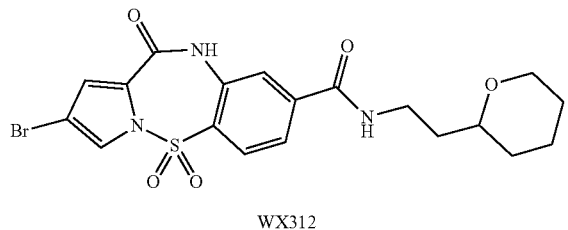

WX312

Step 1: Synthesis of Compound WX312

The synthesis of compound WX312 was referred to the step 1 of the synthesis of WX189 in Embodiment 24. $^1$H NMR (400 MHz, DMSO-d$_6$) δ=11.38 (s, 1H), 8.75 (br t, J=5.5 Hz, 1H), 8.11 (d, J=8.3 Hz, 1H), 7.87 (dd, J=1.6, 4.0 Hz, 2H), 7.81 (dd, J=1.4, 8.3 Hz, 1H), 7.23 (d, J=1.9 Hz, 1H), 3.90-3.83 (m, 1H), 3.33-3.23 (m, 4H), 1.75 (br d, J=3.6 Hz, 1H), 1.66-1.56 (m, 3H), 1.47-1.46 (m, 1H), 1.44 (br s, 2H), 1.24-1.13 (m, 1H).

Embodiment 75: WX221 and WX222

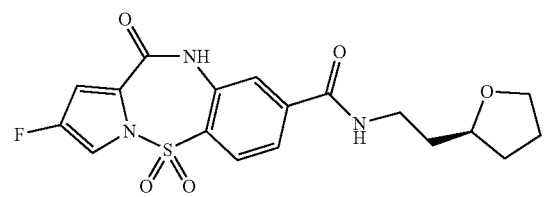

WX221 or WX222

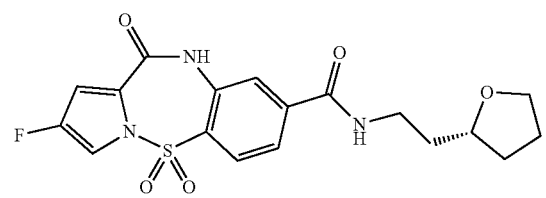

WX222 or WX221

Synthetic Route

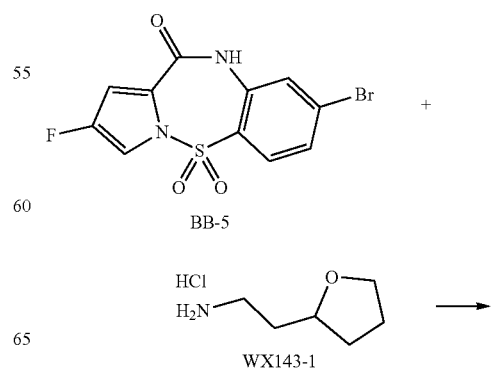

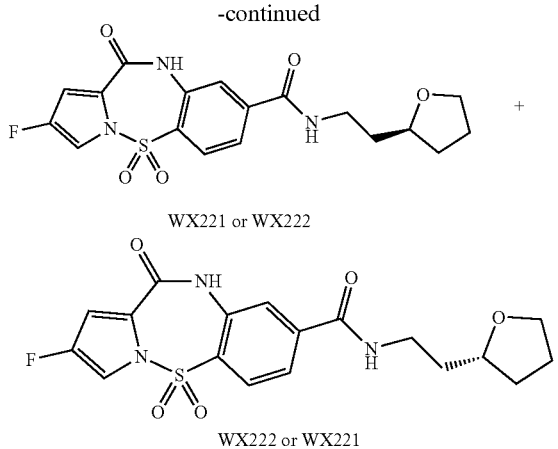

WX221 or WX222

WX222 or WX221

Step 1: Synthesis of Compound WX221 and WX222

Compound BB-5 (100 mg, 289.73 μmol), compound WX143-1 (65.90 mg, 434.60 μmol), Pd(dppf)Cl$_2$ (21.20 mg, 28.97 μmol), Et$_3$N (73.29 mg, 724.33 μmol, 100.82 μL) and DMF (5 mL) were added into a dry hydrogenation flask. The reaction mixture was purged with CO gas for three times, pressurized to 50 psi and stirred under an oil bath at 80° C. for 16 hours. 400 mg of silica gel for removing palladium was added and the mixture was stirred at 25° C. for 12 hours, followed by filtration. The filtrate was concentrated under reduced pressure, and the concentrated filtrate was purified by prep-HPLC to give a racemic mixture. The racemic mixture was isolated by SFC to give WX221 and WX222.

Compound WX221: $^1$H NMR (400 MHz, DMSO-d$_6$) δ=8.83-8.76 (m, 1H), 8.10 (d, J=8.3 Hz, 1H), 7.88 (s, 1H), 7.81 (d, J=8.3 Hz, 1H), 7.73 (br s, 1H), 7.15 (d, J=1.9 Hz, 1H), 3.83-3.70 (m, 2H), 3.66-3.54 (m, 1H), 3.32-3.25 (m, 2H), 2.03-1.91 (m, 1H), 1.80 (dd, J=6.9, 14.2 Hz, 2H), 1.69 (m, 2H), 1.47-1.35 (m, 1H);

Compound WX222: $^1$H NMR (400 MHz, DMSO-d$_6$) δ=8.79 (t, J=5.4 Hz, 1H), 8.10 (d, J=8.3 Hz, 1H), 7.88 (d, J=1.4 Hz, 1H), 7.81 (dd, J=1.5, 8.3 Hz, 1H), 7.73 (dd, J=2.1, 3.4 Hz, 1H), 7.15 (d, J=2.0 Hz, 1H), 3.82-3.71 (m, 2H), 3.63-3.55 (m, 1H), 3.32-3.26 (m, 2H), 2.01-1.91 (m, 1H), 1.86-1.76 (m, 2H), 1.69 (m, 2H), 1.47-1.36 (m, 1H).

Chiral resolution conditions: chiral column: AD (250 mm*30 mm, 5 μm); mobile phase: [Neu-MeOH]; B %: 48%-48%.

Retention time of compound 222: 6.62 min (peak 2); retention time of compound 221: 5.70 min (peak 1).

Embodiment 76: WX279

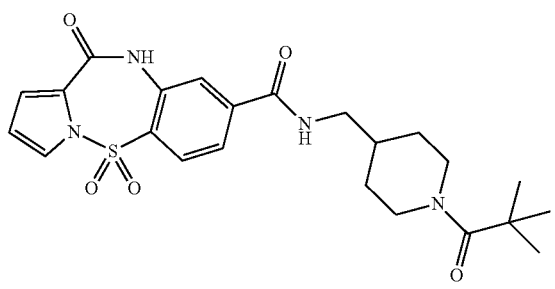 [SMILES: CC(C)(C)C(=O)N1CCC(CNC(=O)c2ccc3c(c2)NC(=O)c2cccn2S3(=O)=O)CC1]

Synthetic Route

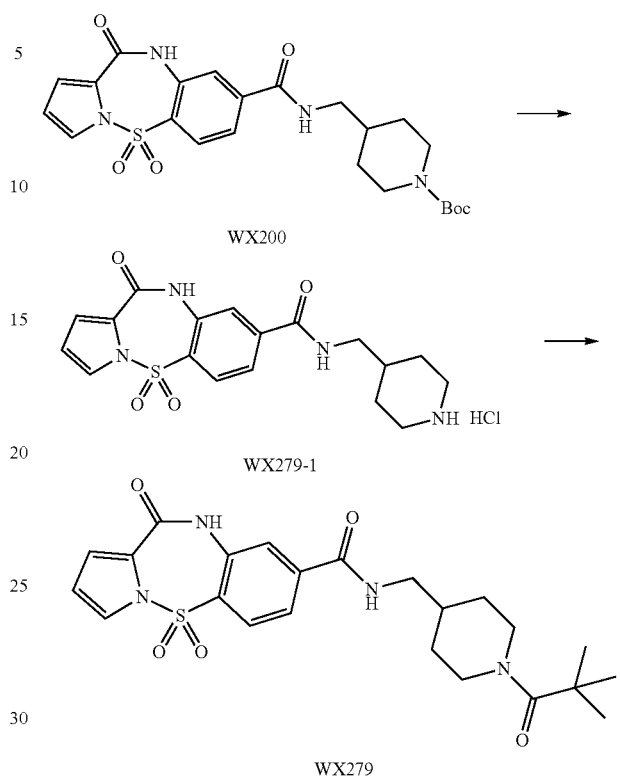

Step 1: Synthesis of Compound WX279-1

WX200 (1 g, 2.05 mmol) was added to HCl/EtOAc (50 mL). The reaction was carried out at 20° C. while stirring for 2 hours. The reaction mixture was filtered, and the filter cake was collected to give WX279-1. $^1$H NMR (400 MHz, DMSO-d$_6$) δ=11.21 (s, 1H), 8.90 (br s, 2H), 8.66-8.53 (m, 1H), 8.10 (d, J=8.2 Hz, 1H), 7.89 (s, 1H), 7.82 (br d, J=8.2 Hz, 1H), 7.60 (dd, J=1.8, 2.9 Hz, 1H), 7.14 (dd, J=1.8, 3.5 Hz, 1H), 6.53 (t, J=3.3 Hz, 1H), 3.17 (br t, J=6.0 Hz, 2H), 2.84-2.78 (m, 2H), 1.79 (br d, J=12.1 Hz, 5H), 1.36 (br d, J=12.1 Hz, 3H).

Step 2: Synthesis of Compound WX279

WX279-1 (100 mg, 235.35 μmol), pivaloyl chloride (31.22 mg, 258.89 μmol, 31.85 μL) and DCM (2 mL) were added into a dry flask, followed by addition of TEA (47.63 mg, 470.70 μmol, 65.52 μL). The reaction mixture was purged with nitrogen gas for three times, and stirred at 20° C. for 12 hours. The reaction mixture was filtered to give a crude product. The crude product was isolated to give WX279.

$^1$H NMR (400 MHz, DMSO-d$_6$) δ=11.21 (s, 1H), 8.81 (br t, J=5.5 Hz, 1H), 8.10 (d, J=8.3 Hz, 1H), 7.87 (s, 1H), 7.79 (d, J=8.3 Hz, 1H), 7.62 (dd, J=1.8, 3.0 Hz, 1H), 7.15 (dd, J=1.6, 3.5 Hz, 1H), 6.54 (t, J=3.4 Hz, 1H), 4.25 (br d, J=12.8 Hz, 2H), 3.16 (br t, J=6.2 Hz, 2H), 2.74 (br t, J=12.4 Hz, 2H), 1.81 (br s, 1H), 1.69 (br d, J=12.9 Hz, 2H), 1.17 (s, 9H), 1.10-0.94 (m, 2H).

Embodiment 77: WX285

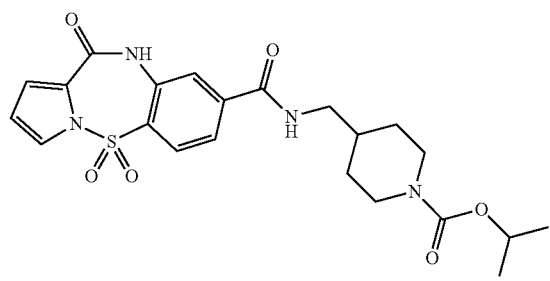 [SMILES: CC(C)CC(=O)N1CCC(CNC(=O)c2ccc3c(c2)NC(=O)c2cccn2S3(=O)=O)CC1]

Synthetic Route

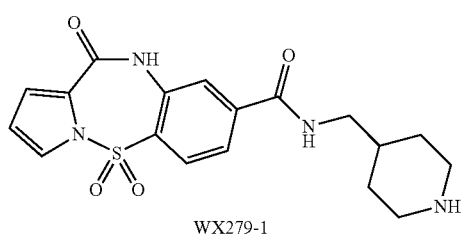

WX279-1

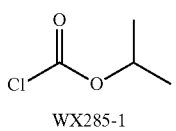

WX285-1

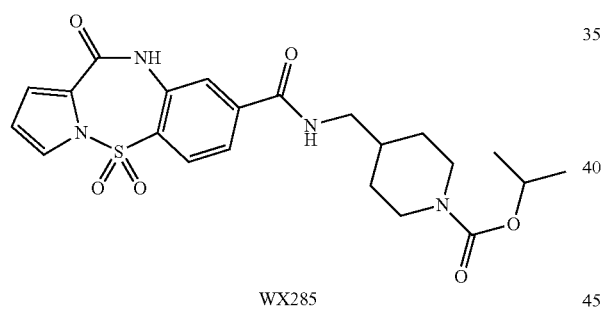

WX285

Step 1: Synthesis of Compound WX285

WX279-1 (90 mg, 211.81 μmol) and DMF (1 mL) were added into a pre-dried vial, followed by addition of Et$_3$N (32.15 mg, 317.72 μmol, 44.22 μL). After stirring for 30 minutes, the reaction system was cooled to 0° C., followed by addition of WX285-1 (25.96 mg, 211.81 μmol, 29.40 μL). The reaction mixture was heated to 25° C. under nitrogen atmosphere and stirred for 10 hours. The reaction mixture was filtered to give a crude product. The crude product was isolated to give WX285. $^1$H NMR (400 MHz, DMSO-d$_6$) δ=11.21 (s, 1H), 8.80 (br t, J=5.5 Hz, 1H), 8.10 (d, J=8.3 Hz, 1H), 7.87 (s, 1H), 7.83-7.75 (m, 1H), 7.62 (dd, J=1.7, 2.9 Hz, 1H), 7.15 (dd, J=1.6, 3.5 Hz, 1H), 6.54 (t, J=3.3 Hz, 1H), 4.74 (dt, J=6.3, 12.5 Hz, 1H), 3.95 (d, J=11.4 Hz, 2H), 3.15 (t, J=6.1 Hz, 2H), 2.69 (d, J=17.7 Hz, 2H), 1.78-1.62 (m, 3H), 1.16 (d, J=6.3 Hz, 6H), 1.10-1.09 (m, 1H), 1.10-0.98 (m, 1H).

Embodiment 78: WX286

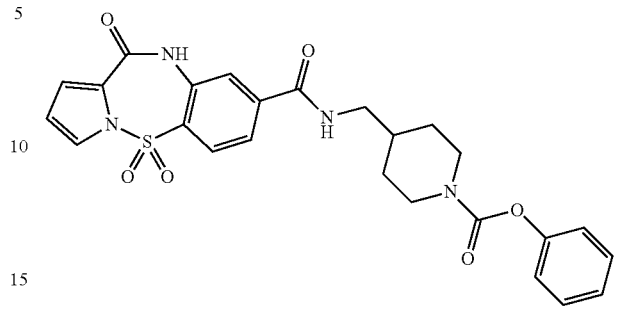

Synthetic Route

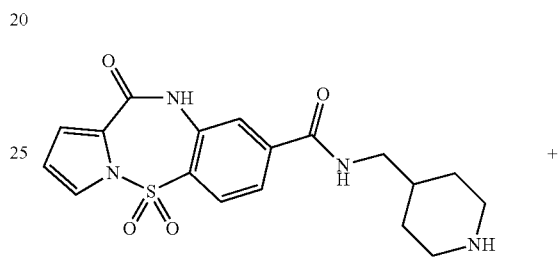

WX279-1

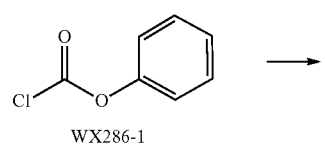

WX286-1

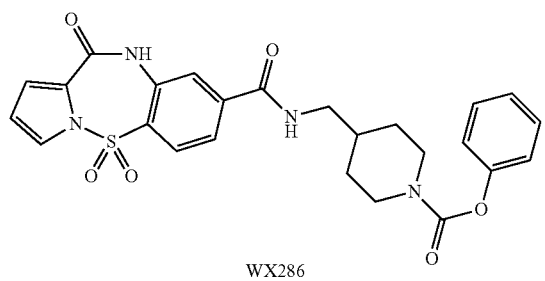

WX286

Step 1: Synthesis of Compound WX286

The synthesis of compound WX286 was referred to the step 1 of the synthesis of WX285 in Embodiment 77. $^1$H NMR (400 MHz, DMSO-d$_6$) δ=11.21 (s, 1H), 8.82 (s, 1H), 8.11 (d, J=8.4 Hz, 1H), 7.89 (s, 1H), 7.82 (d, J=8.2 Hz, 1H), 7.62 (br s, 1H), 7.41-7.34 (m, 2H), 7.20 (s, 1H), 7.15 (dd, J=1.7, 3.4 Hz, 1H), 7.10 (d, J=7.7 Hz, 2H), 6.54 (t, J=3.3 Hz, 1H), 4.20-3.97 (m, 2H), 3.21 (br t, J=6.0 Hz, 2H), 3.06-2.78 (m, 2H), 1.87-1.70 (m, 3H), 1.21 (br d, J=16.3 Hz, 2H).

Embodiment 79: WX287
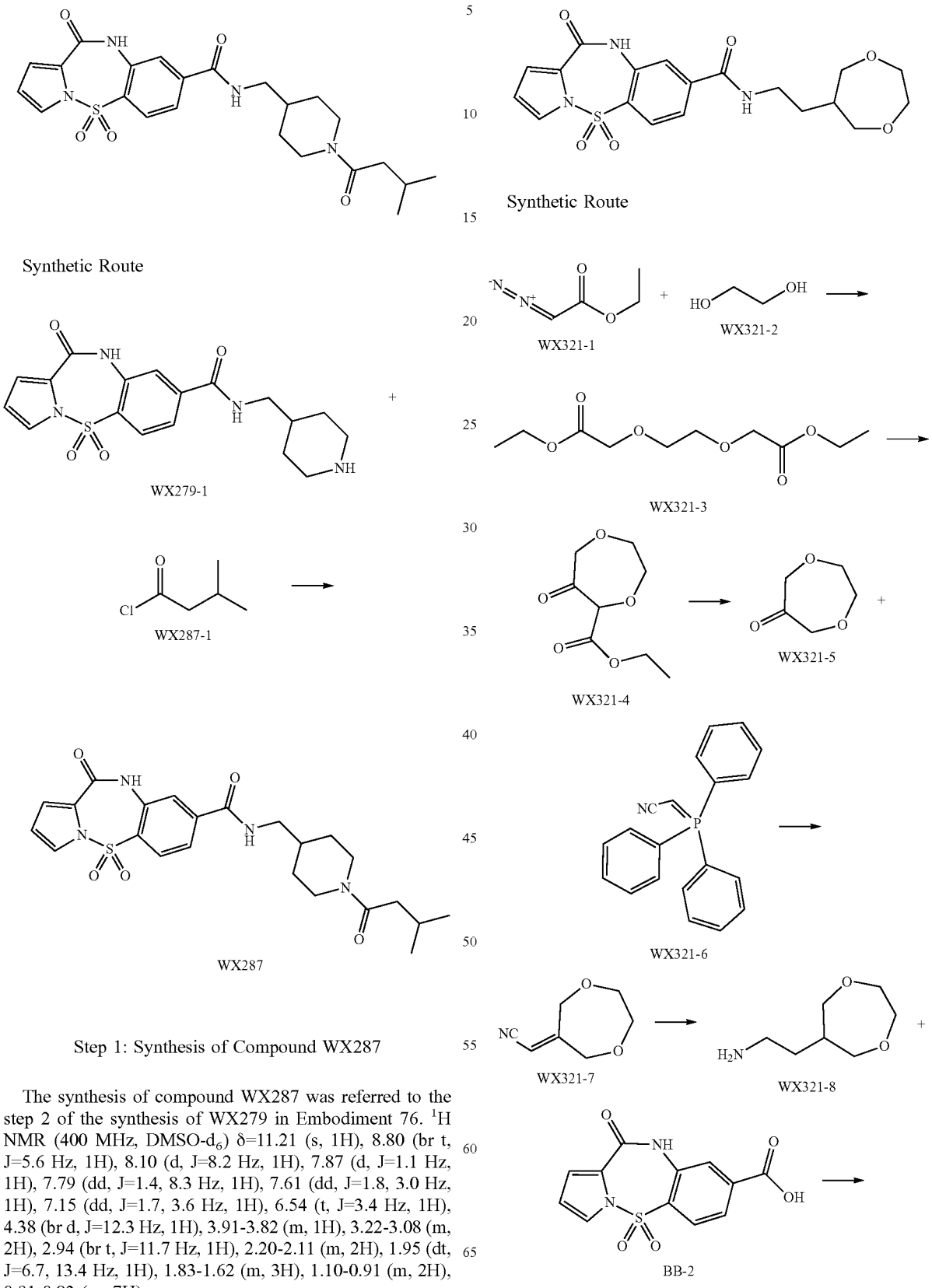
Embodiment 80: WX321
Synthetic Route
Step 1: Synthesis of Compound WX287
The synthesis of compound WX287 was referred to the step 2 of the synthesis of WX279 in Embodiment 76. $^1$H NMR (400 MHz, DMSO-d$_6$) δ=11.21 (s, 1H), 8.80 (br t, J=5.6 Hz, 1H), 8.10 (d, J=8.2 Hz, 1H), 7.87 (d, J=1.1 Hz, 1H), 7.79 (dd, J=1.4, 8.3 Hz, 1H), 7.61 (dd, J=1.8, 3.0 Hz, 1H), 7.15 (dd, J=1.7, 3.6 Hz, 1H), 6.54 (t, J=3.4 Hz, 1H), 4.38 (br d, J=12.3 Hz, 1H), 3.91-3.82 (m, 1H), 3.22-3.08 (m, 2H), 2.94 (br t, J=11.7 Hz, 1H), 2.20-2.11 (m, 2H), 1.95 (dt, J=6.7, 13.4 Hz, 1H), 1.83-1.62 (m, 3H), 1.10-0.91 (m, 2H), 0.91-0.83 (m, 7H).

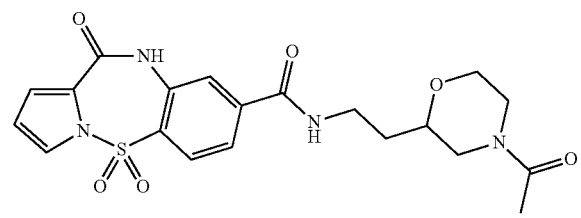

WX321

Step 1: Synthesis of Compound WX321-3

Ethylene glycol (10 g, 161.11 mmol, 9.01 mL) and WX321-1 (36.77 g, 322.23 mmol) were dissolved in DCM (350 mL), followed by slow dropwise addition of BF$_3$.Et$_2$O (345.29 mg, 2.43 mmol, 300.25 μL) at 0° C. The reaction mixture was stirred at 0° C. for 2 hours, then slowly heated to 25° C. and stirred for another 36 hours.

The reaction mixture was concentrated under reduced pressure to give the crude product of WX321-3. $^1$H NMR (400 MHz, CHLOROFORM-d) δ=4.24-4.18 (m, 4H), 4.16 (s, 4H), 3.78 (s, 4H), 1.28 (t, J=7.2 Hz, 6H).

Step 2: Synthesis of Compound WX321-4 t-BuOLi (23.92 g, 298.83 mmol, 26.94 mL) and WX321-3 (35 g, 149.42 mmol) were dissolved in DMF (350 mL). The reaction mixture was stirred at 90° C. for 12 hours and concentrated under reduced pressure, followed by addition of EA (200 mL) to the crude product. The mixture was washed with 2 M HCl (100 mL*2) and water (50 mL). The EA phase was dried over anhydrous sodium sulfate, filtered and concentrated under reduced pressure to give the crude product of WX321-4. $^1$H NMR (400 MHz, CHLOROFORM-d) δ=4.39-4.08 (m, 7H), 3.92-3.85 (m, 1H), 3.79-3.75 (m, 1H), 1.34-1.28 (m, 3H).

Step 3: Synthesis of Compound WX321-5

WX321-4 (19 g, 100.97 mmol) was added to HCl (120 mL). The reaction was carried out at 100° C. while stirring for 4 hours. The reaction mixture was extracted with EA (50 mL*2). The EA phases were combined, dried over anhydrous sodium sulfate, filtered, and concentrated under reduced pressure to give the crude product of WX321-5. $^1$H NMR (400 MHz, CHLOROFORM-d) δ=4.23 (s, 4H), 3.96 (s, 4H).

Step 4: Synthesis of Compound WX321-7

WX321-5 (0.2 g, 1.72 mmol) and WX321-6 (570.90 mg, 1.89 mmol) were dissolved in DCM (5 mL). The reaction mixture was stirred at 25° C. for 12 hours, and concentrated under reduced pressure. The crude product was purified by silica gel column chromatography to give WX321-7. $^1$H NMR (400 MHz, CHLOROFORM-d) δ=5.29 (tt, J=1.2, 2.0 Hz, 1H), 4.68-4.65 (m, 2H), 4.36 (d, J=0.7 Hz, 2H), 3.86-3.79 (m, 4H).

Step 5: Synthesis of Compound WX321-8

WX321-7 (0.25 g, 1.80 mmol) was dissolved in MeOH (10 mL), followed by addition of NH$_3$—H$_2$O (227.50 mg, 1.82 mmol, 0.25 mL, 28% purity) and Raney-Ni (0.25 g). The reaction mixture was purged with hydrogen gas for three times, pressurized to 50 psi and stirred at 50° C. for 3 hours, followed by filtration. The filtrate was concentrated under reduced pressure. The crude product WX321-8 was used directly in the next step. $^1$H NMR (400 MHz, CHLOROFORM-d) δ=3.87 (ddd, J=2.6, 5.2, 12.2 Hz, 2H), 3.80-3.75 (m, 1H), 3.82-3.66 (m, 4H), 3.55 (ddd, J=1.2, 7.1, 12.3 Hz, 2H), 2.74-2.69 (m, 1H), 2.63-2.57 (m, 1H), 2.20-2.07 (m, 1H), 1.69 (br s, 2H), 1.48-1.35 (m, 2H).

Step 6: Synthesis of Compound WX321

The synthesis of compound WX321 was referred to the step 1 of the synthesis of WX189 in Embodiment 24. $^1$H NMR (400 MHz, DMSO-d$_6$) δ=11.19 (s, 1H), 8.73 (t, J=5.5 Hz, 1H), 8.07 (d, J=8.2 Hz, 1H), 7.83 (d, J=1.3 Hz, 1H), 7.75 (dd, J=1.5, 8.2 Hz, 1H), 7.58 (dd, J=1.8, 3.1 Hz, 1H), 7.12 (dd, J=1.8, 3.5 Hz, 1H), 6.51 (t, J=3.3 Hz, 1H), 3.75 (dd, J=5.0, 12.2 Hz, 2H), 3.65-3.53 (m, 4H), 3.43 (dd, J=6.8, 12.3 Hz, 2H), 3.26-3.20 (m, 2H), 2.02-1.92 (m, 1H), 1.43 (q, J=7.1 Hz, 2H).

Embodiment 81: WX322

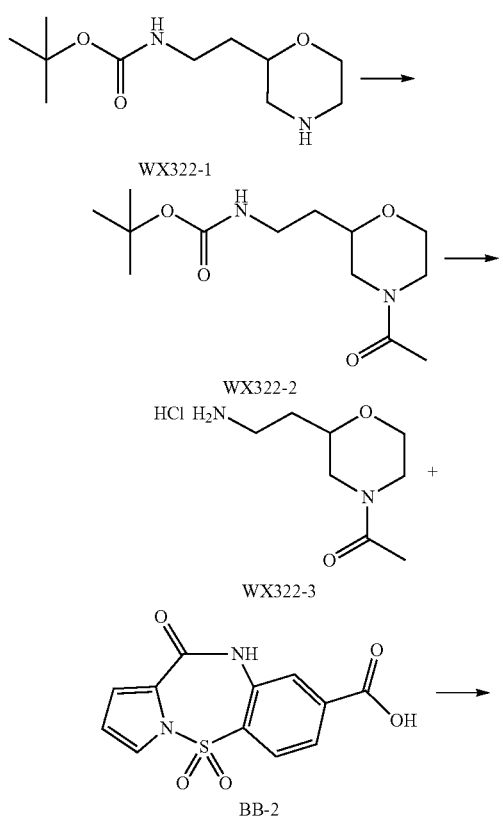

157

-continued

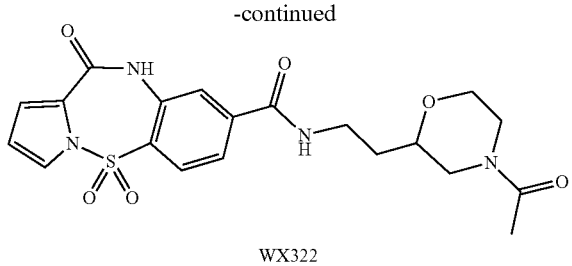

WX322

Step 1: Synthesis of Compound WX322-2

WX322-1 (0.2 g, 868.42 µmol) was dissolved in DCM (5 mL), followed by addition of TEA (131.81 mg, 1.30 mmol, 181.31 µL). Acetyl chloride (74.99 mg, 955.26 µmol, 68.17 µL) was slowly added dropwise at 0° C. The reaction was carried out at 0° C. while stirring for 1.5 hours. DCM (30 mL) was added to the reaction system, and the mixture was washed with water (20 mL*2). The DCM phase was dried over anhydrous sodium sulfate, filtered and concentrated under reduced pressure to give WX322-2. $^1$H NMR (400 MHz, CHLOROFORM-d) δ=4.84 (br s, 1H), 4.41 (br dd, J=2.1, 13.1 Hz, 1H), 3.96-3.89 (m, 1H), 3.69-3.38 (m, 3H), 3.35-3.17 (m, 3H), 3.04-2.90 (m, 1H), 2.76 (br s, 1H), 2.47 (dd, J=10.6, 13.2 Hz, 1H), 2.10 (s, 3H), 1.74-1.57 (m, 2H), 1.45 (s, 9H), 1.32 (s, 1H).

Step 2: Synthesis of Compound WX322-3

WX322-2 (0.2 g, 734.37 µmol) was dissolved in HCl/EtOAc (10 mL). The reaction mixture was stirred at 25° C. for 12 hours, and concentrated under reduced pressure to give WX322-3. $^1$H NMR (400 MHz, DMSO-$d_6$) δ=8.08 (br d, J=19.2 Hz, 3H), 4.20-4.09 (m, 1H), 3.81 (dd, J=2.6, 11.5 Hz, 1H), 3.75-3.61 (m, 1H), 3.44 (br dd, J=2.3, 11.8 Hz, 2H), 3.18-2.99 (m, 1H), 2.92-2.79 (m, 3H), 2.00 (d, J=4.2 Hz, 3H), 1.70 (br dd, J=8.3, 14.7 Hz, 2H).

Step 3: Synthesis of Compound WX322

The synthesis of compound WX322 was referred to the step 1 of the synthesis of WX189 in Embodiment 24. $^1$H NMR (400 MHz, DMSO-$d_6$) δ=11.21 (d, J=3.5 Hz, 1H), 8.78 (br d, J=18.5 Hz, 1H), 8.10 (dd, J=3.6, 8.3 Hz, 1H), 7.87 (s, 1H), 7.79 (d, J=8.4 Hz, 1H), 7.61 (dd, J=1.8, 3.1 Hz, 1H), 7.15 (dd, J=1.8, 3.5 Hz, 1H), 6.54 (t, J=3.4 Hz, 1H), 4.23-4.09 (m, 1H), 3.83 (dd, J=2.5, 11.4 Hz, 1H), 3.79-3.60 (m, 1H), 3.38-3.27 (m, 3H), 3.13 (br s, 1H), 2.89-2.82 (m, 1H), 2.68-2.61 (m, 1H), 2.43-2.43 (m, 1H), 2.44-2.31 (m, 1H), 1.99 (d, J=4.2 Hz, 3H), 1.74-1.58 (m, 2H).

Embodiment 82: WX323

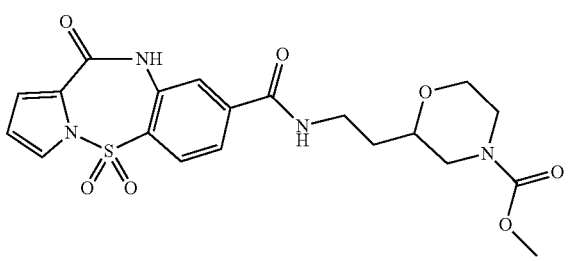 [SMILES: COC(=O)N1CCOC(CCNC(=O)c2ccc3c(c2)NC(=O)c2cccn2S3(=O)=O)C1]

158

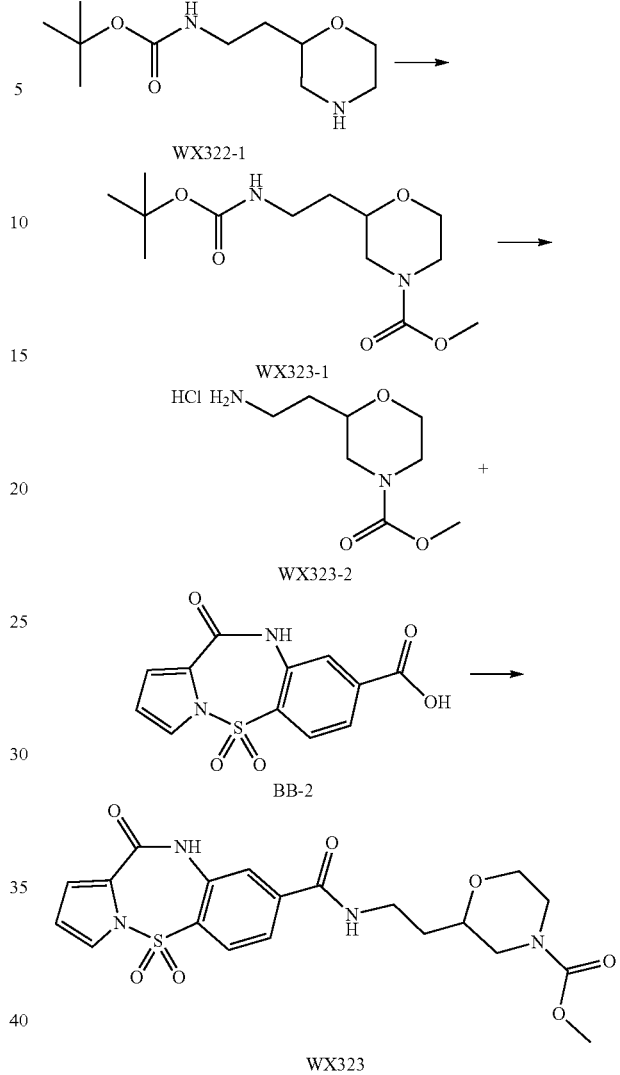

Step 1: Synthesis of Compound WX323-1

WX322-1 (0.2 g, 868.42 µmol) was dissolved in DCM (5 mL), followed by addition of TEA (131.81 mg, 1.30 mmol, 181.31 µL). Methyl chloroformate (90.27 mg, 955.26 µmol, 73.99 µL) was slowly added dropwise at 0° C. The reaction mixture was stirred at 0° C. for 1.5 hours. DCM (30 mL) was added to the reaction mixture, and the reaction mixture was washed with water (20 mL*2). The DCM phase was dried over anhydrous sodium sulfate, filtered and concentrated under reduced pressure to give WX323-1. $^1$H NMR (400 MHz, CHLOROFORM-d) δ=4.86 (br s, 1H), 3.88 (br d, J=9.7 Hz, 3H), 3.71 (s, 3H), 3.51 (br s, 2H), 3.30 (br d, J=6.6 Hz, 1H), 3.26-3.17 (m, 1H), 2.97 (br s, 1H), 2.67 (br s, 1H), 1.66-1.55 (m, 2H), 1.44 (s, 9H).

Step 2: Synthesis of Compound WX323-2

The synthesis of compound WX323-2 was referred to the step 2 of the synthesis of WX22-2 in Embodiment 81.

Step 3: Synthesis of Compound WX323

The synthesis of compound WX323 was referred to the step 1 of the synthesis of WX189 in Embodiment 24. $^1$H NMR (400 MHz, DMSO-d$_6$) δ=11.21 (s, 1H), 8.75 (t, J=5.4 Hz, 1H), 8.10 (d, J=8.2 Hz, 1H), 7.86 (d, J=1.5 Hz, 1H), 7.78 (dd, J=1.5, 8.4 Hz, 1H), 7.61 (dd, J=1.8, 3.1 Hz, 1H), 7.15 (dd, J=1.8, 3.5 Hz, 1H), 6.54 (t, J=3.4 Hz, 1H), 3.85-3.68 (m, 3H), 3.59 (s, 3H), 3.37 (br dd, J=2.9, 11.9 Hz, 5H), 2.90 (br s, 1H), 1.72-1.58 (m, 2H).

Embodiment 83: WX313 and 315

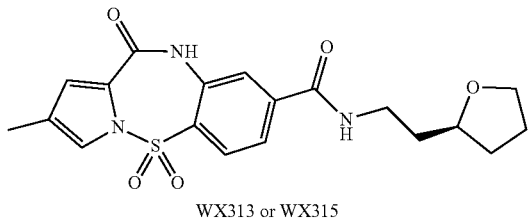

WX313 or WX315

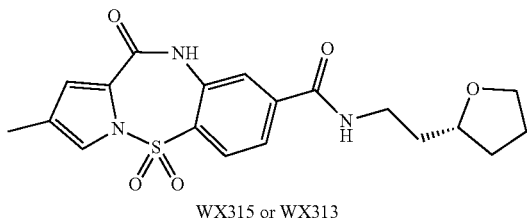

WX315 or WX313

Synthetic Route

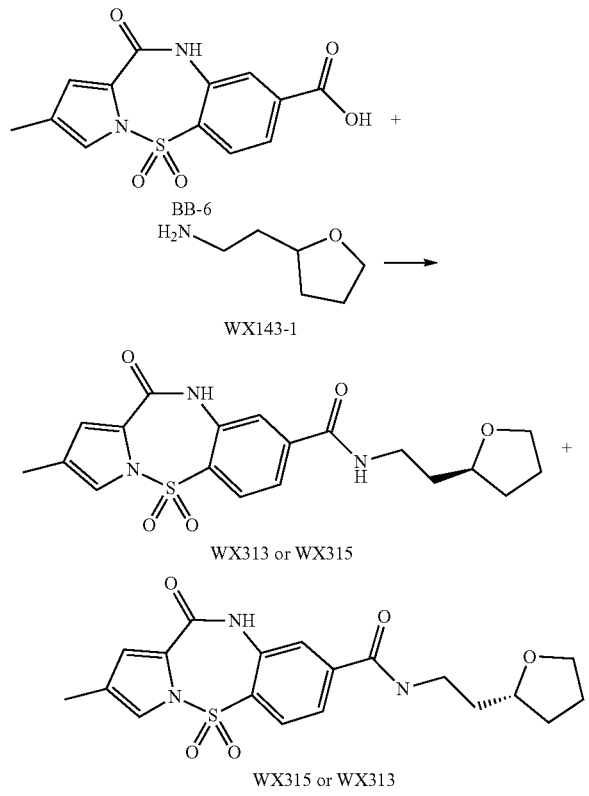

Step 1: Synthesis of Compound WX313 and WX315

The synthesis of compound WX313 and WX315 was referred to the step 1 of the synthesis of WX189 in Embodiment 24.

Compound WX313: $^1$H NMR (400 MHz, DMSO-d$_6$) δ=8.77 (br d, J=5.1 Hz, 1H), 8.06 (d, J=8.4 Hz, 1H), 7.85 (s, 1H), 7.77 (d, J=8.2 Hz, 1H), 7.39 (s, 1H), 7.00 (d, J=1.3 Hz, 1H), 3.80-3.71 (m, 2H), 3.65-3.50 (m, 2H), 3.28-3.24 (m, 1H), 2.05 (s, 3H), 1.99-1.92 (m, 1H), 1.85-1.76 (m, 2H), 1.69 (q, J=7.1 Hz, 2H), 1.40 (s, 1H);

Compound WX315: $^1$H NMR (400 MHz, DMSO-d$_6$) δ=11.17 (br s, 1H), 8.78 (br t, J=5.5 Hz, 1H), 8.06 (d, J=8.4 Hz, 1H), 7.85 (s, 1H), 7.78 (d, J=8.4 Hz, 1H), 7.39 (s, 1H), 7.00 (d, J=1.8 Hz, 1H), 3.81-3.71 (m, 2H), 3.61-3.54 (m, 1H), 3.31-3.25 (m, 2H), 2.05 (s, 3H), 1.99-1.91 (m, 1H), 1.85-1.76 (m, 2H), 1.69 (q, J=7.1 Hz, 2H), 1.46-1.37 (m, 1H).

Chiral resolution conditions: chiral column: OJ (250 mm*50 mm, 10 μm); mobile phase: 0.1% NH$_3$.H$_2$O MeOH; flow rate: 200 mL/min; column temperature: 40° C.

Retention time of compound 315: 4.825 min (peak 2); retention time of compound 313: 4.495 min (peak 1).

Embodiment 84: WX318

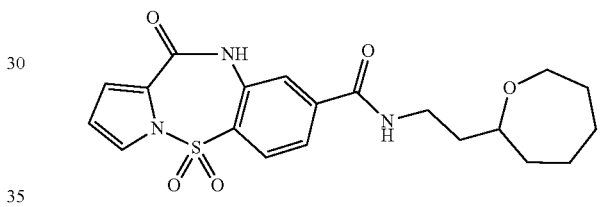

Synthetic Route

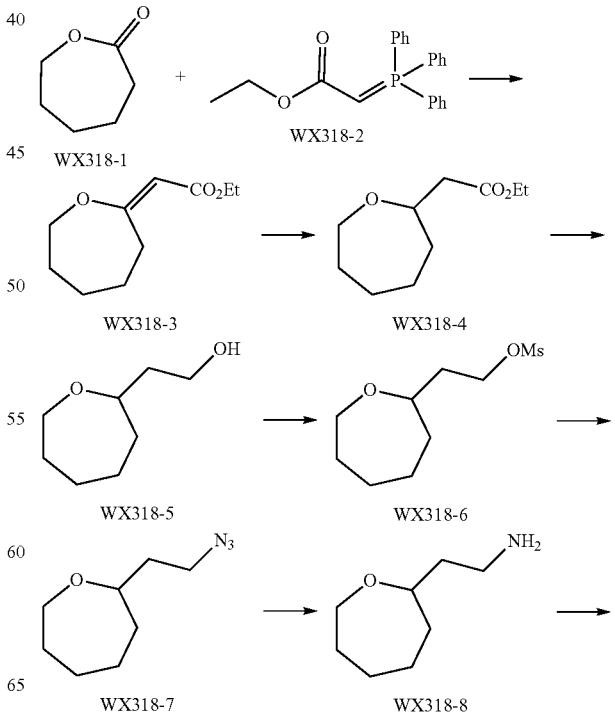

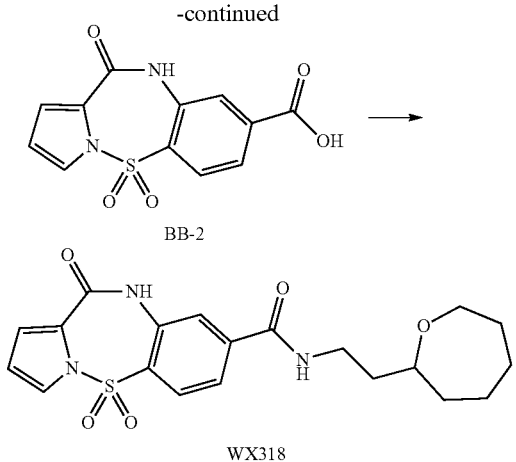

Step 1: Synthesis of Compound WX318-3

WX318-1 (1 g, 8.76 mmol) and WX318-2 (4.69 g, 13.47 mmol) were added into a pre-dried 20 mL microwave reaction tube, followed by addition of chlorobenzene (10 mL). The mixture was stirred at 180° C. for 6 hours under microwave, and then concentrated under reduced pressure to give a crude product. The crude product was subjected to automatic column chromatography to give WX318-3. $^1$H NMR (400 MHz, CHLOROFORM-d) δ=4.87 (s, 1H), 4.30-4.25 (m, 2H), 4.11 (q, J=7.1 Hz, 2H), 2.46-2.36 (m, 2H), 1.91-1.77 (m, 6H), 1.25 (t, J=7.2 Hz, 3H).

Step 2: Synthesis of Compound WX318-4

WX318-3 (2.5 g, 13.57 mmol) was dissolved in EtOAc (10 mL), followed by addition of Pd/C (0.3 g, 5% purity). The reaction mixture was purged with hydrogen gas for three times, pressurized to 40 psi and stirred at 25° C. for 16 hours, followed by filtration through diatomite. The filtrate was concentrated under reduced pressure to give a crude product. The crude product was subjected to automatic column chromatography to give WX318-4. $^1$H NMR (400 MHz, CHLOROFORM-d) δ=4.15 (q, J=7.2 Hz, 2H), 4.02-3.92 (m, 1H), 3.88-3.77 (m, 1H), 3.58 (d, J=4.3, 7.4, 12.1 Hz, 1H), 2.57-2.29 (m, 2H), 1.87-1.50 (m, 8H), 1.26 (t, J=7.2 Hz, 3H).

Step 3: Synthesis of Compound WX318-5

Compound WX318-4 (700 mg, 3.76 mmol, 1 eq) and THF (8 mL) were added into a dry single-necked flask. The mixture was purged with nitrogen gas for three times and cooled to 0° C., followed by addition of LiAlH$_4$ (213.97 mg, 5.64 mmol). The reaction mixture was stirred at 0° C. for 2 hours. Water (0.21 mL), 10% aqueous sodium hydroxide solution (0.63 mL) and water (0.21 mL) were slowly added into the reaction mixture sequentially to quench the reaction, followed by addition of 10 mL of ethyl acetate. The mixture was stirred for 10 minutes and filtered through a five-hole funnel padded with diatomite. The filtrate was concentrated under reduced pressure to give WX318-5. $^1$H NMR (400 MHz, CHLOROFORM-d) δ=3.95-3.84 (m, 1H), 3.82-3.67 (m, 3H), 3.62-3.49 (m, 1H), 2.92 (br s, 1H), 1.84-1.48 (m, 10H).

Step 4: Synthesis of Compound WX318-6

Compound WX318-5 (480 mg, 3.33 mmol) and DCM (8 mL) were added into a dry flask. The mixture was cooled to 0° C., followed by addition of MsCl (457.53 mg, 3.99 mmol, 309.14 μL) and Et$_3$N (673.61 mg, 6.66 mmol, 926.57 μL). The reaction mixture was stirred at 20° C. for 1 hour. 10 mL of saturated aqueous solution of sodium bicarbonate and 10 mL of dichloromethane were added to the reaction mixture, followed by separation. The organic phase was washed with water (5 mL), dried over anhydrous sodium sulfate, followed by filtration. The filtrate was concentrated under reduced pressure to give WX318-6. $^1$H NMR (400 MHz, CHLOROFORM-d) δ=4.44-4.35 (m, 1H), 4.34-4.26 (m, 1H), 3.90-3.80 (m, 1H), 3.67-3.50 (m, 2H), 3.01 (s, 3H), 1.86-1.49 (m, 10H).

Step 5: Synthesis of Compound WX318-7

Compound WX318-6 (866 mg, 3.90 mmol) and DMF (8 mL) were added into a dry vial, and cooled to 0° C., followed by addition of NaN$_3$ (379.88 mg, 5.84 mmol). The reaction mixture was heated to 20° C. and stirred for 16 hours. 10 mL of water was added to the reaction mixture, and the mixture was extracted with ethyl acetate (15 mL*2). The organic phases were combined, washed with saturated brine (10 mL*3), and dried over anhydrous sodium sulfate, followed by filtration. The filtrate was concentrated under reduced pressure to give WX318-7. $^1$H NMR (400 MHz, CHLOROFORM-d) δ=3.93-3.82 (m, 1H), 3.60-3.52 (m, 2H), 3.44-3.35 (m, 2H), 1.76-1.49 (m, 10H).

Step 6: Synthesis of Compound WX318-8

Compound WX318-7 (150 mg, 886.40 μmol), THF (2 mL) and H$_2$O (0.4 mL) were sequentially added into a vial. The system was cooled to 0° C., followed by addition of PPh$_3$ (348.74 mg, 1.33 mmol). The reaction mixture was heated to 25° C. and stirred for 16 hours. The reaction mixture was directly concentrated under reduced pressure to give a white solid crude product of WX318-8, which was used directly in the next step.

Step 7: Synthesis of Compound WX318

The synthesis of compound WX318 was referred to the step 1 of the synthesis of WX189 in Embodiment 24. $^1$H NMR (400 MHz, DMSO-d$_6$) δ=11.22 (s, 1H), 8.71 (br t, J=5.5 Hz, 1H), 8.10 (d, J=8.3 Hz, 1H), 7.86 (d, J=1.4 Hz, 1H), 7.78 (dd, J=1.5, 8.3 Hz, 1H), 7.64-7.59 (m, 1H), 7.15 (dd, J=1.7, 3.6 Hz, 1H), 6.54 (t, J=3.3 Hz, 1H), 3.80-3.68 (m, 1H), 3.53-3.40 (m, 2H), 3.32-3.27 (m, 2H), 1.78-1.68 (m, 1H), 1.67-1.54 (m, 6H), 1.52-1.34 (m, 3H).

Embodiment 85: WX326

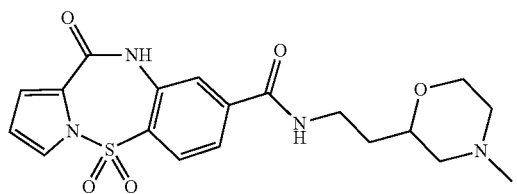 [SMILES: CN1CCOC(CCNC(=O)c2ccc3c(c2)NC(=O)c2cccn2S3(=O)=O)C1]

Synthetic Route

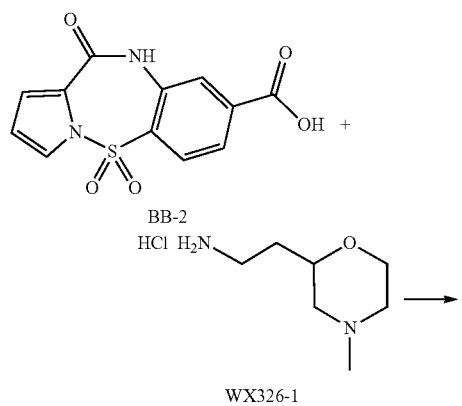

BB-2

WX326-1

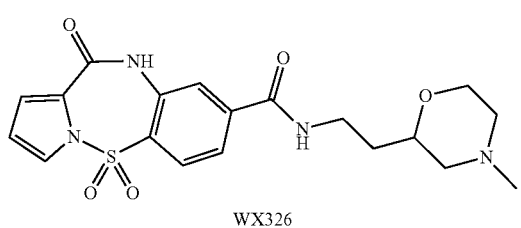

WX326

Step 1: Synthesis of Compound WX326

The synthesis of compound WX326 was referred to the step 1 of the synthesis of WX189 in Embodiment 24. $^1$H NMR (400 MHz, DMSO-$d_6$) δ=11.24 (s, 1H), 8.88 (t, J=5.4 Hz, 1H), 8.12 (d, J=8.3 Hz, 1H), 7.88 (s, 1H), 7.81 (d, J=8.3 Hz, 1H), 7.62 (dd, J=1.6, 3.0 Hz, 1H), 7.15 (dd, J=1.7, 3.6 Hz, 1H), 6.54 (t, J=3.4 Hz, 1H), 4.02 (dd, J=3.0, 12.8 Hz, 1H), 3.80-3.64 (m, 2H), 3.33 (s, 1H), 2.98 (d, J=12.8 Hz, 1H), 2.90-2.71 (m, 4H), 1.79-1.55 (m, 2H).

Embodiment 86: WX319 and 320

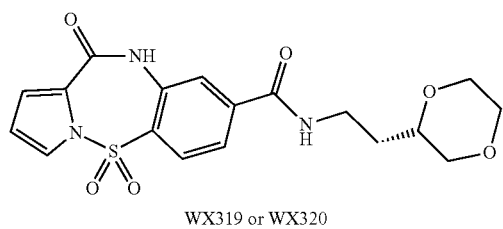

WX319 or WX320

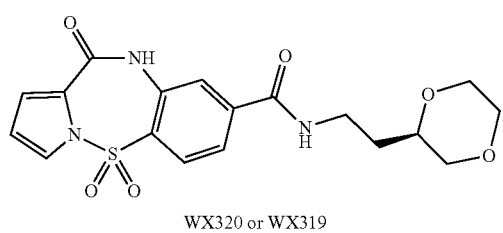

WX320 or WX319

Synthetic Route

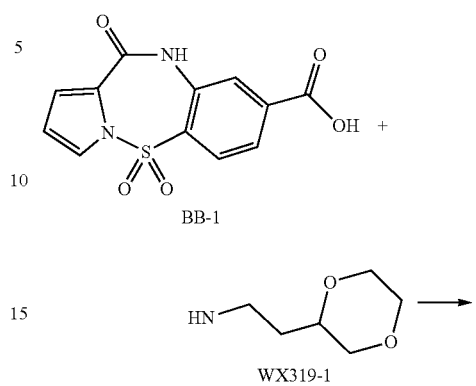

BB-1

WX319-1

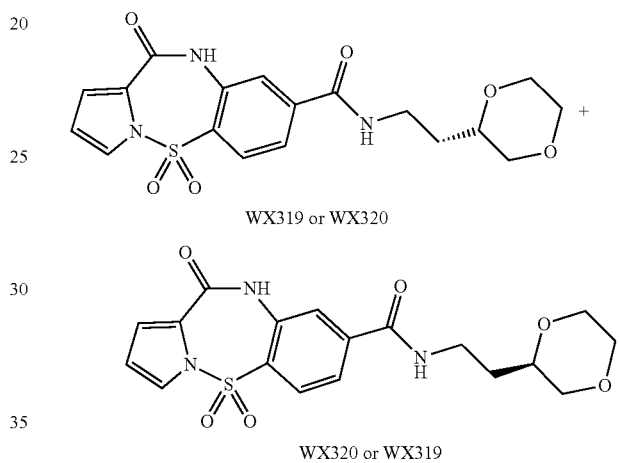

WX319 or WX320

WX320 or WX319

Step 1: Synthesis of Compound WX319 and WX320

The synthesis of compound WX319 and WX320 was referred to the step 1 of the synthesis of WX189 in Embodiment 24.

Compound WX320: $^1$H NMR (400 MHz, DMSO-$d_6$) δ=11.21 (br s, 1H), 8.81-8.70 (m, 1H), 8.09 (d, J=8.2 Hz, 1H), 7.85 (d, J=1.3 Hz, 1H), 7.77 (s, 1H), 7.60 (dd, J=1.6, 3.0 Hz, 1H), 7.12 (dd, J=1.6, 3.5 Hz, 1H), 6.53 (t, J=3.3 Hz, 1H), 3.74-3.36 (m, 7H), 3.29 (br s, 1H), 3.16 (s, 1H), 1.55 (br d, J=7.0 Hz, 2H);

Compound WX319: $^1$H NMR (400 MHz, ACETONITRILE-$d_3$) δ=9.00 (br s, 1H), 8.08 (d, J=8.4 Hz, 1H), 7.77 (d, J=1.5 Hz, 1H), 7.67 (dd, J=1.5, 8.4 Hz, 1H), 7.46 (dd, J=1.8, 3.1 Hz, 1H), 7.29 (br s, 1H), 7.14 (dd, J=1.8, 3.7 Hz, 1H), 6.47 (t, J=3.3 Hz, 1H), 3.73 (d, J=2.9 Hz, 1H), 3.70-3.60 (m, 4H), 3.54-3.47 (m, 1H), 3.44 (d, J=6.0 Hz, 2H), 3.24 (dd, J=9.9, 11.2 Hz, 1H), 1.65-1.57 (m, 1H), 1.61 (s, 1H).

Chiral resolution conditions: chiral column: OJ (250 mm*50 mm, 10 μm); mobile phase: 0.1% NH$_3$.H$_2$O MeOH; flow rate: 200 mL/min; column temperature: 40° C.

Retention time of compound 319: 3.874 min (peak 2); retention time of compound 320: 3.475 min (peak 1).

Embodiment 87: WX328

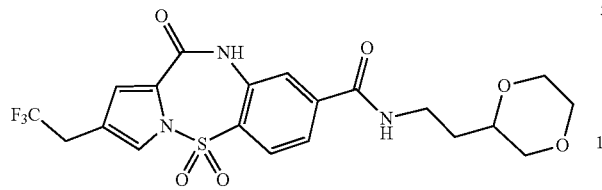

Synthetic Route

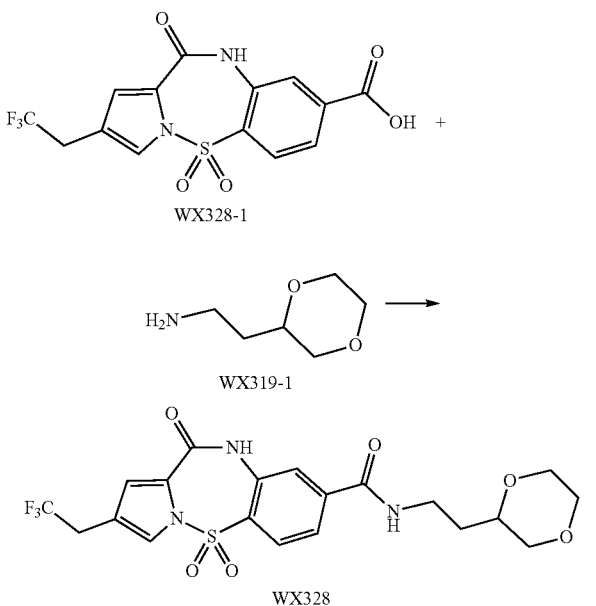

Step 1: Synthesis of Compound WX328

The synthesis of compound WX328 was referred to the step 1 of the synthesis of WX189 in Embodiment 24. δ=11.23 (br s, 1H), 8.83-8.76 (m, 1H), 8.09 (d, J=8.2 Hz, 1H), 7.85 (d, J=1.3 Hz, 1H), 7.77 (s, 1H), 7.60 (dd, J=1.6, 3.0 Hz, 1H), 7.12 (dd, J=1.6, 3.5 Hz, 1H), 3.74-3.36 (m, 7H), 3.29 (br s, 1H), 3.16 (s, 1H), 2.97 (s, 2H), 1.55 (br d, J=7.0 Hz, 2H).

Embodiment 88: WX325 and 329

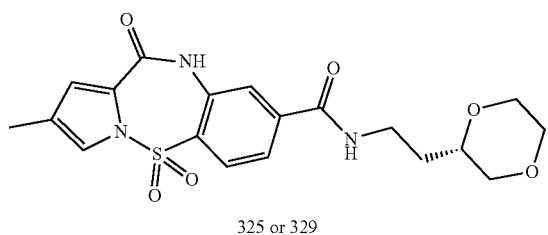

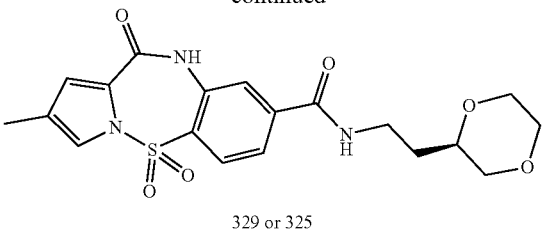

Synthetic Route

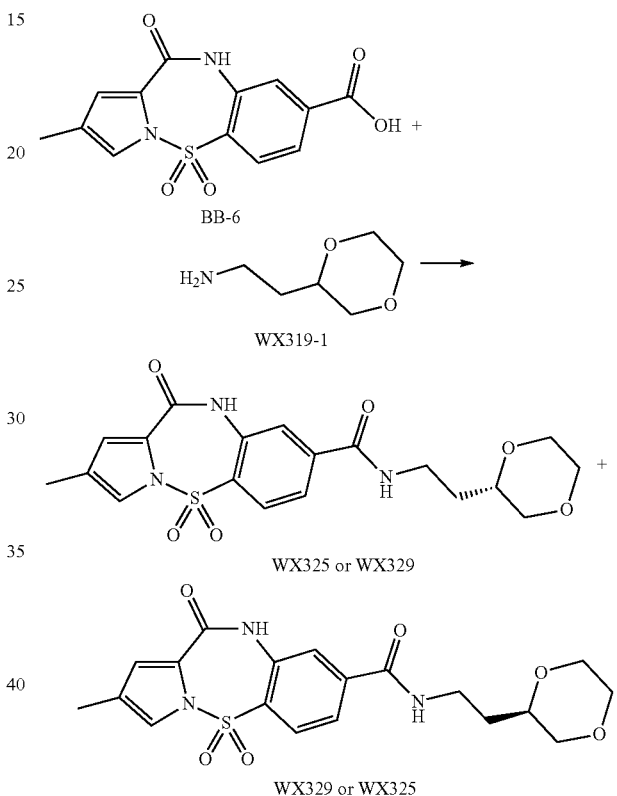

Step 1: Synthesis of Compound WX325 and WX329

BB-6 (500 mg, 1.63 mmol), WX319-1 (278.37 mg, 2.12 mmol), HBTU (928.62 mg, 2.45 mmol) and TEA (495.55 mg, 4.90 mmol, 681.64 μL) were dissolved in DMF (5 mL). The reaction mixture was stirred at 30° C. for 12 hours, concentrated under reduced pressure and isolated by column chromatography. The crude product was concentrated under reduced pressure, and isolated by SFC to give WX325 and WX329.

Compound WX329: $^1$H NMR (400 MHz, DMSO-$d_6$) δ=11.11 (br s, 1H), 8.73 (br t, J=5.5 Hz, 1H), 8.05 (d, J=8.2 Hz, 1H), 7.83 (d, J=1.3 Hz, 1H), 7.74 (dd, J=1.5, 8.4 Hz, 1H), 7.36 (s, 1H), 6.98 (d, J=2.0 Hz, 1H), 3.71-3.48 (m, 5H), 3.45-3.31 (m, 1H), 3.45-3.30 (m, 1H), 3.27-3.21 (m, 1H), 3.14 (dd, J=9.9, 11.2 Hz, 1H), 2.03 (s, 3H), 1.53 (q, J=7.0 Hz, 2H);

Compound WX325: $^1$H NMR (400 MHz, DMSO-$d_6$) δ=11.13 (br s, 1H), 8.73 (br t, J=5.5 Hz, 1H), 8.05 (d, J=8.2

Hz, 1H), 7.83 (d, J=1.3 Hz, 1H), 7.74 (dd, J=1.5, 8.4 Hz, 1H), 7.36 (s, 1H), 6.98 (d, J=2.0 Hz, 1H), 3.71-3.48 (m, 5H), 3.45-3.31 (m, 1H), 3.45-3.30 (m, 1H), 3.27-3.21 (m, 1H), 3.14 (dd, J=9.9, 11.2 Hz, 1H), 2.03 (s, 3H), 1.53 (q, J=7.0 Hz, 2H).

Chiral resolution conditions: chiral column: OJ-3 150×4.6 mm; mobile phase: A: carbon dioxide, B: MeOH (0.1% NH$_3$.H$_2$O); gradient: B %=33%; flow rate: 60 mL/min; column temperature: 40° C.

Retention time of compound 325: 4.919 min (peak 2); retention time of compound 329: 4.563 min (peak 1).

Embodiment 89: WX339 and 350

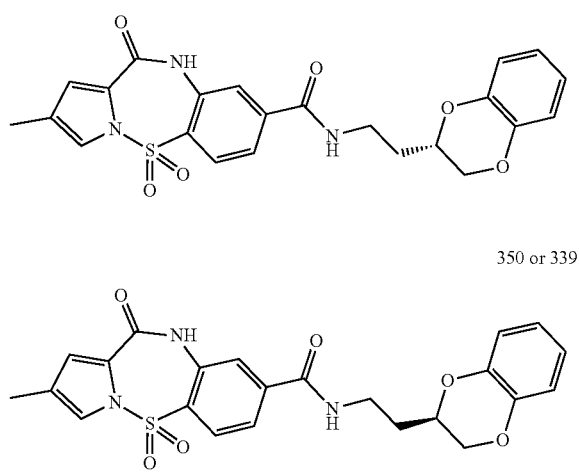

Synthetic Route

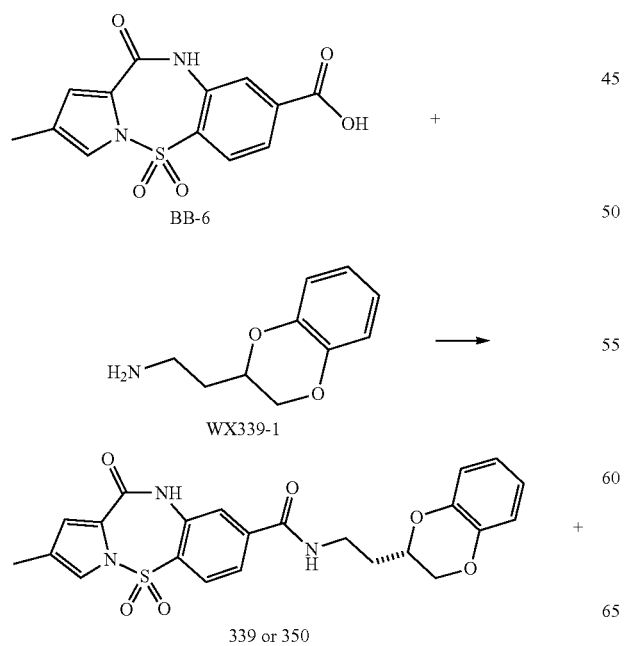

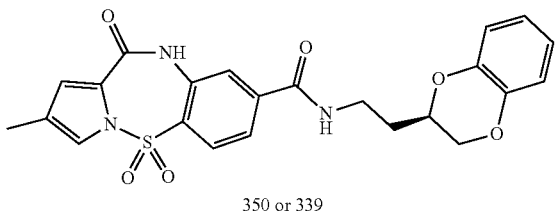

350 or 339

Step 1: Synthesis of Compound WX339 and WX350

BB-6 (0.16 g, 522.37 μmol, 1 eq) and WX339-1 (102.98 mg, 574.61 μmol) were dissolved in DMF (1 mL), followed by addition of HATU (297.93 mg, 783.56 μmol) and DIEA (202.54 mg, 1.57 mmol, 272.96 μL). The reaction was carried out at 30° C. while stirring for 12 hours. The reaction mixture was poured into water (20 mL), followed by filtration. The filter cake was dissolved in ethyl acetate (20 mL). The ethyl acetate phase was dried over anhydrous sodium, filtered and concentrated under reduced pressure. The crude product was purified by silica gel column chromatography to give a racemic mixture, which was isolated by SFC to give WX339 and WX350.

Compound WX350: $^1$H NMR (400 MHz, DMSO-d$_6$) δ=11.15 (s, 1H), 8.88 (t, J=5.5 Hz, 1H), 8.08 (d, J=8.4 Hz, 1H), 7.87 (d, J=1.3 Hz, 1H), 7.79 (dd, J=1.3, 8.4 Hz, 1H), 7.39 (s, 1H), 7.00 (d, J=1.8 Hz, 1H), 6.90-6.75 (m, 4H), 4.32 (dd, J=2.1, 11.4 Hz, 1H), 4.28-4.20 (m, 1H), 3.91 (dd, J=7.5, 11.2 Hz, 1H), 3.56-3.40 (m, 2H), 2.05 (s, 3H), 1.89-1.81 (m, 2H);

Compound WX339: $^1$H NMR (400 MHz, DMSO-d$_6$) δ=11.13 (s, 1H), 8.86 (t, J=5.5 Hz, 1H), 8.08 (d, J=8.4 Hz, 1H), 7.87 (d, J=1.3 Hz, 1H), 7.79 (dd, J=1.3, 8.4 Hz, 1H), 7.39 (s, 1H), 7.00 (d, J=1.8 Hz, 1H), 6.90-6.75 (m, 4H), 4.32 (dd, J=2.1, 11.4 Hz, 1H), 4.28-4.20 (m, 1H), 3.91 (dd, J=7.5, 11.2 Hz, 1H), 3.56-3.40 (m, 2H), 2.05 (s, 3H), 1.89-1.81 (m, 2H).

Chiral resolution conditions: chiral column: AS (250 mm*30 mm, 5 μm); mobile phase: A: carbon dioxide, B: methanol; gradient: B %=45%; flow rate: 80 mL/min; column temperature: 40° C.

Retention time of compound 339: 4.078 min (peak 2); retention time of compound 350: 3.952 min (peak 1).

Embodiment 90: WX352 and 353

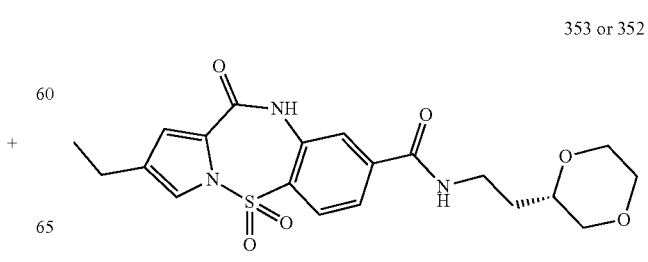

353 or 352

352 or 353
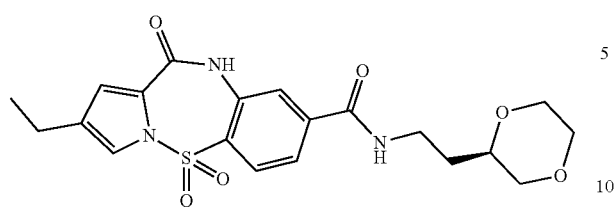
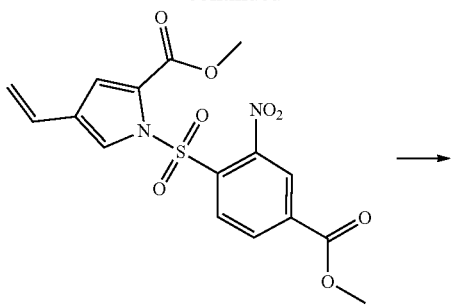
WX353-7
WX353-1
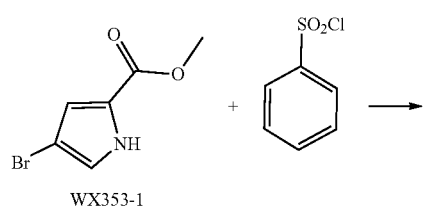
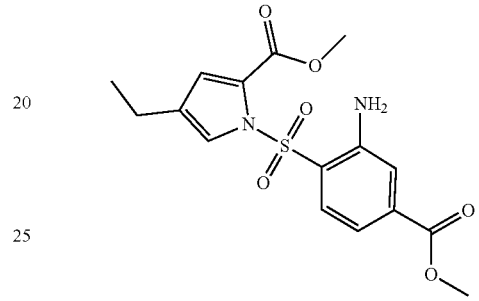
WX353-8
WX353-2
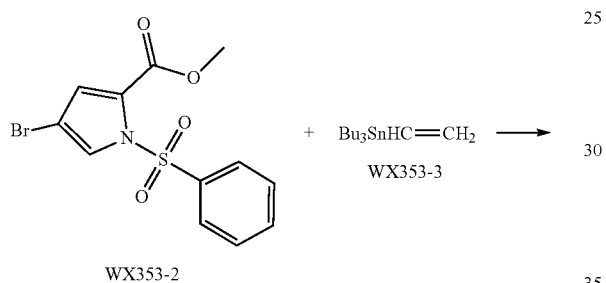
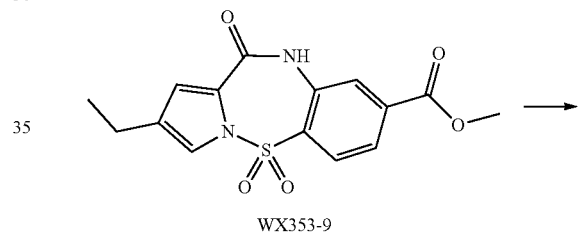
WX353-9
WX353-4
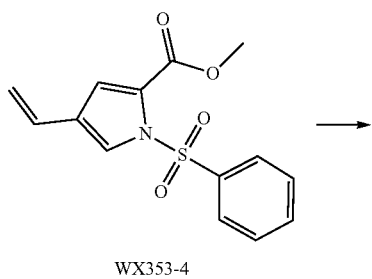
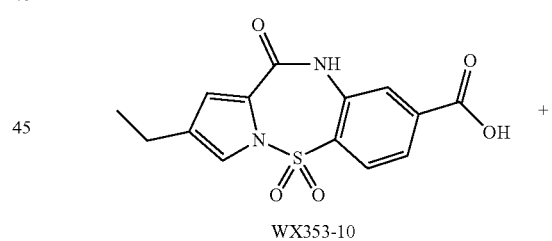
WX353-10 +
WX353-5
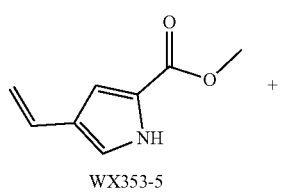
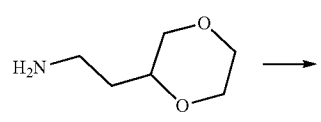
WX319-1
WX353-6
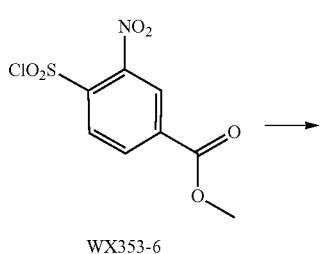
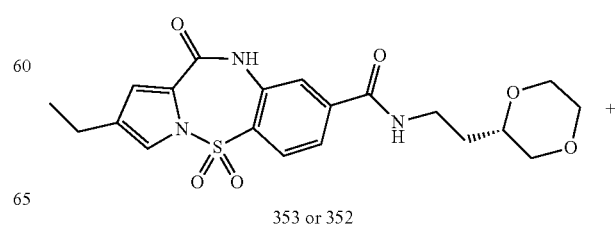
353 or 352 +

-continued

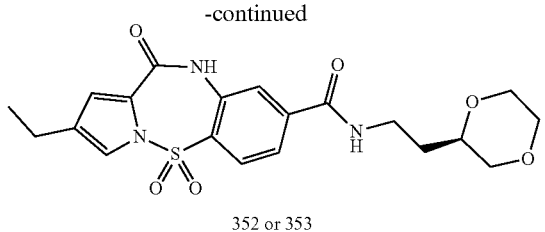

352 or 353

Step 1: Synthesis of Compound WX353-3

WX353-1 (20 g, 98.03 mmol) was dissolved in dichloromethane (200 mL), triethylamine (14.88 g, 147.04 mmol, 20.47 mL) and DMAP (1.20 g, 9.80 mmol) were added, followed by dropwise addition of benzenesulfonyl chloride (19.05 g, 107.83 mmol, 13.80 mL). The reaction mixture was stirred at 30° C. for 5 hours, followed by addition of DCM (100 mL). The mixture was washed with 2 M HCl (30 mL*2). The organic phase was dried over anhydrous sodium sulfate and evaporated under reduced pressure to remove the solvent to give WX353-2. $^1$H NMR (400 MHz, DMSO-$d_6$) δ=8.08-8.02 (m, 3H), 7.83-7.76 (m, 1H), 7.72-7.66 (m, 2H), 7.19 (d, J=2.0 Hz, 1H), 3.68 (s, 3H).

Step 2: Synthesis of Compound WX353-4

WX353-2 (10 g, 29.05 mmol) was dissolved in DMF (80 mL), followed by addition of Pd(PPh$_3$)$_4$ (1.68 g, 1.45 mmol) and WX353-3 (11.98 g, 37.77 mmol, 10.99 mL). The reaction mixture was purged with nitrogen gas for three times. The reaction was carried out at 100° C. while stirring for 24 hours. EA (100 mL) and a solution of 10 g of cesium fluoride in 50 mL of H$_2$O were added to the reaction mixture, and the mixture was stirred for 6 hours, followed by filtration. The filtrate was washed with water (50 mL*3). The EA phase was dried over anhydrous sodium sulfate, filtered and concentrated under reduced pressure. The crude product was purified by silica gel column chromatography to give WX353-4. $^1$H NMR (400 MHz, DMSO-$d_6$) δ=8.04-7.94 (m, 3H), 7.80-7.75 (m, 1H), 7.71-7.63 (m, 2H), 7.37 (d, J=1.5 Hz, 1H), 6.60 (dd, J=11.0, 17.6 Hz, 1H), 5.72 (d, J=17.6 Hz, 1H), 5.21 (d, J=11.2 Hz, 1H), 3.67 (s, 3H).

Step 3: Synthesis of Compound WX353-5

WX353-4 (7.6 g, 26.09 mmol) was dissolved in MeOH (80 mL), followed by addition of CH$_3$ONa (2.82 g, 52.18 mmol). The reaction was carried out at 50° C. for 12 hours. The reaction mixture was concentrated under reduced pressure. The crude product was purified by silica gel column chromatography to give WX353-5. $^1$H NMR (400 MHz, CHLOROFORM-d) δ=9.02 (br s, 1H), 7.05-6.94 (m, 2H), 6.57 (dd, J=10.9, 17.5 Hz, 1H), 5.48 (dd, J=1.1, 17.6 Hz, 1H), 5.06 (dd, J=1.2, 10.9 Hz, 1H), 3.87 (s, 3H).

Step 4: Synthesis of Compound WX353-7 t-BuOK (1 M, 28.58 mL) was added dropwise to a solution of WX353-5 (3.6 g, 23.82 mmol) in THF (36 mL) at 0° C. The mixture was heated to 30° C. and stirred for 30 minutes. The mixture was then cooled to 0° C., followed by addition of a solution of WX353-6 (7.99 g, 28.58 mmol) in THF (36 mL). The reaction mixture was then slowly heated to 30° C. and stirred for 12 hours. The solvent was removed under reduced pressure. EA (100 mL) was added to the crude product, and the mixture was washed with saturated NH$_4$Cl (50 mL) and water (50 mL*2). The EA phase was dried over anhydrous sodium sulfate, filtered and concentrated under reduced pressure. The crude product was purified by silica gel column chromatography to give WX353-7. $^1$H NMR (400 MHz, CHLOROFORM-d) δ=8.45 (s, 1H), 8.41-8.38 (m, 2H), 7.62 (d, J=2.0 Hz, 1H), 7.27 (d, J=2.2 Hz, 1H), 6.56 (dd, J=10.9, 17.5 Hz, 1H), 5.59 (d, J=17.6 Hz, 1H), 5.27 (d, J=11.5 Hz, 1H), 4.01 (s, 3H), 3.73 (s, 3H).

Step 5: Synthesis of Compound WX353-8

WX353-7 (3 g, 7.61 mmol) was dissolved in EtOAc (60 mL) and MeOH (60 mL), followed by addition of Raney-Ni (1.5 g). The reaction mixture was purged with hydrogen gas for three times, pressurized to 30 psi, and stirred at 30° C. for 6 hours, followed by filtration. The filtrate was concentrated under reduced pressure. The crude product was purified by silica gel column chromatography to give WX353-8. $^1$H NMR (400 MHz, CHLOROFORM-d) δ=7.63 (d, J=8.4 Hz, 1H), 7.49 (s, 1H), 7.40 (d, J=0.9 Hz, 1H), 7.33 (d, J=8.6 Hz, 1H), 6.98 (d, J=2.0 Hz, 1H), 5.28 (br s, 2H), 3.91 (s, 3H), 3.73 (s, 3H), 2.49 (q, J=7.6 Hz, 2H), 1.25-1.19 (m, 1H), 1.22 (t, J=7.5 Hz, 2H).

Step 6: Synthesis of Compound WX353-9

WX353-8 (1 g, 2.73 mmol) was added to DMSO (10 mL), followed by addition of t-BuOK (459.39 mg, 4.09 mmol). The reaction mixture was stirred at 30° C. for 0.5 hour, followed by addition of EA (100 mL). The mixture was washed with saturated NH$_4$Cl (30 mL*2) and water (30 mL). The EA phase was dried over anhydrous sodium sulfate, filtered, and concentrated under reduced pressure to give WX353-9. $^1$H NMR (400 MHz, CHLOROFORM-d) δ=9.36 (s, 1H), 8.12 (d, J=8.4 Hz, 1H), 8.04 (d, J=1.1 Hz, 1H), 8.00-7.95 (m, 1H), 7.27-7.25 (m, 1H), 7.19 (d, J=1.8 Hz, 1H), 3.99 (s, 3H), 2.52 (q, J=7.5 Hz, 2H), 1.22 (t, J=7.5 Hz, 3H).

Step 7: Synthesis of Compound WX353-10

WX353-8 (0.35 g, 1.05 mmol) was dissolved in THF (9 mL), followed by addition of a solution of LiOH—H$_2$O (43.93 mg, 1.05 mmol) in H$_2$O (3 mL). The reaction mixture was stirred at 30° C. for 12 hours, followed by addition of EA (100 mL). The mixture was washed with water (50 mL*2). The EA phase was discarded. EA (100 mL) was added to the aqueous layer, and 2 M HCl was slowly added while stirring to adjust the pH of the aqueous phase to 3-4, followed. The mixture was partitioned, the EA phase was dried over anhydrous sodium sulfate, filtered, and concentrated under reduced pressure to give WX353-9. $^1$H NMR (400 MHz, DMSO-$d_6$) δ=13.70 (br s, 1H), 11.22 (s, 1H), 8.10 (d, J=8.4 Hz, 1H), 8.01 (d, J=1.3 Hz, 1H), 7.89 (dd, J=1.4, 8.3 Hz, 1H), 7.40 (d, J=0.9 Hz, 1H), 7.08 (d, J=1.8 Hz, 1H), 2.45 (d, J=7.7 Hz, 2H), 1.13 (t, J=7.5 Hz, 3H).

Step 8: Synthesis of Compound WX353 and WX352

The synthesis of compound WX352 and WX353 was referred to the step 1 of the synthesis of compound WX339 and WX350 in Embodiment 89.

Compound WX352: $^1$H NMR (400 MHz, DMSO-$d_6$) δ=11.18 (s, 1H), 8.79 (t, J=5.6 Hz, 1H), 8.08 (d, J=8.4 Hz, 1H), 7.85 (d, J=1.5 Hz, 1H), 7.77 (dd, J=1.5, 8.2 Hz, 1H), 7.43-7.36 (m, 1H), 7.07 (d, J=2.0 Hz, 1H), 3.73-3.66 (m, 2H), 3.62 (dd, J=2.1, 11.1 Hz, 1H), 3.58-3.49 (m, 2H), 3.45 (dd, J=2.6, 11.0 Hz, 1H), 3.33-3.23 (m, 2H), 3.16 (dd, J=10.0, 11.4 Hz, 1H), 2.44 (d, J=7.5 Hz, 2H), 1.60-1.50 (m, 2H), 1.12 (t, J=7.5 Hz, 3H);

Compound WX353: $^1$H NMR (400 MHz, DMSO-$d_6$) δ=11.18 (s, 1H), 8.79 (t, J=5.4 Hz, 1H), 8.08 (d, J=8.4 Hz, 1H), 7.85 (d, J=1.1 Hz, 1H), 7.77 (dd, J=1.3, 8.4 Hz, 1H), 7.39 (d, J=0.7 Hz, 1H), 7.07 (d, J=1.8 Hz, 1H), 3.74-3.66 (m, 2H), 3.60 (s, 1H), 3.59-3.48 (m, 2H), 3.44 (dd, J=2.4, 11.0 Hz, 1H), 3.33-3.24 (m, 2H), 3.20-3.12 (m, 1H), 2.44 (d, J=7.7 Hz, 2H), 1.59-1.51 (m, 2H), 1.12 (t, J=7.5 Hz, 3H).

Chiral resolution conditions: chiral column: OJ-H 250 mm*30 mm i.d. 5 μm; mobile phase: A: carbon dioxide, B: methanol; gradient: B %=30%; flow rate: 70 mL/min; column temperature: 40° C.

Retention time of compound 352: 0.86 min (peak 1); retention time of compound 353: 0.98 min (peak 2).

Embodiment 91: WX355 and 356

355 or 356

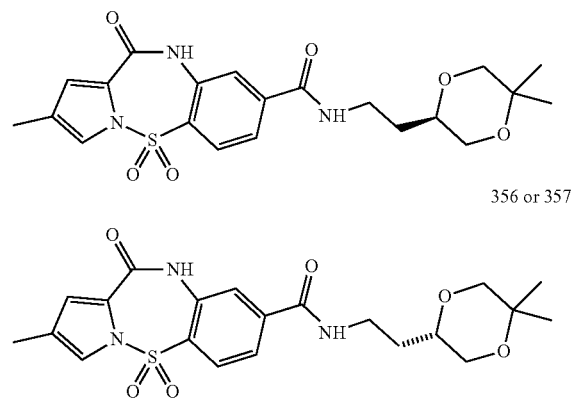

356 or 357

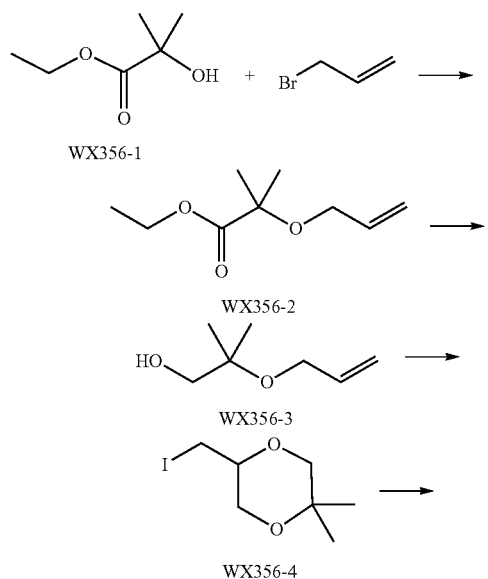

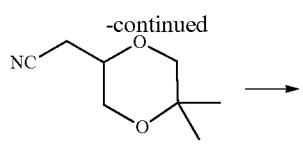

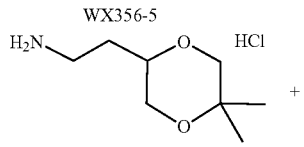

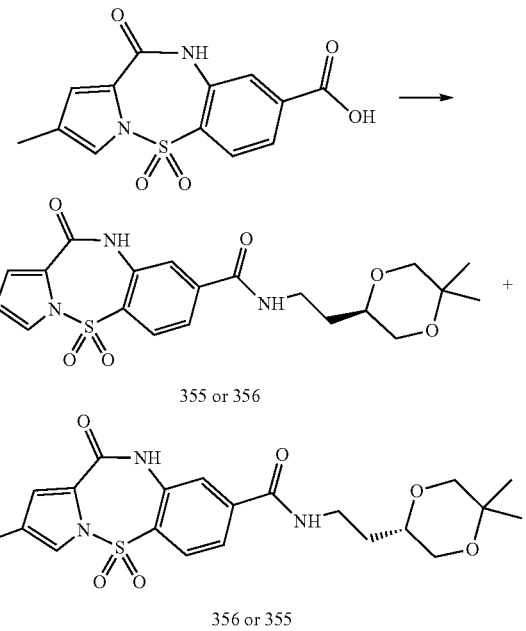

355 or 356

356 or 355

Step 1: Synthesis of Compound WX356-2

NaH (1.66 g, 41.62 mmol, 60% purity) and DMF (50 mL) were added into a pre-dried 100 mL three-necked flask, and then vacuumized and charged with nitrogen for three times. The mixture was cooled to 0° C., then a solution of WX356-1 (5 g, 37.83 mmol) in DMF (5 mL) was added dropwise while maintaining the temperature at 0-5° C. The solution was stirred for 30 minutes, and became a white suspension. The mixture was cooled to 0° C., a solution of bromopropene (4.12 g, 34.05 mmol) in DMF (5 mL) was slowly added dropwise while maintaining the temperature below 5° C., and the solution turned into a yellow liquid. After completion of the addition, the solution was heated to 25° C. and stirred for 12 hours, and the color of the solution turned yellow. The reaction mixture was poured into 50 mL of $H_2O$ to quench the reaction, followed by addition of 50 mL of EtOAc. The mixture was partitioned, the aqueous phase was extracted with EtOAc (2*50 mL). The organic phases were combined, washed with 20 mL of saturated brine, dried over anhydrous sodium sulfate, filtered and concentrated to give WX356-2.

Step 2: Synthesis of Compound WX356-3

The raw material WX356-2 (4.5 g, 26.13 mmol) and THF (60 mL) were added into a pre-dried 250 mL single-necked flask, followed by slow dropwise addition of LiBH$_4$ (1.14 g, 52.26 mmol). After completion of the addition, the reaction mixture was stirred at 25° C. for 16 hours. The reaction mixture was poured into 50 mL of H₂O to quench the reaction, followed by addition of 50 mL of EtOAc. The mixture was partitioned, the aqueous phase was extracted with EtOAc (2*50 mL). The organic phases were combined, washed with 20 mL of saturated brine, and dried over anhydrous sodium sulfate, followed by filtration. The organic phase was concentrated by a water pump to give WX356-3.

Step 3: Synthesis of Compound WX356-4

WX356-3 (3 g, 23.04 mmol) and MeCN (200 mL) were added into a pre-dried 250 mL flask, followed by addition of NaHCO₃ (5.81 g, 69.13 mmol, 2.69 mL) and I₂ (17.55 g, 69.13 mmol, 13.93 mL). The reaction mixture was stirred at 25° C. for 16 hours. The reaction mixture was poured into 100 mL of water to quench the reaction, followed by addition of 200 mL EtOAc. The mixture was partitioned, the aqueous phase was extracted with EtOAc (2*200 mL). The organic phases were combined, washed with 100 mL of saturated brine, and dried over anhydrous sodium sulfate, followed by filtration. The organic phase was concentrated by a water pump to give WX356-4.

Step 4: Synthesis of Compound WX356-5

WX356-4 (500 mg, 1.95 mmol) and DMSO (5 mL) were added into a dry single-necked flask, followed by addition of KCN (508.56 mg, 7.81 mmol, 334.58 µL) and NaI (585.34 mg, 3.91 mmol). The reaction mixture was purged with nitrogen gas for three times and stirred at 100° C. for 2 hours, followed by addition of 20 mL of (water:ethyl acetate=1:1). The pH value of the system was adjusted greater than 12 with 4M NaOH solution, followed by extraction with ethyl acetate (5 mL*3). The organic phase was washed with saturated brine (5 mL*2), dried over anhydrous sodium sulfate, filtered, and concentrated under reduced pressure to give WX356-5. ¹H NMR (400 MHz, CHLOROFORM-d) δ=3.79-3.72 (m, 1H), 3.71-3.52 (m, 4H), 2.52 (dt, J=0.9, 5.1 Hz, 2H), 1.34 (s, 3H), 1.14 (s, 3H).

Step 5: Synthesis of Compound WX356-6

WX356-5 (300 mg, 1.93 mmol) and THF (1 mL) were added into a dry single-necked flask, followed by addition of BH₃.THF (1 M, 3.87 mL). The reaction mixture was purged with nitrogen gas for three times, stirred at 70° C. for 5 hours, followed by addition of 10 mL of water. The pH value of the system was adjusted to 2 with 2M hydrochloric acid, and the aqueous phase was washed with ethyl acetate (5 mL*2). The mixture was partitioned, the aqueous phase was concentrated under reduced pressure with an oil pump to give WX356-6. ¹H NMR (400 MHz, METHANOL-d₄) δ=3.61-3.55 (m, 5H), 3.12-3.06 (m, 2H), 1.78-1.68 (m, 2H), 1.31 (s, 3H), 1.09 (s, 3H).

Step 6: Synthesis of Compound WX356 and WX355

BB-6 (521.74 mg, 1.70 mmol) and DMF (2 mL) were added into a single-necked flask, followed by addition of HATU (971.53 mg, 2.56 mmol) and DIPEA (550.37 mg, 4.26 mmol, 741.74 µL), and finally WX356-6 (400 mg, 2.04 mmol, HCl) was added. The reaction mixture was purged with nitrogen gas for three times, then stirred at 28° C. for 12 hours. The reaction mixture was filtered through an organic phase needle filter to give a crude product. The crude product was isolated by column chromatography to give a racemic product, which was further isolated by SFC to give WX355 and WX356.

Compound WX355: ¹H NMR (400 MHz, DMSO-d₆) δ=11.17 (s, 1H), 8.79 (t, J=5.5 Hz, 1H), 8.08 (d, J=8.4 Hz, 1H), 7.85 (d, J=1.3 Hz, 1H), 7.77 (dd, J=1.5, 8.4 Hz, 1H), 7.81-7.72 (m, 1H), 7.40 (dd, J=1.1, 1.8 Hz, 1H), 7.01 (d, J=1.8 Hz, 1H), 3.52-3.37 (m, 5H), 3.31-3.21 (m, 2H), 2.05 (s, 3H), 1.65-1.52 (m, 2H), 1.21 (s, 3H);

Compound WX356: ¹H NMR (400 MHz, DMSO-d₆) (Peak 2) δ=11.17 (br s, 1H), 8.79 (br t, J=5.3 Hz, 1H), 8.08 (d, J=8.2 Hz, 1H), 7.85 (s, 1H), 7.77 (d, J=8.2 Hz, 1H), 7.40 (s, 1H), 7.01 (d, J=1.3 Hz, 1H), 3.53-3.38 (m, 5H), 3.30-3.20 (m, 2H), 2.05 (s, 3H), 1.58 (br d, J=5.3 Hz, 2H), 1.21 (s, 3H), 1.01 (s, 3H).

Chiral resolution conditions: chiral column: AD (250 mm*30 mm, 5 µm); mobile phase: A: water (10 mM ammonium bicarbonate), B: isopropanol; gradient: B from 0.4% to 0.4% in 20 min; flow rate: 75 mL/min; column temperature: 35° C.

Retention time of compound 355: 2.5 min (peak 1); retention time of compound 356: 2.7 min (peak 2).

Embodiment 92: WX338

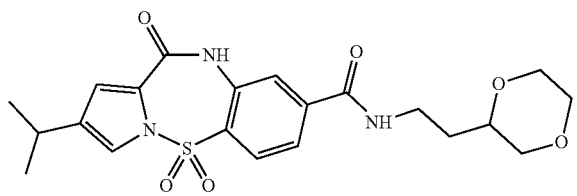

WX338

Synthetic Route

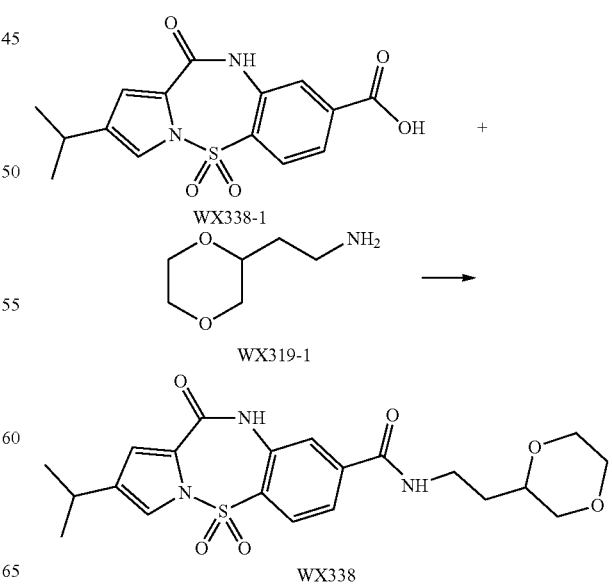

Step 1: Synthesis of Compound WX338

The synthesis of compound WX338 was referred to the step 1 of the synthesis of compound WX339 and WX350 in Embodiment 89. $^1$H NMR (400 MHz, DMSO-d$_6$) δ=11.17 (s, 1H), 8.76 (t, J=5.4 Hz, 1H), 8.08 (d, J=8.4 Hz, 1H), 7.86 (d, J=1.3 Hz, 1H), 7.77 (dd, J=1.5, 8.2 Hz, 1H), 7.37-7.34 (m, 1H), 7.12 (d, J=2.0 Hz, 1H), 3.74-3.35 (m, 7H), 3.16 (dd, J=10.1, 11.2 Hz, 1H), 2.80 (td, J=6.9, 13.7 Hz, 1H), 1.60-1.50 (m, 2H), 1.15 (d, J=6.8 Hz, 6H).

HBV In Vitro Test in Quantitative qPCR Assay

1 Experimental purpose:

The HBV DNA content in HepG2.2.15 cells was determined by real-time quantitative qPCR assay (real time-qPCR), and the inhibitory effect of the compound on HBV was evaluated by the EC$_{50}$ value of the compound.

2 Experimental materials:

2.1 Cell line: HepG2.2.15 cells

HepG2.2.15 cell culture medium (DMEM/F12, Invitrogen-11330057; 10% serum, Invitrogen-10099141; 100 units/mL penicillin and 10 μg/mL streptomycin, Invitrogen-15140122; 1% non-essential amino acids, Invitrogen-11140076; 2 mM L-glutamine, Invitrogen-25030081; 300 μg/mL Geneticin, Invitrogen-10131027

2.2 Reagents:

Trypsin (Invitrogen-25300062)

DPBS (Hyclone-SH30028.01B)

DMSO (Sigma-D2650-100 Ml)

High-throughput DNA purification kit (QIAamp 96 DNA Blood Kit, Qiagen-51162)

Quantitative Fast Start Universal Probe Reagent (Fast-Start Universal Probe Master, Roche-04914058001)

2.3 Consumables and equipment:

96-well cell culture plate (Corning-3599)

CO$_2$ incubator (HERA-CELL-240)

Optical sealing membrane (ABI-4311971)

Quantitative PCR 96-well plate (Applied Biosystems-4306737)

Quantitative fluorescence PCR system (Applied Biosystems-7500 real time PCR system)

3. Experimental procedures and methods:

3.1 HepG2.2.15 cells (4×10$^4$ cells/well) were seeded into a 96-well plate and incubated overnight at 37° C. under 5% CO$_2$.

3.2 On the 2$^{nd}$ day, the compound was diluted into 8 concentrations with 3-time gradient. The compounds with different concentrations were added into the culture wells in duplicate wells. The final concentration of DMSO in the culture medium was 1%. 1 μM GLS4 was used as a 100% inhibition control, and 1% DMSO was used as a 0% inhibition control.

3.3 On the 5$^{th}$ day, the culture medium was replaced with a fresh medium containing the compound.

3.4 On the 8$^{th}$ day, the culture medium in the culture well was collected, and the DNA was extracted with a high-throughput DNA purification kit (Qiagen-51162), of which specific procedure was referred to the product specification.

3.5 The preparation of the PCR reaction solution was shown in Table 1:

TABLE 1

The preparation of the PCR reaction solution

| Item | The volume for preparing 1 hole (μL) | The volume for preparing 80 holes (μL) |
|---|---|---|
| Quantitative Fast Start Universal Probe Reagent | 12.5 | 1000 |
| Upstream primer (10 μL) | 1 | 80 |
| Downstream primer (10 μL) | 1 | 80 |
| Probe (10 μL) | 0.5 | 40 |

Upstream primer sequence:
(SEQ ID NO: 1)
GTGTCTGCGGCGTTTTATCA

Downstream primer sequence:
(SEQ ID NO: 2)
GACAAACGGGCAACATACCTT

Probe sequence:
(SEQ ID NO: 3)
5' + FAM + CCTCTKCATCCTGCTGCTATGCCTCATC + TAMRA-3'

3.6 15 μL of the reaction mixture was added into each well of a 96-well PCR plate, followed by addition of 10 μL of sample DNA or HBV DNA standards into each well.

3.7 PCR reaction conditions: heating at 95° C. for 10 minutes; then denaturation at 95° C. for 15 seconds, extension at 60° C. for 1 minute, a total of 40 cycles.

3.8 Data Analysis:

3.8.1 Calculation of the percentage of inhibition: % Inh.=[1−(DNA copy number in sample−DNA copy number in 1 μM GLS4)/(DNA copy number in DMSO control−DNA copy number in 1 μM GLS4)]×100

3.8.2 Calculation of EC$_{50}$: The 50% inhibitory concentration (EC$_{50}$) value of the compound on HBV was calculated by GraphPad Prism software.

4. The experimental results were shown in Table 2:

TABLE 2

EC$_{50}$ test results measured in qPCR assay

| Test compound | 50% inhibitory concentration (EC$_{50}$) value of HBV | Test compound | 50% inhibitory concentration (EC$_{50}$) value of HBV |
|---|---|---|---|
| WX143 | A | WX145 | B |
| WX146 | D | WX163 | C |
| WX170 | A | WX171 | B |
| WX175 | B | WX176 | D |
| WX254 | B | WX255 | A |
| WX257 | A | WX258 | B |
| WX259 | B | WX260 | A |
| WX261 | B | WX262 | B |
| WX263 | C | WX265 | D |
| WX266 | B | WX267 | B |
| WX270 | B | WX185 | A |
| WX186 | A | WX184 | B |
| WX187 | B | WX189 | B |
| WX190 | C | WX195 | C |
| WX196 | A | WX197 | B |
| WX198 | B | WX200 | A |
| WX201 | C | WX206 | B |
| WX208 | C | WX289 | B |
| WX290 | A | WX211 | C |
| WX215 | B | WX216 | A |
| WX217 | A | WX218 | A |
| WX219 | A | WX220 | A |
| WX223 | C | WX225 | B |

TABLE 2-continued

EC$_{50}$ test results measured in qPCR assay

| Test compound | 50% inhibitory concentration (EC$_{50}$) value of HBV | Test compound | 50% inhibitory concentration (EC$_{50}$) value of HBV |
|---|---|---|---|
| WX226 | C | WX227 | B |
| WX228 | B | WX229 | B |
| WX230 | B | WX231 | B |
| WX232 | C | WX233 | A |
| WX235 | B | WX237 | A |
| WX239 | A | WX271 | C |
| WX272 | B | WX275 | C |
| WX278 | A | WX280 | B |
| WX288 | B | WX292 | C |
| WX293 | A | WX295 | B |
| WX297 | A | WX298 | A |
| WX299 | B | WX300 | B |
| WX301 | A | WX305 | A |
| WX306 | A | WX308 | A |
| WX309 | A | WX311 | A |
| WX312 | A | WX221 | A |
| WX222 | A | WX279 | B |
| WX285 | B | WX286 | C |
| WX287 | C | WX321 | B |
| WX322 | A | WX323 | A |
| WX313 | A | WX315 | A |
| WX318 | A | WX326 | A |
| WX319 | A | WX320 | B |
| WX328 | A | WX338 | B |
| WX325 | A | WX329 | B |
| WX339 | A | WX350 | B |
| WX352 | B | WX353 | A |
| WX355 | C | WX356 | B |

Note:
A: EC$_{50}$ ≤100 nM;
B: 100 nM <EC$_{50}$ ≤500 nM;
C: 500 nM <EC$_{50}$ ≤1000 nM;
D: 1000 nM <EC$_{50}$ ≤10000 nM;

Conclusion: The compounds of the invention have a significant inhibitory effect on HBV.

Study on the Inhibition of Cytochrome P450 Isoenzyme

The experimental purpose was to determine the inhibitory effect of test compounds on the activity of human liver microsomal cytochrome P450 isoenzymes (CYP1A2, CYP2C9, CYP2C19, CYP2D6 and CYP3A4).

Experimental procedures: The test compound (10 mM) was subjected to a gradient dilution to prepare a working solution (100× final concentration). The working solution concentrations were: 5, 1.5, 0.5, 0.15, 0.05, 0.015, 0.005 mM. The working solutions of the mixture of P450 isoenzymes (CYP1A2, CYP2C9, CYP2C19, CYP2D6, and CYP3A4) positive inhibitors and the specific substrate thereof (5 in 1) were prepared simultaneously. Human liver microsomes frozen in a −80° C. refrigerator were thawed on ice. After all of the human liver microsomes were dissolved, it was diluted with PB to prepare the working solution with a specific concentration (0.253 mg/mL). 20 µL of the substrate mixture was added into the reaction plate (20 µL of PB was added into the Blank well) while 158 µL of human liver microsomes working solution were added into the reaction plate. The reaction plate was placed on ice for use. 2 µL of test compound with varying concentration (N=1) and a specific inhibitor (N=2) were added into the corresponding wells. The group without inhibitor (test compound or positive inhibitor) was added with the corresponding organic solvent as a control sample (the test compound control sample was 1:1 DMSO:MeOH; the positive control sample was 1:9 DMSO:MeOH). After pre-incubation under a 37° C. water bath for 10 minutes, 20 µL of coenzyme factor (NADPH) solution was added into the reaction plate and incubated under a 37° C. water bath for 10 minutes. 400 µL of cold acetonitrile solution (the internal standard was 200 ng/mL Tolbutamide and Labetalol) was added to terminate the reaction. The reaction plate was placed on a shaker and shaken for 10 minutes. After centrifugation at 4,000 rpm for 20 minutes, 200 µL of the supernatant was collected and added to 100 µL of water to dilute the sample. Finally, the plate was sealed, oscillated, shaken evenly, and subjected to LC/MS/MS measurement. The experimental results were shown in Table 3:

TABLE 3

Inhibitory effects of test compounds on the activity of human liver microsomal cytochrome P450 isoenzyme

| | IC$_{50}$ (µM) | | | | |
|---|---|---|---|---|---|
| Compound | CYP1A2 | CYP2C9 | CYP2C19 | CYP2D6 | CYP3A4-M |
| WX171 | >50 | >50 | >50 | >50 | >50 |
| WX290 | >50 | >50 | >50 | >50 | >50 |
| WX319 | >50 | >50 | >50 | >50 | >50 |
| WX325 | >50 | >50 | >50 | >50 | >50 |

Conclusion: The test compounds have no significant inhibitory effect on CYP1A2, CYP2C9, CYP2C19, CYP2D6 and CYP3A4.

Study on the Plasma Protein Binding Rate

The experimental purpose was to determine the protein binding rate of test compounds in human and CD-1 mice plasma.

Experimental procedures: 796 µL of blank plasma was taken from human and CD-1 mice, and 4 µL of test compound working solution (400 µM) or warfarin working solution (400 µM) was added to achieve a final concentration of the test compound and the warfarin in plasma samples of 2 µM. The samples were mixed thoroughly. The final concentration of organic phase DMSO was 0.5%. 50 µL of the test compound and warfarin plasma sample were transferred into sample receiving plates (three parallels), and a relative volume of corresponding blank plasma or buffer was immediately added, insuring that the final volume of each sample well was 100 µL, and the volume ratio of plasma to dialysis buffer was 1:1. 400 µL of stop solution was added to these samples, which was used as a T$_0$ sample for the determination of recovery and stability. The T$_0$ sample was stored at 2-8° C., waiting for subsequent processing with other dialyzed samples. 150 µL of test compound and warfarin plasma sample were added into the drug delivery end of each dialysis well, and 150 µL of blank dialysis buffer were added into the receiving end of the dialysis well. The dialysis plate was then sealed with a gas permeable membrane, placed in a humidified 5% CO$_2$ incubator and incubated at 37° C. while shaking at about 100 rpm for 4 hours. After completion of the dialysis, 50 µL of the dialyzed buffer sample and the dialyzed plasma sample were pipetted into a new sample receiving plate. A relative volume of corresponding blank plasma or buffer was added to the sample, insuring that the final volume of each sample well was 100 µL and the plasma to dialysis buffer volume ratio was 1:1. All samples were subjected to protein precipitation, followed by LC/MS/MS analysis. The protein binding rate and the recovery rate were calculated by the formulas: % Unbound (unbinding rate)=100*FC/TC; % Bound (binding rate)=100−% Unbound; % Recovery (recovery rate)=100*(FC+TC)/T0. The experimental results were shown in Table 4:

TABLE 4

Protein binding rates of test compounds in
human and CD-1 mice plasma

| | Plasma protein binding rate | |
|---|---|---|
| Compound | Human | CD-1 mouse |
| WX171 | 76% | 88% |
| WX290 | 90% | 93% |
| WX319 | 67% | 81% |
| WX325 | 81% | 94% |

Conclusion: The test compounds exhibit a lower protein binding rate in human and CD-1 mice plasma.

In Vivo Pharmacokinetic Study

Pharmacokinetic study of oral and intravenous administration of WX325 on Balb/c mice WX325 was mixed with a 400/40% aqueous solution of 5% DMSO/55% polyethylene glycol, followed by vortexing and sonication to prepare a 1 mg/mL nearly clear solution, which was filtered through microporous membrane for use. Balb/c female mice of 7-10 weeks old were selected and the candidate compound solution was intravenously administered at a dose of 1 mg/kg. WX325 was mixed with a 10% aqueous solution of solutol (polyethylene glycol-15 hydroxystearate), followed by vortexing and sonication to prepare a 1 mg/mL nearly clear solution, which was filtered through microporous membrane for use. Balb/c female mice of 7-10 weeks old were selected and the candidate compound solution was orally administered at a dose of 10 mg/kg.

Whole blood was collected within a certain period of time, which was treated to prepare the plasma. The drug concentration was analyzed by LC-MS/MS method, and the pharmacokinetic parameters were calculated by Phoenix WinNonlin software (Pharsight, USA).

Pharmacokinetic study of oral and intravenous administration of WX325 on SD rats WX325 was mixed with a 400/40% aqueous solution of 5% DMSO/55% polyethylene glycol, followed by vortexing and sonication to prepare a 1 mg/mL nearly clear solution, which was filtered through microporous membrane for use. SD male rats of 7-10 weeks old were selected and the candidate compound solution was intravenously administered at a dose of 1 mg/kg.

WX325 was mixed with a 10% aqueous solution of solutol, followed by vortexing and sonication to prepare a 1 mg/mL nearly clear solution, which was filtered through microporous membrane for use. SD male rats of 7-10 weeks old were selected and the candidate compound solution was orally administered at a dose of 10 mg/kg.

Whole blood was collected within a certain period of time, which was treated to prepare the plasma. The drug concentration was analyzed by LC-MS/MS method, and the pharmacokinetic parameters were calculated by Phoenix WinNonlin software (Pharsight, USA).

Pharmacokinetic study of oral and intravenous administration of WX325 on Beagle dogs WX325 was mixed with a 400/40% aqueous solution of 5% DMSO/55% polyethylene glycol, followed by vortexing and sonication to prepare a 1 mg/mL nearly clear solution, which was filtered through microporous membrane for use. A male beagle dog of about 10 kg was selected and the candidate compound solution was intravenously administered at a dose of 1 mg/kg.

WX325 was mixed with a 10% aqueous solution of solutol, followed by vortexing and sonication to prepare a 2 mg/mL uniform suspension, which was filtered through microporous membrane for use. A male beagle dog of about 10 kg was selected and the candidate compound solution was orally administered at a dose of 10 mg/kg.

Whole blood was collected within a certain period of time, which was treated to prepare the plasma. The drug concentration was analyzed by LC-MS/MS method, and the pharmacokinetic parameters were calculated by Phoenix WinNonlin software (Pharsight, USA).

The experimental results were shown in Table 5:

TABLE 5

Pharmacokinetic results of test compound

| | | | WX325 | | |
|---|---|---|---|---|---|
| | Compound | | Mouse | Rat | Dog |
| PK | iv | $T_{1/2}$ (h) | 1.2 | 0.95 | 2.87 |
| | (1 mpk) | $Vd_{ss}$ (L/kg) | 0.45 | 0.56 | 2.95 |
| | | Cl (ml/min/kg) | 8.5 | 8.5 | 15.6 |
| | | $AUC_{0\text{-}last}$ (nM · h) | 4672 | 4818 | 2679 |
| | po | $T_{max}$ (h) | 0.5 | 0.5 | 1.67 |
| | (10 mpk) | $C_{max}$ (nM) | 19933 | 8573 | 5847 |
| | | $AUC_{0\text{-}24\,h}$ (nM · h) | 32543 | 31132 | 33218 |
| | | F % | 70 | 65 | 126 |

Note:
$T_{1/2}$ refers to half-life;
$Vd_{ss}$ refers to apparent volume of distribution;
Cl refers to clearance rate;
$AUC_{0\text{-}last}$ refers to area under the curve;
$T_{max}$ refers to peak time;
$C_{max}$ refers to peak concentration;
F % refers to oral bioavailability;
iv refers to intravenous injection;
PO refers to oral administration; mpk refers to mg/kg.

Experimental conclusion: The compound of the invention has a good pharmacokinetic property in single or partial parameter on canine.

In Vivo Pharmacodynamic Study

AAV/HBV model

Experimental purpose was to determine the anti-HBV effect of the compounds on mice by AAV/HBV mouse model.

Figure 2:
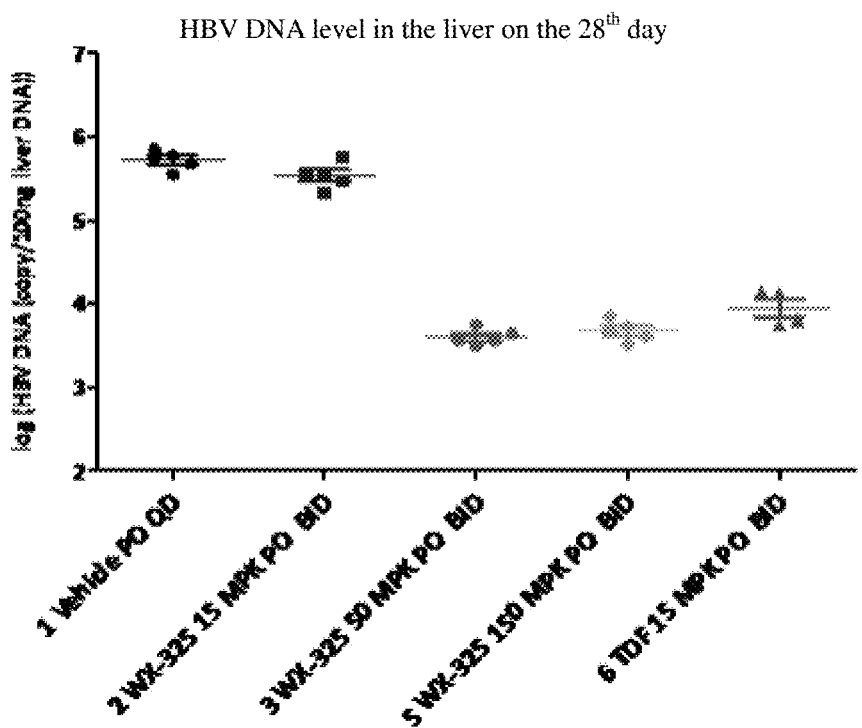
FIG. 2: Hepatitis B virus DNA level in the liver on the 28$^{th}$ day; Note: QD refers to once a day; BID refers to twice a day; MPK refers to mg/kg; Vehicle refers to a blank control.

Experimental procedures: The day of the first administration was designated as day 0, one day before administration was day −1, one day after administration was day 1, and so forth. On the $28^{th}$ day before administration, all animals were injected with $1*10^{11}$ v.g. rAAV8-1.3 HBV virus via the tail vein, and each animal was injected with 200 μL. On the $14^{th}$ day and $7^{th}$ day before administration, the blood of all the mice injected with rAAV8-1.3 HBV virus was taken from the submandibular vein for collection of the serum. The collected blood samples were placed at 37° C. for about 30 minutes, followed by centrifugation at 13,200 g at 4° C. for 3 minutes, and the supernatant was taken. The serum was used to detect the content of HBV DNA, HBeAg and HBsAg. Mice, with a low HBV DNA, HBeAg and HBsAg level and a light weight would be removed from the experiment. 25 mice were selected and equally distributed into each group, and it was ensured that there was no statistical difference in HBV DNA, HBsAg, HBeAg level and body weight of the mice in each compound treatment group on the $21^{st}$ day after the virus injection (P>0.05). The test compound WX325 was mixed with a 10% aqueous solution of solutol, followed by vortexing and sonication to prepare a uniform suspension, which was filtered through microporous membrane for use. Tenofovir was used as a positive compound and dissolved in physiological saline, sonicated and stirred until dissolved, formulated into a 0.1 mg/mL mother liquor, and then diluted to 0.01 mg/mL with physiological saline, and stored at 4° C. before use. The test compound WX325 was administered twice a day (BID) at an interval of 8 hour by oral gavage (PO). The reference compound tenofovir was administered by oral gavage twice a day. Both drugs were administered for 28 days, in which blood samples were taken on the $3^{rd}$, $7^{th}$, $10^{th}$ and $28^{th}$ day after administration, and the HBV DNA level in plasma was measured by qPCR. On the $28^{th}$ day, the mice were euthanized by $CO_2$ inhalation, and the livers were collected. The HBV DNA level in the livers of the mice was determined by qPCR. The experimental results were shown in FIG. 1 and FIG. 2.

Experimental conclusion: The compounds of the invention exhibit good in vivo efficacy and a dose-dependent effect.

What is claimed is:

1. A compound of formula (I), a tautomer or stereoisomer thereof or a pharmaceutically acceptable salt thereof,

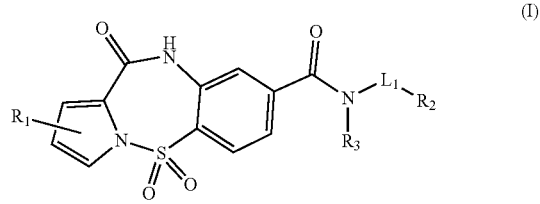

(I)

$L_1$ is a single bond or —$C_{1-6}$ alkyl-;

$R_1$ is H, Cl, F, Br I or $C_{1-3}$ alkyl which is optionally substituted by 1, 2 or 3 R;

$R_2$ is selected from the group consisting of $C_{1-3}$ heteroalkyl, 4-8 membered heterocycloalkyl, 5-10 membered heteroaryl, 4-8 membered partially unsaturated heterocycloalkyl, phenyl, $C_{1-3}$ alkyl, $C_{3-8}$ cycloalkyl, 4-8 membered heterocycloalkyl-O— and 5-10 membered heteroaryl-O—, each of which is optionally substituted by 1, 2 or 3 R;

$R_3$ is H or $C_{1-3}$ alkyl;

---

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Upstream primer

<400> SEQUENCE: 1
gtgtctgcgg cgttttatca                                                   20

<210> SEQ ID NO 2
<211> LENGTH: 21
<212> TYPE: DNA
<213> ORGANISM: Artificial Sequence
<220> FEATURE:
<223> OTHER INFORMATION: Downstream primer

<400> SEQUENCE: 2
gacaaacggg caacatacct t                                                 21

<210> SEQ ID NO 3
<211> LENGTH: 28
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (1)..(1)
<223> OTHER INFORMATION: FAM modification
<220> FEATURE:
<221> NAME/KEY: misc_feature
<222> LOCATION: (28)..(28)
<223> OTHER INFORMATION: TAMRA modification

<400> SEQUENCE: 3
cctctkcatc ctgctgctat gcctcatc                                          28
``` each of R is independently H, Cl, F, Br, I, NH$_2$, OH or CN, or selected from the group consisting of C$_{1-6}$ alkyl, C$_{1-6}$ heteroalkyl, phenyl, phenyl-O—C(=O)— and 5-6 membered heteroaryl, each of which is optionally substituted by 1, 2 or 3 R';

each of R' is independently selected from the group consisting of Cl, F, Br, I, NH$_2$, CH$_3$, CN and N(CH$_3$)$_2$;

each of the "hetero" in the C$_{1-3}$ heteroalkyl, 4-8 membered heterocycloalkyl, 5-10 membered heteroaryl, C$_{1-6}$ heteroalkyl, 5-6 membered heteroaryl and 4-8 membered partially unsaturated heterocycloalkyl is independently selected from the group consisting of —S—, —O—, —NH—, N, —C(=O)—, —O—C(=O)—, —S(=O)$_2$—, —S(=O)—, —NH—C(=O)— and —NH—C(=O)—O—;

in any of the above cases, the number of the heteroatom or the heteroatomic group is independently 1, 2, 3 or 4.

2. The compound, the tautomer or stereoisomer thereof or the pharmaceutically acceptable salt thereof according to claim 1, wherein, R is H, Cl, F, Br, I, NH$_2$, OH or CN, or selected from the group consisting of

C$_{1-3}$ alkyl, C$_{1-6}$ alkyl-O—C(=O)—, C$_{1-6}$ alkyl-C(=O)—, C$_{1-3}$ alkyl-S(=O)$_2$—, C$_{1-3}$ alkyl-S(=O)—, C$_{1-3}$ alkylamino, phenyl, phenyl-O—C(=O)— and pyridyl, each of which is optionally substituted by 1, 2 or 3 R'.

3. The compound, the tautomer or stereoisomer thereof or the pharmaceutically acceptable salt thereof according to claim 2, wherein, R is H, Cl, F, Br, I, NH$_2$, OH or CN, or selected from the group consisting of CH$_3$,

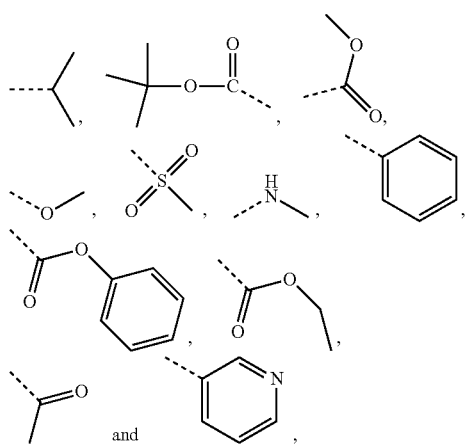

each of which is optionally substituted by 1, 2 or 3 R'.

4. The compound, the tautomer or stereoisomer thereof or the pharmaceutically acceptable salt thereof according to claim 3, wherein, R is selected from the group consisting of H, Cl, F, Br, I, NH$_2$, OH, CH$_3$, CN,

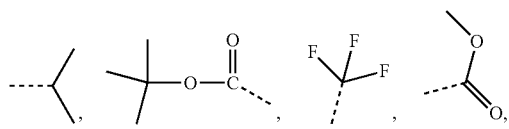

-continued

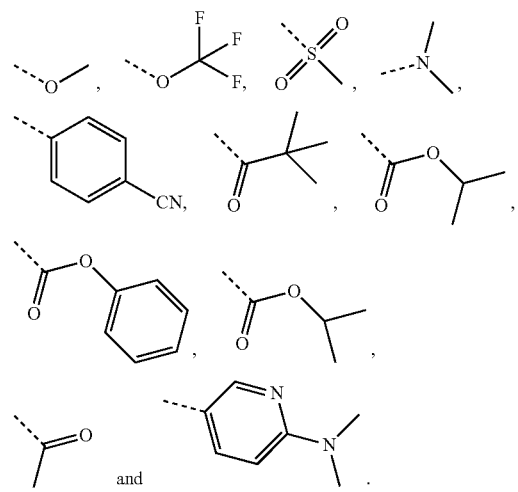

5. The compound, the tautomer or stereoisomer thereof or the pharmaceutically acceptable salt thereof according to claim 1, wherein, R$_1$ is selected from the group consisting of H, Cl, F, Br, I, Me, Et,

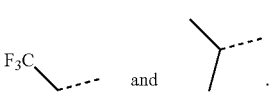

6. The compound, the tautomer or stereoisomer thereof or the pharmaceutically acceptable salt thereof according to claim 1, wherein, R$_2$ is selected from the group consisting of C$_{1-3}$ alkoxy, tetrahydrofuranyl, thiazolyl, 3-azabicyclo[3.1.0]hexyl, pyridyl, benzimidazolyl, thienyl, pyrazolyl, benzothiazolyl, imidazo[1,2-α]pyridyl, methyl, C$_{1-3}$ alkyl-thio, C$_{1-3}$ alkyl-S(=O)$_2$—, cyclopentyl, phenyl, azetidinyl, piperidinyl, pyrrolidinyl, oxazolyl, 2-oxo-pyrrolidinyl, 2(1H)-oxo-pyridinyl, cyclohexyl, cyclopropyl, 1,1-dioxo-isothiazolidinyl, pyrimidinyl, 1,3,4-thiadiazolyl, 2-oxo-oxazolidinyl, tetrahydropyranyl, cyclopentyl-O—, pyridyl-O—, oxepanyl, 1,4-dioxanyl, 1,4-dioxepanyl, morpholinyl and 2,3-dihydrobenzo[b][1,4]dioxinyl, each of which is optionally substituted by 1, 2 or 3 R.

7. The compound, the tautomer or stereoisomer thereof or the pharmaceutically acceptable salt thereof according to claim 6, wherein, R$_2$ is selected from the group consisting of CH$_3$,

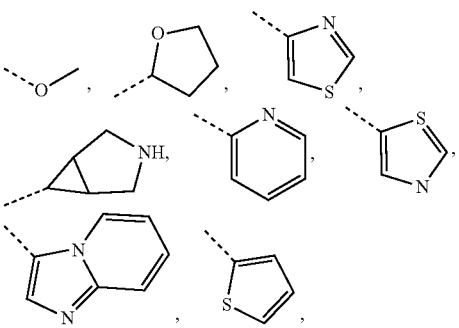

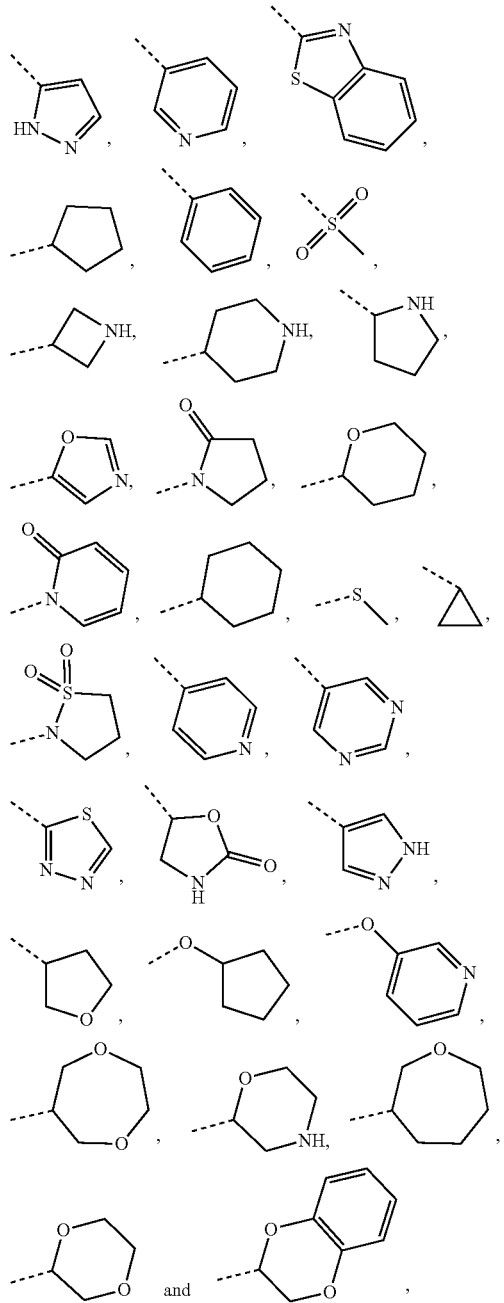
each of which is optionally substituted by 1, 2 or 3 R.
8. The compound, the tautomer or stereoisomer thereof or the pharmaceutically acceptable salt thereof according to claim 7, wherein, R₂ is selected from the group consisting of
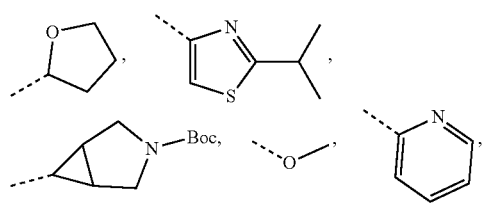
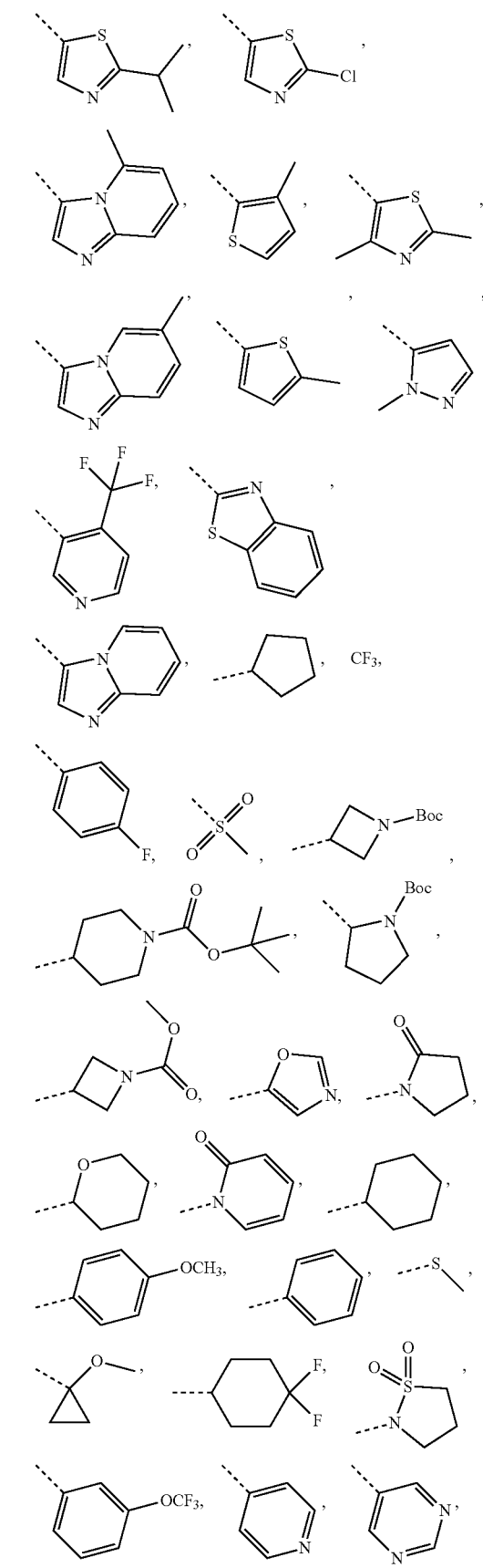

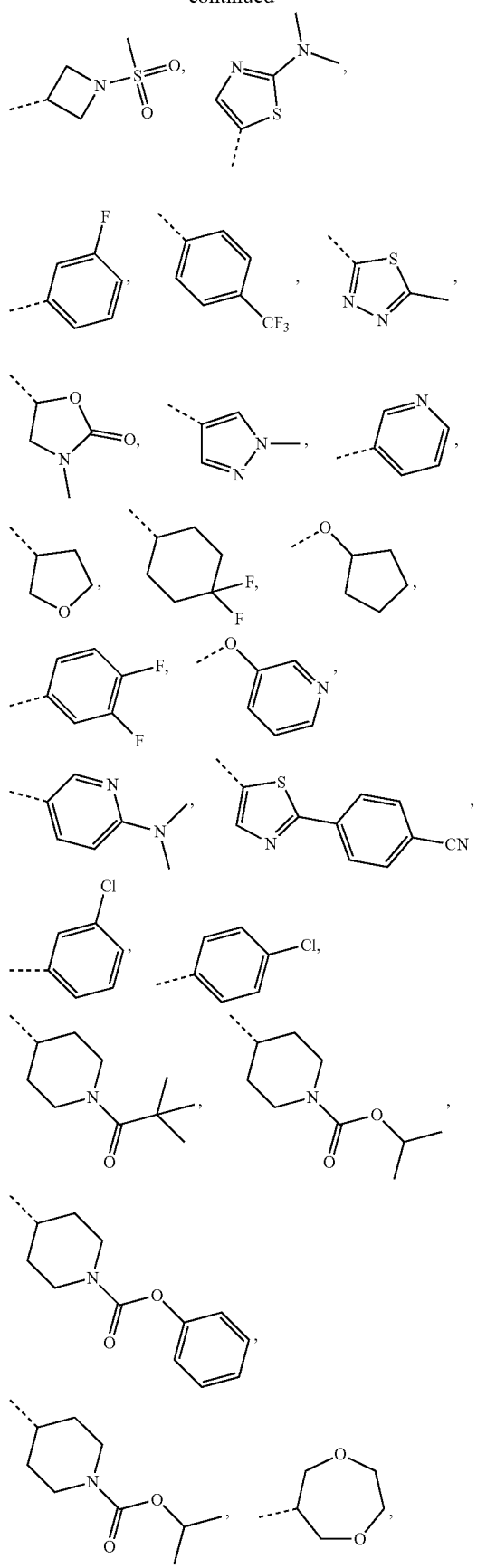

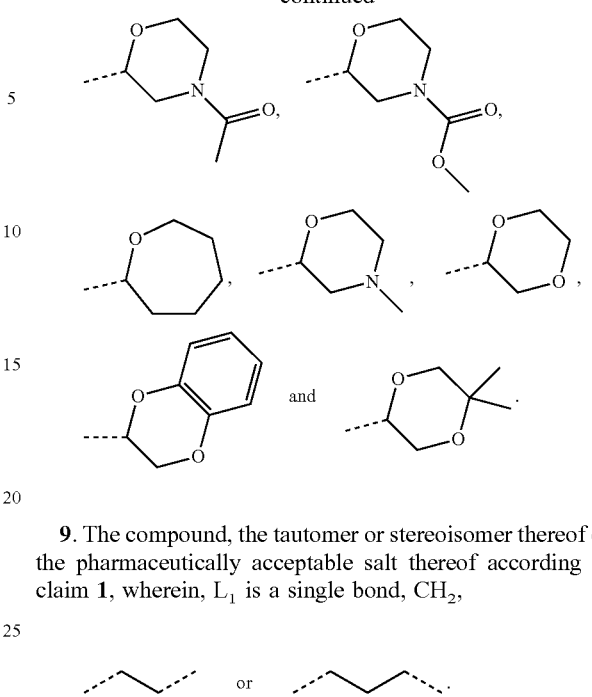

9. The compound, the tautomer or stereoisomer thereof or the pharmaceutically acceptable salt thereof according to claim 1, wherein, L₁ is a single bond, CH₂, or 10. The compound, the tautomer or stereoisomer thereof or the pharmaceutically acceptable salt thereof according to claim 1, wherein, R₃ is H, CH₃ or —CH₂CH₃.

11. The compound, the tautomer or stereoisomer thereof or the pharmaceutically acceptable salt thereof according to claim 1, wherein, the moiety $\cdots$ L₁ $-$ R₂ is selected from the group consisting of

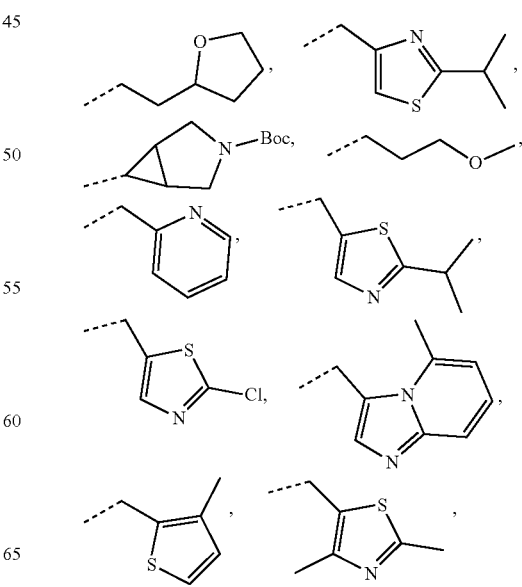

-continued
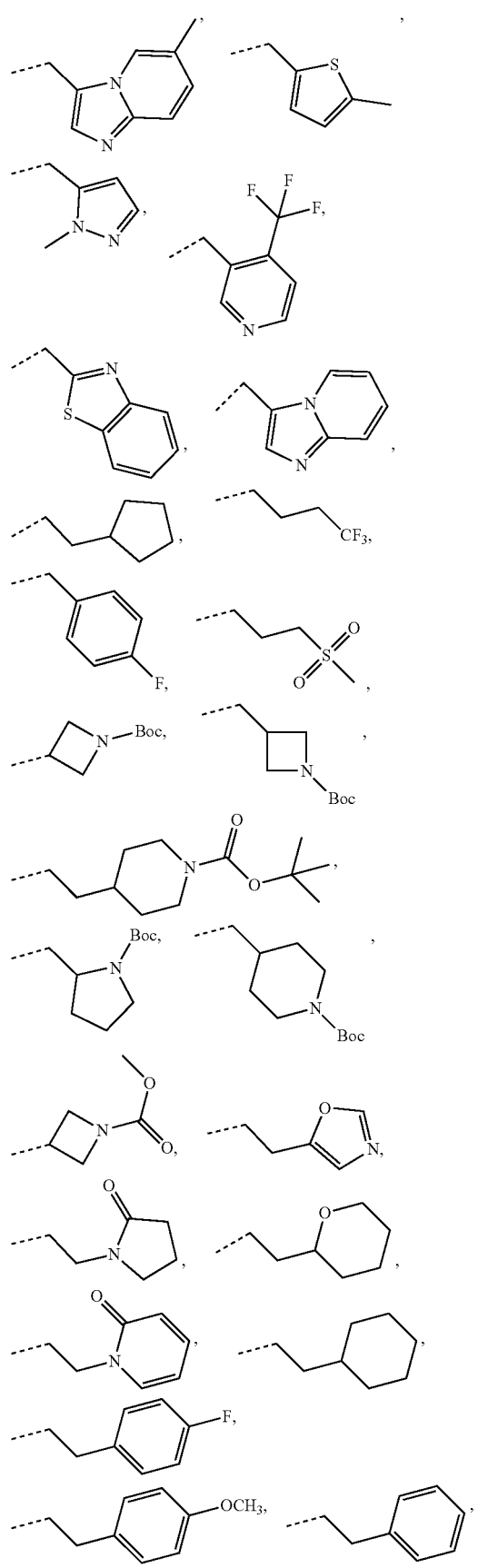
-continued
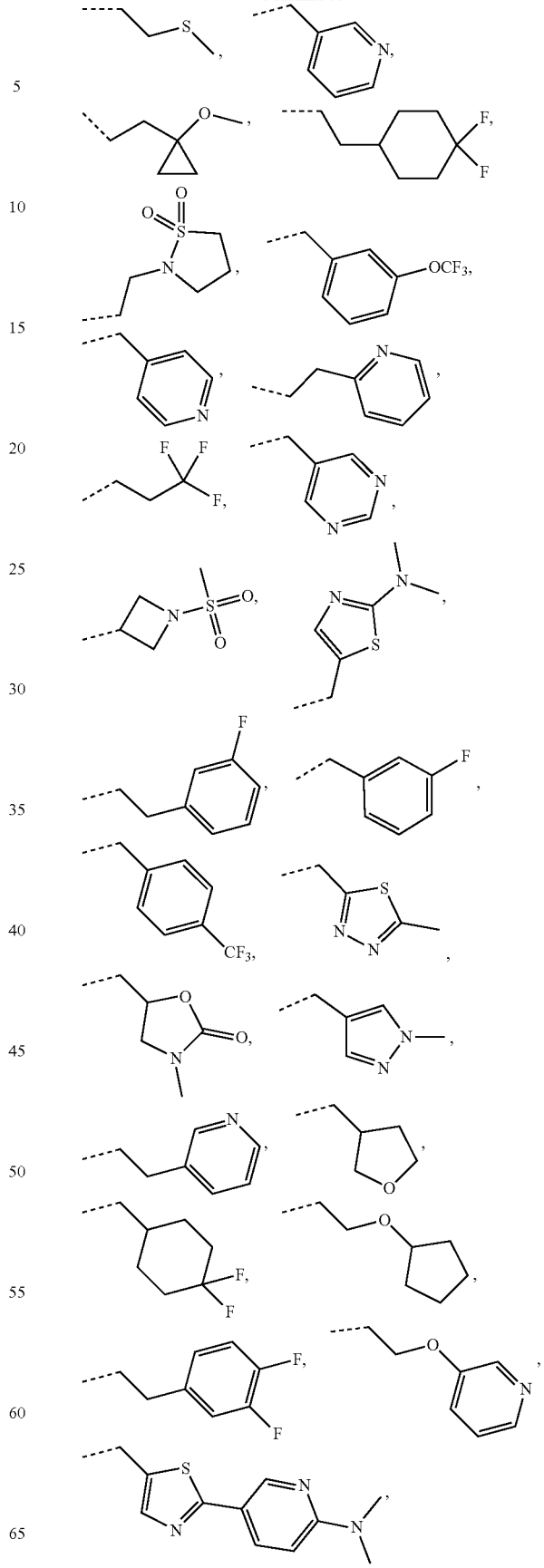

-continued
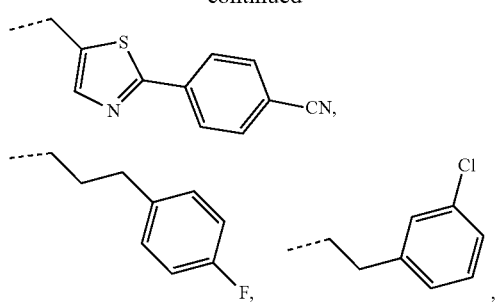
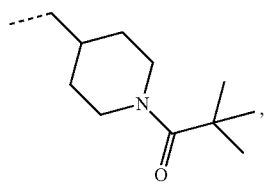
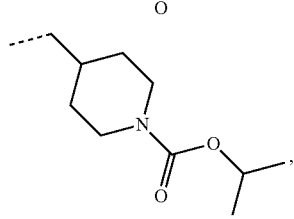
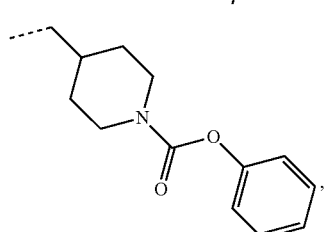
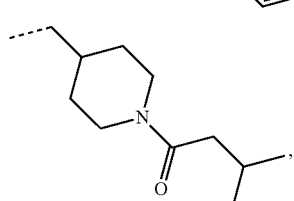
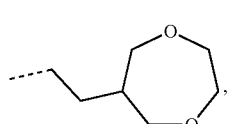
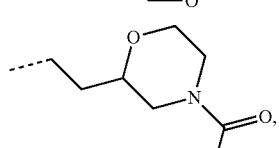
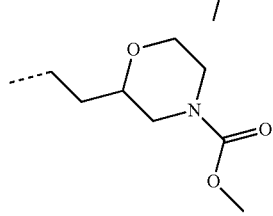
-continued
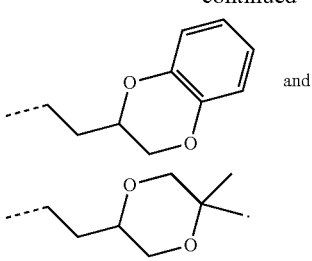 and
12. The compound, the tautomer or stereoisomer thereof or the pharmaceutically acceptable salt thereof according to claim 1, wherein the compound is selected from the group consisting of:
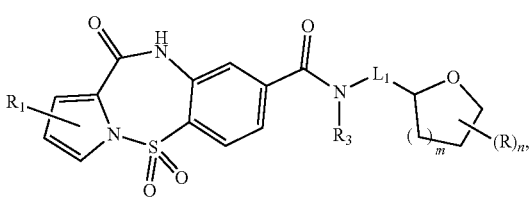 (I-1)
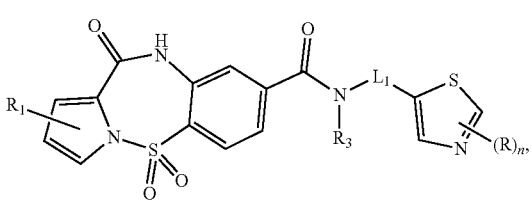 (I-2)
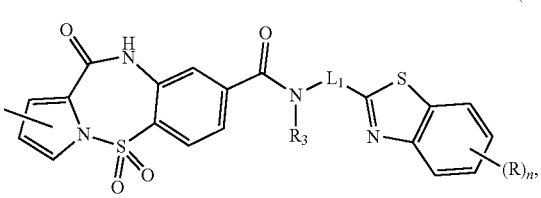 (I-3)
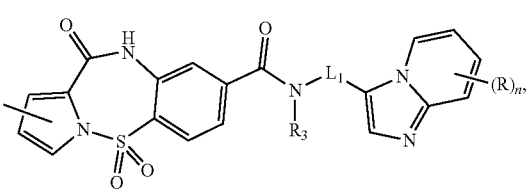 (I-4)
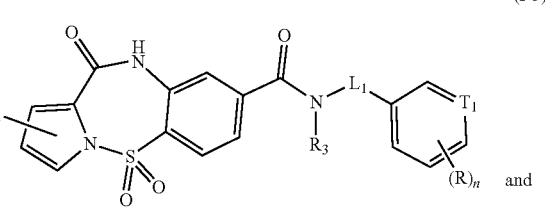 (I-5) and (I-6)

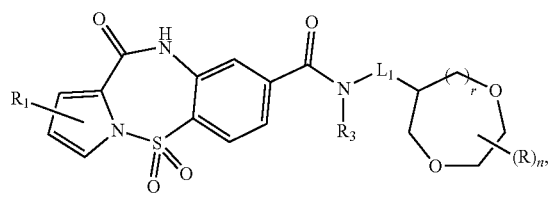

wherein, m is 1, 2 or 3;

n is 1 or 2;

r is 0 or 1;

T₁ is N or CH;

R is as defined in claim 1;

L₁ is as defined in claim 1;

R₁ is as defined in claim 1;

R₃ is as defined in claim 1.

13. The compound, the tautomer or stereoisomer thereof or the pharmaceutically acceptable salt thereof according to claim 12, wherein the compound is selected from the group consisting of:

(I-7)

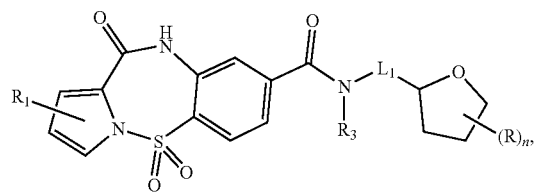

(I-8)

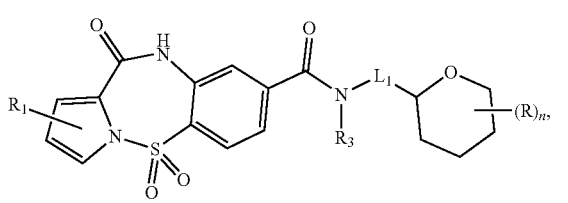

(I-9)

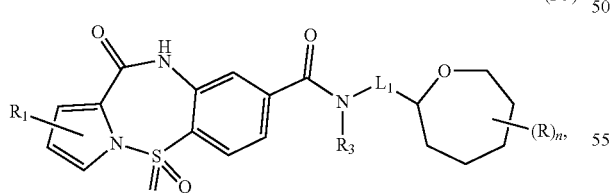

(I-10)

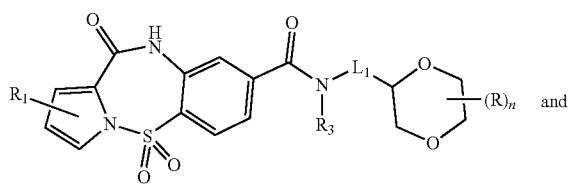 and (I-11)

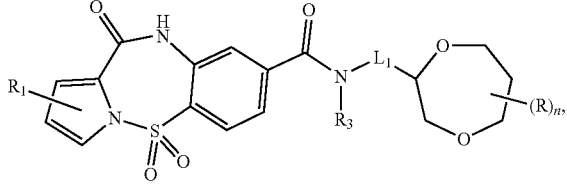

wherein, each of R is independently H, Cl, F, Br, I, NH₂, OH or CN, or selected from the group consisting of C₁₋₆ alkyl, C₁₋₆ heteroalkyl, phenyl, phenyl-O—C(=O)— and 5-6 membered heteroaryl, each of which is optionally substituted by 1, 2 or 3 R';

each of R' is independently selected from the group consisting of Cl, F, Br, I, NH₂, CH₃, CN and N(CH₃)₂;

L₁ is a single bond or —C₁₋₆ alkyl-;

R₁ is H, Cl, F, Br, I or C₁₋₃ alkyl which is optionally substituted by 1, 2 or 3 R;

R₃ is H or C₁₋₃ alkyl;

each of the "hetero" in the C₁₋₆ heteroalkyl and 5-6 membered heteroaryl is independently selected from the group consisting of —S—, —O—, —NH—, N, —C(=O)—, —O—C(=O)—, —S(=O)₂—, —S(=O)—, —NH—C(=O)— and —NH—C(=O)—O—;

in any of the above cases, the number of the heteroatom or the heteroatomic group is independently 1, 2, 3 or 4;

n is as defined in claim 12.

14. The compound, the tautomer or stereoisomer thereof or the pharmaceutically acceptable salt thereof according to claim 1, wherein the compound is selected from the group consisting of:

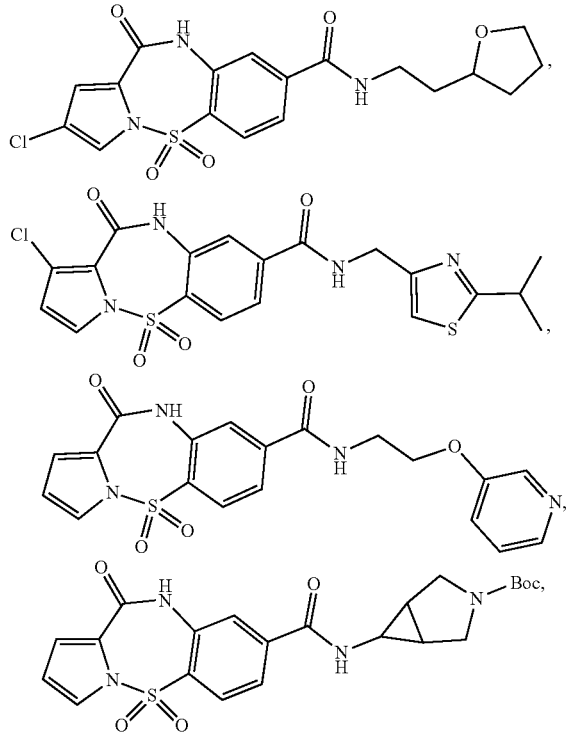

197
-continued

198
-continued

199
-continued
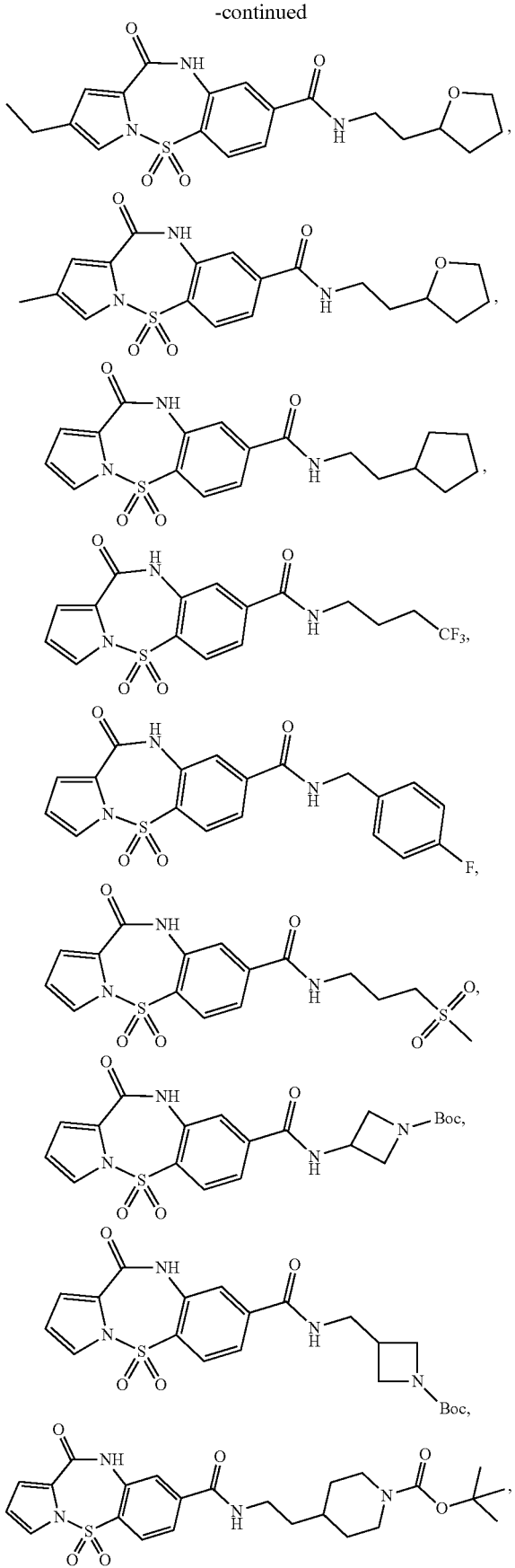
200
-continued
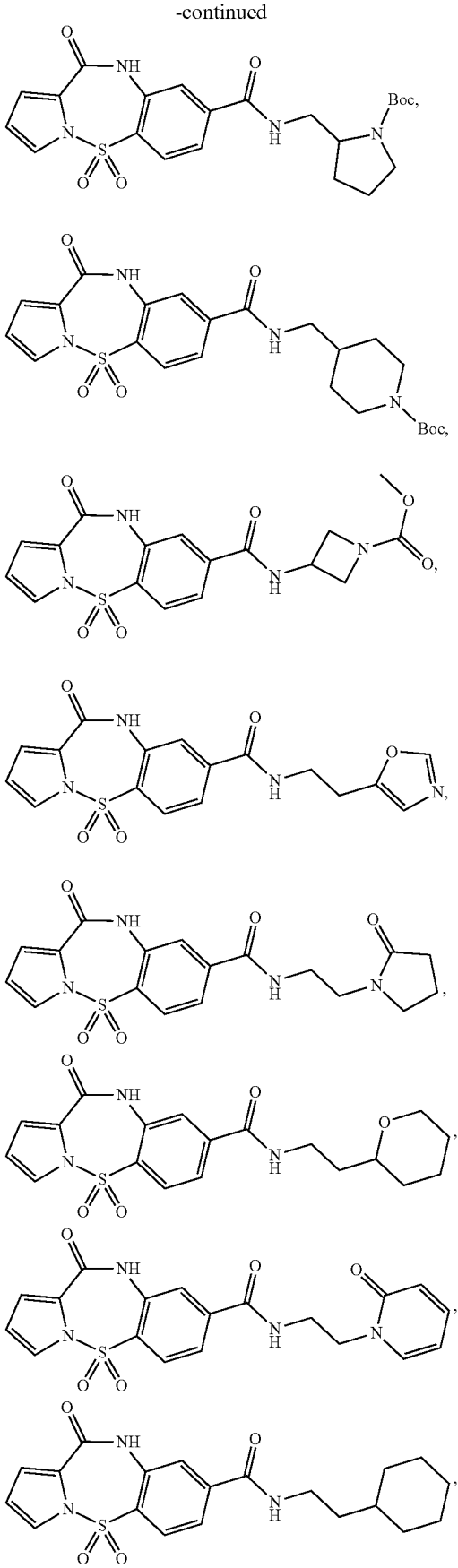

201
-continued

202
-continued

203
-continued
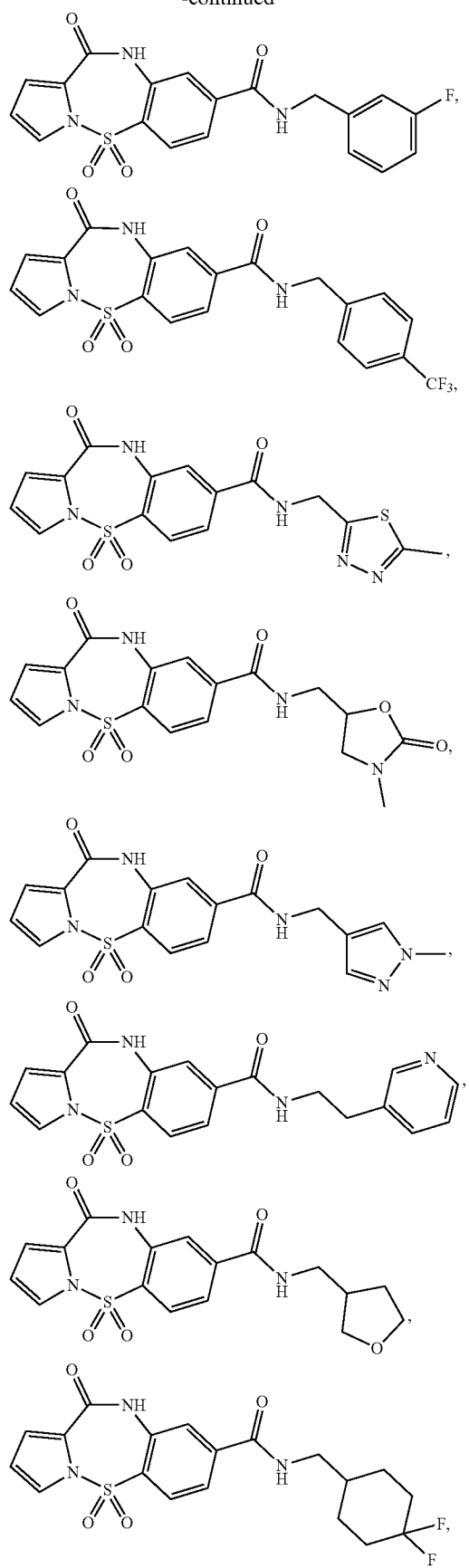
204
-continued
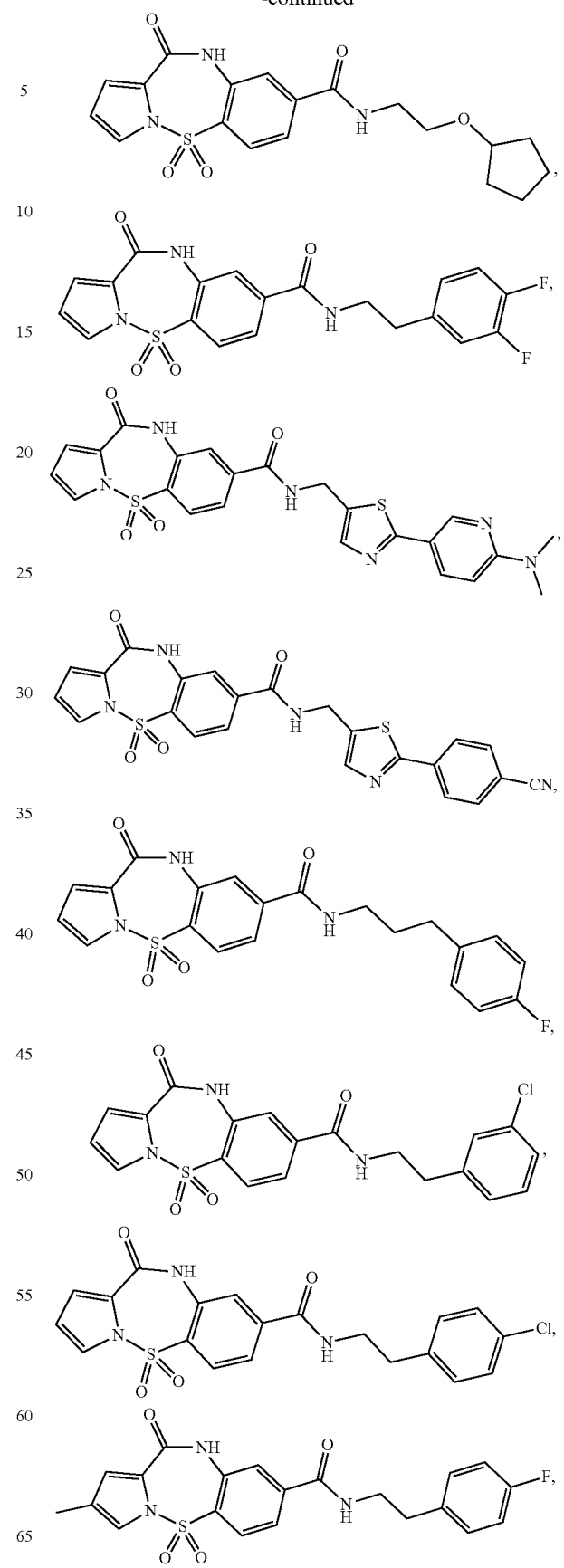

205
-continued
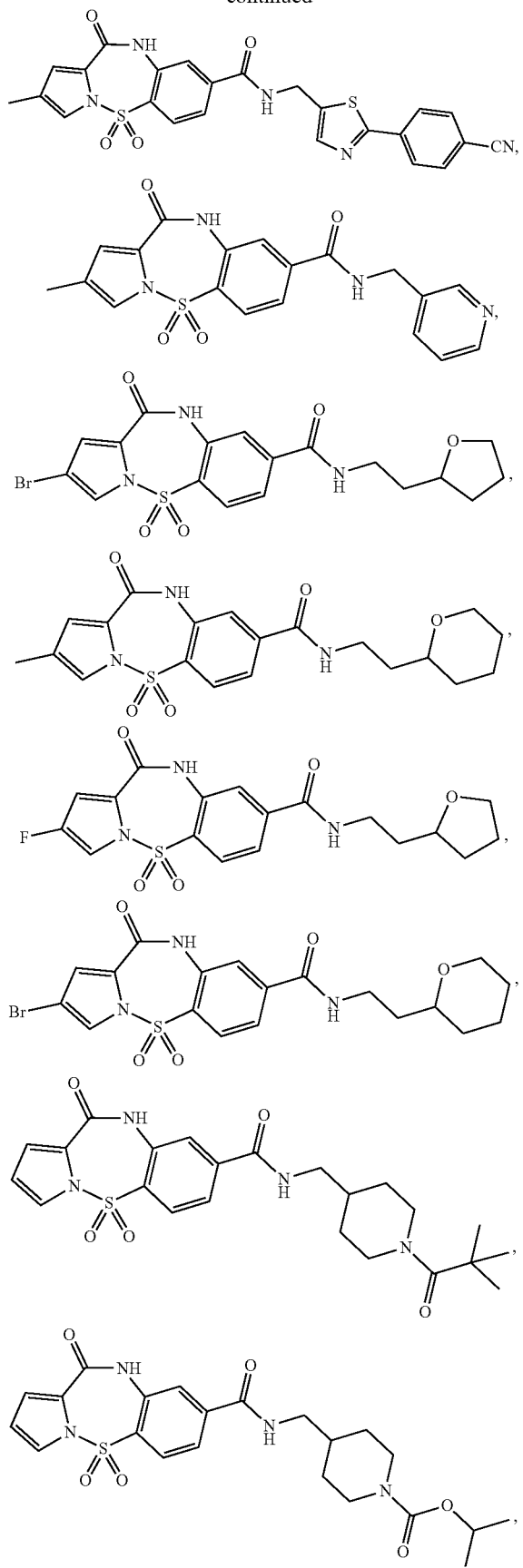
206
-continued
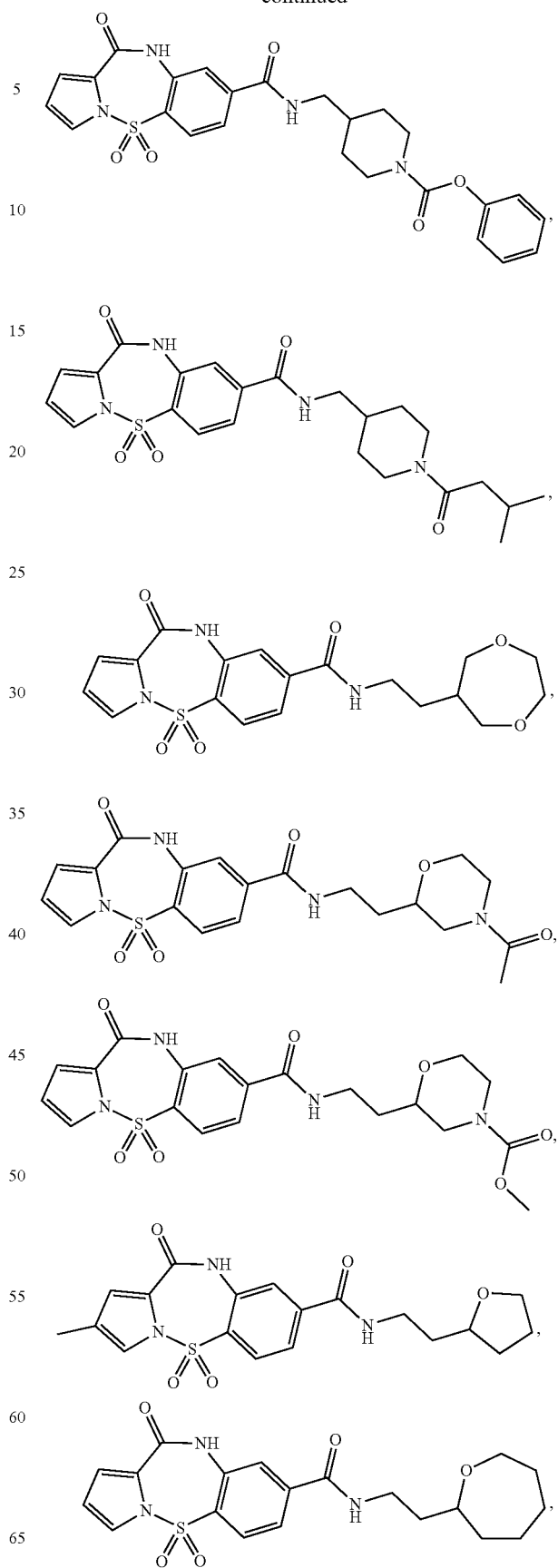

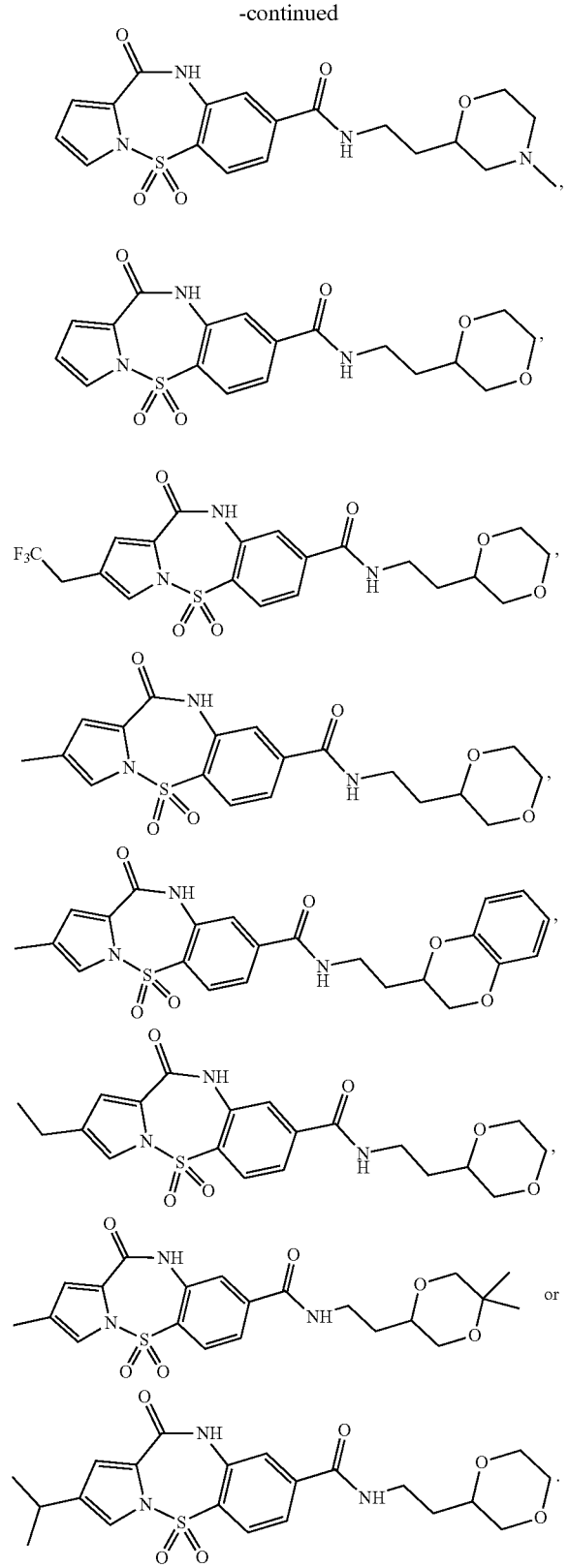
15. The compound, the tautomer or stereoisomer thereof or the pharmaceutically acceptable salt thereof according to claim 14, wherein the compound is selected from the group consisting of:
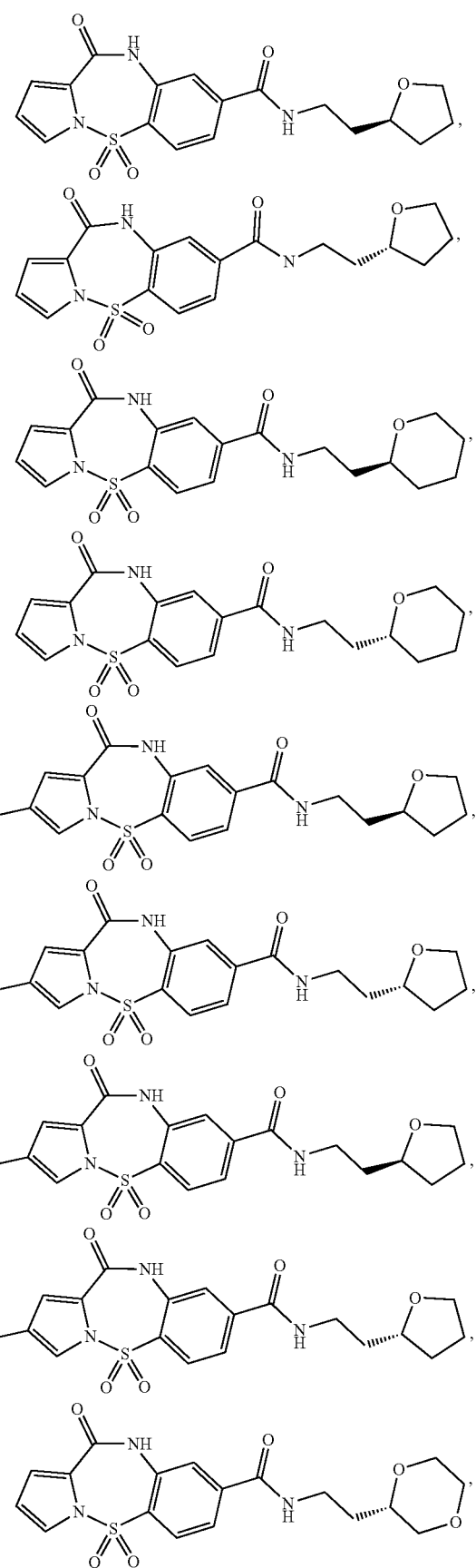

-continued

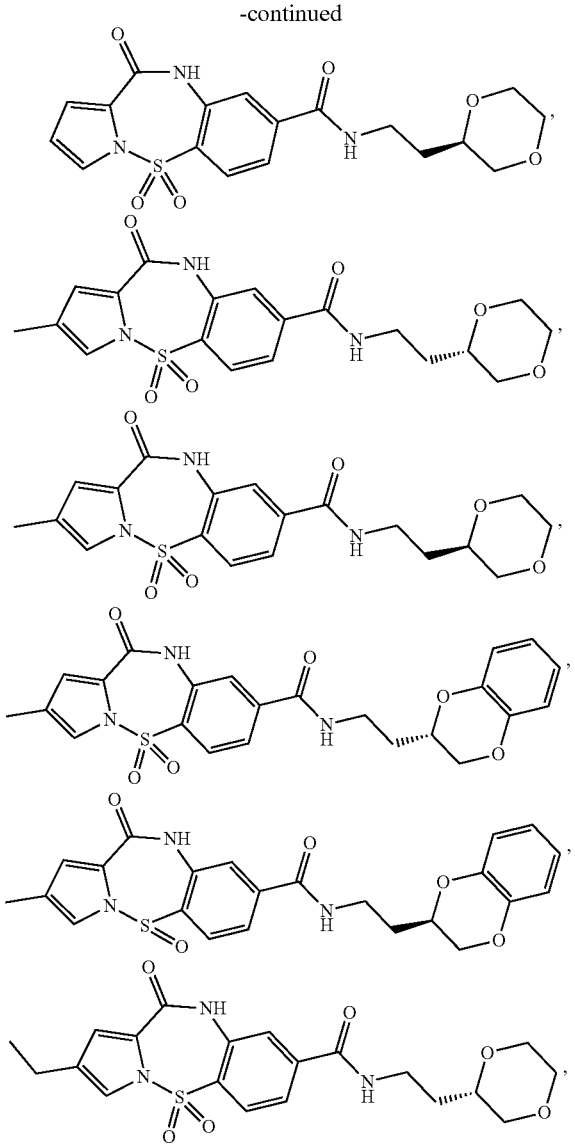

-continued

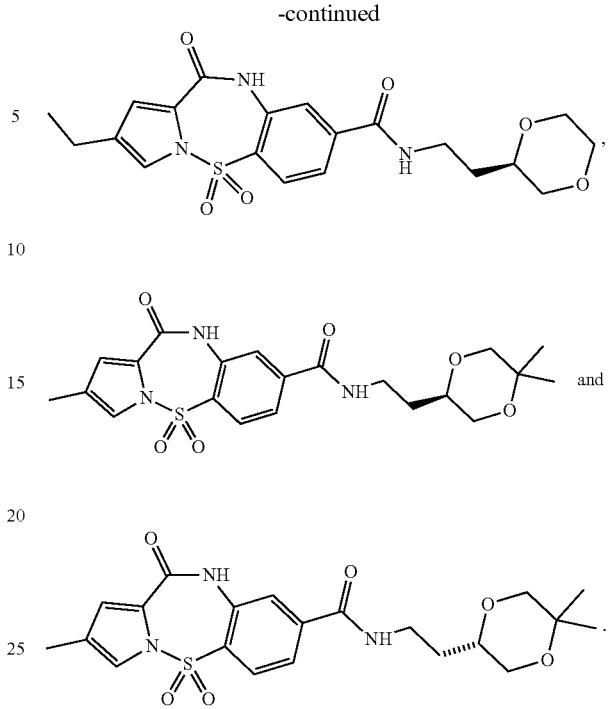

16. A pharmaceutical composition comprising a therapeutically effective amount of the compound, the tautomer or stereoisomer thereof or the pharmaceutically acceptable salt thereof according to claim 1 as the active ingredient, and a pharmaceutically acceptable carrier.

17. A method for treating hepatitis B comprising: administering an effective amount of the compound, the tautomer or stereoisomer thereof or the pharmaceutically acceptable salt thereof according to claim 1 to the patient in need thereof.

18. A method for treating hepatitis B comprising: administering an effective amount of the pharmaceutical composition according to claim 16 to the patient in need thereof.

* * * * *